US008124605B2

(12) United States Patent
Hangauer, Jr.

(10) Patent No.: US 8,124,605 B2
(45) Date of Patent: Feb. 28, 2012

(54) COMPOSITIONS AND METHODS FOR MODULATING A KINASE CASCADE

(75) Inventor: David G. Hangauer, Jr., East Amherst, NY (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 411 days.

(21) Appl. No.: 12/217,721

(22) Filed: Jul. 7, 2008

(65) Prior Publication Data
US 2009/0149510 A1 Jun. 11, 2009

Related U.S. Application Data

(60) Provisional application No. 60/958,526, filed on Jul. 6, 2007.

(51) Int. Cl.
A61K 31/44 (2006.01)
A61K 31/535 (2006.01)
C07D 211/82 (2006.01)
C07D 413/00 (2006.01)

(52) U.S. Cl. ............... 514/235.5; 514/340; 514/357; 544/131; 546/337

(58) Field of Classification Search ............... 514/235.5, 514/340, 357; 544/131; 546/337
See application file for complete search history.

(56) References Cited

U.S. PATENT DOCUMENTS

| 3,699,227 | A | 10/1972 | Doyle et al. ............... 424/263 |
| 3,761,477 | A | 9/1973 | Schwartz et al. |
| 3,868,380 | A | 2/1975 | Molteni et al. ............... 260/295 |
| 4,010,279 | A | 3/1977 | Griss et al. ............... 424/309 |
| 5,849,912 | A | 12/1998 | Akasaka et al. ............... 544/360 |
| 6,207,697 | B1 | 3/2001 | Han et al. ............... 514/409 |
| 6,538,960 | B1 | 3/2003 | Sabi et al. ............... 369/13.38 |
| 6,624,180 | B2 | 9/2003 | South et al. |
| 6,844,367 | B1 | 1/2005 | Zhu et al. ............... 514/620 |
| 6,969,726 | B2 | 11/2005 | Lou et al. |
| 7,300,931 | B2 | 11/2007 | Hangauer, Jr. |
| 2003/0130253 | A1 | 7/2003 | Dorwald et al. ............... 514/10.2 |
| 2003/0186963 | A1 | 10/2003 | Dorwald ............... 514/217.03 |
| 2004/0092598 | A1 | 5/2004 | Watkins et al. ............... 514/575 |
| 2004/0234622 | A1 | 11/2004 | Muto et al. ............... 424/649 |
| 2004/0242572 | A1 | 12/2004 | Stenkamp et al. ............... 514/227.2 |
| 2005/0059713 | A1 | 3/2005 | Mjalli et al. ............... 514/357 |
| 2006/0014830 | A1 | 1/2006 | Abouabdellah et al. ...... 514/430 |
| 2006/0160800 | A1 | 7/2006 | Hangauer, Jr. ............... 514/235.2 |
| 2006/0223805 | A1 | 10/2006 | Abouabdellah et al. ...... 514/241 |
| 2007/0015752 | A1 | 1/2007 | Hangauer, Jr. ............... 514/235.2 |
| 2007/0197783 | A1 | 8/2007 | Hangauer, Jr. |
| 2008/0287436 | A1 | 11/2008 | Hangauer, Jr. et al. |
| 2008/0318976 | A1* | 12/2008 | Wood et al. ............... 514/256 |

FOREIGN PATENT DOCUMENTS

| EP | 0 463 638 A1 | 1/1992 |
| EP | 1 745 800 A1 | 1/2007 |
| GB | 1 121 922 | 7/1968 |
| WO | WO-9219208 A1 | 11/1992 |
| WO | WO 96/12473 | 5/1996 |
| WO | WO 99/01127 | 1/1999 |
| WO | WO 01/19788 A2 | 3/2001 |
| WO | WO 02/079197 A1 | 10/2002 |
| WO | WO 03/059903 A2 | 7/2003 |
| WO | WO 03/078404 A1 | 9/2003 |
| WO | WO 03/087057 A1 | 10/2003 |
| WO | WO 03/093248 A1 | 11/2003 |
| WO | WO-03093297 A2 | 11/2003 |
| WO | WO 03/099771 A2 | 12/2003 |
| WO | WO 2004/011427 A2 | 2/2004 |
| WO | WO 2004/041833 A1 | 5/2004 |
| WO | WO 2004/043925 A2 | 5/2004 |
| WO | WO 2004/056774 A2 | 7/2004 |
| WO | WO 2005/013914 A2 | 2/2005 |
| WO | WO 2005/032493 A2 | 4/2005 |
| WO | WO 2006/009876 A2 | 1/2006 |
| WO | WO 2006/071960 A2 | 7/2006 |
| WO | WO-2007026920 A2 | 3/2007 |
| WO | WO 2007/087441 A2 | 8/2007 |
| WO | WO 2007/095383 A3 | 8/2007 |
| WO | WO 2007/136790 A2 | 11/2007 |
| WO | WO 2008/002676 A3 | 1/2008 |
| WO | WO 2008/005338 A1 | 1/2008 |
| WO | WO 2008/076356 A1 | 6/2008 |
| WO | WO 2008/082637 A1 | 7/2008 |
| WO | WO 2008/127727 A1 | 10/2008 |
| WO | WO 2008/127728 A1 | 10/2008 |

OTHER PUBLICATIONS

Vippagunt, Sr. et al. Crystalline solids. Advanced Drug Delivery Reviews 48 (2001) 3-26.*
Salehi et al. Facile conversion of alcohols into N-substituted amides by magnesium hydrogensulfate under heterogeneous conditions. Synthetic Communications, 31(13), 1947-1951 (2001).*
Honma et al., *J. Med. Chem.* 26:1499-1504 (1983).
Artico et al., "Aromatic hydrazides as specific inhibitors of bovine serum amine oxidase", *Eur. J. Med. Chem.*, 27(3):219-228 (1992).
Becalli et al., "An effective contribution to functionalized pyridines synthesis by way of an unusual rearrangement of amidines", *Tetrahedron*, 58(6):1213-1222 (2002).
Database Beilstein, Beilstein Institute for Organic Chemistry, Frankfurt-Main, XP002470813, (1995).
Database Beilstein, Beilstein Institute for Organic Chemistry, Frankfurt-Main, XP002470814, (2004).
Database Beilstein, Beilstein Institute for Organic Chemistry, Frankfurt-Main, XP002470815, (2004).
Database Beilstein, Beilstein Institute for Organic Chemistry, Frankfurt-Main, XP002470816, (1968).
Database Beilstein, Beilstein Institute for Organic Chemistry, Frankfurt-Main, XP002495954, (1990).
Hadjeri et al., "Antimitotic Activity of 5-Hydroxy-7-methoxy-2-phenyl-4-quinolones" *J. Med. Chem.*, 47(20):4964-4970 (2004).
An et al., "Oxidation of N-Benzylaldimines to N-Benzylamides by MCPBA and $BF_3OEt_2$", *Synlett*, 6:876-878 (2003).
Byrn et al., "Hydrates and Solvates", in *Solid-State Chemistry of Drugs*, 2nd Ed., SSCI, Inc., West Lafayette, IN, Ch. 11, pp. 233-247 (1999).
Cain et al., "Potential Antitumor Agents. IX. Bisquaternary Salts", *J. Med. Chem.*, 11(5):963-966 (1968).

(Continued)

Primary Examiner — Sreeni Padmanabhan
Assistant Examiner — Renee Claytor
(74) Attorney, Agent, or Firm — Mintz, Levin, Cohn, Ferris, Glovsky and Popeo, P.C.; Ivor R. Elrifi; Heidi A. Erlacher

(57) ABSTRACT

The invention relates to compounds and methods for modulating one or more components of a kinase cascade.

18 Claims, No Drawings

OTHER PUBLICATIONS

Davidson et al., "Discovery and Characterization of a Substrate Selective p38α Inhibitor", *Biochemistry*, 43:11658-11671 (2004).

Duong et al., "Inhibition of Osteoclast Function by Adenovirus Expressing Antisense Protein-tyrosine Kinase 2", *J. Biol. Chem.*, 276(10):7484-7492 (2001).

Frame, M.C., "Src in cancer:deregulation and consequences for cell behaviour", *Biochem. Biophys. Acta*, 1602:114-130 (2002).

Garrido et al., "Synthesis of N,N'-Diacyl-1,2-di-(4-pyridyl)ethylenediamines", *J. Het. Chem.*, 18:1305-1308 (1981).

Golub et al., "Molecular Classification of Cancer: Class Discovery and Class Prediction by Gene Expression Monitoring", *Science*, 286:531-537 (1999).

Guo et al., "Tyrosine Phosphorylation of the NR2B Subunit of the NMDA Receptor in the Spinal Cord during the Development and Maintenance of Inflammatory Hyperalgesia", *J. Neurosci.*, 22(14):6208-6217 (2002).

Huff, J.R., "HIV Protease: A Novel Chemotherapeutic Target for AIDS", *J. Med. Chem.*, 34(8):2305-2314 (1991).

Lala et al., "Role of nitric oxide in tumor progression: Lessons from experimental tumors", *Cancer Metastasis Rev.*, 17(1):91-106 (1998).

Liechti et al., "Salicylanilides as inhibitors of the protein tyrosine kinase epidermal growth factor receptor", *Eur. J. Med. Chem.*, 39(1):11-26 (2004).

Million et al, "Inhibition of the EGF-Stimulated Cellular Proliferation of ER 22 Cells by Hydroxybiphenyl Derivatives", *J. Med. Chem.*, 38(23):4693-4703 (1995).

Miyazaki et al., "Src Kinase Activity is Essential for Osteoclast Function", *J. Biol. Chem.*, 279(17):17660-17666 (2004).

Parang et al., "Recent advances in the discovery of Src kinase inhibitors", *Expert Opin. Ther. Patents*, 15(9):1183-1207 (2005).

Paul et al., "Src deficiency or blockade of Src activity in mice provides cerebral protection following stroke", *Nat. Med.*, 7(2):222-227 (2001).

Planas-Silva et al., "Targeting c-Src kinase enhances tamoxifen's inhibitory effect on cell growth by modulating expression of cell cycle and survival proteins", *Cancer Chemotherapy Pharmacol.*, 60(4):535-543 (2006).

Rouhi et al., "The Right Stuff: From research and development to the clinic, getting drug crystals right is full of pitfalls", *Chem. Eng. News*, pp. 32-35 (2003).

U.S. Pharmacopia #23, National Formulary #18, pp. 1843-1844 (1995).

Yu et al., "Src, a molecular switch governing gain control of synaptic transmission mediated by N-methyl-D-aspartate receptors", *Proc. Natl. Acad. Sci. USA*, 96:7697-7704 (1999).

Zhang et al., "Design, synthesis, and SAR of anthranilamide-based factor Xa inhibitors incorporating substituted biphenyl P4 motifs", *Bioorg. Med. Chem. Lett.*, 14(4):983-987 (2004).

* cited by examiner

COMPOSITIONS AND METHODS FOR MODULATING A KINASE CASCADE

RELATED APPLICATIONS

This non-provisional patent application claims priority under 35 U.S.C. §119(e) to U.S. Application No. 60/958,526, filed Jul. 6, 2007. The entire contents of the above-identified application are hereby incorporated by reference.

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers. In many transduction processes, an increasing number of enzymes and other molecules become engaged in the events that proceed from the initial stimulus. In such cases the chain of steps is referred to as a "signaling cascade" or a "second messenger pathway" and often results in a small stimulus eliciting a large response. One class of molecules involved in signal transduction is the kinase family of enzymes. The largest group of kinases are protein kinases, which act on and modify the activity of specific proteins. These are used extensively to transmit signals and control complex processes in cells.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate, ATP, in a highly conserved pocket. Protein phosphatases catalyze the transfer of phosphate in the opposite direction.

A tyrosine kinase is an enzyme that can transfer a phosphate group from ATP to a tyrosine residue in a protein. Phosphorylation of proteins by kinases is an important mechanism in signal transduction for regulation of enzyme activity. The tyrosine kinases are divided into two groups; those that are cytoplasmic proteins and the transmembrane receptor-linked kinases. In humans, there are 32 cytoplasmic protein tyrosine kinases and 58 receptor-linked protein-tyrosine kinases. The hormones and growth factors that act on cell surface tyrosine kinase-linked receptors are generally growth-promoting and function to stimulate cell division (e.g., insulin, insulin-like growth factor 1, epidermal growth factor).

Inhibitors of various known protein kinases or protein phosphatases have a variety of therapeutic applications. One promising potential therapeutic use for protein kinase or protein phosphatase inhibitors is as anti-cancer agents. About 50% of the known oncogene products are protein tyrosine kinases (PTKs) and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products). There are at least 9 members of the Src family of non-receptor PTK's with pp60$^{csrc}$ (hereafter referred to simply as "Src") being the prototype PTK of the family wherein the approximately 300 amino acid catalytic domains are highly conserved. The hyperactivation of Src has been reported in a number of human cancers, including those of the colon, breast, lung, bladder, and skin, as well as in gastric cancer, hairy cell leukemia, and neuroblastoma. Overstimulated cell proliferation signals from transmembrane receptors (e.g. EGFR and p185HER2/Neu) to the cell interior also appear to pass through Src. Because Src hyperactivation (without mutation) is involved in tumor initiation, progression, and metastasis for many important human tumor types, this kinase is an important target for cancer therapy.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders.

SUMMARY OF THE INVENTION

Compounds of the invention are useful in modulation of a component of the kinase signaling cascade. Some compounds may be useful in modulation of more than one component of a kinase signaling cascade. The compounds of the present invention are useful as pharmaceutical agents. The compounds of the invention may be useful for modulating regulation of a kinase which may be involved in a normal cellular signal transduction pathway (e.g., cell growth, differentiation, survival, adhesion, migration, etc.), or a kinase involved in a disease or disorder. Such diseases and disorders include, without limitation, cancers, osteoporosis, cardiovascular disorders, immune system dysfunction, type II diabetes, obesity, immune disease (rheumatoid arthritis, MS, psoriasis) and transplant rejection.

The compounds of the invention are useful in treating diseases and disorders that are modulated by tyrosine kinase inhibition. For example, the compounds of the invention are useful in treating diseases and disorders that are modulated by Src kinase. The compounds of the invention may also be useful in treating diseases and disorders that are modulated by focal adhesion kinase (FAK). The compounds of the invention may also be useful in treating diseases and disorders that are modulated by a Janus kinase (JAK).

For example the compounds may be useful as anti-proliferative agents, for treating mammals, such as for treating humans and animals. The compounds may be used without limitation, for example, as anti-cancer, anti-angiogenesis, anti-metastatic, anti-microbial, anti-bacterial, anti-fungal, anti-parasitic and/or anti-viral agents. The compounds of the invention are useful, for example, in treating lung cancer. The compounds of the invention are also useful, for example, in treating colon cancer. The compounds of the invention are also useful, for example, in treating breast cancer.

Compounds of the invention include compounds of Formula I

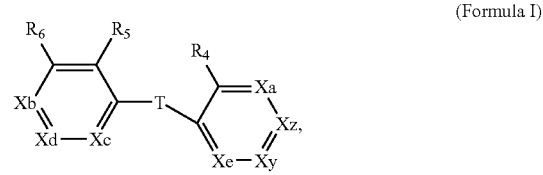

(Formula I)

or a salt, solvate, hydrate, or prodrug thereof, wherein:

T is a bond, $CR_{12}R_{13}$, C(O), O, S, S(O), $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, $C_1$, $C_2$, $C_3$, $C_4$, $C_5$, or $C_6$ alkyl, $C_3$, $C_4$, $C_5$, $C_6$, $C_7$ or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$)alkyl-aryl, ($C_3$, $C_4$, $C_5$, $C_6$, $C_7$, or $C_8$)cycloalkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, G, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COOH, COO—($C_1$, $C_2$, $C_3$, $C_4$, $C_5$, or $C_6$) alkyl, $SO_2H$, $SO_2$—($C_1$, $C_2$, $C_3$, $C_4$, $C_5$, or $C_6$) alkyl, wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl, or $C_3$, $C_4$, $C_5$, $C_6$, $C_7$, or $C_8$ cycloalkyl;

G is $SO_3H$, $OSO_3H$, $OPO_3H_2$, $OPO_2H_2$, $NH_2$, $NHR_{19}$, $NR_{20}R_{21}$, tetrazole, O—($C_1$, $C_2$, $C_3$, $C_4$, $C_5$, or $C_6$) alkyl-K, O—($C_3$, $C_4$, $C_5$, $C_6$, $C_7$, or $C_8$)cycloalkyl-K, O—C(O)—($C_1$, $C_2$, $C_3$, $C_4$, $C_5$, or $C_6$) alkyl-L, O—C(O)($C_3$, $C_4$, $C_5$, $C_6$, $C_7$, or $C_8$)cycloalkyl-L, NH—($C_1$, $C_2$, $C_3$, $C_4$, $C_5$, or $C_6$) alkyl-M, NH—($C_3$, $C_4$, $C_5$, $C_6$, $C_7$, or $C_8$)cycloalkyl-M or O-aryl-Q, further wherein ($C_1$, $C_2$, $C_3$, $C_4$, $C_5$, or $C_6$) alkyl is linear or branched alkyl;

K is aryl, heteroaryl, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, $C_1$, $C_2$, $C_3$, $C_4$, $C_5$, $C_6$ alkoxy, or L is aryl, heteroaryl, OH, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or M is aryl, heteroaryl, OH, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or Q is aryl, heteroaryl, OH, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

Z is —$(CR_1R_{1'})_n$—C(O)—$NR_2(CR_3R_{3'})_m$—B, —$(CR_1R_{1'})_n$—$NR_2$—C(O)—$(CR_3R_{3'})_m$—B, —$(CR_1R_{1'})_n$—$NR_2$—C(O)—$NR_2(CR_3R_{3'})_m$—B, —$(CR_1R_{1'})_n$—$S(O)_p$—$NR_2$—$(CR_3R_{3'})_m$—B, —$(CR_1R_{1'})_n$—$NR_2$—$S(O)_p$—$(CR_3R_{3'})_m$—B, —$(CR_1R_{1'})_n$—O—C(O)—$NR_2$—$(CR_3R_{3'})_m$—B, —$(CR_1R_{1'})_n$—$NR_2$—C(O)—O—$(CR_3R_{3'})_m$—B, —$(CR_1R_{1'})_n$—CH(OH)—$CR_2R_{2'}$—$NR_2$—$(CR_3R_{3'})_m$—B, —$(CR_1R_{1'})_n$—S—C(O)—$NR_2(CR_3R_{3'})_m$—B, —$(CR_1R_{1'})_n$—O—$(CR_3R_{3'})_m$—B, —$(CR_1R_{1'})_n$—C(S)—$NR_2(CR_3R_{3'})_m$—B, —$(CR_1R_{1'})_n$—$NR_2$—C(S)—$(CR_3R_{3'})_m$—B, —$(CR_1R_{1'})_n$—P(=O)(O—)—$CH_2$—$NR_2$—$(CR_3R_{3'})_m$—B, —$(CR_1R_{1'})_n$—P(=O)(OH)—$CH_2$—$(CR_3R_{3'})_m$—B, —$(CR_1R_{1'})_n$$NR_2$—$CH_2$—P(=O)(O—)—$(CR_3R_{3'})_m$—B, —$(CR_1R_{1'})_n$—P(=O)(O—)$NR_2$—$(CR_3R_{3'})_m$—B, —$(CR_1R_{1'})_n$—$NR_2$P(=O)(O—)—$(CR_3R_{3'})_m$—B, —$(CR_1R_{1'})_n$—CH(CN)—$NR_2(CR_3R_{3'})_m$—B, —$(CR_1R_{1'})_n$—$CH_2$—$(CR_3R_{3'})_m$—B, —$(CR_1R_{1'})_n$—C(O)—CHF—$(CR_3R_{3'})_m$—B, —$(CR_1R_{1'})_n$—$CR_2(OH)$—$CR_{2'}(OH)$—$(CR_3R_{3'})_m$—B, —$(CR_1R_{1'})_n$—$CR_2(OH)$—$CR_{2'}(NH_2)$—$(CR_3R_{3'})_m$—B, —$(CR_1R_{1'})_n$—CH(OH)—C(O)$NR_2(CR_3R_{3'})_m$—B,

—(CR$_1$R$_{1'}$)$_n$—NR$_2$—(CR$_3$R$_{3'}$)$_m$—B, —(CR$_1$R$_{1'}$)$_n$—C(O)C(OH)R$_2$—(CR$_3$R$_{3'}$)—B, —(CR$_1$R$_{1'}$)$_n$—C(O)—(CR$_3$R$_{3'}$)—B, —(CR$_1$R$_{1'}$)$_n$—S(O)$_p$—(CR$_3$R$_{3'}$)—B,

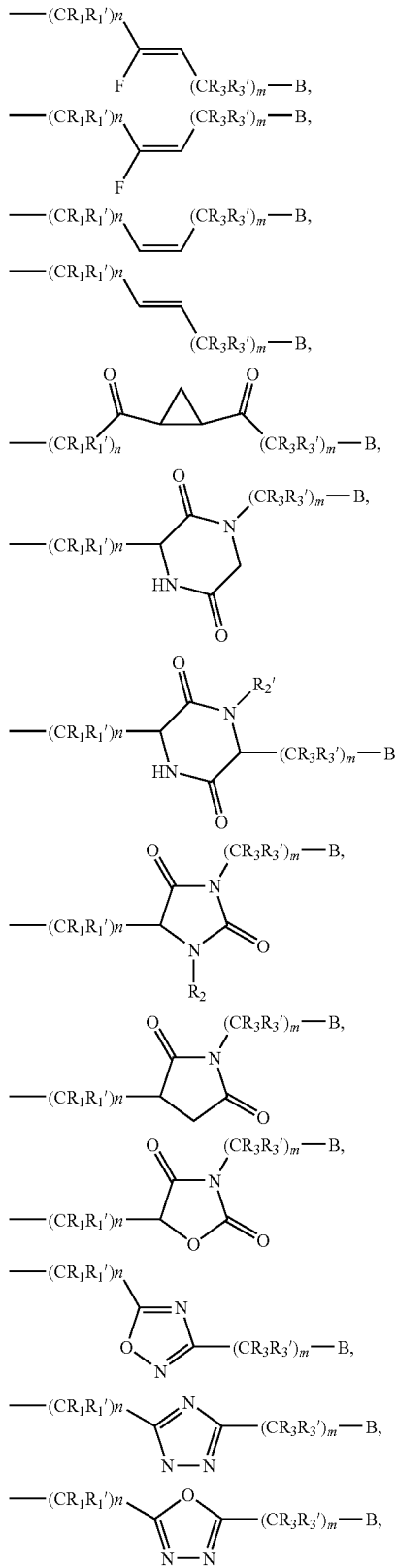

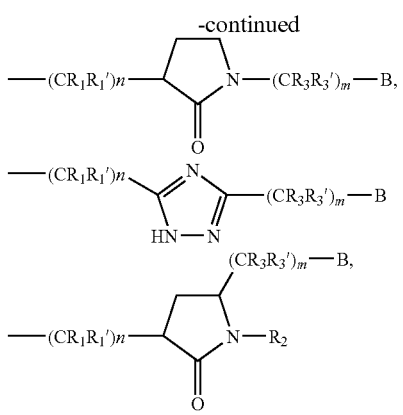

B is Ar or —(CR$_{22}$R$_{23}$)$_s$-J;

Ar is unsubstituted aryl, unsubstituted nitrogen-containing heteroaryl group, aryl substituted with D, or nitrogen-containing heteroaryl group substituted with D;

J is selected from hydrogen, OH, CN, CF$_3$, NR$_{31}$R$_{32}$, C$_1$, C$_2$, C$_3$, C$_4$, C$_5$, or C$_6$ alkyl, C$_3$, C$_4$, C$_5$, C$_6$, C$_7$, or C$_8$ cycloalkyl, C$_1$, C$_2$, C$_3$, C$_4$, C$_5$, or C$_6$ alkoxy, non-aromatic heterocycle, partially unsaturated carbocycle, COOH, COOR$_{30}$, and CONR$_{31}$R$_{32}$; further wherein alkyl, cycloalkyl, non-aromatic heterocycle, and partially unsaturated carbocycle are optionally substituted with D;

D is selected from halogen, C$_1$, C$_2$, C$_3$, C$_4$, C$_5$, or C$_6$ alkoxy, C$_1$, C$_2$, C$_3$, C$_4$, C$_5$, or C$_6$ alkyl, C$_3$, C$_4$, C$_5$, C$_6$, C$_7$, or C$_8$ cycloalkyl, non-aromatic heterocycle, partially unsaturated carbocycle, (C$_1$, C$_2$, C$_3$, C$_4$, C$_5$, or C$_6$)alkyl-non-aromatic heterocycle, (C$_3$, C$_4$, C$_5$, C$_6$, C$_7$, or C$_8$)cycloalkyl-non-aromatic heterocycle, (C$_1$, C$_2$, C$_3$, C$_4$, C$_5$, or C$_6$)alkyl-partially unsaturated carbocycle, (C$_3$, C$_4$, C$_5$, C$_6$, C$_7$, or C$_8$)cycloalkyl-partially unsaturated carbocycle, —OR$_{26}$, —SR$_{27}$, —NR$_{28}$R$_{29}$, and —(CR$_{24}$R$_{25}$)$_t$—U;

U is cyano, —OR$_{26}$, —SR$_{27}$, C$_1$, C$_2$, C$_3$, C$_4$, C$_5$, or C$_6$ alkyl, C$_3$, C$_4$, C$_5$, C$_6$, C$_7$, or C$_8$ cycloalkyl, non-aromatic heterocycle, partially unsaturated carbocycle, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, or glycoside;

R$_{22}$ and R$_{23}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl;

R$_{24}$ and R$_{25}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl;

R$_{26}$, R$_{27}$, R$_{28}$, and R$_{29}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl, or together R$_{28}$ and R$_{29}$ form a ring;

R$_{30}$, R$_{31}$ and R$_{32}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl, or together R$_{31}$ and R$_{32}$ form a ring;

s is 0, 1, 2, 3, 4, 5, 6, 7, 8, 9, or 10;

t is 0, 1, 2, 3, 4, 5, or 6;

p is 0, 1 or 2;

n and m are, independently 0, 1, or 2; and

R$_1$, R$_{1'}$, R$_2$, R$_{2'}$, R$_3$, and R$_{3'}$ are independently H or C$_1$, C$_2$, C$_3$, C$_4$, C$_5$, or C$_6$ alkyl, or C$_3$, C$_4$, C$_5$, C$_6$, C$_7$, or C$_8$ cycloalkyl.

The invention relates to compounds wherein Z is selected from —(CR$_1$R$_{1'}$)$_n$—NR$_2$—C(O)—(CR$_3$R$_{3'}$)$_m$—B, —(CR$_1$R$_{1'}$)$_n$—NR$_2$—(CR$_3$R$_{3'}$)$_m$—B, —(CR$_1$R$_{1'}$)$_n$—NR$_2$—C(O)—NR$_2$(CR$_3$R$_{3'}$)$_m$, —(CR$_1$R$_{1'}$)$_n$—O—C(O)—NR$_2$(CR$_3$R$_{3'}$)$_m$—B, —(CR$_1$R$_{1'}$)$_n$—NR$_2$—S(O)$_p$—(CR$_3$R$_{3'}$)$_m$—B, —(CR$_1$R$_{1'}$)$_n$—S(O)$_p$—(CR$_3$R$_{3'}$)—B, and —(CR$_1$R$_{1'}$)$_n$—C(O)—CR$_2$R$_{2'}$—NR$_2$—(CR$_3$R$_{3'}$)—B.

The invention relates to compounds wherein n is selected from 0, 1, and 2. The invention relates to compounds wherein m is selected from 0, 1, and 2.

The invention relates to compounds wherein $R_1$ and $R_{1'}$ are both hydrogen. The invention relates to compounds wherein $R_2$ and $R_{2'}$ are both hydrogen. The invention relates to compounds wherein $R_3$ and $R_{3'}$ are both hydrogen.

The invention relates to compounds wherein at least one of $X_a$, $X_b$, $X_c$, $X_d$, $X_e$, $X_y$ and $X_z$ is N. The invention relates to compounds wherein $X_c$ is N.

The invention relates to compounds wherein T is selected from a bond, $CH_2O$, O, and $OCH_2$.

The invention relates to compounds wherein $X_z$ is CZ.

The invention relates to compounds wherein B is Ar.

The invention relates to compounds wherein Ar is:

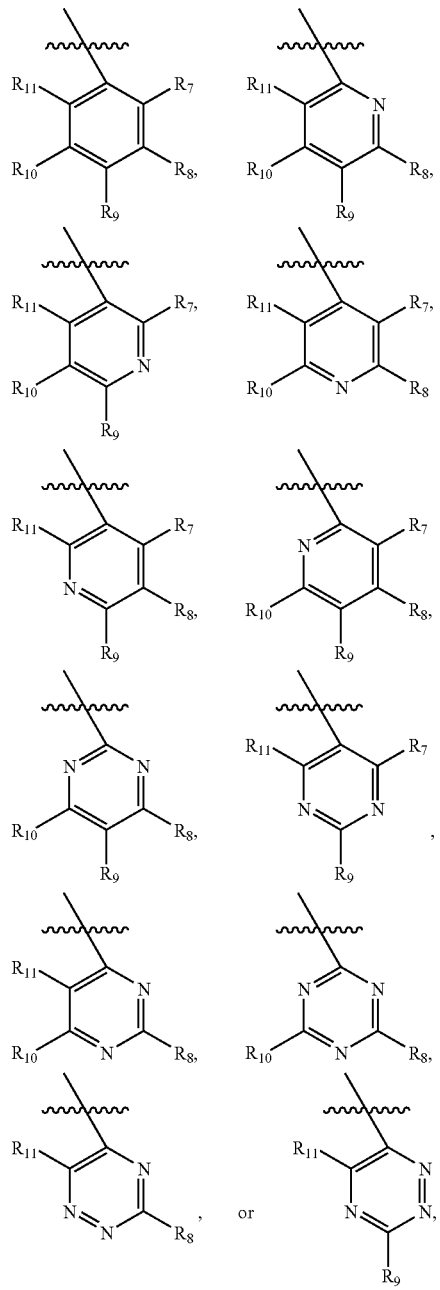

where $R_7$, $R_8$, $R_9$, $R_{10}$, and $R_{11}$ are, independently, hydrogen, hydroxyl, halogen, G, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl, ($C_1$, $C_2$, $C_3$, $C_4$, $C_5$, or $C_6$) alkyl-aryl, ($C_3$, $C_4$, $C_5$, or $C_6$) cycloalkyl-aryl, ($C_1$, $C_2$, $C_3$, $C_4$, $C_5$, or $C_6$) alkyl-heteroaryl, ($C_3$, $C_4$, $C_5$, or $C_6$) cycloalkyl-heteroaryl; $C_3$, $C_4$, $C_5$, $C_6$, $C_7$, or $C_8$ cycloalkyl, ($C_1$, $C_2$, $C_3$, $C_4$, $C_5$, or $C_6$)alkyl-non-aromatic heterocycle, ($C_3$, $C_4$, $C_5$, $C_6$, $C_7$, or $C_8$)cycloalkyl-non-aromatic heterocycle, ($C_1$, $C_2$, $C_3$, $C_4$, $C_5$, or $C_6$)alkyl-partially unsaturated carbocycle, ($C_3$, $C_4$, $C_5$, $C_6$, $C_7$, or $C_8$)cycloalkyl-partially unsaturated carbocycle, $C_1$, $C_2$, $C_3$, $C_4$, $C_5$, or $C_6$ alkyl-O—$C_1$, $C_2$, $C_3$, $C_4$, $C_5$, or $C_6$ alkyl, —$OR_{26}$, —$SR_{27}$, —$NR_{28}R_{29}$, —$(CR_{24}R_{25})_t$—U;

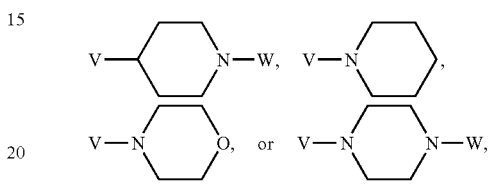

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$;

U is cyano, —$OR_{26}$, —$SR_{27}$, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, or glycoside;

$R_{24}$ and $R_{25}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl;

$R_{26}$, $R_{27}$, $R_{28}$, and $R_{29}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl, or together $R_{28}$ and $R_{29}$ form a ring;

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

G is $SO_3H$, $OSO_3H$, $OPO_3H_2$, $OPO_3H_2$, $NH_2$, $NHR_{19}$, $NR_{20}R_{21}$,

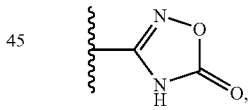

tetrazole, O-lower $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, aryl, heteroaryl, or

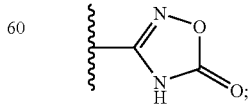

L is aryl, heteroaryl, OH, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

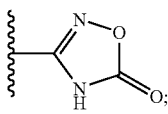

M is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

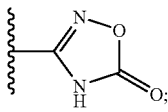

Q is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

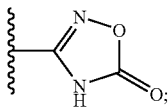

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring; and t is 0, 1, 2, 3, 4, 5, or 6.

The invention relates to compounds, wherein B is —(CR$_{22}$R$_{23}$)$_s$-J. The invention relates to compounds, wherein J is alkyl. The invention relates to compounds, wherein J is a non-aromatic heterocycle.

The invention relates to compounds, wherein R$_4$, R$_5$, and R$_6$ are each H.

The invention relates to a composition comprising a compound of the invention and at least one pharmaceutically acceptable carrier or excipient.

Certain compounds of the invention are selected from Compounds 1-183. For example, the compound of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, or 183.

The invention includes a solvate of a compound according to Formula I.

The invention also includes a hydrate of a compound according to Formula I.

The invention also includes an acid addition salt of a compound according to Formula I. For example, a hydrochloride salt, e.g., dihydrochloride.

The invention also includes a prodrug of a compound according to Formula I.

The invention also includes a pharmaceutically acceptable salt of a compound of Formula I.

The invention also includes a composition of a compound according to Formula I and at least one pharmaceutically acceptable excipient.

The invention relates to a compound of Formula I, having a structure according to one of Formulae II-CCCXIX.

The invention relates to a solvate of a compound according to one of Formulae II-CCCXIX.

The invention also relates to a hydrate of a compound according to one of Formulae II-CCCXIX.

The invention also relates to an acid addition salt of a compound according to one of Formulae II-CCCXIX. For example, a hydrochloride salt.

Further, the invention relates to a prodrug of a compound according to one of Formulae II-CCCXIX.

The invention also relates to a pharmaceutically acceptable salt of a compound according to one of Formulae II-CCCXIX.

The invention includes compositions comprising a compound according to one of Formulae II-CCCXIX and at least one pharmaceutically acceptable excipient.

The invention relates to compounds and methods of using the compounds to modulate a component of the kinase signaling cascade. Some compounds may be useful in modulation of more than one component of a kinase signaling cascade. The compounds of the present invention are useful as pharmaceutical agents.

Certain compounds of the invention are non-ATP competitive kinase inhibitors.

The invention relates to compounds and methods of using the compounds to treat cell proliferation disorders.

The invention also includes a method of preventing or treating a cell proliferation disorder by administering a pharmaceutical composition that includes a compound according to one of Formulae I-CCCXIX, or a salt, solvate, hydrate, or prodrug thereof, and at least one pharmaceutically acceptable excipient to a subject in need thereof.

The invention includes use of a compound of the present invention in the manufacture of a medicament to prevent or treat a cell proliferation disorder.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriasis.

For example, the treatment or prevention of the proliferative disorder may occur through the inhibition of a tyrosine kinase. For example, the tyrosine kinase can be a Src kinase or focal adhesion kinase (FAK). The tyrosine kinase can be a Janus (JAK) kinase e.g., JAK3 and/or JAK1.

The invention relates to a method of treating or preventing a disease or disorder that is modulated by tyrosine kinase inhibition, by administering a pharmaceutical composition that includes a compound according to one of Formulae I-CCCXIX, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection. For example, the compound is a compound according to Formula I.

The invention relates to use of a compound of the present invention in the manufacture of a medicament to treat or prevent a disease or disorder that is modulated by tyrosine kinase inhibition.

The pharmaceutical composition of the invention may modulate a kinase pathway. For example, the kinase pathway is a Src kinase pathway, or a focal adhesion kinase pathway.

The pharmaceutical composition of the invention may modulate a kinase directly. For example, the kinase is Src kinase, or focal adhesion kinase. For example, the composition of the invention may modulate JAK kinase e.g., JAK1 and/or JAK3.

Certain pharmaceutical compositions of the invention are non-ATP competitive kinase inhibitors.

The compounds of the invention are also useful to treat or prevent a microbial infection, such as a bacterial, fungal, parasitic or viral infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, and 183.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriases. Anti-cancer agents include anti-metastatic agents.

A compound of the present invention may be used in the manufacture of a medicament to be used as an anti-proliferative agent. A compound may be used in the manufacture of a medicament as an anti-cancer, anti-angiogenesis, anti-microbial, anti-bacterial, anti-fungal, anti-parasitic and/or anti-viral agent. Additionally, a compound may be used in the manufacture of a medicament for the treatment or prevention of other cell-proliferation-related disorders such as diabetic retinopathy, macular degeneration and psoriasis.

The compound of the invention used as a pharmaceutical agent includes a compound selected from Compounds 1-183. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, or 183.

In one aspect of the invention, a compound of the invention, for example, a compound according to one of Formulae I-CCCXIX, is used to modulate a kinase cascade. For example, the compound is used to modulate a component of a kinase cascade which is responsible for the manifestation of a disease or disorder.

Such diseases and disorders include cancers, osteoporosis, cardiovascular disorders, immune system dysfunction, type II diabetes, obesity, and transplant rejection.

For example, a compound of the invention may be used to treat or prevent a cell proliferation disorder in a subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase, focal adhesion kinase (FAK), or JAK. In another embodiment, the subject is a mammal. In one embodiment, the subject is human.

The invention relates to a method of treating or preventing a disease or disorder by administering to a subject a compound of Formula I, or a salt, solvate, hydrate, or prodrug thereof, wherein the disorder or disease is selected from a cell proliferation disorder, pre-cancer, microbial infection, an immune disease, osteoporosis, hearing loss, ophthalmic disease, macular edema, a cardiovascular disorder, stroke, atherosclerosis, type II diabetes, obesity, immune system dysfunction, chronic neuropathic pain, and transplant rejection. For example, the disease or disorder treated by the method of the invention is modulated by tyrosine kinase inhibition.

In one embodiment, the disease or disorder treated by the method of the invention is a microbial infection such as a bacterial, fungal, parasitic or viral infection.

In one embodiment, the disease or disorder treated by the method of the invention is a cell proliferation disorder which is a hyperproliferative disorder selected from psoriases, diabetic retinopathy and macular degeneration.

In one embodiment, the disease or disorder treated by the method of the invention is a cell proliferation disorder such as cancer. For example, the cancer is lung cancer, breast cancer, colon cancer, ovarian cancer, brain cancer, liver cancer, pancreatic cancer, prostate cancer, malignant melanoma, non-melanoma skin cancer, a hematologic tumor, hematologic malignancy, childhood leukemia, lymphoma, multiple myeloma, Hodgkin's disease, lymphoma of lymphocytic or cutaneous origin, acute or chronic leukemia, lymphoblastic leukemia, acute myelocytic leukemia, chronic myelocytic leukemia, plasma cell neoplasm, lymphoid neoplasm or a cancer associated with AIDS.

In one embodiment, the disease or disorder treated by the method of the invention is a cell proliferation disorder which is an epidermic cyst, dermoid cyst, lipoma, adenoma, capillary hemangioma, cutaneous hemangioma, lymphangioma, nevi lesion, teratoma, nephroma, myofibromatosis, osteoplastic tumor, or a dysplastic mass.

In one embodiment, the disease or disorder treated by the method of the invention is a cardiovascular disorder such as stroke or atherosclerosis.

In one embodiment, the disease or disorder treated by the method of the invention is an immune disease such as multiple sclerosis, rheumatoid arthritis, or is transplant rejection.

In one embodiment, in the methods of the invention, the compound or pharmaceutical composition is to be administered orally or topically.

The invention is also drawn to a method of treating or preventing cancer or a proliferation disorder in a subject, comprising administering an effective amount of a compound of the invention, for example, a compound according to one of Formulae I-CCCXIX. For example, the compound of the invention may be a kinase inhibitor. The compound of the invention may be a non-ATP competitive kinase inhibitor. The compound of the invention may inhibit a kinase directly, or it may affect the kinase pathway.

Another aspect of the invention is a method of preventing or treating a cell proliferation disorder comprising administering to a subject in need thereof a compound according to one of Formulae I-CCCXIX. Another aspect of the invention includes use of a compound of the invention in the manufacture of a medicament to protect against or treat a cell proliferation disorder. In one embodiment, the compound inhibits one or more components of a protein kinase signaling cascade. In another embodiment, the compound is an allosteric inhibitor. In another embodiment, the compound is a peptide substrate inhibitor. In another embodiment, the compound does not inhibit ATP binding to a protein kinase. In one embodiment, the compound inhibits a Src family protein kinase. In another embodiment, the Src family protein kinase is pp60$^{c-src}$ tyrosine kinase. In another embodiment, the compound inhibits a JAK family protein kinase.

Another aspect of the invention includes a method of protecting against or treating hearing loss in a subject comprising administering a compound according to one of Formulae I-CCCXIX. One aspect of the invention includes a method of reducing the amount of hearing loss. In one embodiment, the compound inhibits one or more components of a kinase signaling cascade. In one embodiment, the compound is an allosteric inhibitor. In one embodiment, the compound is a peptide substrate inhibitor. In one embodiment, the compound does not inhibit ATP binding to the protein kinase. In one embodiment, the compound inhibits a Src family protein kinase. In one embodiment, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically e.g., by administering drops into the ear, intraarterially, intralesionally, by metering pump, or by application to mucous membranes. In another embodiment, the compound is administered with a pharmaceutically acceptable carrier.

In one embodiment, the compound is administered before initiation of hearing loss. In another embodiment, the compound is administered after initiation of hearing loss.

In one embodiment, the compound is administered in combination with a drug that causes hearing loss e.g., cis platinum or an aminoglycoside antibiotic. In another embodiment, the compound is administered in combination with a drug that targets hairy cells.

Another aspect of the invention includes a method of protecting against or treating osteoporosis in a subject comprising administering a compound according to one of Formulae I-CCCXIX. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before initiation of osteoporosis. In another embodiment, the compound is administered after initiation of osteoporosis.

Another aspect of the invention includes a method of protecting against or treating ophthalmic diseases e.g., macular degeneration, retinopathy, macular edema, etc. in a subject comprising administering a compound according to one of Formulae I-CCCXIX. Another aspect of the invention includes use of a compound of the invention in the manufacture of a medicament to protect against or treat ophthalmic diseases. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits one or more components in the VEGF pathway.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops to the eye), intraarterially, intralesionally, by metering pump, or by application to mucous membranes. In one embodiment, the compound is administered with a pharmaceutically acceptable carrier. In one embodiment, the compound is administered before initiation of the ophthalmic disease. In another embodiment, the compound is administered after initiation of ophthalmic disease.

Another aspect of the invention includes a method of protecting against or treating diabetes in a subject comprising administering a compound according to one of Formulae I-CCCXIX. Another aspect of the invention includes use of a compound of the invention in the manufacture of a medicament to protect against or treat diabetes. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of diabetes. In another embodiment, the compound is administered after the onset of diabetes.

Another aspect of the invention includes a method of protecting against or treating obesity in a subject comprising administering a compound according to one of Formulae I-CCCXIX. Another aspect of the invention includes use of a compound of the invention in the manufacture of a medicament to protect against or treat obesity. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the subject is obese. In another embodiment, the compound is administered after the subject is obese.

Another aspect of the invention includes a method of protecting against or treating stroke in a subject comprising administering a compound according to one of Formulae I-CCCXIX Another aspect of the invention includes use of a compound of the invention in the manufacture of a medicament to protect against or treat stroke. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before a stroke has occurred. In another embodiment, the compound is administered after a stroke has occurred.

Another aspect of the invention includes a method of protecting against or treating atherosclerosis in a subject comprising administering a compound according to one of Formulae I-CCCXIX. Another aspect of the invention includes use of a compound of the invention in the manufacture of a medicament to protect against or treat atherosclerosis. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of atherosclerosis. In another embodiment, the compound is administered after the onset of atherosclerosis.

Another aspect of the invention includes a method of regulating immune system activity in a subject comprising administering a compound according to one of Formulae I-CCCXIX. For example, modulating immune system activity includes modulating autoimmune diseases such as transplant rejection (e.g., kidney, heart, lung, liver, pancreas, skin, host versus graft reaction (HVGR), etc.), rheumatoid arthritis, and amyotrophic lateral sclerosis. Another aspect of the invention includes use of a compound of the invention in the manufacture of a medicament to regulate immune system activity. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of immune system irregularity. In another embodiment, the compound is administered after the onset of immune system irregularity.

Another aspect of the invention includes a method of protecting against or treating chronic neuropathic pain in a subject comprising administering a compound according to one of Formulae I-CCCXIX. Another aspect of the invention includes use of a compound of the invention in the manufacture of a medicament to protect against or treat chronic neuropathic pain. In one embodiment, the compound, inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of chronic neuropathic pain. In another embodiment, the compound is administered after the onset of chronic neuropathic pain.

Another aspect of the invention includes a method of protecting against or treating hepatitis B in a subject comprising administering a compound according to one of Formulae I-CCCXIX. Another aspect of the invention includes use of a compound of the invention in the manufacture of a medicament to protect against or treat hepatitis B. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of hepatitis B. In another embodiment, the compound is administered after the onset of hepatitis B.

Accordingly, another aspect of the invention is a method for treating leukemia in a host comprising administering to a patient a compound according to one of Formulae I-CCCXIX. Another aspect of the invention includes use of a compound of the invention in the manufacture of a medicament to treat leukemia. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits a JAK family protein kinase. In one embodiment, the compound is administered before the onset of leukemia. In another embodiment, the compound is administered after the onset of leukemia.

In another embodiment, there is provided a method for treating leukemia in a host comprising administering to a patient a therapeutically effective amount of a compound according to one of Formulae I-CCCXIX, as defined above, and at least one further therapeutic agent selected from the group consisting of anti-proliferative agents, cytotoxic agents, cytostatic agents, and chemotherapeutic agents and salts and derivatives thereof. According to certain embodiments, the compound of the present invention may be used in the treatment of a leukemia in combination therapy with one or more of the drugs selected from a group consisting of an alkaloid, an alkylating agent, an antitumor antibiotic, an anti-metabolite, an Bcr-Abl tyrosine kinase inhibitor, a nucleoside analog, a multidrug resistance reversing agent, a DNA binding agent, microtubule binding drug, a toxin and a DNA antagonist. Those of skill in the art will recognize the chemotherapeutic agents classified into one or more particular classes of drugs described above.

In one embodiment, there is provide a method for treating leukemia in a host comprising administering to a patient that has been previously treated with a Bcr-Abl tyrosine kinase inhibitor and has become resistant to the Bcr-Abl tyrosine kinase inhibitor treatment, a therapeutically effective amount of a compound according to one of Formulae I-CCCXIX.

Another aspect of the invention includes a method of regulating allergy in a subject comprising administering a compound according to one of Formulae I-CCCXIX. Another aspect of the invention includes use of a compound of the invention in the manufacture of a medicament to regulate allergy in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of allergy. In another embodiment, the compound is administered after the onset of allergy.

Another aspect of the invention includes a method of regulating asthma in a subject comprising administering a compound according to one of Formulae I-CCCXIX. Another aspect of the invention includes use of a compound of the invention in the manufacture of a medicament to regulate asthma in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of asthma. In another embodiment, the compound is administered after the onset of asthma.

Another aspect of the invention includes a method of regulating multiple sclerosis in a subject comprising administering a compound according to one of Formulae I-CCCXIX. Another aspect of the invention includes use of a compound of the invention in the manufacture of a medicament to regulate multiple sclerosis in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of multiple sclerosis. In another embodiment, the compound is administered after the onset of multiple sclerosis.

Another aspect of the invention includes a method of regulating psoriasis in a subject comprising administering a compound according to one of Formulae I-CCCXIX. Another aspect of the invention includes use of a compound of the invention in the manufacture of a medicament to regulate psoriasis in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of psoriasis. In another embodiment, the compound is administered after the onset of psoriasis.

Another aspect of the invention includes a method of regulating Sjogren's syndrome in a subject comprising administering a compound according to one of Formulae I-CCCXIX. Another aspect of the invention includes use of a compound of the invention in the manufacture of a medicament to regulate Sjogren's syndrome in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of Sjogren's syndrome. In another embodiment, the compound is administered after the onset of Sjogren's syndrome.

Another aspect of the invention includes a method of regulating Type II inflammatory disease such as vascular inflammation (including vasculitis, ateritis, atherosclerosis and coronary artery disease) in a subject comprising administering a compound according to one of Formulae I-CCCXIX. Another aspect of the invention includes use of a compound of the invention in the manufacture of a medicament to regulate Type II inflammatory disease in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of Type II inflammatory disease. In another embodiment, the compound is administered after the onset of Type II inflammatory disease.

Another aspect of the invention includes a method of regulating pulmonary diseases such as bronchitis obliterous and primary and primary pulmonary hypertension, delayed or cell-mediated, Type IV hypersensitivity in a subject comprising administering a compound according to one of Formulae I-CCCXIX. Another aspect of the invention includes use of a compound of the invention in the manufacture of a medicament to regulate pulmonary disease in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of pulmonary disease. In another embodiment, the compound is administered after the onset of pulmonary disease.

Another aspect of the invention includes a method of regulating lymphoma in a subject comprising administering a compound according to one of Formulae I-CCCXIX. Another aspect of the invention includes use of a compound of the invention in the manufacture of a medicament to regulate lymphoma in a host. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a JAK family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of lymphoma. In another embodiment, the compound is administered after the onset of lymphoma.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders. Such diseases and disorders include, for example, cancers, osteoporosis, cardiovascular disorders, immune system dysfunction, type II diabetes, obesity, and transplant rejection.

Compounds of the invention are useful in modulation a component of the kinase signaling cascade. Some compounds may be useful in modulation of more than one component of a kinase signaling cascade. The phrase "modulates one or more components of a protein kinase signaling cascade" means that one or more components of the kinase signaling cascade are affected such that the functioning of a cell changes. Components of a protein kinase signaling cascade include any proteins involved directly or indirectly in the kinase signaling pathway including second messengers and upstream and downstream targets.

A number of protein kinases and phosphatases are known, and are targets for the development of therapeutics. See, e.g., Hidaka and Kobayashi, Annu. Rev. Pharmacol. Toxicol, 1992, 32:377-397 and Davies et al., Biochem. J., 2000, 351: 95-105, each of which is incorporated by reference herein.

One family of kinases, the protein tyrosine kinases are divided into two large families: receptor tyrosine kinases, or RTKs (e.g., insulin receptor kinase (IRK), epidermal growth factor receptor (EGFR), basic fibroblast growth factor receptor (FGFR), platelet-derived growth factor receptor (PDGFR), vascular endothelial growth factor receptor (VEGFR-2 or Flk1/KDR), and nerve growth factor receptor (NGFR)) and nonreceptor tyrosine kinases, or NRTKs (e.g., the Src family (Src, Fyn, Yes, Blk, Yrk, Fgr, Hck, Lck, and Lyn), Fak, Jak, Abl and Zap70). See, for example, Parang and Sun, Expert Opin. Ther. Patents, 2005, 15:1183-1207, incorporated by reference herein.

Because of the role of Src kinases in a variety of cancers, these kinases are the subject of a number of studies relating to the development of Src inhibitors as cancer therapeutics, including highly metastatic cancer cell growth. Src inhibitors are sought as therapeutics for a variety of cancers, including, for example, colon cancer, precancerous colon lesions, ovarian cancer, breast cancer, epithelial cancers, esophageal cancer, non-small cell lung cancer, pancreatic cancer, and others. See, e.g., Frame, Biochim. Biophys. Acta, 2002, 1602:114-130 and Parang and Sun, Expert Opin. Ther. Patents, 2005, 15:1183-1207.

Inhibition of other kinases may be useful in the treatment and modulation of other types of diseases and disorders. For example, various eye diseases may be inhibited or prevented by administration of VEGF receptor tyrosine kinase inhibitors. Inhibitors of the tyrosine phosphatase PTP-1B and/or glycogen phosphorylase may provide treatments for Type II diabetes or obesity. Inhibitors of p56lck may be useful in treating immune system disorders. Other targets include HIV reverse transcriptase, thromboxane synthase, EGFRTK, p55 fyn, etc.

The Janus kinases (JAK) are a family of tyrosine kinases consisting of JAK1, JAK2, JAK3 and TYK2. The JAKs play a crucial role in cytokine signaling. The downstream substrates of the JAK family of kinases include the signal tranducer activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, 1999, Mol. Med. 5:432:456 and Seidel et al., 2000, Oncogene 19:2645-2656.

Compounds of the invention may be Src signaling inhibitors that bind in the Src peptide substrate site. The activity of various compounds of the invention has been studied in c-Src (527F, constitutively active and transforming) transformed NIH3T3 cells and in human colon cancer cells (HT29). For example, in these cell lines, compounds which reduce the phosphorylation level of known Src protein substrates in a dose-dependent fashion and in good correlation with growth inhibitory effects may directly inhibit Src, and may do so by binding in the peptide binding site (as opposed to binding at an allosteric site).

Molecular modeling experiments have been performed which show that compounds of the invention fit into the model Src substrate site (See, e.g., U.S. Pat. Nos. 7,005,445 and 7,070,936). Modeling is also used to retool the Src kinase inhibitor scaffolds in order to target other kinases, simply by using a different set of side chains present on the molecules and/or modifying the scaffold itself.

Without wishing to be bound by theory, it is believed that the conformation of some kinases (e.g., Src) outside cells relative to the conformation inside cells is markedly different, because inside cells, many kinases are is embedded in multi-protein signaling complexes. Thus, because the peptide substrate binding site is not well formed in an isolated kinase (as shown by Src x-ray structures), it is believed that the activity against isolated kinase for a peptide substrate binding inhibitor would be weak. Binding to this site in an isolated kinase assay requires the inhibitor to capture the very small percentage of total protein in an isolated enzyme assay that is in the same conformation that exists inside cells. This requires a large excess of the inhibitor to drain significant amounts of the enzyme from the catalytic cycle in the assay in order to be detectable.

However, for cell-based assays, a large inhibitor excess is not needed because the peptide binding site is expected to be formed. In cell-based Src assays, SH2 & SH3 domain binding proteins have already shifted the Src conformation so that the peptide substrate binding site is fully formed. Thus, low concentrations of the inhibitor can remove the enzyme from the catalytic cycle since all of the enzyme is in the tight binding conformation.

The vast majority of known kinase inhibitors are ATP competitive and show poor selectivity in a panel of isolated kinase assays. However, many of the compounds of the invention are thought to be peptide substrate binding inhibitors. Thus, traditional high throughput screening of compounds against isolated enzymes, such as Src, would not result in the discovery of compounds of the invention.

There is considerable recent literature support for targeting pp60c-src (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al. (1999) Oncogene 18(33): 4654-4662). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano, et al., Proc. Annu. Meet. Am. Assoc. Cancer Res. 38:A1925 (1997)). Additionally, reduced VEGF mRNA expression was noted upon Src inhibition and tumors derived from these Src-inhibited cell lines showed reduced angiogenic development (Ellis et al., Journal of Biological Chemistry 273 (2):1052-1057 (1998)).

For example, a knock-out of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., (1997) Genes & Development 11: 2835-2844). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors (Levitzki, Current Opinion in Cell Biology, 8, 239-244 (1996); Levitzki, Anti-Cancer Drug Design, 11, 175-182 (1996)). The potential benefits of Src inhibition for cancer therapy appear to be four-fold inhibition of uncontrolled cell growth caused by autocrine growth factor loop effects, inhibition of metastasis due to triggering apoptosis upon breaking free from the cell matrix, inhibition of tumor angiogenesis via reduced VEGF levels, low toxicity.

Prostate cancer cells have been reported to have both an over expression of paxillin and p130cas and are hyperphosphorylated (Tremblay et al., Int. J. Cancer, 68, 164-171, 1996) and may thus be a prime target for Src inhibitors.

Thus, the invention relates to compounds and methods of using compounds to treat cell proliferation disorders.

The compounds of the present invention are useful as pharmaceutical agents, for example, as therapeutic agents for treating humans and animals. The compounds may be used without limitation, for example, as anti-cancer, anti-angiogenesis, anti-metastatic, anti-microbial, anti-bacterial, anti-fungal, anti-parasitic and/or anti-viral agents. The compounds may be used for other cell proliferation-related disorders such as psoriasis.

As described herein, a compound of the invention may be used to protect against or prevent hearing loss in a subject. Another aspect of the invention includes use of a compound of the invention in the manufacture of a medicament to protect against or treat hearing loss. In order to protect against hearing loss, the compound may be administered prior to noise exposure or exposure to a drug which induces hearing loss. Such drugs may include chemotherapeutic drugs (e.g., platinum-based drugs which target hair cells) and aminoglycoside antibiotics. A compound of the invention may provide a synergistic effect with certain cancer drugs. For example, promising inhibitors can be screened in primary human tumor tissue assays, particularly to look for synergy with other known anti-cancer drugs. In addition, the protein kinase inhibitors may reduce toxicity of certain cancer drugs (e.g., platinum-based drugs which are toxic to the cochlea and kidney), thereby allowing increased dosage.

Alternatively, a compound of the invention may be used to treat hearing loss in a subject. In this embodiment, the compound is administered to the subject subsequent to the initiation of hearing loss to reduce the level of hearing loss. A compound of the invention may be involved in modulating a kinase cascade, e.g. a kinase inhibitor, a non-ATP competitive inhibitor, a tyrosine kinase inhibitor, a Src inhibitor or a focal adhesion kinase (FAK) modulator. Although not wishing to be bound by theory, it is believed that the administration of kinase inhibitors prevents apoptosis of cochlear hair cells, thereby preventing hearing loss. In one embodiment, administration of a compound of the invention is administered to a subject suffering from hearing loss in order to prevent further hearing loss. In another embodiment, administration of a compound of the invention is administered to a subject suffering from hearing loss in order to restore lost hearing. In particular, following noise exposure, the tight cell junctures between the cochlear hair cells, as well as the cell-extracellular matrix interaction, are torn and stressed. The stressing of these tight cell junctures initiates apoptosis in the cells through a complex signaling pathway in which tyrosine kinases act as molecular switches, interacting with focal adhesion kinase to transduce signals of cell-matrix disruptions to the nucleus. It is believed that the administration of kinase inhibitors prevents the initiation of apoptosis in this cascade.

The identification of apoptosis in the noise-exposed cochlea has generated a number of new possibilities for the prevention of noise-induced hearing loss (NIHL) (Hu, et al.; 2000, *Acta. Otolaryngol.*, 120, 19-24). For example, the ear can be protected from NIHL by administration of antioxidant drugs to the round window of the ear (Hight, et al.; 2003, *Hear. Res.*, 179, 21-32; Hu, et al.; *Hear. Res.* 113, 198-206). Specifically, NIHL has been reduced by the administration of FDA-approved antioxidant compounds (N-L-acetylcysteine (L-NAC) and salicylate) in the chinchilla (Kopke, et al.; 2000, *Hear. Res.*, 149, 138-146). Moreover, Harris et al. have recently described prevention of NIHL with Src-PTK inhibitors (Harris, et al.; 2005, *Hear. Res.*, 208, 14-25). Thus, it is hypothesized that the administration of a compound of the instant invention which modulates the activity of kinases, is useful for treating hearing loss.

Changes in cell attachment or cell stress can activate a variety of signals through the activation of integrins and through the phosphorylation of PTKs, including the Src family of tyrosine kinases. Src interactions have been linked to signaling pathways that modify the cytoskeleton and activate a variety of protein kinase cascades that regulate cell survival and gene transcription (reviewed in Giancotti and Ruoslahti; 1999, *Science*, 285, 1028-1032). In fact, recent results have indicated that outer hair cells (OHC), which had detached at the cell base following an intense noise exposure, underwent apoptotic cell death. Specifically, the Src PTK signaling cascade is thought to be involved in both metabolic- and mechanically-induced initiation of apoptosis in sensory cells of the cochlea. In a recent study, Src inhibitors provided protection from a 4 hour, 4 kHz octave band noise at 106 dB, indicating that Src-PTKs might be activated in outer hair cells following noise exposure (Harris, et al.; 2005, *Hear. Res.*, 208, 14-25). Thus, compounds of the instant invention that modulate the activity of Src, are useful in treating hearing loss.

The present invention relates to a method for protecting against or treating osteoporosis in a subject. Another aspect of the invention includes use of a compound of the invention in the manufacture of a medicament to protect against or treat osteoporosis. This method involves administering an effective amount of a compound of the invention to the subject to protect against or to treat osteoporosis. In order to protect against osteoporosis, the compound may be administered prior to the development of osteoporosis. Alternatively, the compound may be used to treat osteoporosis in a subject. In this embodiment, the compound is administered to the subject subsequent to the initiation of osteoporosis to reduce the level of osteoporosis.

A compound of the invention can be, e.g. a non-ATP competitive inhibitor. The compound of the invention can modulate a kinase signaling cascade, depending upon the particular side chains and scaffold modifications selected. The compound of the invention can be a kinase inhibitor. For example, the compound can be a protein tyrosine kinase (PTK) inhibitor. The proline-rich tyrosine kinase (PYK2; also known as cell adhesion kinase β, related adhesion focal tyrosine kinase, or calcium-dependent tyrosine kinase) and focal adhesion kinase (FAK) are members of a distinct family of non receptor protein-tyrosine kinases that are regulated by a variety of extracellular stimuli (Avraham, et al.; 2000, *Cell Signal.*, 12, 123-133; Schlaepfer, et al.; 1999, *Prog. Biophys. Mol. Biol.*, 71, 435-478). The compound of the invention can be a Src inhibitor. It has been shown that Src deficiency is associated with osteoporosis in mice, because of loss of osteoclast function (Soriano, et al.; 1991, *Cell*, 64, 693-702). Alternatively, the compound of the invention can modulate the expression of interleukin-1 receptor associated kinase M (IRAK-M). Mice that lack IRAK-M develop severe osteoporosis, which is associated with the accelerated differentiation of osteoclasts, an increase in the half-life of osteoclasts, and their activation (Hongmei, et al.; 2005, *J. Exp. Med.*, 201, 1169-1177).

Multinucleated osteoclasts originate from the fusion of mononuclear phagocytes and play a major role in bone development and remodeling via the resorption of bone. Osteoclasts are multinucleated, terminally differentiated cells that degrade mineralized matrix. In normal bone tissue, there is a balance between bone formation by osteoblasts and bone resorption by osteoclasts. When the balance of this dynamic and highly regulated process is disrupted, bone resorption can exceed bone formation resulting in quantitative bone loss. Because osteoclasts are essential for the development and remodeling of bone, increases in their number and/or activity lead to diseases that are associated with generalized bone loss (e.g., osteoporosis) and others with localized bone loss (e.g., rheumatoid arthritis, periodontal disease).

Osteoclasts and osteoblasts both command a multitude of cellular signaling pathways involving protein kinases. Osteoclast activation is initiated by adhesion to bone, cytoskeletal rearrangement, formation of the sealing zone, and formation of the polarized ruffled membrane. It is believed that protein-tyrosine kinase 2 (PYK2) participates in the transfer of signals from the cell surface to the cytoskeleton, as it is tyrosine phosphorylated and activated by adhesion-initiated signaling in osteoclasts (Duong, et al.; 1998, *J. Clin. Invest.*, 102, 881-892). Recent evidence has indicated that the reduction of PYK2 protein levels results in the inhibition of osteoclast formation and bone resorption in vitro (Duong, et al.; 2001, *J. Bio. Chem.*, 276, 7484-7492). Therefore, the inhibition of PYK2 or other protein tyrosine kinases might reduce the level of osteoporosis by decreasing osteoclast formation and bone resorption. Thus, without wishing to be bound by theory, it is hypothesized that the administration of a compound of the instant invention will modulate kinase (e.g. PTK) activity and therefore result in the inhibition of osteoclast formation and/or bone resorption, thereby treating osteoporosis.

Src tyrosine kinase stands out as a promising therapeutic target for bone disease as validated by Src knockout mouse studies and in vitro cellular experiments, suggesting a regulatory role for Src in both osteoclasts (positive) and osteoblasts (negative). In osteoclasts, Src plays key roles in motility, polarization, survival, activation (ruffled border formation) and adhesion, by mediating various signal transduction pathways, especially in cytokine and integrin signaling (Parang and Sun; 2005, *Expert Opin. Ther. Patents*, 15, 1183-1207). Moreover, targeted disruption of the src gene in mice induces osteopetrosis, a disorder characterized by decreased bone resorption, without showing any obvious morphological or functional abnormalities in other tissues or cells (Soriano, et al.; 1991, *Cell*, 64, 693-702). The osteopetrotic phenotype of src$^{-/-}$ mice is cell-autonomous and results from defects in mature osteoclasts, which normally express high levels of Src protein (Horne, et al.; 1991, *Cell*, 119, 1003-1013). By limiting the effectiveness of Src tyrosine kinase, which triggers osteoclast activity and inhibits osteoblasts, Src inhibitors are thought to lessen bone break down and encourage bone formation. Because osteoclasts normally express high levels of Src, inhibition of Src kinase activity might be useful in the treatment of osteoporosis (Missbach, et al.; 1999, *Bone*, 24, 437-449). Thus, the PTK inhibitors of the instant invention that modulate the activity of Src, are useful in treating osteoporosis.

As described herein, a compound of the invention may be used to protect against or prevent obesity in a subject. Another aspect of the invention includes use of a compound of the invention in the manufacture of a medicament to protect against or treat obesity. In order to protect against obesity, the compound may be administered prior to the development of obesity in a subject. Alternatively, the compound may be used to treat obesity in a subject. A compound of the instant invention may be involved in modulating a kinase signaling cascade, e.g., a kinase inhibitor, a non-ATP competitive inhibitor, a tyrosine kinase inhibitor, a protein tyrosine phosphatase inhibitor, or a protein-tyrosine phosphatase 1B inhibitor.

Obesity is associated with diabetes and increased insulin resistance in insulin responsive tissues, such as skeletal muscle, liver, and white adipose tissue (Klaman, et al.; 2000, *Mol. Cell. Biol.*, 20, 5479-5489). Insulin plays a critical role in the regulation of glucose homeostasis, lipid metabolism, and energy balance. Insulin signaling is initiated by binding of insulin to the insulin receptor (IR), a receptor tyrosine kinase. Insulin binding evokes a cascade of phosphorylation events, beginning with the autophosphorylation of the IR on multiple tyrosyl residues. Autophosphorylation enhances IR kinase activity and triggers downstream signaling events. The stimulatory effects of protein tyrosine kinases and the inhibitory effects of protein tyrosine phosphatases largely define the action of insulin. Appropriate insulin signaling minimizes large fluctuations in blood glucose concentrations and ensures adequate delivery of glucose to cells. Since insulin stimulation leads to multiple tyrosyl phosphorylation events, enhanced activity of one or more protein-tyrosine phosphatases (PTPs) could lead to insulin resistance, which may lead to obesity. Indeed, increased PTP activity has been reported in several insulin-resistant states, including obesity (Ahmad, et al.; 1997, *Metabolism*, 46, 1140-1145). Thus, without wishing to be bound by theory, the administration of a compound of the instant invention modulates kinase (e.g., PTP) activity, thereby treating obesity in a subject.

Insulin signaling begins with the activation of the IR via tyrosine phosphorylation and culminates in the uptake of glucose into cells by the glucose transporter, GLUT4 (Saltiel and Kahn; 2001, *Nature*, 414, 799-806). The activated IR must then be deactivated and returned to a basal state, a process that is believed to involve protein-tyrosine phosphatase-1B (PTP-1B) (Ahmad, et al; 1997, *J. Biol. Chem.*, 270, 20503-20508). Disruption of the gene that codes for PTP-1B in mice results in sensitivity to insulin and increased resistance to diet-induced obesity (Elchebly, et al.; 1999, *Science*, 283, 1544-1548; Klaman, et al.; 2000, *Mol. Cell. Biol.*, 20, 5479-5489). The decreased adiposity in PTP-1B deficient mice was due to a marked reduction in fat cell mass without a decrease in adipocyte number (Klaman, et al.; 2000, *Mol. Cell. Biol.*, 20, 5479-5489). Moreover, leanness in PTP-1B-deficient mice was accompanied by increased basal metabolic rate and total energy expenditure, without marked alteration of uncoupling protein mRNA expression. The disruption of the PTP-1B gene demonstrated that altering the activity of PTP-1B can modulate insulin signaling and dietary-induced obesity in vivo. Thus, without wishing to be bound by theory, the administration of a compound of the instant invention that modulates insulin signaling (e.g., PTP-1B activity), is useful in treating obesity in a subject.

As described herein, a compound of the invention may be used to protect against or prevent diabetes in a subject. Another aspect of the invention includes use of a compound of the invention in the manufacture of a medicament to protect against or prevent diabetes. In order to protect against diabetes, the compound may be administered prior to the development of diabetes in a subject. Alternatively, the compound may be used to treat diabetes in a subject. The compound of the instant invention may be involved in modulating a kinase signaling cascade, e.g. a kinase inhibitor, a non-ATP competitive inhibitor, a tyrosine kinase inhibitor, a phosphatase and tension homologue on chromosome 10 (PTEN) inhibitor, or a sequence homology 2-containing inositol 5'-phosphatase 2 (SHIP2) inhibitor.

Type 2 diabetes mellitus (T2DM) is a disorder of dysregulated energy metabolism. Energy metabolism is largely controlled by the hormone insulin, a potent anabolic agent that promotes the synthesis and storage of proteins, carbohydrates and lipids, and inhibits their breakdown and release back into the circulation. Insulin action is initiated by binding to its tyrosine kinase receptor, which results in autophosphorylation and increased catalytic activity of the kinase (Patti, et al.; 1998, *J. Basic Clin. Physiol. Pharmacol.* 9, 89-109). Tyrosine phosphorylation causes insulin receptor substrate (IRS) proteins to interact with the p85 regulatory subunit of phosphatidylinositol 3-kinase (PI3K), leading to the activation of the enzyme and its targeting to a specific subcellular location, depending on the cell type. The enzyme generates the lipid product phosphatidylinositol-3,4,5-trisphosphate (PtdIns(3,4,5)$P_3$), which regulates the localization and activity of numerous proteins (Kido, et al.; 2001, *J. Clin. Endocrinol. Metab.,* 86, 972-979). PI3K has an essential role in insulin-stimulated glucose uptake and storage, inhibition of lipolysis and regulation of hepatic gene expression (Saltiel, et al.; 2001, *Nature,* 414, 799-806). Overexpression of dominant-interfering forms of PI3K can block glucose uptake and translocation of glutamate transporter four, GLUT4, to the plasma membrane (Quon, et al.; 1995, *Mol. Cell. Biol.,* 15, 5403-5411). Thus, the administration of a compound of the instant invention that modulates kinase (e.g. PI3K) activity, and therefore results in increased glucose uptake, is useful in treating diabetes.

PTEN is a major regulator of PI3K signaling in may cell types, and functions as a tumor suppressor due to antagonism of the anti-apoptotic, proliferative and hypertrophic activities of the PI3K pathway (Goberdhan, et al.; 2003, *Hum. Mol. Genet.,* 12, R239-R248; Leslie, et al.; 2004, *J. Biochem.,* 382, 1-11). Although not wishing to be bound by theory, it is believed that PTEN attenuates the PI3K pathway by dephosphorylation of the PtdIns(3,4,5)$P_3$ molecule, degrading this important lipid second messenger to PtdIns(4,5)$P_2$. In a recent study, reduction of endogenous PTEN protein by 50% using small interfering RNA (siRNA) enhanced insulin-dependent increases in PtdIns(3,4,5)$P_3$ levels, and glucose uptake (Tang, et al.; 2005, *J. Biol. Chem.,* 280, 22523-22529). Thus, without wishing to be bound by theory, it is hypothesized that the administration of a compound of the instant invention that modulates PTEN activity, and therefore results in increased glucose uptake, is useful for treating diabetes.

PtdIns(3,4,5)$P_3$ levels are also controlled by the family of SRC homology 2 (SH2)—containing inositol 5'-phosphatase (SHIP) proteins, SHIP I and SHIP2 (Lazar and Saltiel; 2006, *Nature Reviews,* 5, 333-342). SHIP2, expressed in skeletal muscle, among other insulin-sensitive tissues, catalyzes the conversion of PtdIns(3,4,5)$P_3$ into PtdIns(3,4)$P_2$ (Pesesse, et al.; 1997; *Biochem Biophys. Res. Commun.,* 239, 697-700; Backers, et al.; 2003, *Adv. Enzyme Regul.,* 43, 15-28; Chi, et al.; 2004, *J. Biol. Chem.,* 279, 44987-44995; Sleeman, et al.; 2005, *Nature Med.,* 11, 199-205). Overexpression of SHIP2 markedly reduced insulin-stimulated PtdIns(3,4,5)$P_3$ levels, consistent with the proposed capacity of SHIP2 to attenuate the activation of downstream effectors of PI3K (Ishihara, et al.; 1999, *Biochem. Biophys. Res. Commun.,* 260, 265-272). Thus, without wishing to be bound by theory, it is hypothesized that the administration of a compound of the instant invention which modulates SHIP2 activity, and therefore results in increased glucose uptake, is useful for treating diabetes.

As described herein, a compound of the invention may be used to protect against or prevent eye disease in a subject. Another aspect of the invention includes use of a compound of the invention in the manufacture of a medicament to protect against or prevent eye disease. In order to protect against eye disease, the compound may be administered prior to the development of eye disease in a subject. Alternatively, the compound may be used to treat eye disease in a subject, e.g. macular degeneration, retinopathy, and macular edema. The compound of the instant invention may be involved in modulating a kinase cascade, e.g. a kinase inhibitor, a non-ATP competitive inhibitor, a tyrosine kinase inhibitor, e.g. a vascular endothelial growth factor (VEGF) receptor tyrosine kinase inhibitor.

Vision-threatening neovascularization of the physiologically avascular cornea can occur. The proliferative retinopathies, principally diabetic retinopathy and age-related macular degeneration, are characterized by increased vascular permeability, leading to retinal edema and subretinal fluid accumulation, and the proliferation of new vessels that are prone to hemorrhage. Angiogenesis, the formation of new blood vessels from preexisting capillaries, is an integral part of both normal development and numerous pathological processes. VEGF, a central mediator of the complex cascade of angiogenesis and a potent permeability factor, is an attractive target for novel therapeutics. VEGF is the ligand for two membrane-bound tyrosine kinase receptors, VEGFR-1 and VEGFR-2. Ligand binding triggers VEGFR dimerization and transphosphorylation with subsequent activation of an intracellular tyrosine kinase domain. The ensuing intracellular signaling axis results in vascular endothelial cell proliferation, migration, and survival. Thus, without wishing to be bound by theory, it is hypothesized that the administration of a compound of the instant invention which modulates kinase activity, e.g. tyrosine kinase activity, and results in the inhibition of angiogenesis and/or neovascularization, is useful for treating an eye disease, e.g. macular degeneration, retinopathy and/or macular edema.

Macular degeneration is characterized by VEGF-mediated retinal leakage (an increase in vascular permeability) and by the abnormal growth of small blood vessels in the back of the eye (angiogenesis). VEGF has been identified in neovascular membranes in both diabetic retinopathy and age-related macular degeneration, and intraocular levels of the factor correlate with the severity of neovascularization in diabetic retinopathy (Kvanta, et al.; 1996, *Invest. Ophthal. Vis. Sci.,* 37, 1929-1934.; Aiello, et al.; 1994, *N. Engl. J. Med.,* 331, 1480-1487). Therapeutic antagonism of VEGF in these models results in significant inhibition of both retinal and choroidal neovascularization, as well as a reduction in vascular permeability (Aiello, et al.; 1995, *Proc. Natl. Acad. Sci. USA.,* 92, 10457-10461; Krzystolik, et al.; 2002, *Arch. Ophthal.,* 120, 338-346; Qaum, et al.; 2001, *Invest. Ophthal. Vis. Sci.,* 42, 2408-2413). Thus, without wishing to be bound by theory, it is hypothesized that the administration of a compound of the instant invention which modulates VEGF activity, and results in the inhibition of angiogenesis and/or neovascularization, is useful for treating an eye disease, e.g. macular degeneration, retinopathy and/or macular edema.

The compounds of the invention are used in methods of treating, preventing, or ameliorating a stroke in a subject who is at risk of suffering a stroke, is suffering from a stroke or has suffered a stroke. The compounds of the invention are useful in methods of treating patients who are undergoing post-stroke rehabilitation. Another aspect of the invention includes use of a compound of the invention in the manufacture of a medicament to treat, prevent, or ameliorate stroke.

A stroke, also known as a cerebrovascular accident (CVA), is an acute neurological injury whereby the blood supply to a part of the brain is interrupted due to either blockage of an artery or rupture of a blood vessel. The part of the brain in which blood supply is interrupted no longer receives oxygen and/or nutrients carried by the blood. The brain cells become damaged or necrotic, thereby impairing function in or from that part of the brain. Brain tissue ceases to function if deprived of oxygen for more than 60 to 90 seconds and after a few minutes will suffer irreversible injury possibly leading to a death of the tissue, i.e., infarction.

Strokes are classified into two major types: ischemic, i.e., blockage of a blood vessel supplying the brain, and hemorrhagic, i.e., bleeding into or around the brain. The majority of all strokes are ischemic strokes. Ischemic stroke is commonly divided into thrombotic stroke, embolic stroke, systemic hypoperfusion (Watershed stroke), or venous thrombosis. In thrombotic stroke, a thrombus-forming process develops in the affected artery, the thrombus, i.e., blood clot, gradually narrows the lumen of the artery, thereby impeding blood flow to distal tissue. These clots usually form around atherosclerotic plaques. There are two types of thrombotic strokes, which are categorized based on the type of vessel on which the thrombus is formed. Large vessel thrombotic stroke involves the common and internal carotids, vertebral, and the Circle of Willis. Small vessel thrombotic stroke involves the intracerebral arteries, branches of the Circle of Willis, middle cerebral artery stem, and arteries arising from the distal vertebral and basilar artery.

A thrombus, even if non-occluding, can lead to an embolic stroke if the thrombus breaks off, at which point it becomes an embolus. An embolus refers to a traveling particle or debris in the arterial bloodstream originating from elsewhere. Embolic stroke refers to the blockage of arterial access to a part of the brain by an embolus. An embolus is frequently a blood clot, but it can also be a plaque that has broken off from an atherosclerotic blood vessel or a number of other substances including fat, air, and even cancerous cells. Because an embolus arises from elsewhere, local therapy only solves the problem temporarily. Thus, the source of the embolus must be identified. There are four categories of embolic stroke: those with a known cardiac source; those with a potential cardiac or aortic source (from trans-thoracic or trans-esophageal echocardiogram); those with an arterial source; and those with unknown source.

Systemic hypoperfusion is the reduction of blood flow to all parts of the body. It is most commonly due to cardiac pump failure from cardiac arrest or arrhythmias, or from reduced cardiac output as a result of myocardial infarction, pulmonary embolism, pericardial effusion, or bleeding. Hypoxemia (i.e., low blood oxygen content) may precipitate the hypoperfusion. Because the reduction in blood flow is global, all parts of the brain may be affected, especially the "watershed" areas which are border zone regions supplied by the major cerebral arteries. Blood flow to these area has not necessary stopped, but instead may have lessened to the point where brain damage occurs.

Veins in the brain function to drain the blood back to the body. When veins are occluded due to thrombosis, the draining of blood is blocked and the blood backs up, causing cerebral edema. This cerebral edema can result in both ischemic and hemorrhagic strokes. This commonly occurs in the rare disease sinus vein thrombosis.

Stroke is diagnosed in a subject or patient using one or more of a variety of techniques known in the art, such as, for example, neurological examination, blood tests, CT scans (without contrast enhancements), MRI scans, Doppler ultrasound, and arteriography (i.e., roentgenography of arteries after injection of radiopacque material into the blood stream). If a stroke is confirmed on imaging, various other studies are performed to determine whether there is a peripheral source of emboli. These studies include, e.g., an ultrasound/doppler study of the carotid arteries (to detect carotid stenosis); an electrocardiogram (ECG) and echocardiogram (to identify arrhythmias and resultant clots in the heart which may spread to the brain vessels through the bloodstream); a Holter monitor study to identify intermittent arrhythmias and an angiogram of the cerebral vasculature (if a bleed is thought to have originated from an aneurysm or arteriovenous malformation).

Compounds useful in these methods of treating, preventing or ameliorating stroke or a symptom associated with stroke are compounds that modulate kinase signaling cascade preceding, during or after a stroke. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating stroke or a symptom associated with stroke described herein is an allosteric inhibitor of kinase signaling cascade preceding, during or after a stroke. Preferably, the compound used in the methods of treating, preventing or ameliorating stroke or a symptom associated with stroke described herein is a non-ATP competitive inhibitor of kinase signaling cascade preceding, during or after a stroke.

Inhibition of Src activity has been shown to provide cerebral protection during stroke. (See Paul et al., Nature Medicine, vol. 7(2):222-227 (2001), which is hereby incorporated by reference in its entirety). Vascular endothelia growth factor (VEGF), which is produced in response to the ischemic injury, has been shown to promote vascular permeability. Studies have shown that the Src kinase regulates VEGF-mediated VP in the brain following stroke, and administration of an Src inhibitor before and after stroke reduced edema, improved cerebral perfusion and decreased infarct volume after injury occurred. (Paul et al., 2001). Thus, Src inhibition may be useful in the prevention, treatment or amelioration of secondary damage following a stroke.

The compounds of the invention prevent, treat or ameliorate stroke or a symptom associated with stroke. Another aspect of the invention includes use of a compound of the invention in the manufacture of a medicament to prevent, treat, or ameliorate stroke or a symptom associated with stroke. Symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause.

Generally there are three treatment stages for stroke: prevention, therapy immediately after the stroke, and post-stroke rehabilitation. Therapies to prevent a first or recurrent stroke are based on treating the underlying risk factors for stroke, such as, e.g., hypertension, high cholesterol, atrial fibrillation, and diabetes. Acute stroke therapies try to stop a stroke while it is happening by quickly dissolving the blood clot causing an ischemic stroke or by stopping the bleeding of a hemorrhagic stroke. Post-stroke rehabilitation helps individuals overcome disabilities that result from stroke damage. Medication or drug therapy is the most common treatment for stroke. The most popular classes of drugs used to prevent or treat stroke are anti-thrombotics (e.g., anti-platelet agents and anticoagulants) and thrombolytics. The compounds are administered to a patient who is at risk of suffering a stroke, is suffering from a stroke or has suffered a stroke at a time before, during, after, or any combination thereof, the occurrence of a stroke. The compounds of the invention are administered alone, in pharmaceutical compositions, or in combination with any of a variety of known treatments, such as, for example, an anti-platelet medication (e.g., aspirin, clopidogrel, dipyridamole), an anti-coagulant (e.g., warfarin), or a thrombolytic medication (e.g., tissue plasminogen activator (t-PA), reteplase, Urokinase, streptokinase, tenectaplase, lanoteplase, or anistreplase.

The compounds of the invention are used in methods of treating, preventing, ameliorating atherosclerosis or a symptom thereof in a subject who is at risk for or suffering from atherosclerosis. Another aspect of the invention includes use of a compound of the invention in the manufacture of a medicament to treat, prevent, or ameliorate atherosclerosis.

Atherosclerosis is a disease affecting the arterial blood vessel and is commonly referred to as a "hardening" of the arteries. It is caused by the formation of multiple plaques within the arteries. Atherosclerotic plaques, though compensated for by artery enlargement, eventually lead to plaque ruptures and stenosis (i.e., narrowing) of the artery, which, in turn, leads to an insufficient blood supply to the organ it feeds. Alternatively, if the compensating artery enlargement process is excessive, a net aneurysm results. These complications are chronic, slowly progressing and cumulative. Most commonly, soft plaque suddenly ruptures, causing the formation of a blood clot (i.e., thrombus) that rapidly slows or stops blood flow, which, in turn, leads to death of the tissues fed by the artery. This catastrophic event is called an infarction. For example, coronary thrombosis of a coronary artery causes a myocardial infarction, commonly known as a heart attack. A myocardial infarction occurs when an atherosclerotic plaque slowly builds up in the inner lining of a coronary artery and then suddenly ruptures, totally occluding the artery and preventing blood flow downstream.

Atherosclerosis and acute myocardial infarction are diagnosed in a patient using any of a variety of clinical and/or laboratory tests such as, physical examination, radiologic or ultrasound examination and blood analysis. For example, a doctor or clinical can listen to a subject's arteries to detect an abnormal whooshing sound, called a bruit. A bruit can be heard with a stethoscope when placed over the affected artery. Alternatively, or in addition, the clinician or physician can check pulses, e.g., in the leg or foot, for abnormalities such as weakness or absence. The physician or clinical may perform blood work to check for cholesterol levels or to check the levels of cardiac enzymes, such as creatine kinase, troponin and lactate dehydrogenase, to detect abnormalities. For example, troponin sub-units I or T, which are very specific for the myocardium, rise before permanent injury develops. A positive troponin in the setting of chest pain may accurately predict a high likelihood of a myocardial infarction in the near future. Other tests to diagnose atherosclerosis and/or myocardial infarction include, for example, EKG (electrocardiogram) to measure the rate and regularity of a subject's heartbeat; chest X-ray, measuring ankle/brachial index, which compares the blood pressure in the ankle with the blood pressure in the arm; ultrasound analysis of arteries; CT scan of areas of interest; angiography; an exercise stress test, nuclear heart scanning; and magnetic resonance imaging (MRI) and positron emission tomography (PET) scanning of the heart.

Compounds useful in these methods of treating, preventing or ameliorating atherosclerosis or a symptom thereof are compounds that modulate kinase signaling cascade in a patient at risk for or suffering from atherosclerosis. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating atherosclerosis or a symptom thereof described herein is an allosteric inhibitor of kinase signaling cascade involved in atherosclerosis. Preferably, the compound used in the methods of treating, preventing or ameliorating atherosclerosis or a symptom associated with atherosclerosis described herein is a non-ATP competitive inhibitor of kinase signaling cascade involved in atherosclerosis.

Cellular signal transduction by Src is believed to play a key role in increased permeability of vessels, known as vascular permeability (VP). Vascular endothelia growth factor (VEGF), which is produced in response to the ischemic injury, including, e.g., myocardial infarction, has been shown to promote vascular permeability. Studies have shown that the inhibition of Src kinase decreases VEGF-mediated VP. (See Parang and Sun, Expert Opin. Ther. Patents, vol. 15(9): 1183-1206 (2005), which is hereby incorporated by reference in its entirety). Mice treated with an Src inhibitor demonstrated reduced tissue damage associated with trauma or injury to blood vessels after myocardial infarction, as compared to untreated mice. (See e.g., U.S. Patent Publication Nos. 20040214836 and 20030130209 by Cheresh et al., the contents of which are hereby incorporated by reference in their entirety). Thus, Src inhibition may be useful in the prevention, treatment or amelioration of secondary damage following injury due to atherosclerosis, such as, for example, myocardial infarction.

The compounds of the invention prevent, treat or ameliorate stroke or a symptom associated with atherosclerosis. Another aspect of the invention includes use of a compound of the invention in the manufacture of a medicament to prevent, treat, or ameliorate stroke or a symptom associated with atherosclerosis. Atherosclerosis generally does not produce symptoms until it severely narrows the artery and restricts blood flow, or until it causes a sudden obstruction. Symptoms depend on where the plaques and narrowing develop, e.g., in the heart, brain, other vital organs and legs or almost anywhere in the body. The initial symptoms of atherosclerosis may be pain or cramps when the body requires more oxygen, for example during exercise, when a person may feel chest pain (angina) because of lack of oxygen to the heart or leg cramps because of lack of oxygen to the legs. Narrowing of the arteries supplying blood to the brain may cause dizziness or transient ischemic attacks (TIA's) where the symptoms and signs of a stroke last less than 24 hours. Typically, these symptoms develop gradually.

Symptoms of myocardial infarction are characterized by varying degrees of chest pain, discomfort, sweating, weakness, nausea, vomiting, and arrhythmias, sometimes causing loss of consciousness. Chest pain is the most common symptom of acute myocardial infarction and is often described as a tightness, pressure, or squeezing sensation. Pain may radiate to the jaw, neck, arms, back, and epigastrium, most often to the left arm or neck. Chest pain is more likely caused by myocardial infarction when it lasts for more than 30 minutes. Patients suffering from a myocardial infarction may exhibit shortness of breath (dyspnea) especially if the decrease in myocardial contractility due to the infarct is sufficient to cause left ventricular failure with pulmonary congestion or even pulmonary edema.

The compounds of the invention are administered alone, in pharmaceutical compositions, or in combination with any of a variety of known treatments for atherosclerosis, such as, for example, cholesterol-lowering drugs (e.g., statins), antiplatelet medications, or anti-coagulants.

The compounds of the invention are used in methods of treating, preventing, ameliorating neuropathic pain, such as chronic neuropathic pain, or a symptom thereof in a subject who is at risk of suffering from, is suffering from, or has suffered neuropathic pain. Another aspect of the invention includes use of a compound of the invention in the manufacture of a medicament to treat, prevent or ameliorate neuropathic pain.

Neuropathic pain, also known as neuralgia, is qualitatively different from ordinary nociceptive pain. Neuropathic pain usually presents as a steady burning and/or "pins and needles" and/or "electric shock" sensations. The difference between nociceptive pain and neuropathic pain is due to the fact that "ordinary", nociceptive pain stimulates only pain nerves, while a neuropathy often results in the stimulation of both pain and non-pain sensory nerves (e.g., nerves that respond to touch, warmth, cool) in the same area, thereby producing signals that the spinal cord and brain do not normally expect to receive.

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

Neuropathic pain is diagnosed in a subject or patient using one or more of a variety of laboratory and/or clinical techniques known in the art, such as, for example, physical examination.

Compounds useful in these methods of treating, preventing or ameliorating neuropathic pain, such as chronic neuropathic pain, or a symptom associated with neuropathic pain are compounds that modulate kinase signaling cascade involved in neuropathic pain. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating neuropathic pain or a symptom thereof is an allosteric inhibitor of kinase signaling cascade involved in neuropathic pain. Preferably, the compound used in the methods of treating, preventing or ameliorating neuropathic pain or a symptom thereof is a non-ATP competitive inhibitor of kinase signaling cascade involved in neuropathic pain.

c-Src has been shown to regulate the activity of N-methyl-D-aspartate (NMDA) receptors. (See Yu et al., Proc. Natl. Acad. Sci. USA, vol. 96:7697-1704 (1999), which is hereby incorporated by reference in its entirety). Studies have shown that PP2, a low molecular weight Src kinase inhibitor, decreases phosphorylation of the NMDA receptor NM2 subunit. (See Guo et al., J. Neuro., vol. 22:6208-6217 (2002), which is hereby incorporated by reference in its entirety). Thus, Src inhibition, which in turn, inhibits the activity NMDA receptors, may be useful in the prevention, treatment or amelioration of neuropathic pain, such as chronic neuropathic pain.

The compounds of the invention prevent, treat or ameliorate neuropathic pain, such as chronic neuropathic pain, or a symptom associated with neuropathic pain. Symptoms of neuropathic pain include shooting and burning pain, tingling and numbness.

The compounds of the invention are administered alone, in pharmaceutical compositions, or in combination with any of a variety of known treatments, such as, for example, analgesics, opioids, tricyclic antidepressants, anticonvulsants and serotonin norepinephrine reuptake inhibitors.

The compounds of the invention are used in methods of treating, preventing, ameliorating hepatitis B or a symptom thereof in a subject who is at risk for or suffering from hepatitis B. Another aspect of the invention includes use of a compound of the invention in the manufacture of a medicament to treat, prevent, or ameliorate hepatitis B.

The hepatitis B virus, a member of the Hepadnavirus family, consists of a proteinaceous core particle containing the viral genome in the form of double stranded DNA with single-stranded regions and an outer lipid-based envelope with embedded proteins. The envelope proteins are involved in viral binding and release into susceptible cells. The inner capsid relocates the DNA genome to the cell's nucleus where viral mRNAs are transcribed. Three subgenomic transcripts encoding the envelope proteins are made, along with a transcript encoding the X protein. A fourth pre-genomic RNA is transcribed, which is exported to the cytosol and translates the viral polymerase and core proteins. Polymerase and pre-genomic RNA are encapsidated in assembling core particles, where reverse transcription of the pre-genomic RNA to genomic DNA occurs by the polymerase protein. The mature core particle then exits the cell via normal secretory pathways, acquiring an envelope along the way.

Hepatitis B is one of a few known non-retroviral viruses that employ reverse transcription as part of the replication process. Other viruses which use reverse transcription include, e.g., HTLV or HIV.

During HBV infection, the host immune response is responsible for both hepatocellular damage and viral clearance. While the innate immune response does not play a significant role in these processes, the adaptive immune response, particularly virus-specific cytotoxic T lymphocytes (CTLs), contributes to nearly all of the liver injury associated with HBV infection. By killing infected cells and by producing antiviral cytokines capable of purging HBV from viable hepatocytes, CTLs also eliminate the virus. Although liver damage is initiated and mediated by the CTLs, antigen-nonspecific inflammatory cells can worsen CTL-induced immunopathology and platelets may facilitate the accumulation of CTLs into the liver.

Hepatitis B is diagnosed in a patient using any of a variety of clinical and/or laboratory tests such as, physical examination, and blood or serum analysis. For example, blood or serum is assayed for the presence of viral antigens and/or antibodies produced by the host. In a common test for Hepatitis B, detection of hepatitis B surface antigen (HBsAg) is used to screen for the presence of infection. It is the first detectable viral antigen to appear during infection with this virus; however, early in an infection, this antigen may not be present and it may be undetectable later in the infection as it is being cleared by the host. During this 'window' in which the host remains infected but is successfully clearing the virus, IgM antibodies to the hepatitis B core antigen (anti-HBc IGM) may be the only serologic evidence of disease.

Shortly after the appearance of the HBsAg, another antigen named as the hepatitis B e antigen (HBeAg) will appear. Traditionally, the presence of HBeAg in a host's serum is associated with much higher rates of viral replication; however, some variants of the hepatitis B virus do not produce the "e" antigen at all. During the natural course of an infection, the HBeAg may be cleared, and antibodies to the "e" antigen (anti-HBe) will arise immediately afterward. This conversion is usually associated with a dramatic decline in viral replication. If the host is able to clear the infection, eventually the HBsAg will become undetectable and will be followed by antibodies to the hepatitis B surface antigen (anti-HBs). A person negative for HBsAg but positive for anti-HBs has either cleared an infection or has been vaccinated previously. A number of people who are positive for HBsAg may have very little viral multiplication, and hence may be at little risk of long-term complications or of transmitting infection to others.

Compounds useful in these methods of treating, preventing or ameliorating hepatitis B or a symptom thereof are compounds that modulate kinase signaling cascade in a patient at risk for or suffering from hepatitis B. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating hepatitis B or a symptom thereof described herein is an allosteric inhibitor of kinase signaling cascade involved in hepatitis B. Preferably, the compound used in the methods of treating, preventing or ameliorating hepatitis B or a symptom associated with hepatitis B described herein is a non-ATP competitive inhibitor of kinase signaling cascade involved in hepatitis B.

Src plays a role in the replication of the hepatitis B virus. The virally encoded transcription factor HBx activates Src in a step that is required from propagation of the HBV virus. (See, e.g., Klein et al., EMBO J., vol. 18:5019-5027 (1999); Klein et al., Mol. Cell. Biol., vol. 17:6427-6436 (1997), each of which is hereby incorporated by reference in its entirety). Thus, Src inhibition, which in turn, inhibits Src-mediated propagation of the HBV virus, may be useful in the prevention, treatment or amelioration of hepatitis B or a symptom thereof The compounds of the invention prevent, treat or ameliorate hepatitis B or a symptom associated with hepatitis B. Symptoms of hepatitis B typically develop within 30-180 days of exposure to the virus. However, up to half of all people infected with the hepatitis B virus have no symptoms. The symptoms of hepatitis B are often compared to flu, and include, e.g., appetite loss; fatigue; nausea and vomiting, itching all over the body; pain over the liver (e.g., on the right side of the abdomen, under the lower rib cage), jaundice, and changes in excretory functions.

The compounds of the invention are administered alone, in pharmaceutical compositions, or in combination with any of a variety of known treatments for hepatitis B, such as, for example, interferon alpha, lamivudine (Epivir-HBV) and baraclude (entecavir).

As described herein, the compounds of the invention may be used to regulate immune system activity in a subject, thereby protecting against or preventing autoimmune disease, e.g., lupus, transplant rejection (e.g., kidney, heart, lung, liver, pancreas, skin, host versus graft reaction (HVGR), etc.), rheumatoid arthritis, and amyotrophic lateral sclerosis, sepsis, T-cell mediated autoimmune diseases such as multiple sclerosis, psoriasis and Sjogren's syndrome, and hypersensitivity reactions. The compounds of the invention may also be used to protect against or prevent solid and hematologic malignancies, e.g., leukemia and lymphomas. Another aspect of the invention includes use of a compound of the invention in the manufacture of a medicament to regulate the immune system. Alternatively, the compound may be used to treat autoimmune disease in a subject. Yet another aspect of the invention includes use of a compound of the invention in the manufacture of a medicament to protect against or treat solid and hematologic malignancies. For example, the compound may result in reduction in the severity of symptoms or halt impending progression of the autoimmune disease, or solid or hematologic malignancy in a subject. The compound of the invention may be involved in modulating a kinase signaling cascade, e.g., a kinase inhibitor, a non-ATP competitive inhibitor, a tyrosine kinase inhibitor, e.g., a Src inhibitor, a p59fyn (Fyn) inhibitor, a p56lck (Lck) inhibitor or a Janus kinase (JAK) inhibitor such as a JAK1, JAK2, JAK3 or TYK2 inhibitor.

Autoimmune diseases are diseases caused by a breakdown of self-tolerance such that the adaptive immune system responds to self antigens and mediates cell and tissue damage. Autoimmune diseases can be organ specific (e.g., thyroiditis or diabetes) or systemic (e.g., systemic lupus erythematosus). T cells modulate the cell-mediated immune response in the adaptive immune system. Under normal conditions, T cells express antigen receptors (T cell receptors) that recognize peptide fragments of foreign proteins bound to self major histocompatibility complex molecules. Among the earliest recognizable events after T cell receptor (TCR) stimulation are the activation of Lck and Fyn, resulting in TCR phosphorylation on tyrosine residues within immunoreceptor tyrosine-based activation motifs (Zamoyska, et al.; 2003, *Immunol. Rev.*, 191, 107-118). Tyrosine kinases, such as Lck (which is a member of the Src family of protein tyrosine kinases) play an essential role in the regulation of cell signaling and cell proliferation by phosphorylating tyrosine residues of peptides and proteins (Levitzki; 2001, *Top. Curr. Chem.*, 211, 1-15; Longati, et al.; 2001, *Curr. Drug Targets*, 2, 41-55; Qian, and Weiss; 1997, *Curr. Opin. Cell Biol.*, 9, 205-211). Thus, although not wishing to be bound by theory, it is hypothesized that the administration of a compound of the instant invention which modulates tyrosine kinase (e.g., Src) activity is useful in the treatment of autoimmune disease.

The tyrosine kinases lck and fyn are both activated in the TCR pathway; thus, inhibitors of lck and/or fyn have potential utility as autoimmune agents (Palacios and Weiss; 2004, *Oncogene*, 23, 7990-8000). Lck and Fyn are predominantly expressed by T cells through most of their lifespan. The roles of Lck and Fyn in T cell development, homeostasis and activation have been demonstrated by animal and cell line studies (Parang and Sun; 2005, *Expert Opin. The Patents*, 15, 1183-1207). Lck activation is involved in autoimmune diseases and transplant rejection (Kamens, et al.; 2001, *Curr. Opin. Investig. Drugs*, 2, 1213-1219). Results have shown that the lck (−) Jurkat cell lines are unable to proliferate, produce cytokines, and generate increases in intracellular calcium, inositol phosphate, and tyrosine phosphorylation in response to T cell receptor stimulation (Straus and Weiss 1992, *Cell*, 70, 585-593; Yamasaki, et al.; 1996, *Mol. Cell. Biol.*, 16, 7151-7160). Therefore, an agent inhibiting lck would effectively block T cell function, act as an immunosuppressive agent, and have potential utility in autoimmune diseases, such as rheumatoid arthritis, multiple sclerosis, and lupus, as well as in the area of transplant rejection and allergic diseases (Hanke and Pollok; 1995, *Inflammation Res.*, 44, 357-371). Thus, although not wishing to be bound by theory, it is hypothesized that the administration of a compound of the instant invention which modulates one or more members of the Src family of protein tyrosine kinases (e.g., lck and/or fyn) is useful in the treatment of autoimmune disease.

JAK kinases have been implicated and/or demonstrated to play a critical role in many disease pathways. For example, JAK3 plays a crucial role in IgE receptor-mediated mast cell degeneration responses (Malaviya et al., 1999, Biochem. Biophys. Res. Commun. 257:807-813), and inhibition of JAK3 kinase has been shown to prevent type I hypersensitivity reactions, including anaphylaxis (Malaviya et al., 1999, J. Biol. Chem. 274:27028-27038). JAK3 inhibition has also resulted in immune suppression for allograft rejection (Kirken, 2001, Transpl. Proc. 33:3268-3270). JAK kinases have also been implicated in the mechanism involved in early and late stages of rheumatoid arthritis (Muller-Ladner et al., 2000, J. Immunal. 164:3894-3901); familial amyotrophic lateral sclerosis (Trieu et al., 2000, Biochem Biophys. Res. Commun. 267:22-25); leukemia (Sudbeck et al., 1999, Clin. Cancer Res. 5:1569-1582); mycosis fungoides, a form of T-cell lymphoma (Nielsen et al., 1997, Prac. Natl. Acad. Sci. USA 94:6764-6769); and abnormal cell growth (Yu et al., 1997, J. Immunal. 159:5206-5210; Catlett-Falcone et al., 1999, Immunity 10:105-115).

Thus, without wishing to be bound by theory, it is hypothesized that the administration of a compound of the instant invention which modulates one or more members of the JAK kinase family (e.g., JAK1, JAK2, JAK3, or TYK2) is useful for the treatment of immune mediated diseases, e.g., hypersensitivity reactions, transplant rejection (e.g., acute and chronic transplant rejection), rheumatoid arthritis, amyotrohopic lateral sclerosis, and malignanices, e.g., leukemia and lymphoma. In a particular embodiment, the compound used in the methods of treating, preventing or ameliorating immune mediated disease is an inhibitor of JAK3.

JAK3 kinase binds the common gamma chain of cytokinetic receptors. This common gamma chain, which is involved in both ligand binding and signal transduction, is a shared subunit of the multichain receptor for cytokines IL-2, IL-4, IL-7, IL-9, IL-15 and IL-21. Without intending to be bound by theory, because the JAK3 kinase binds the common gamma chain of these receptors, the compounds described herein can be used to regulate, and in particular inhibit, these and other cytokine receptor signaling cascades which utilize the common gamma chain. Thus, in another aspect, the invention provides methods of regulating, and in particular inhibiting, signal transduction cascades in which a JAK kinase plays a role, such as signal transduction cascades of cytokine receptors utilizing the common gamma chain, including, but not limited to, the IL-2, IL-4, IL-7, IL-9, IL-15 and IL-21 signal transduction cascades. The methods generally involve contacting a JAK-dependent receptor, or a cell expressing a JAK-dependent receptor, with an amount of JAK inhibitory compound effective to regulate or inhibit the signal transduction cascade, e.g., a compound of the invention. The methods may also be used to regulate, and in particular inhibit, downstream processes or cellular responses elicited by activation of the particular JAK-dependent signal transduction cascade. The methods may be practiced to regulate any signal transduction cascade where JAK kinase is now known or later discovered to play a role. The methods may be practiced in in vitro contexts or in in vivo contexts as a therapeutic approach towards the treatment or prevention of diseases characterized by, caused by or associated with activation of the JAK-dependent signal transduction cascade. Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren's syndrome, Type II inflammatory disease such as vascular inflammation (including vasculitis, ateritis, atherosclerosis and coronary artery disease), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas.

The compounds of the invention can be administered alone, or in combination with or adjunctive to other common immunosuppressive therapies, such as, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also, the prescribing information in the 2005 Edition of The Physician's Desk Reference), the disclosures of which are incorporated herein by reference. Azothiopurine is currently available from Salix Pharmaceuticals, Inc. under the brand name AZASAN; mercaptopurine is currently available from Gate Pharmaceuticals, Inc. under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and Abbott under the brand name GENGRAF; IMPDH inhibitors such as mycophenolate mofetil and mycophenolic acid are currently available from Roche under the brand name CELLCEPT and Novartis under the brand name MYFORTIC; azathioprine is currently available from Glaxo Smith Kline under the brand name IMURAN; and antibodies are currently available from Ortho Biotech under the brand name ORTHOCLONE, Novartis under the brand name SIMULECT (basiliximab) and Roche under the brand name ZENAPAX (daclizumab).

When used to treat or prevent such diseases, the compounds of the invention may be administered singly, as mixtures of one or more compounds of the invention or in mixture or combination with other agents useful for treating such diseases and/or the symptoms associated with such diseases. The compounds of the invention may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds of the invention may be administered per se in the form of prodrugs or as pharmaceutical compositions, comprising an active compound or prodrug.

Compounds of the invention include compounds with water solubilizing groups appended on the compound (Wermuth, C. G., *The Practice of Medicinal Chemistry* 2003, p. 617), e.g., $SO_3H$, $OSO_3H$, $OPO_3H_2$, $OPO_3H_2$, amines,

[structure: 1,2,4-oxadiazol-3-yl-5(4H)-one]

tetrazole, etc.

Compound of the invention include compounds according to Formula I

[structure of Formula I: central T linking two substituted vinyl/ring systems with $R_6$, $R_5$, $R_4$, $X_a$, $X_b$, $X_c$, $X_d$, $X_e$, $X_y$, $X_z$]

(Formula I)

or a salt, solvate, hydrate, or prodrug thereof, wherein:

T is a bond, $CR_{12}R_{13}$, C(O), O, S, S(O), S(O)$_2$, $NR_{14}$, $C(R_{15}R_{16})C(R_{17}R_{18})$, CH$_2$O, or OCH$_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, $C_1$, $C_2$, $C_3$, $C_4$, $C_5$, or $C_6$ alkyl, $C_3$, $C_4$, $C_5$, $C_6$, $C_7$ or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$)alkyl-aryl, ($C_3$, $C_4$, $C_5$, $C_6$, $C_7$, or $C_8$)cycloalkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, G, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COOH, COO—($C_1$, $C_2$, $C_3$, $C_4$, $C_5$, or $C_6$) alkyl, SO$_2$H, SO$_2$—($C_1$, $C_2$, $C_3$, $C_4$, $C_5$, or $C_6$) alkyl,

[structures: V—piperidine—N—W ;  V—N—piperidine ;  V—N—morpholine(O) ; V—N—piperazine—N—W]

wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl, or $C_3$, $C_4$, $C_5$, $C_6$, $C_7$, or $C_8$ cycloalkyl;

G is SO$_3$H, OSO$_3$H, OPO$_3$H$_2$, OPO$_3$H$_2$, NH$_2$, NHR$_{19}$, NR$_{20}$R$_{21}$,

[structure: 1,2,4-oxadiazol-5(4H)-one]

tetrazole, O—($C_1$, $C_2$, $C_3$, $C_4$, $C_5$, or $C_6$) alkyl-K, O—($C_3$, $C_4$, $C_5$, $C_6$, $C_7$, or $C_8$)cycloalkyl-K, O—C(O)—($C_1$, $C_2$, $C_3$, $C_4$, $C_5$, or $C_6$) alkyl-L, O—C(O)($C_3$, $C_4$, $C_5$, $C_6$, $C_7$, or $C_8$)cycloalkyl-L, NH—($C_1$, $C_2$, $C_3$, $C_4$, $C_5$, or $C_6$) alkyl-M, NH—($C_3$, $C_4$, $C_5$, $C_6$, $C_7$, or $C_8$)cycloalkyl-M or O-aryl-Q, further wherein ($C_1$, $C_2$, $C_3$, $C_4$, $C_5$, or $C_6$) alkyl is linear or branched alkyl;

K is aryl, heteroaryl, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, $C_1$, $C_2$, $C_3$, $C_4$, $C_5$, $C_6$ alkoxy, or

[structure: 1,2,4-oxadiazol-5(4H)-one]

L is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, or

[structure: 1,2,4-oxadiazol-5(4H)-one]

M is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, or

[structure: 1,2,4-oxadiazol-5(4H)-one]

Q is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, or

[structure: 1,2,4-oxadiazol-5(4H)-one]

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

Z is —(CR$_1$R$_{1'}$)$_n$—C(O)—NR$_2$(CR$_3$R$_{3'}$)$_m$—B, —(CR$_1$R$_{1'}$)$_n$—NR$_2$—C(O)—(CR$_3$R$_{3'}$)$_m$—B, —(CR$_1$R$_{1'}$)$_n$—NR$_2$—C(O)—NR$_2$(CR$_3$R$_{3'}$)$_m$—B, —(CR$_1$R$_{1'}$)$_n$—S(O)$_p$—NR$_2$—(CR$_3$R$_{3'}$)$_m$—B, —(CR$_1$R$_{1'}$)$_n$—NR$_2$—S(O)$_p$—(CR$_3$R$_{3'}$)$_m$—B, —(CR$_1$R$_{1'}$)$_n$—O—C(O)—NR$_2$—(CR$_3$R$_{3'}$)$_m$—B, —(CR$_1$R$_{1'}$)$_n$—NR$_2$—C(O)—O—

—(CR$_3$R$_3'$)$_m$—B, —(CR$_1$R$_1'$)$_n$—CH(OH)—CR$_2$R$_2'$—NR$_2$(CR$_3$R$_3'$)$_m$—B, —(CR$_1$R$_1'$)$_n$—S—C(O)—NR$_2$(CR$_3$R$_3'$)$_m$—B, —(CR$_1$R$_1'$)$_n$—O—(CR$_3$R$_3'$)$_m$—B, —(CR$_1$R$_1'$)$_n$—C(S)—NR$_2$(CR$_3$R$_3'$)$_m$—B, —(CR$_1$R$_1'$)$_n$—NR$_2$—C(S)—(CR$_3$R$_3'$)$_m$—B, —(CR$_1$R$_1'$)$_n$—P(=O)(O—)—CH$_2$—NR$_2$(CR$_3$R$_3'$)$_m$—B, —(CR$_1$R$_1'$)$_n$—P(=O)(OH)—CH$_2$—(CR$_3$R$_3'$)$_m$—B, —(CR$_1$R$_1'$)$_n$NR$_2$—CH$_2$—P(=O)(O—)(CR$_3$R$_3'$)$_m$—B, —(CR$_1$R$_1'$)$_n$—P(=O)(O—)NR$_2$(CR$_3$R$_3'$)$_m$—B, —(CR$_1$R$_1'$)$_n$—NR$_2$P(=O)(O—)(CR$_3$R$_3'$)$_m$—B, —(CR$_1$R$_1'$)$_n$—CH(CN)—NR$_2$(CR$_3$R$_3'$)$_m$—B, —(CR$_1$R$_1'$)$_n$—CH$_2$—(CR$_3$R$_3'$)$_m$—B, —(CR$_1$R$_1'$)$_n$—C(O)—CHF—(CR$_3$R$_3'$)$_m$—B, —(CR$_1$R$_1'$)$_n$—CR$_2$(OH)—CR$_2$(OH)—(CR$_3$R$_3'$)$_m$—B, —(CR$_1$R$_1'$)$_n$—CR$_2$(OH)—CR$_2'$(NH$_2$)—(CR$_3$R$_3'$)$_m$—B, —(CR$_1$R$_1'$)$_n$—CH(OH)—C(O)NR$_2$(CR$_3$R$_3'$)$_m$—B,

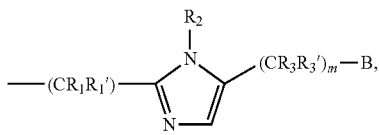

—(CR$_1$R$_1'$)$_n$—NR$_2$—(CR$_3$R$_3'$)$_m$—B, —(CR$_1$R$_1'$)$_n$—C(O)C(OH)R$_2$—(CR$_3$R$_3'$)—B, —(CR$_1$R$_1'$)$_n$—C(O)—(CR$_3$R$_3'$)—B, —(CR$_1$R$_1'$)$_n$—S(O)$_p$—(CR$_3$R$_3'$)—B,

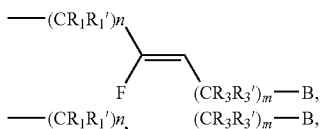

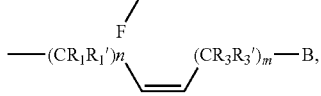


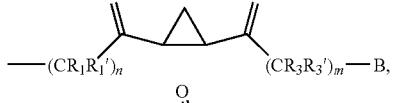

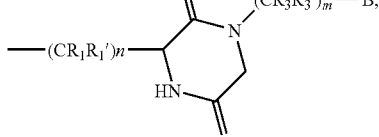

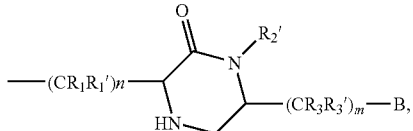

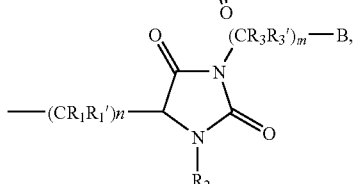

-continued

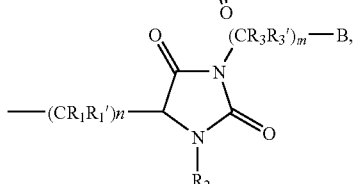

B is Ar or —(CR$_{22}$R$_{23}$)$_s$-J;

Ar is unsubstituted aryl, unsubstituted nitrogen-containing heteroaryl group, aryl substituted with D, or nitrogen-containing heteroaryl group substituted with D;

J is selected from hydrogen, OH, CN, CF$_3$, NR$_{31}$R$_{32}$, C$_1$, C$_2$, C$_3$, C$_4$, C$_5$, or C$_6$ alkyl, C$_3$, C$_4$, C$_5$, C$_6$, C$_7$, or C$_8$ cycloalkyl, C$_1$, C$_2$, C$_3$, C$_4$, C$_5$, or C$_6$ alkoxy, non-aromatic heterocycle, partially unsaturated carbocycle, COOH, COOR$_{30}$, and CONR$_{31}$R$_{32}$; further wherein alkyl, cycloalkyl, non-aromatic heterocycle, and partially unsaturated carbocycle are optionally substituted with D;

D is selected from halogen, C$_1$, C$_2$, C$_3$, C$_4$, C$_5$, or C$_6$ alkoxy, C$_1$, C$_2$, C$_3$, C$_4$, C$_5$, or C$_6$ alkyl, C$_3$, C$_4$, C$_5$, C$_6$, C$_7$, or C$_8$ cycloalkyl, non-aromatic heterocycle, partially unsaturated carbocycle, (C$_1$, C$_2$, C$_3$, C$_4$, C$_5$, or C$_6$)alkyl-non-aromatic heterocycle, (C$_3$, C$_4$, C$_5$, C$_6$, C$_7$, or C$_8$)cycloalkyl-non-aromatic heterocycle, (C$_1$, C$_2$, C$_3$, C$_4$, C$_5$, or C$_6$)alkyl-partially unsaturated carbocycle, (C$_3$, C$_4$, C$_5$, C$_6$, C$_7$, or C$_8$)cycloalkyl-partially unsaturated carbocycle, —OR$_{26}$, —SR$_{27}$, —NR$_{28}$R$_{29}$, and —(CR$_{24}$R$_{25}$)$_t$—U;

U is cyano, —OR$_{26}$, —SR$_{27}$, C$_1$, C$_2$, C$_3$, C$_4$, C$_5$, or C$_6$ alkyl, C$_3$, C$_4$, C$_5$, C$_6$, C$_7$, or C$_8$ cycloalkyl, non-aromatic heterocycle, partially unsaturated carbocycle, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, or glycoside;

R$_{22}$ and R$_{23}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl;

R$_{24}$ and R$_{25}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl;

$R_{26}$, $R_{27}$, $R_{28}$, and $R_{29}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl, or together $R_{28}$ and $R_{29}$ form a ring;

$R_{30}$, $R_{31}$ and $R_{32}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl, or together $R_{31}$ and $R_{32}$ form a ring;

s is 0, 1, 2, 3, 4, 5, 6, 7, 8, 9, or 10;

t is 0, 1, 2, 3, 4, 5, or 6;

p is 0, 1 or 2;

n and m are, independently 0, 1, or 2; and $R_1$, $R_{1'}$, $R_2$, $R_{2'}$, $R_3$, and $R_{3'}$ are independently H or $C_1$, $C_2$, $C_3$, $C_4$, $C_5$, or $C_6$ alkyl, or $C_3$, $C_4$, $C_5$, $C_6$, $C_7$, or $C_8$ cycloalkyl.

In one embodiment, the invention relates to compounds wherein, when $X_z$ is CZ and Z is —$(CR_1R_{1'})_n$—$NR_2$—$(CR_3R_{3'})_m$—B and T is a bond, then n is not 0. In one embodiment, the invention relates to compounds wherein, when $X_z$ is CZ and Z is —$(CR_1R_{1'})_n$—$NR_2$—$(CR_3R_{3'})_m$—B and T is a bond, then n is 1 or 2. In one embodiment, the invention relates to compounds wherein, when $X_z$ is CZ and Z is —$(CR_1R_{1'})_n$—$NR_2$—$(CR_3R_{3'})_m$—B and T is a bond, then $R_6$ is H and $X_b$ and $X_d$ are both CH. In one embodiment, the invention relates to compounds wherein, when $X_z$ is CZ and Z is —$(CR_1R_{1'})_n$—$NR_2$—C(O)—$(CR_3R_{3'})_m$—B and T is a bond, then n is not 0. In one embodiment, the invention relates to compounds wherein, when $X_z$ is CZ and Z is —$(CR_1R_{1'})_n$—$NR_2$—C(O)—$(CR_3R_{3'})_m$—B and T is a bond, then n is 1 or 2.

In one embodiment, the invention relates to compounds wherein, when $X_z$ is CZ and Z is —$(CR_1R_{1'})_n$—$NR_2$—C(O)—$(CR_3R_{3'})_m$—B; T is $CH_2O$; n is 0, then when B is Ar substituted with D, D is not OH or piperidine. In one embodiment, the compound of the invention is not

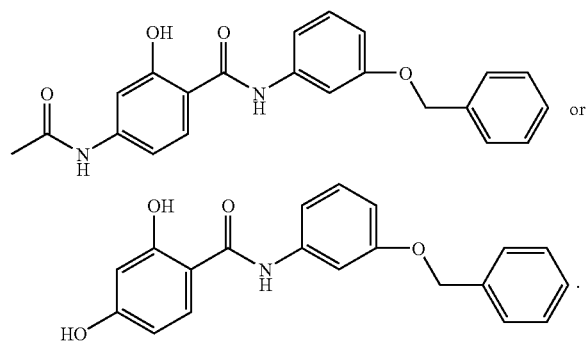

In one embodiment, the invention relates to compounds wherein, Z is selected from —$(CR_1R_{1'})_n$—$NR_2$—C(O)—$(CR_3R_3)_m$—B, —$(CR_1R_{1'})_n$—$NR_2$—$(CR_3R_{3'})_m$—B, —$(CR_1R_{1'})_n$—$NR_2$—C(O)—$NR_2(CR_3R_{3'})_m$, —$(CR_1R_{1'})_n$—O—C(O)—$NR_2(CR_3R_3)_m$—B, —$(CR_1R_{1'})_n$—$NR_2$—$S(O)_p$—$(CR_3R_{3'})_m$—B, —$(CR_1R_{1'})_n$—$S(O)_p$—$(CR_3R_{3'})_m$—B, and —$(CR_1R_{1'})_n$—C(O)—$CR_2R_{2'}$—$NR_2$—$(CR_3R_{3'})_m$—B.

In one embodiment, the invention relates to compounds wherein, Z is —$(CR_1R_{1'})_n$—C(O)—$NR_2(CR_3R_{3'})_m$—B, and at least three of $R_1$, $R_{1'}$, $R_3$, and $R_{3'}$ are not hydrogen. In one embodiment, the invention relates to compounds wherein, Z is —$(CR_1R_{1'})_n$—$NR_2$—C(O)—$(CR_3R_{3'})_m$—B. In one embodiment, the invention relates to compounds wherein, Z is —$(CR_1R_{1'})_n$—$NR_2$—$(CR_3R_{3'})_m$—B. In one embodiment, the invention relates to compounds wherein, Z is —$(CR_1R_{1'})_n$—$NR_2$—C(O)—$NR_2(CR_3R_{3'})_m$—B. In one embodiment, the invention relates to compounds wherein, Z is —$(CR_1R_{1'})_n$—O—C(O)—$NR_2(CR_3R_3)_m$—B. In one embodiment, the invention relates to compounds wherein, Z is —$(CR_1R_{1'})_n$—$NR_2$—C(O)—O—$(CR_3R_3)_m$—B. In one embodiment, the invention relates to compounds wherein, Z is —$(CR_1R_{1'})_n$—$NR_2$—$S(O)_p$—$(CR_3R_{3'})_m$—B or —$(CR_1R_1)_n$—$S(O)_p$—$NR_2$—$(CR_3R_{3'})_m$—B. In one embodiment, the invention relates to compounds wherein, Z is —$(CR_1R_{1'})_n$—$S(O)_p$—$(CR_3R_{3'})_m$—B. In one embodiment, the invention relates to compounds wherein, Z is —$(CR_1R_{1'})_n$—CH(OH)—$CR_2R_{2'}$—$NR_2$—$(CR_3R_{3'})_m$—B. In one embodiment, the invention relates to compounds wherein, Z is —$(CR_1R_{1'})_n$—C(O)—$CR_2R_{2'}$—$NR_2$—$(CR_3R_{3'})_m$—B. In one embodiment, the invention relates to compounds wherein, Z is

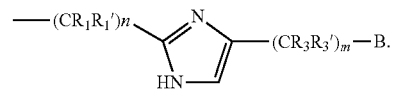

In one embodiment, the invention relates to compounds wherein, Z is —$(CR_1R_{1'})_n$—S—C(O)—$NR_2$—$(CR_3R_{3'})_m$—B. In one embodiment, the invention relates to compounds wherein, Z is

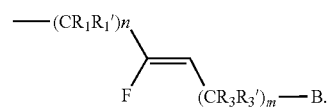

In one embodiment, the invention relates to compounds wherein, Z is —$(CR_1R_{1'})_n$—C(O)—$C(OH)R_2$—$(CR_3R_{3'})_m$—B. In one embodiment, the invention relates to compounds wherein, Z is —$(CR_1R_{1'})_n$—P(=O)(O—)—$NR_2$—$(CR_3R_{3'})_m$—B. In one embodiment, the invention relates to compounds wherein, Z is —$(CR_1R_{1'})_n$—$NR_2$—P(=O)(O—)—$(CR_3R_{3'})_m$—B.

In one embodiment, the invention relates to compounds wherein, n is selected from 0, 1, and 2. In one embodiment, the invention relates to compounds wherein, wherein m is selected from 0, 1, and 2.

In one embodiment, the invention relates to compounds wherein, $R_1$ and $R_{1'}$ are both hydrogen. In one embodiment, the invention relates to compounds wherein, $R_2$ and $R_{2'}$ are both hydrogen. In one embodiment, the invention relates to compounds wherein, $R_3$ and $R_{3'}$ are both hydrogen.

In one embodiment, the invention relates to compounds wherein, at least one of $X_a$, $X_b$, $X_c$, $X_d$, $X_e$, $X_y$ and $X_z$ is N. In one embodiment, the invention relates to compounds wherein, $X_c$ is N.

In one embodiment, the invention relates to compounds wherein, T is selected from a bond, $CH_2O$, O, and $OCH_2$. In one embodiment, the invention relates to compounds wherein, T is a bond. In one embodiment, the invention relates to compounds wherein, T is $CH_2O$ or $OCH_2$. In one embodiment, the invention relates to compounds wherein, T is O.

In one embodiment, the invention relates to compounds wherein, $X_z$ is CZ.

In one embodiment, the invention relates to compounds wherein, B is Ar.

In one embodiment, the invention relates to compounds wherein, Ar is:

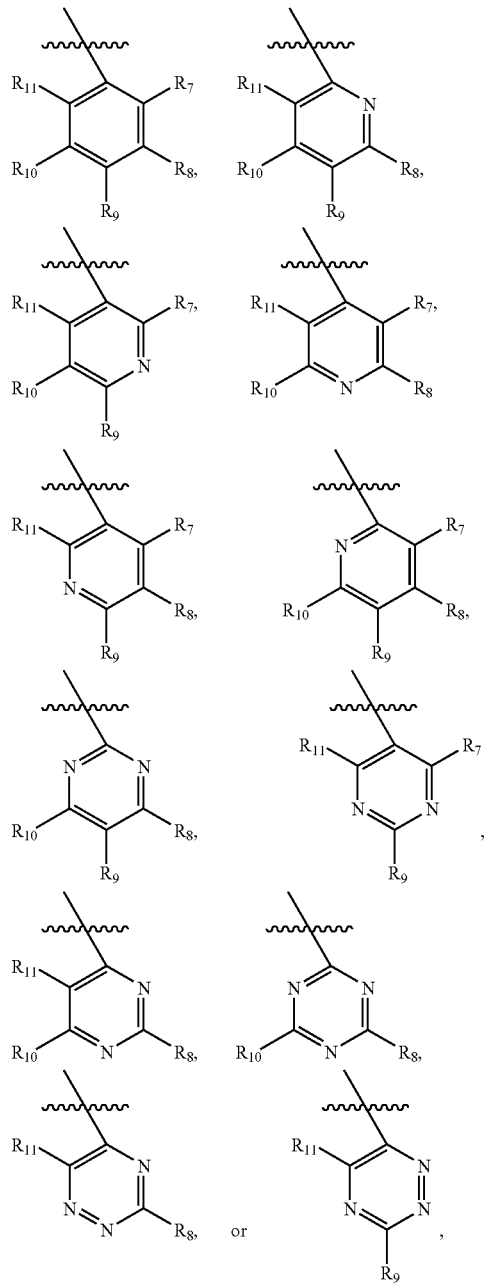

where $R_7$, $R_8$, $R_9$, $R_{10}$, and $R_{11}$ are, independently, hydrogen, hydroxyl, halogen, G, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C^4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl, ($C_1$, $C_2$, $C_3$, $C_4$, $C_5$, or $C_6$) alkyl-aryl, ($C_3$, $C_4$, $C_5$, or $C_6$) cycloalkyl-aryl, ($C_1$, $C_2$, $C_3$, $C_4$, $C_5$, or $C_6$) alkyl-heteroaryl, ($C_3$, $C_4$, $C_5$, or $C_6$) cycloalkyl-heteroaryl; $C_3$, $C_4$, $C_5$, $C_6$, $C_7$, or $C_g$ cycloalkyl, ($C_1$, $C_2$, $C_3$, $C_4$, $C_5$, or $C_6$)alkyl-non-aromatic heterocycle, ($C_3$, $C_4$, $C_5$, $C_6$, $C_7$, or $C_8$)cycloalkyl-non-aromatic heterocycle, ($C_1$, $C_2$, $C_3$, $C_4$, $C_5$, or $C_6$)alkyl-partially unsaturated carbocycle, ($C_3$, $C_4$, $C_5$, $C_6$, $C_7$, or $C_8$)cycloalkyl-partially unsaturated carbocycle, $C_1$, $C_2$, $C_3$, $C_4$, $C_5$, or $C_6$ alkyl-O—$C_1$, $C_2$, $C_3$, $C_4$, $C_5$, or $C_6$ alkyl, —$OR_{26}$, —$SR_{27}$, —$NR_{28}R_{29}$, —$(CR_{24}R_{25})_t$—U;

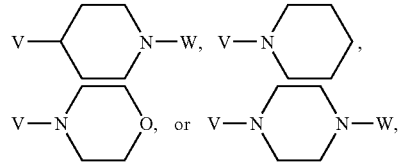

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —$CH_2$—, —$CH_2CH_2$—, —$CH_2CH_2CH_2$—, —$O$—$CH_2$—, —$OCH_2CH_2$— or —$OCH_2CH_2CH_2$;
U is cyano, —$OR_{26}$, —$SR_{27}$, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, or glycoside;
$R_{24}$ and $R_{25}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl;
$R_{26}$, $R_{27}$, $R_{28}$, and $R_{29}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl, or together $R_{28}$ and $R_{29}$ form a ring;
$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;
G is $SO_3H$, $OSO_3H$, $OPO_3H_2$, $OPO_3H_2$, $NH_2$, $NHR_{19}$, $NR_{20}R_{21}$,

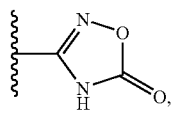

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;
K is $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, aryl, heteroaryl, or

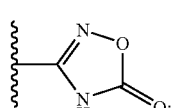

L is aryl, heteroaryl, OH, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

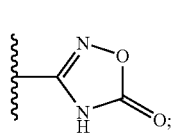

M is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

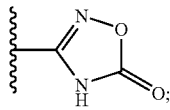

Q is aryl, heteroaryl, OH, C(O)NR$_{28}$R$_{29}$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

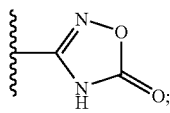

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring; and t is 0, 1, 2, 3, 4, 5, or 6.

In one embodiment, the invention relates to compounds wherein, Ar is

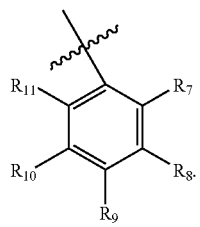

In one embodiment, the invention relates to compounds wherein, R$_7$, R$_3$, R$_9$, R$_{10}$, and R$_{11}$ are each hydrogen. In one embodiment, the invention relates to compounds wherein, at least one of R$_7$, R$_8$, R$_9$, R$_{10}$, and R$_{11}$ is halogen, C$_1$, C$_2$, C$_3$, C$_4$, C$_5$, or C$_6$ alkoxy, or O-benzyl.

In one embodiment, the invention relates to compounds wherein, B is —(CR$_{22}$R$_{23}$)$_s$-J. In one embodiment, the invention relates to compounds wherein, R$_{22}$ and R$_{23}$ are both H. In one embodiment, the invention relates to compounds wherein, one of R$_{22}$ and R$_{23}$ is H. In one embodiment, the invention relates to compounds wherein, one of R$_{22}$ and R$_{23}$ is alkyl or cycloalkyl. In one embodiment, the invention relates to compounds wherein, one of R$_{22}$ and R$_{23}$ is H and the other is alkyl or cycloalkyl.

In one embodiment, the invention relates to compounds wherein, s is 1. In one embodiment, the invention relates to compounds wherein, s is 2.

In one embodiment, the invention relates to compounds wherein J is alkyl, such as methyl, ethyl, propyl, isopropyl, butyl, isobutyl, t-butyl, pentyl, isopentyl, or the like. Alkyl can be substituted for example with cyano, hydroxyl, halo, alkoxy, amino, thiol, or the like.

In one embodiment, the invention relates to compounds wherein J is cycloalkyl.

In one embodiment, the invention relates to compounds wherein J is selected from cyclopropyl, cyclobutyl, cyclohexyl, cyclopentyl, cycloheptyl, and cyclooctyl.

In one embodiment, the invention relates to compounds wherein J is a substituted carbocycle or a heterocycle. Non-limiting examples include

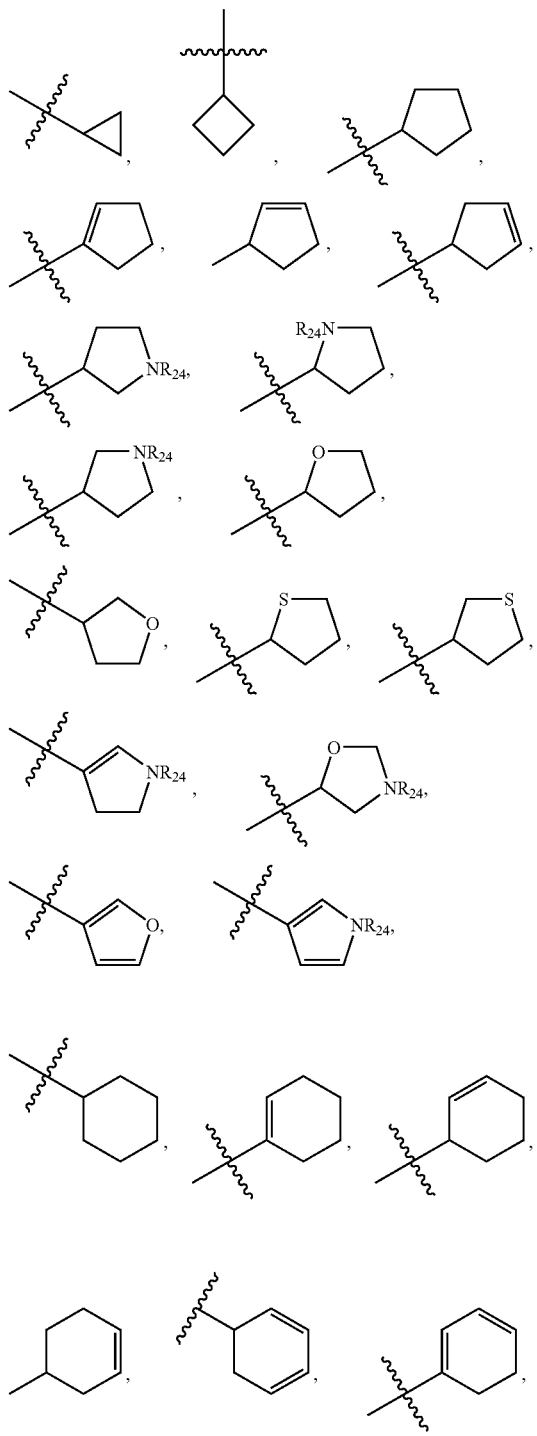

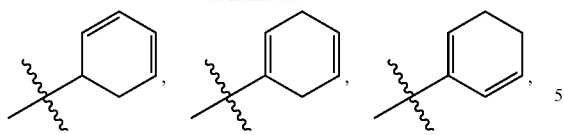
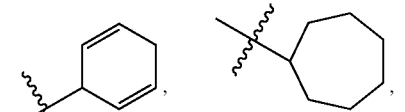
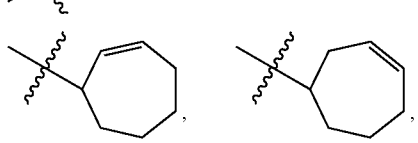
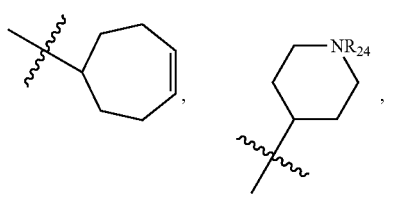
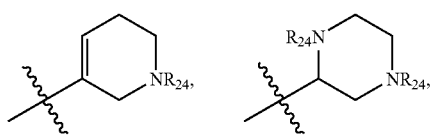
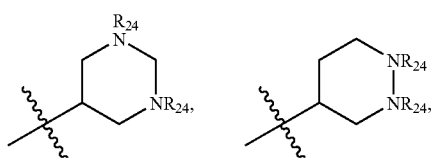
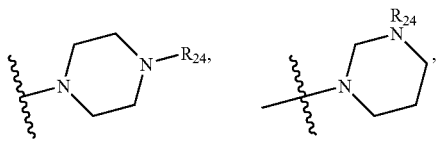
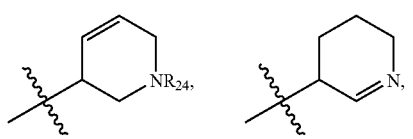
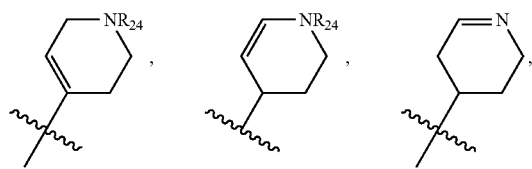
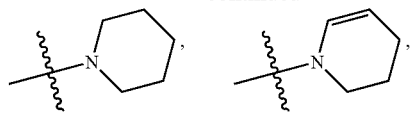
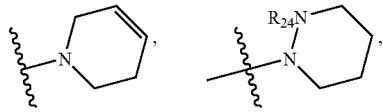
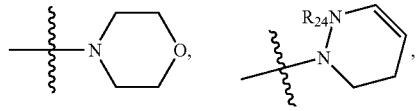
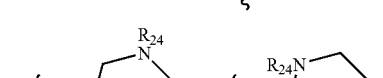
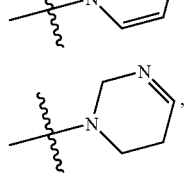

and isomers thereof, and the like.

In one embodiment, the invention relates to compounds wherein J is a non-aromatic heterocycle. In one embodiment, the invention relates to compounds wherein J contains at least one heteroatom selected from N, O, and S. In one embodiment, the invention relates to compounds wherein J contains at least two heteroatoms. In one embodiment, the invention relates to compounds wherein J contains at least two N atoms. In one embodiment, the invention relates to compounds wherein J contains one O. In one embodiment, the invention relates to compounds wherein J contains one S. In one embodiment, the invention relates to compounds wherein J is a 5-membered ring heterocycle. In one embodiment, the invention relates to compounds wherein J is a 6-membered ring heterocycle. In one embodiment, the invention relates to compounds wherein J is a partially unsaturated carbocycle. In one embodiment, the invention relates to compounds wherein J is a 6-membered ring partially unsaturated carbocycle.

In one embodiment, the invention relates to compounds wherein $R_4$, $R_5$, and $R_6$ are each H. In one embodiment, the invention relates to compounds wherein $R_4$ and $R_6$ are each hydrogen. In one embodiment, the invention relates to compounds wherein $X_b$, $X_c$, and $X_d$ are $CR_b$, $CR_x$, and $CR_d$ respectively and $R_b$, $R_c$, and $R_d$ are each hydrogen. In one embodiment, the invention relates to compounds wherein $X_a$, $X_y$, and $X_e$ are $CR_a$, CY, and $CR_e$ respectively and $R_a$, Y, and $R_e$ are each hydrogen.

In one embodiment, the invention relates to compounds wherein the compound is a compound according to one of formulae II-CCCXIX.

The invention relates to a compound of Formula I, having a structure according to one of Formulae II-CCCXIX, depicted in Table A.

TABLE A
Formula II:
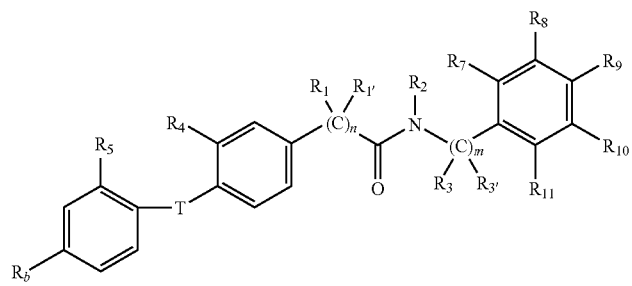
Formula III:
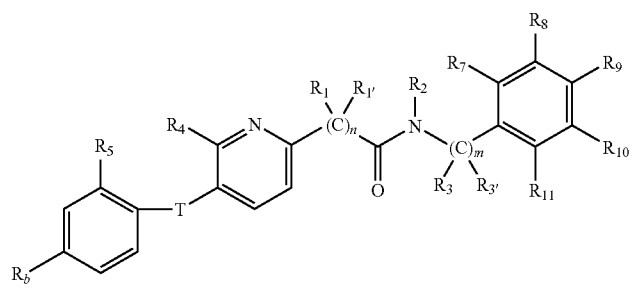
Formula IV:
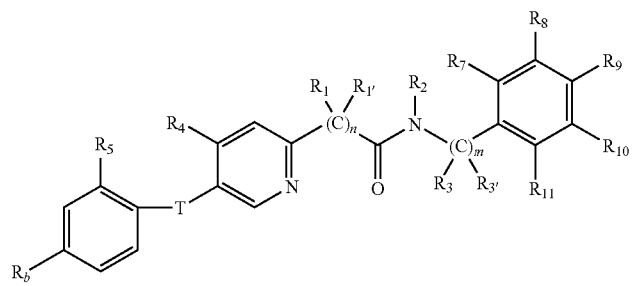
Formula V:
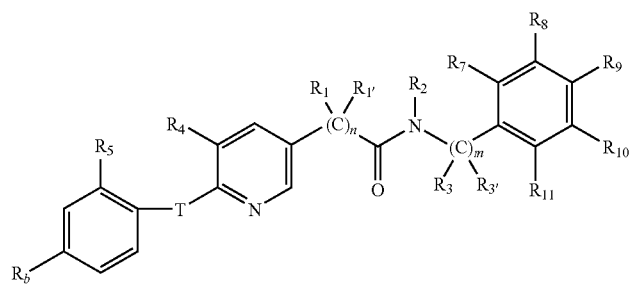
Formula VI:
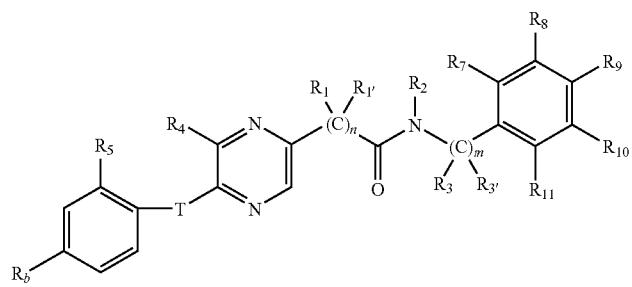

TABLE A-continued
Formula VII:
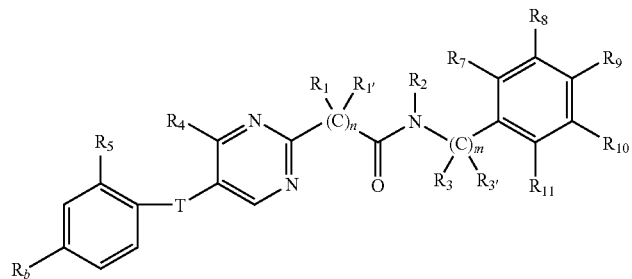
Formula VIII:
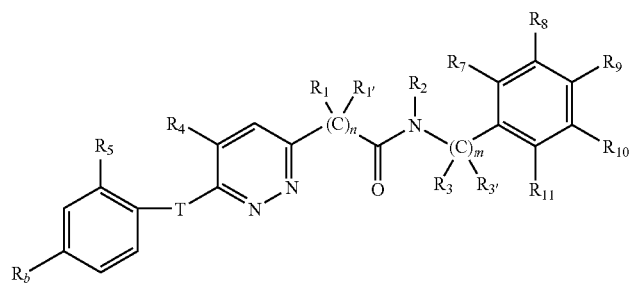
Formula IX:
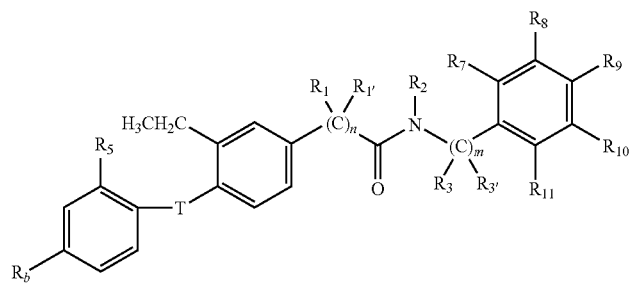
Formula X:
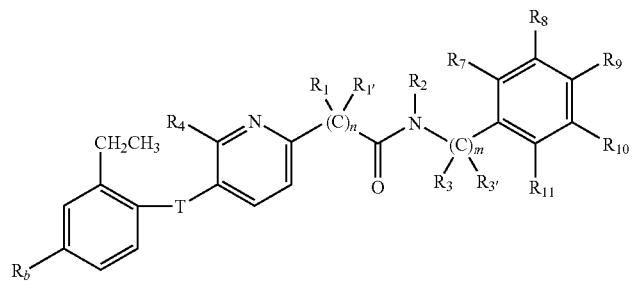

TABLE A-continued
Formula XI:
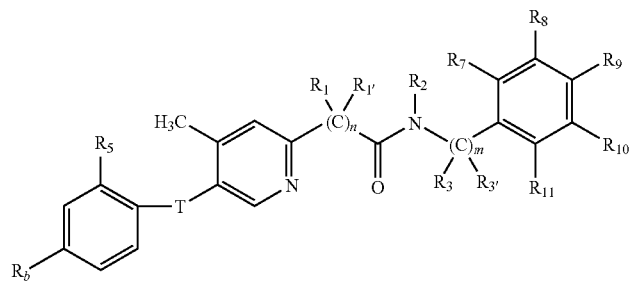
Formula XII:
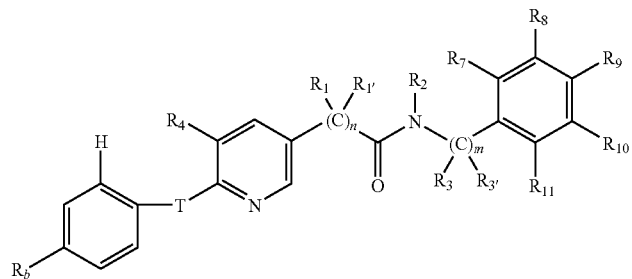
Formula XIII:
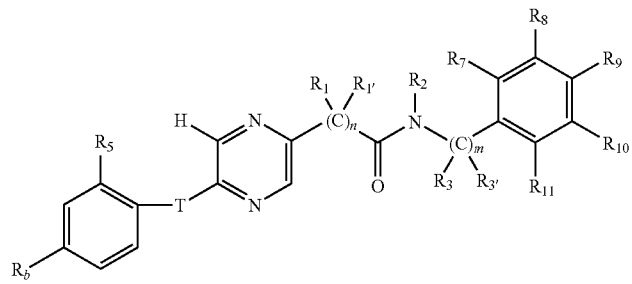
Formula XIV:
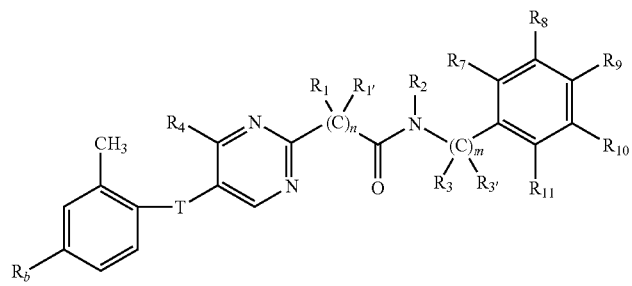
Formula XV:
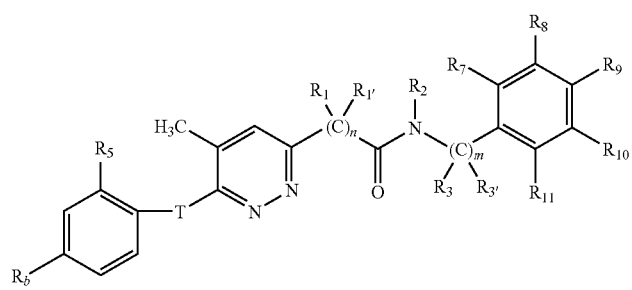

TABLE A-continued
Formula XVI:
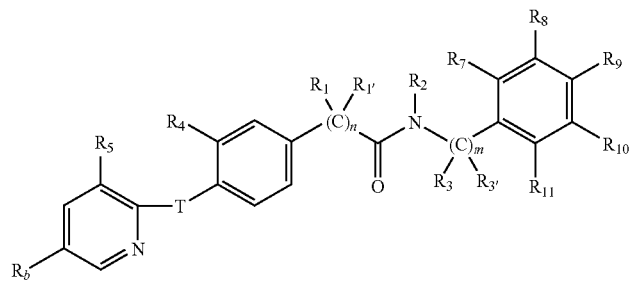
Formula XVII:
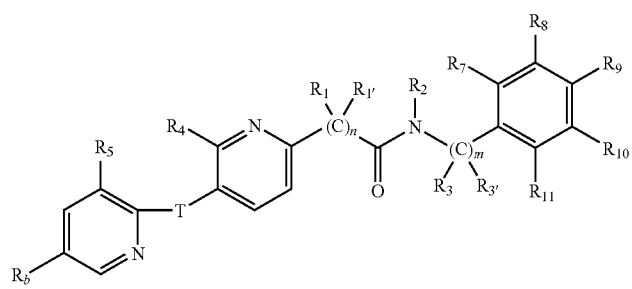
Formula XVIII:
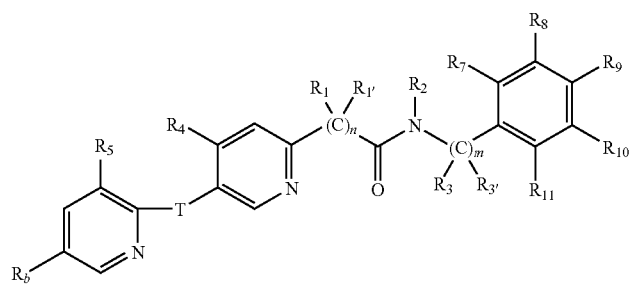
Formula XIX:
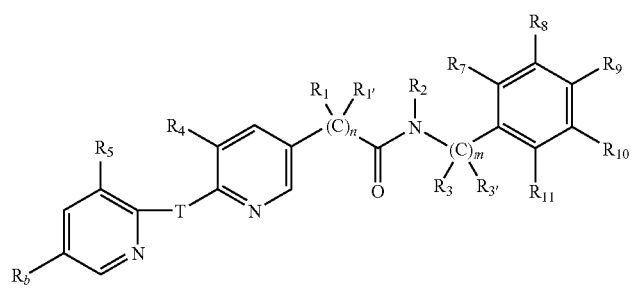

TABLE A-continued
Formula XX:
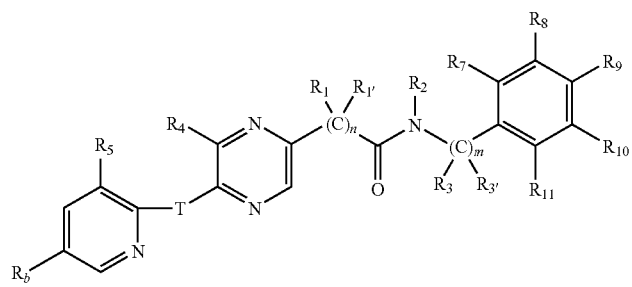
Formula XXI:
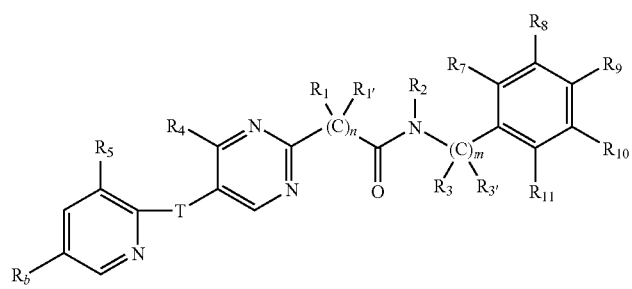
Formula XXII:
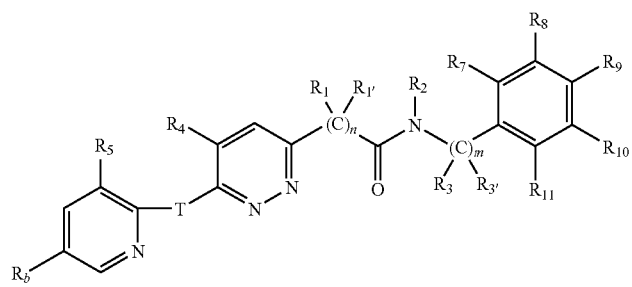
Formula XXIII:
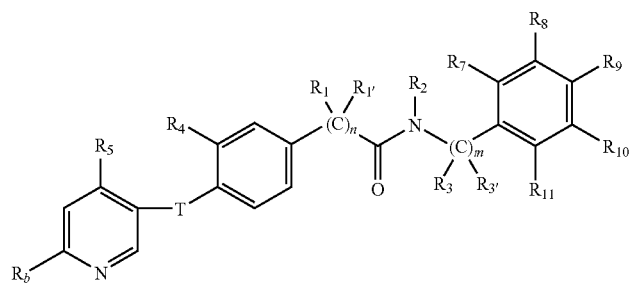
Formula XXIV:
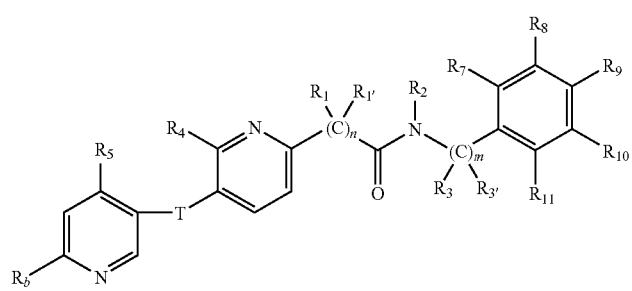

TABLE A-continued
Formula XXV:
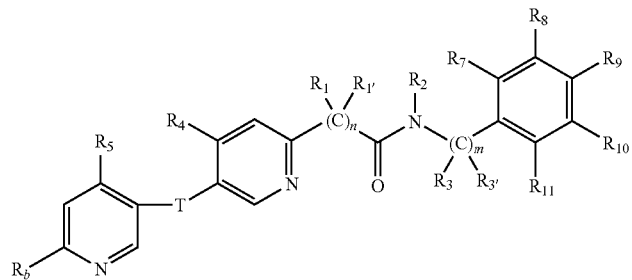
Formula XXVI:
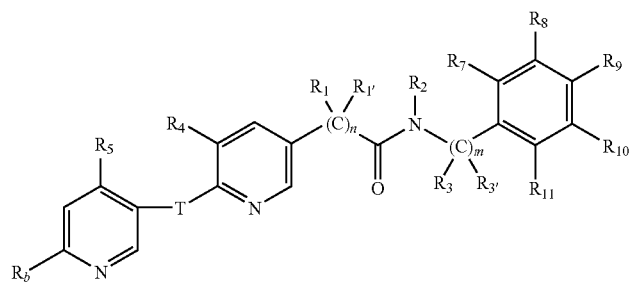
Formula XXVII:
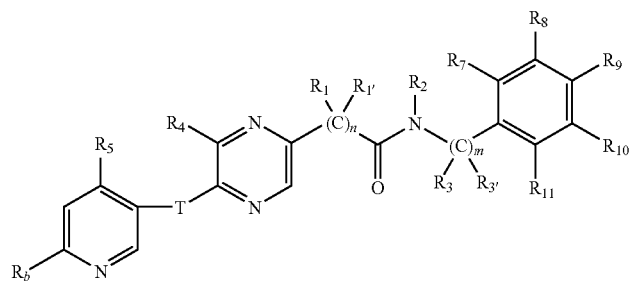
Formula XXVIII:
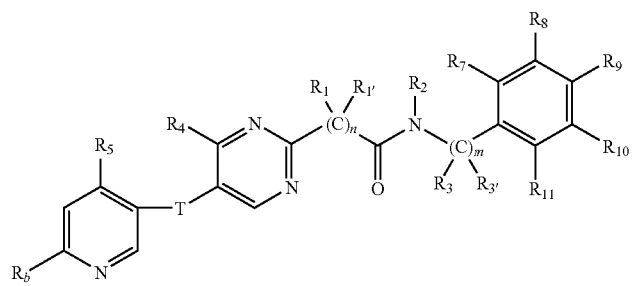

TABLE A-continued
Formula XXIX:
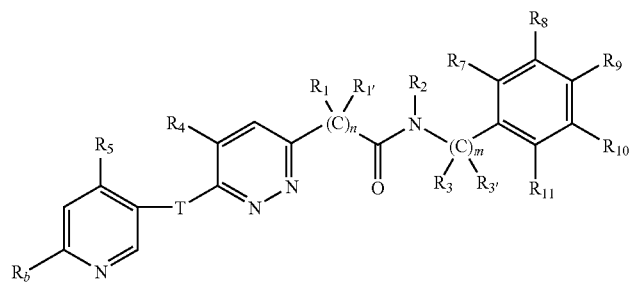
Formula XXX:
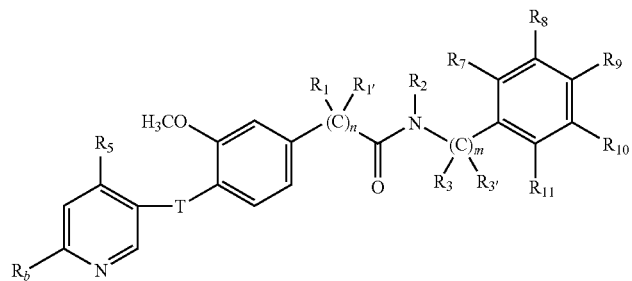
Formula XXXI:
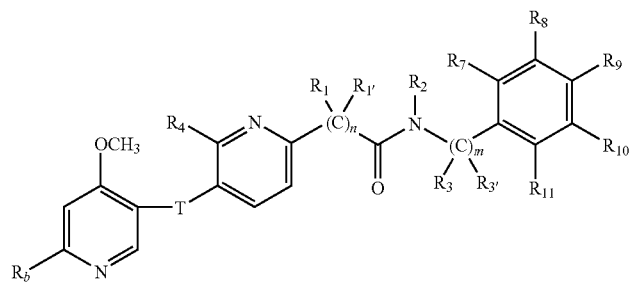
Formula XXXII:
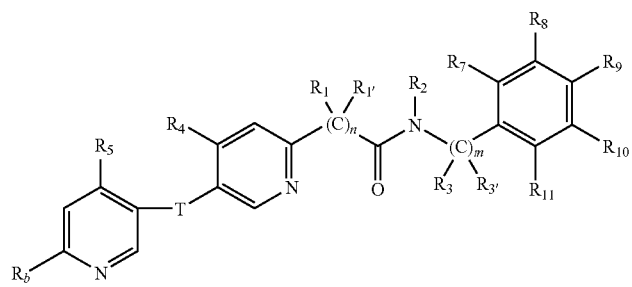
Formula XXXIII:
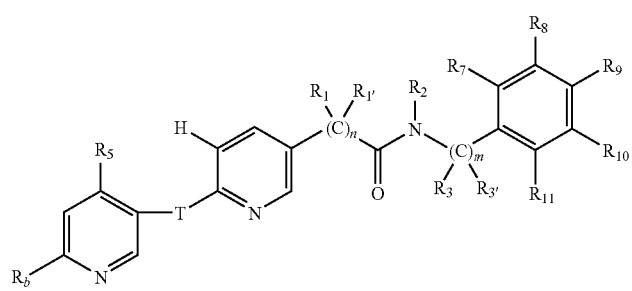

TABLE A-continued
Formula XXXIV:
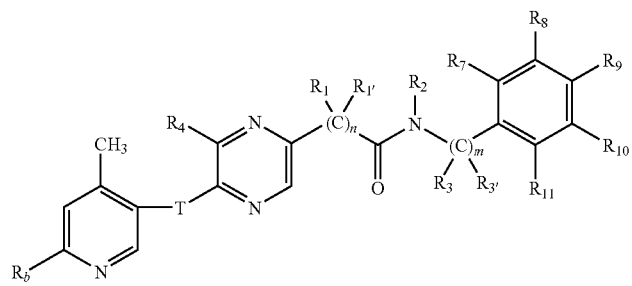
Formula XXXV:
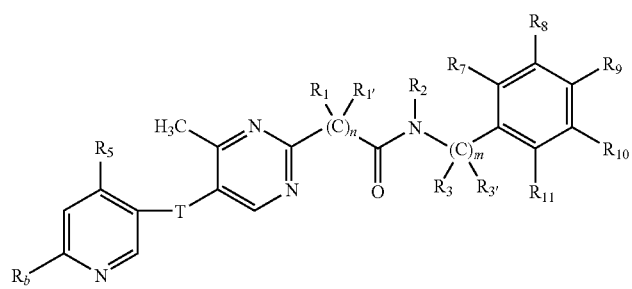
Formula XXXVI:
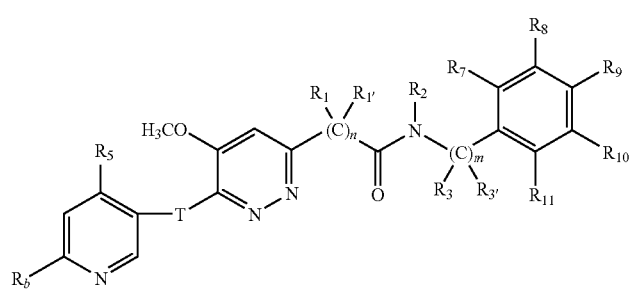
Formula XXXVII:
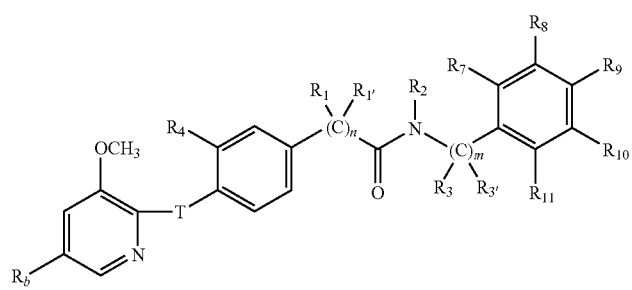

TABLE A-continued
Formula XXXVIII:
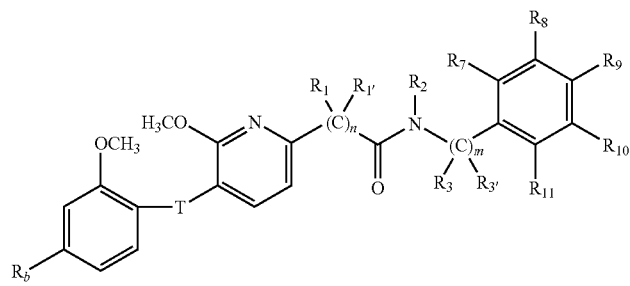
Formula XXXIX:
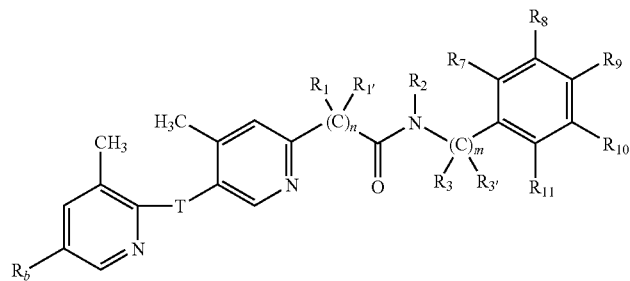
Formula XL:
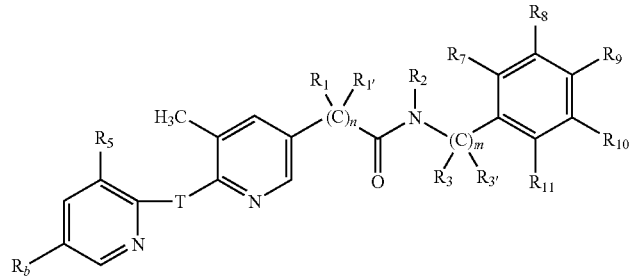
Formula XLI:
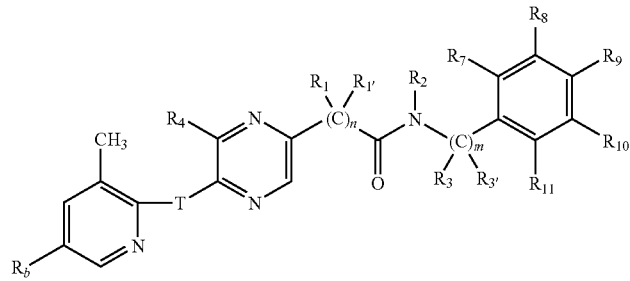
Formula XLII:
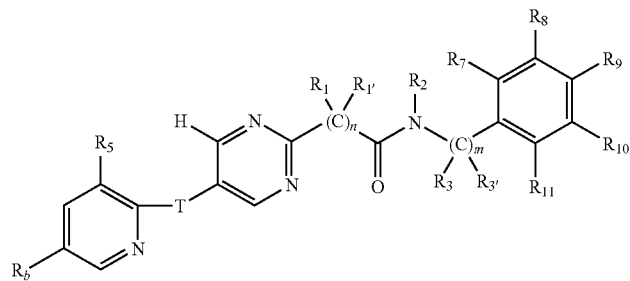

TABLE A-continued
Formula XLIII:
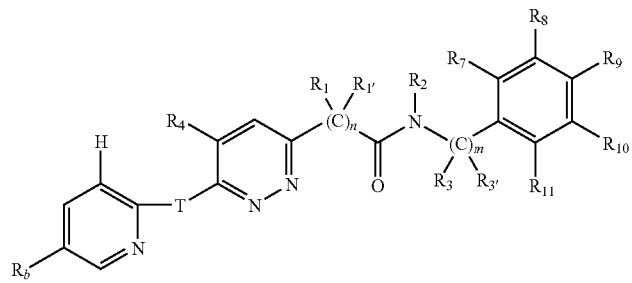
Formula XLIV:
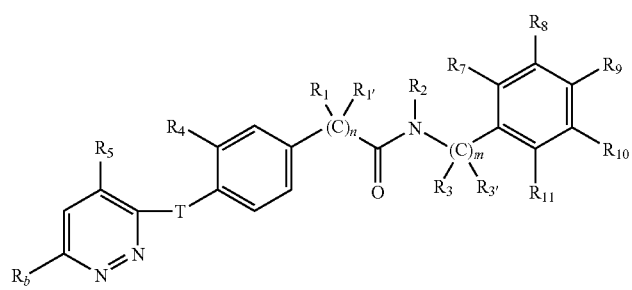
Formula XLV:
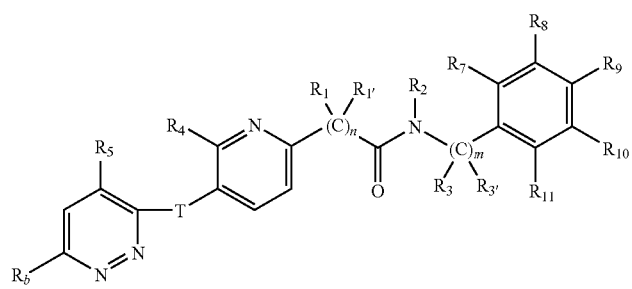
Formula XLVI:
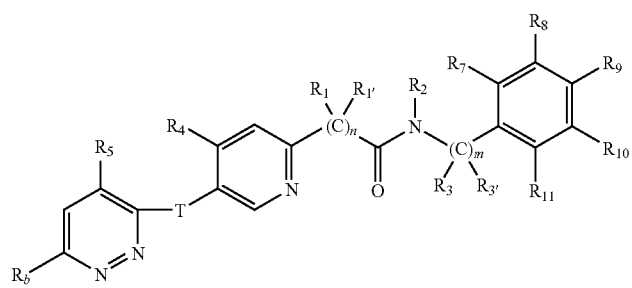

TABLE A-continued
Formula XLVII:
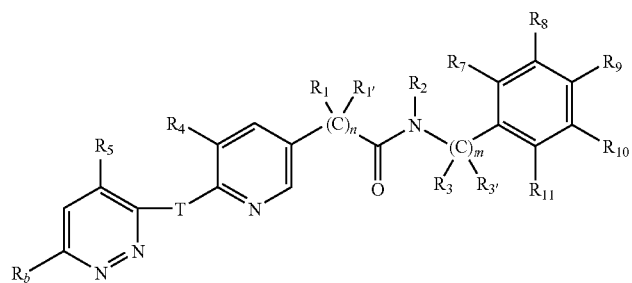
Formula XLVIII:
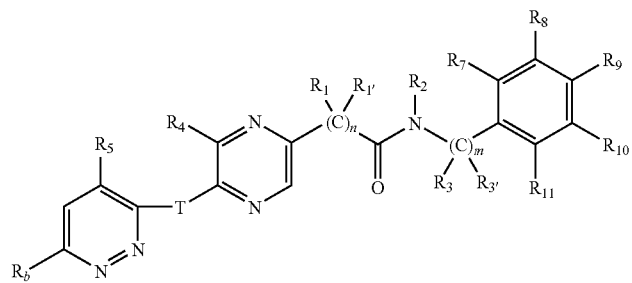
Formula XLIX:
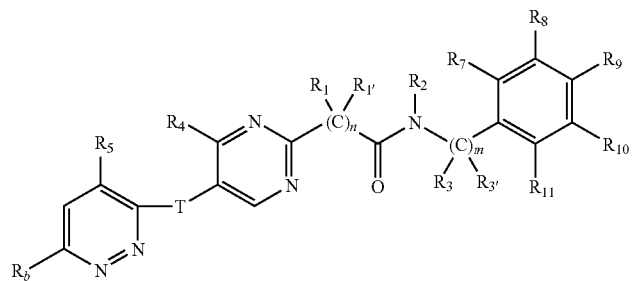
Formula L:
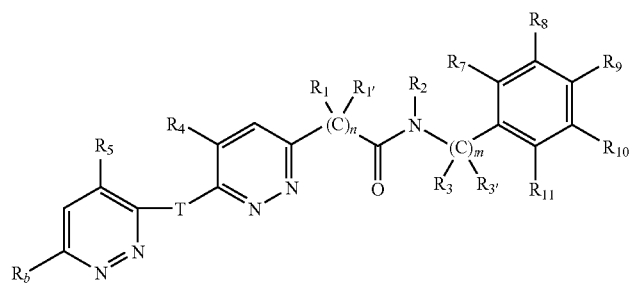
Formula LI:
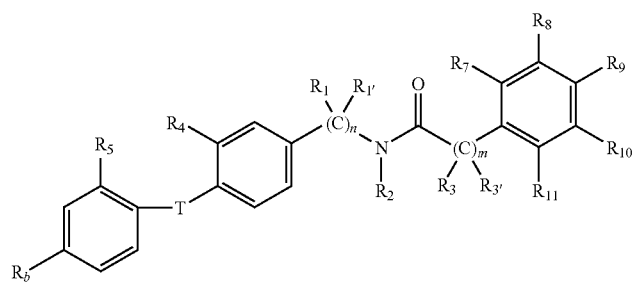

TABLE A-continued
Formula LII:
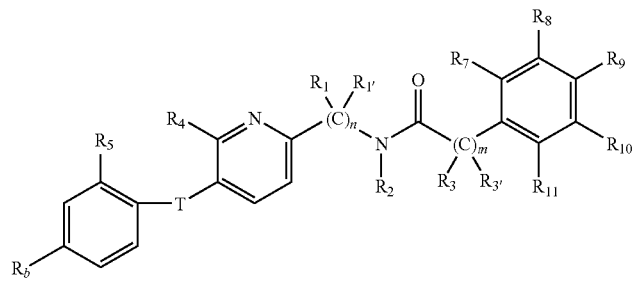
Formula LIII:
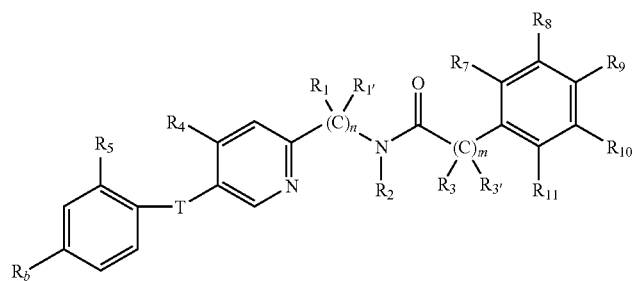
Formula LIV:
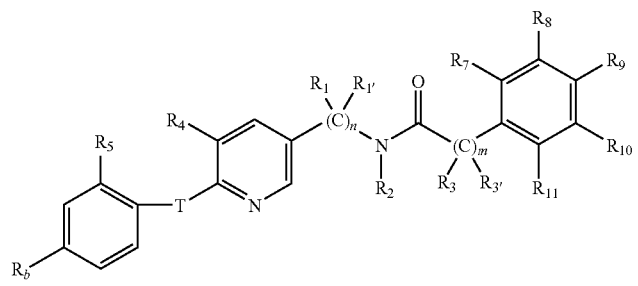
Formula LV:
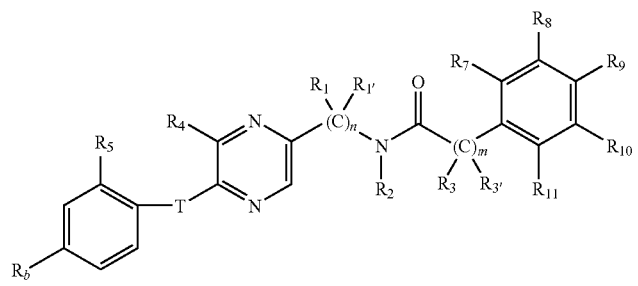
Formula LVI:
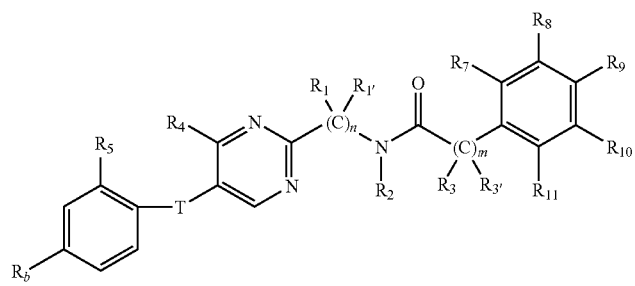

TABLE A-continued
Formula LVII:
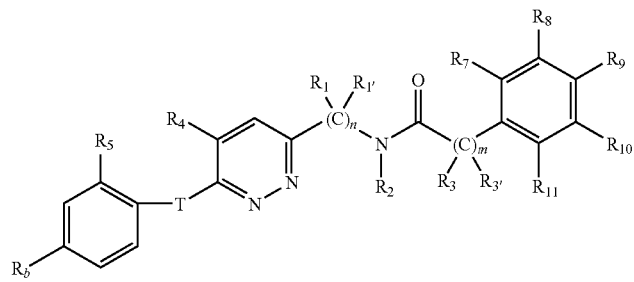
Formula LVIII:
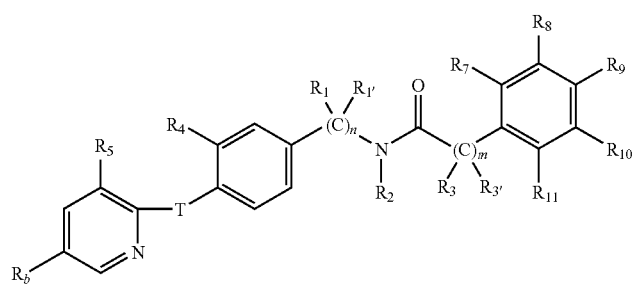
Formula LIX:
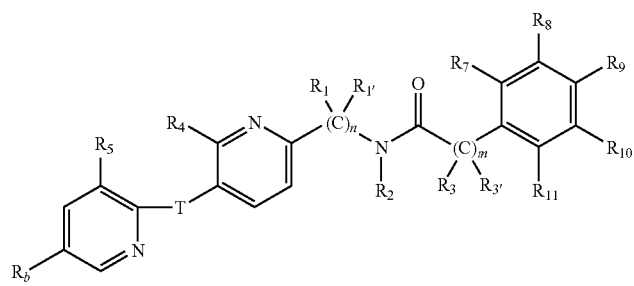
Formula LX:
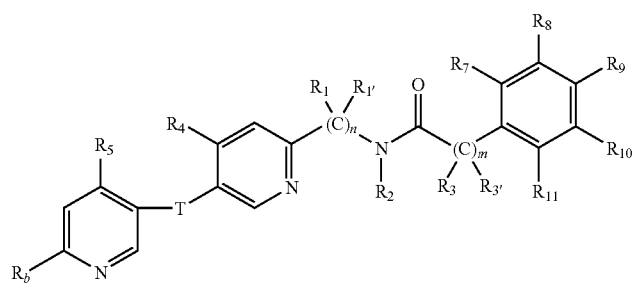

TABLE A-continued
Formula LXI:
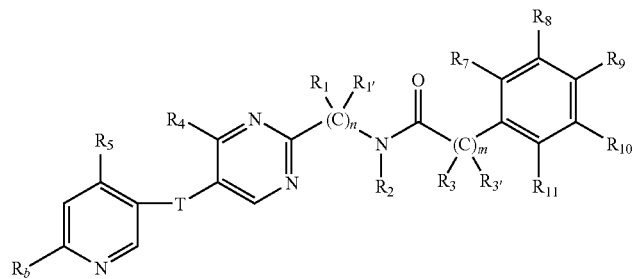
Formula LXII:
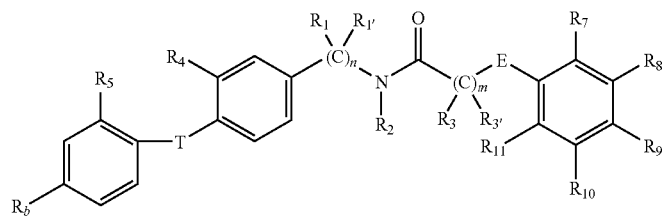
Formula LXIII:
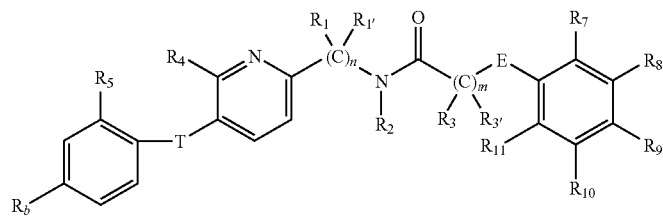
Formula LXIV:
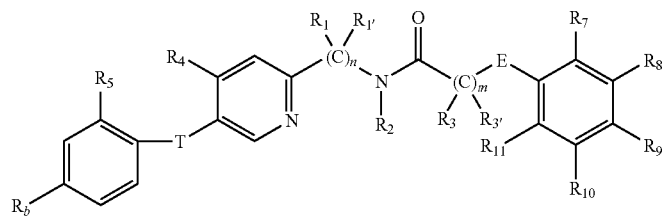
Formula LXV:
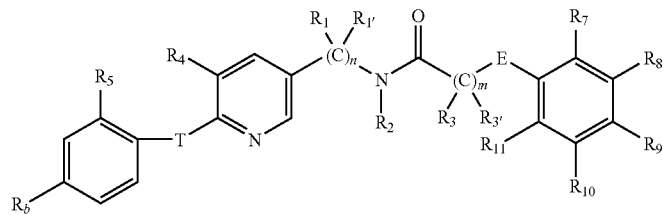

TABLE A-continued
Formula LXVI:
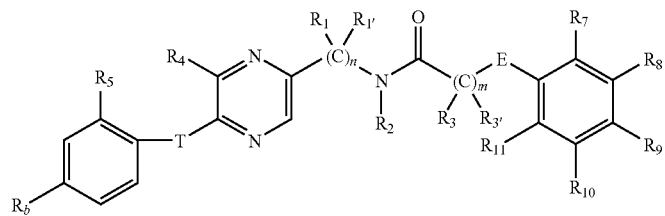
Formula LXVII:
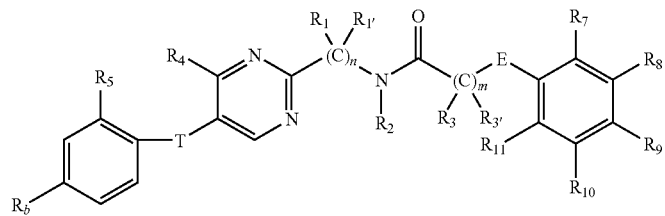
Formula LXVIII:
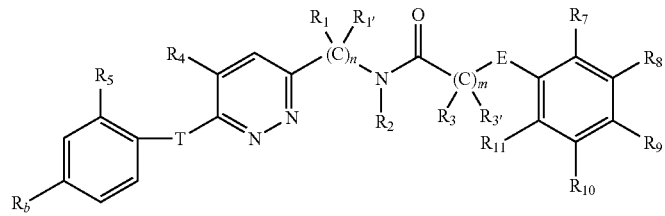
Formula LXIX:
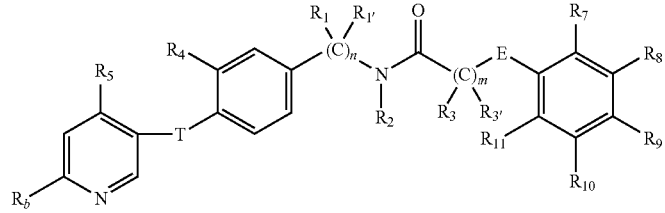
Formula LXX:
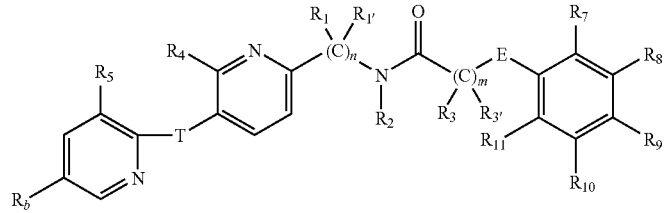
Formula LXXI:
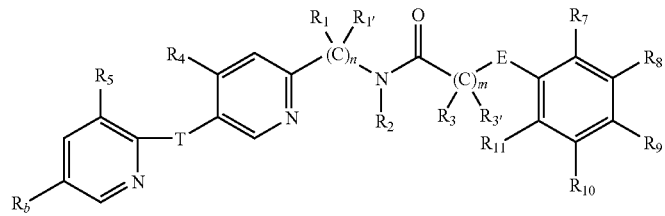

TABLE A-continued
Formula LXXII:
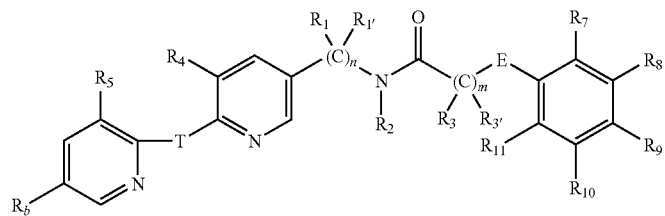
Formula LXXIII:
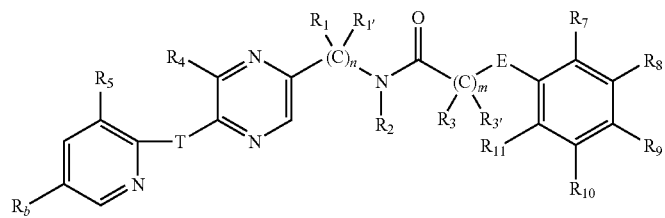
Formula LXXIV:
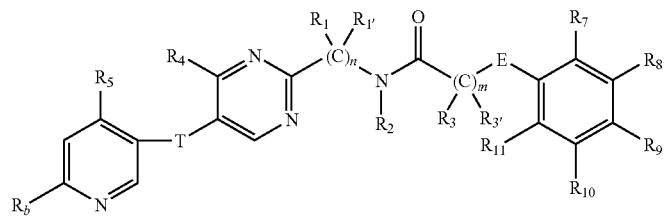
Formula LXXV:
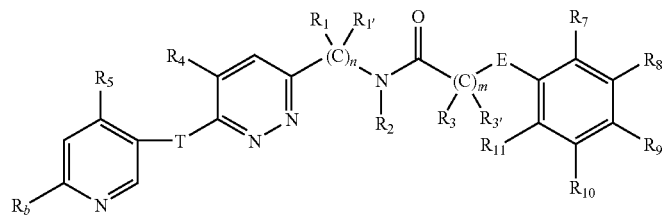
Formula LXXVI:
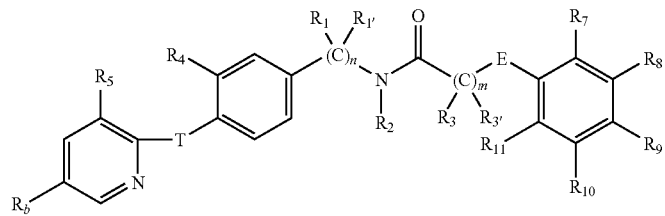
Formula LXXVII:
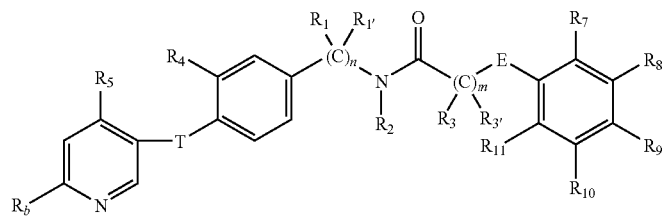

TABLE A-continued
Formula LXXVIII:
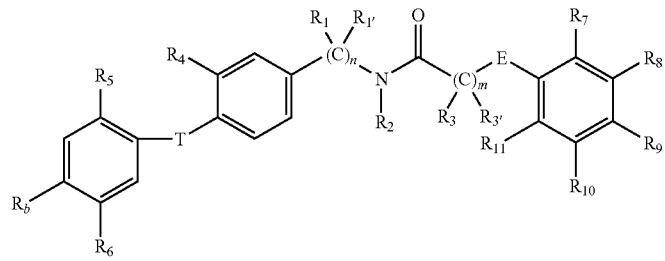
Formula LXXIX:
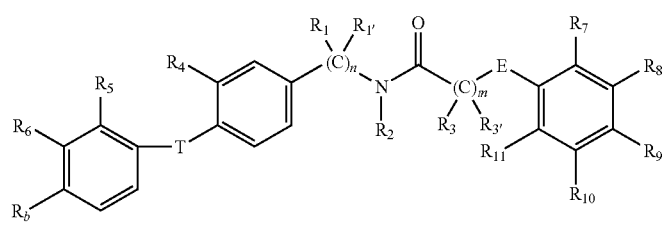
Formula LXXX:
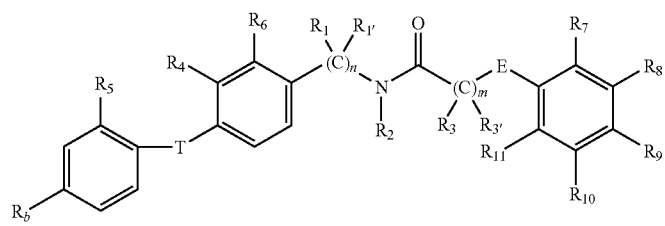
Formula LXXXI:
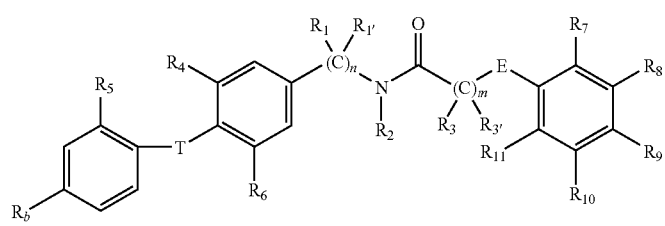
Formula LXXXII:
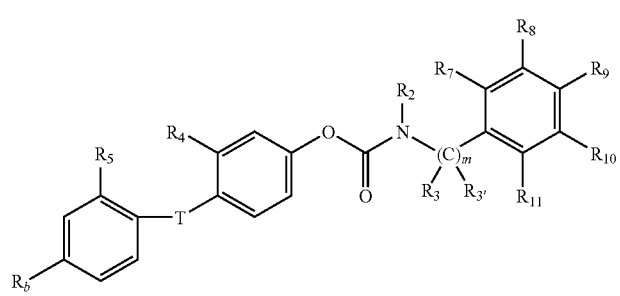

TABLE A-continued
Formula LXXXIII:
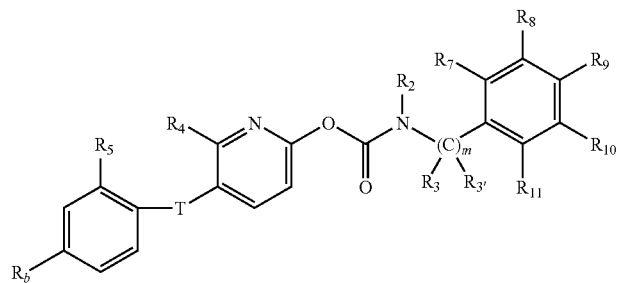
Formula LXXXIV:
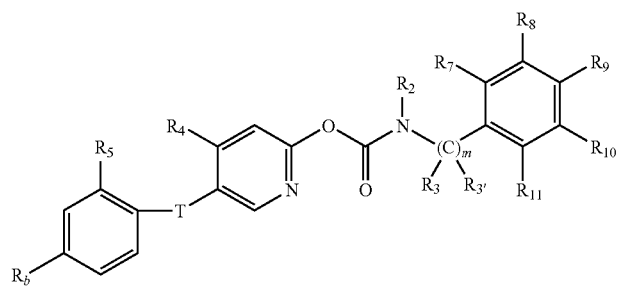
Formula LXXXV:
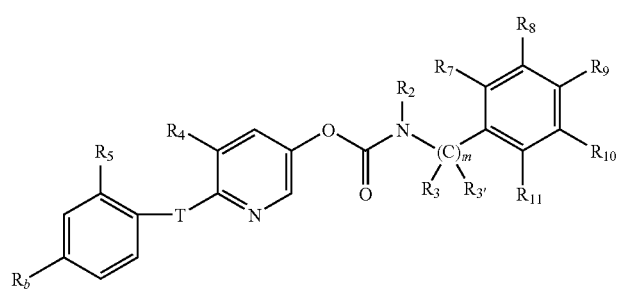
Formula LXXXVI:
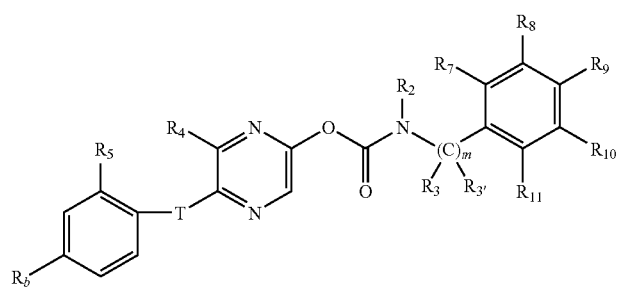

TABLE A-continued
Formula LXXXVII:
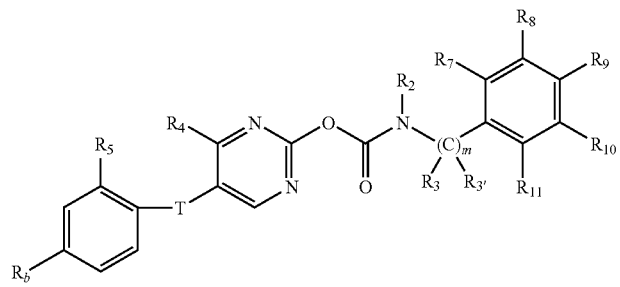
Formula LXXXVIII:
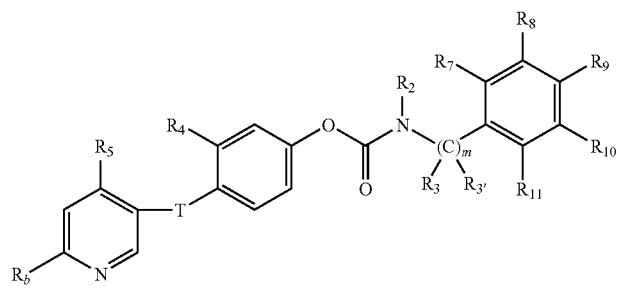
Formula LXXXIX:
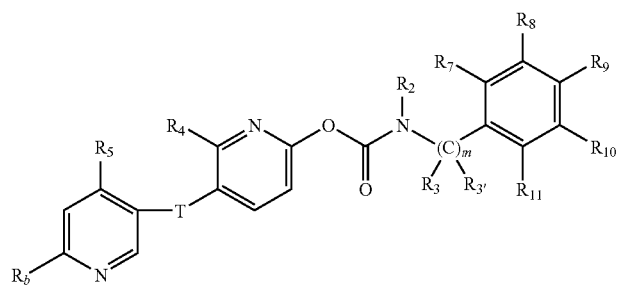
Formula XC:
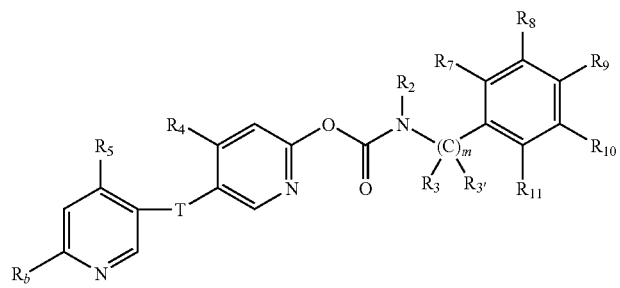

TABLE A-continued
Formula XCI:
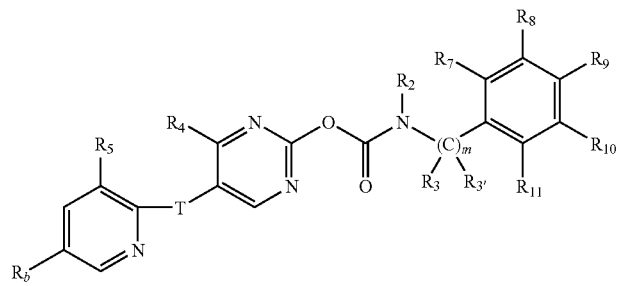
Formula XCII:
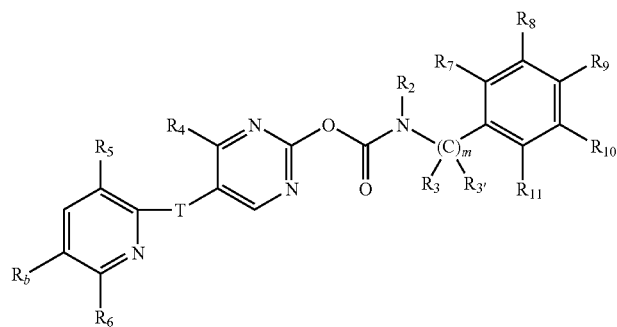
Formula XCIII:
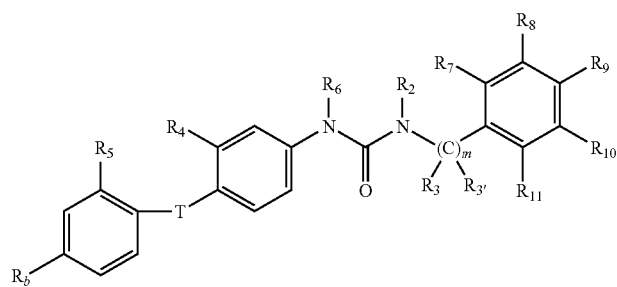
Formula XCIV:
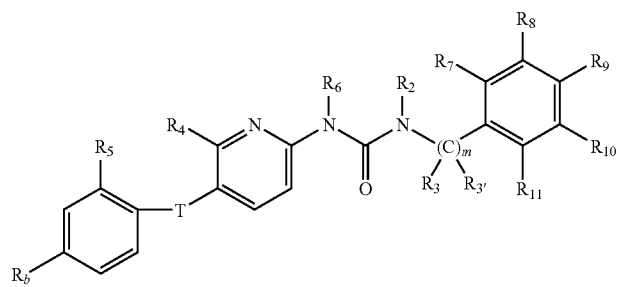

TABLE A-continued
Formula XCV:
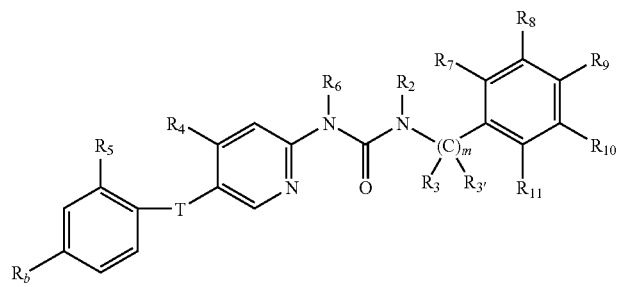
Formula XCVI:
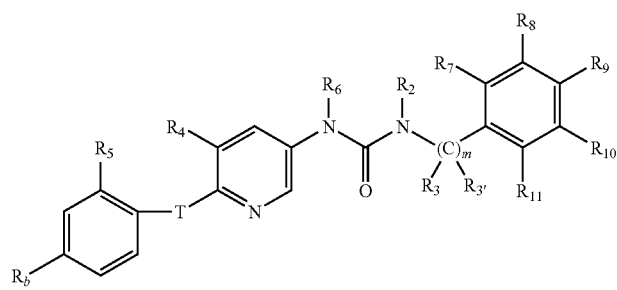
Formula XCVII:
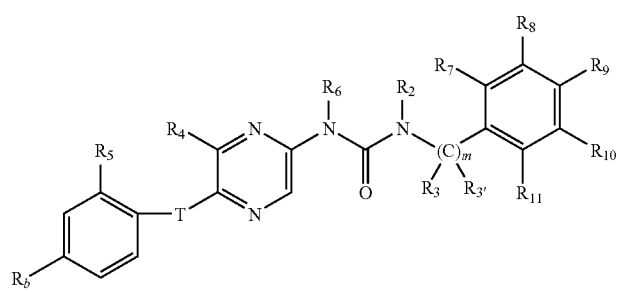
Formula XCVIII:
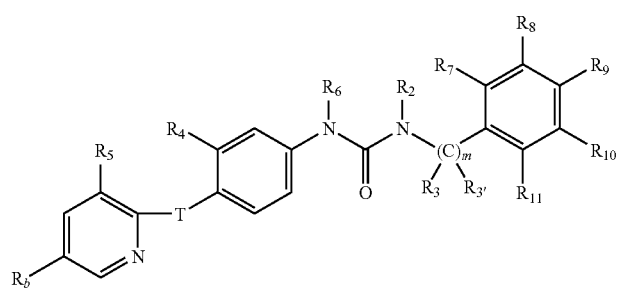

TABLE A-continued
Formula XCIX:
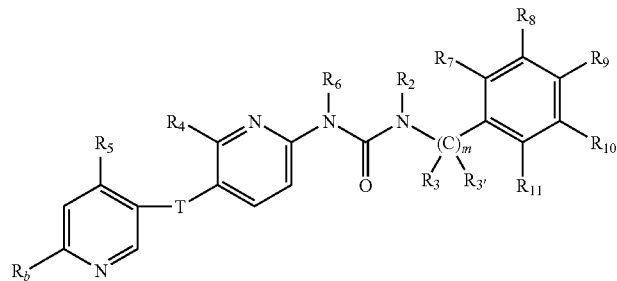
Formula C:
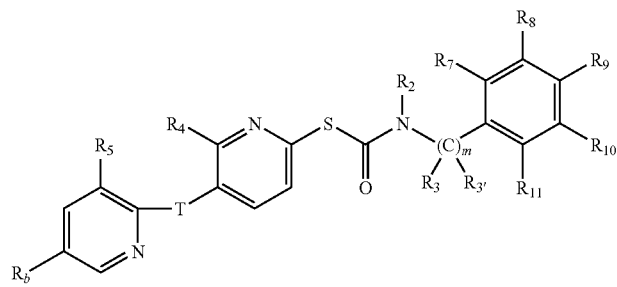
Formula CI:
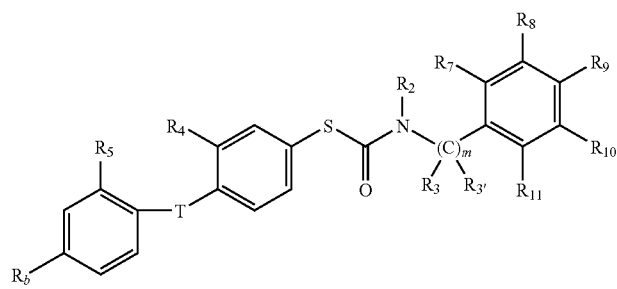
Formula CII:
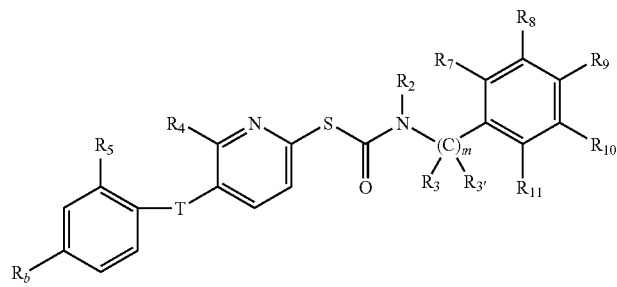

TABLE A-continued
Formula CIII:
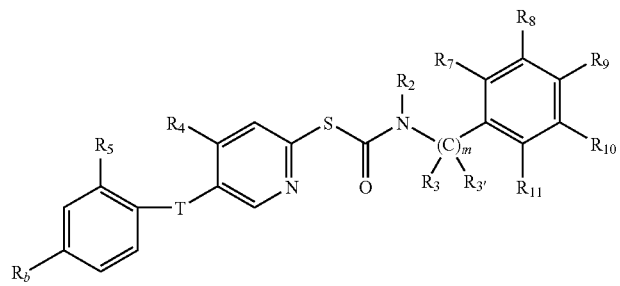
Formula CIV:
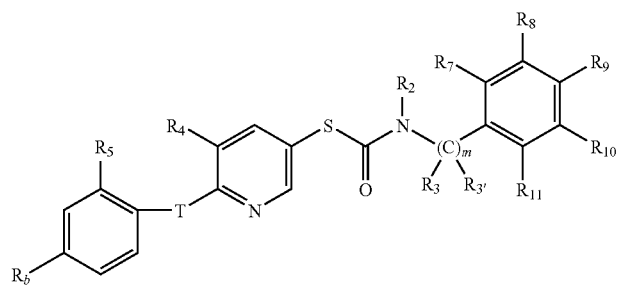
Formula CV:
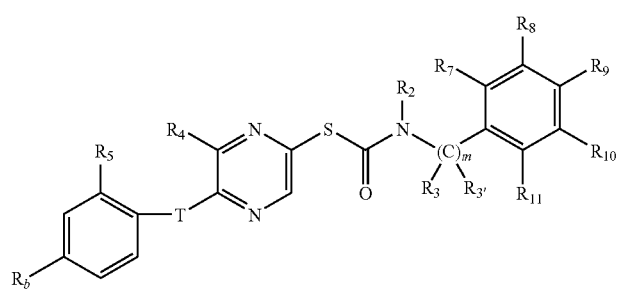
Formula CVI:
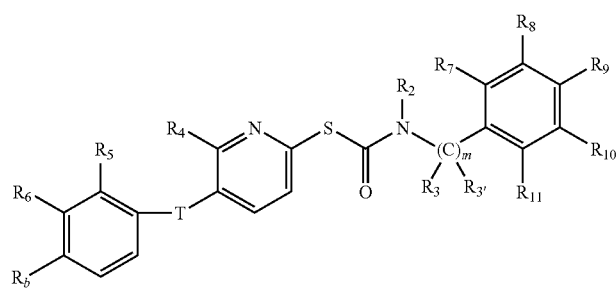

TABLE A-continued
Formula CVII:
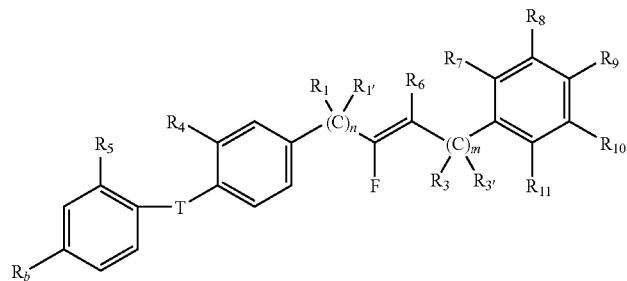
Formula CVIII:
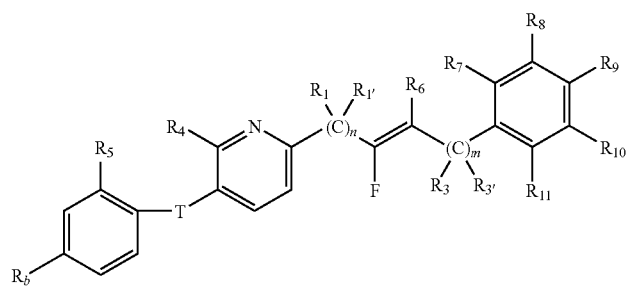
Formula CIX:
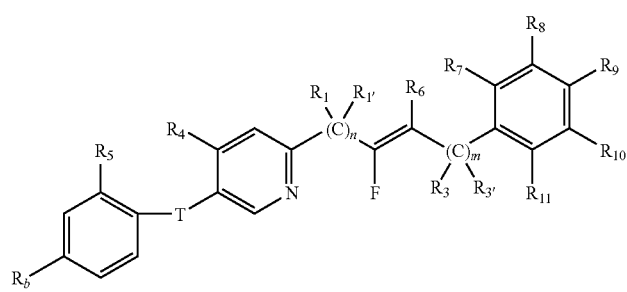
Formula CX:
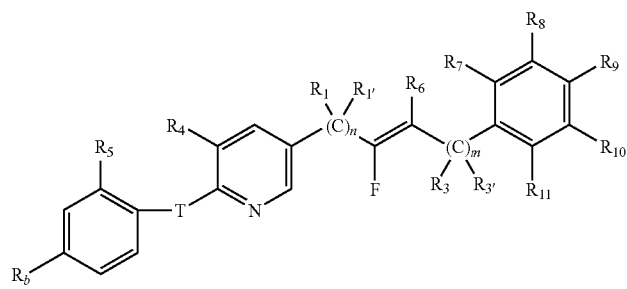

TABLE A-continued
Formula CXI:
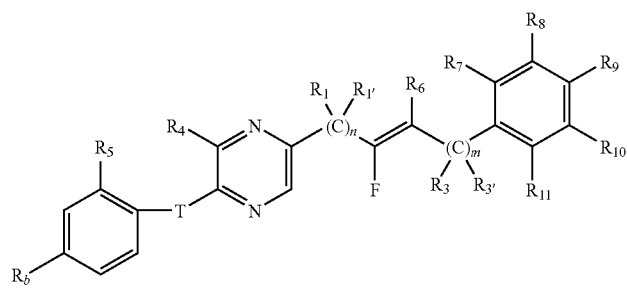
Formula CXII:
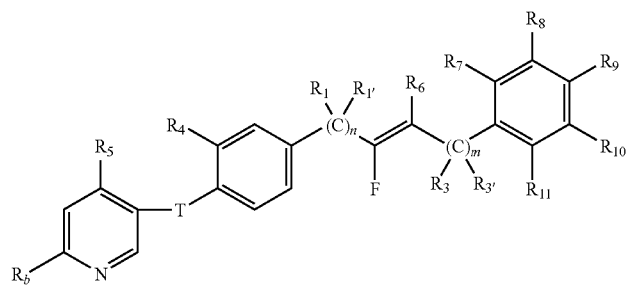
Formula CXIII:
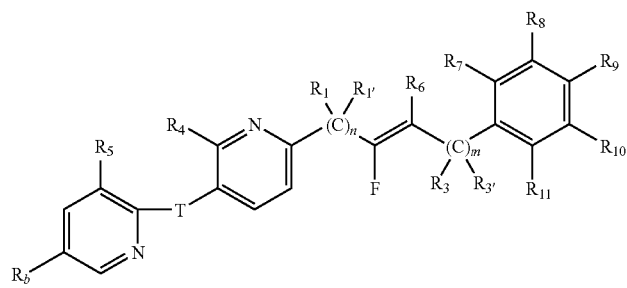
Formula CXIV:
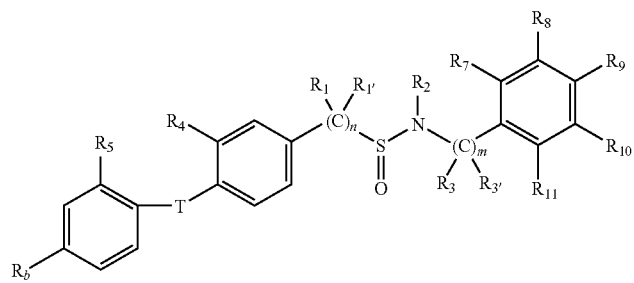
Formula CXV:
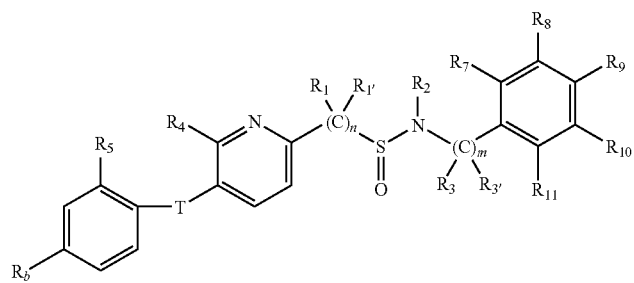

TABLE A-continued
Formula CXVI:
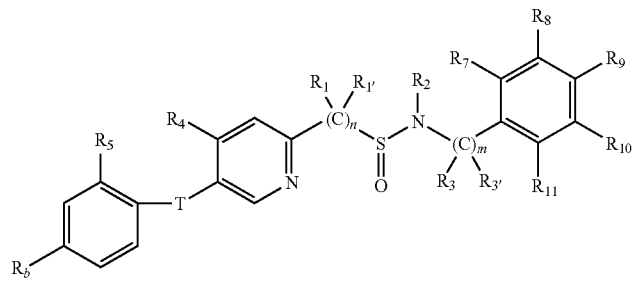
Formula CXVII:
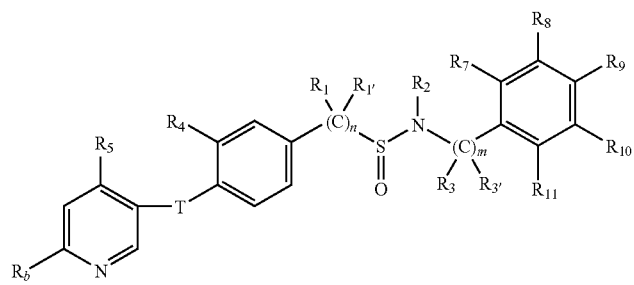
Formula CXVIII:
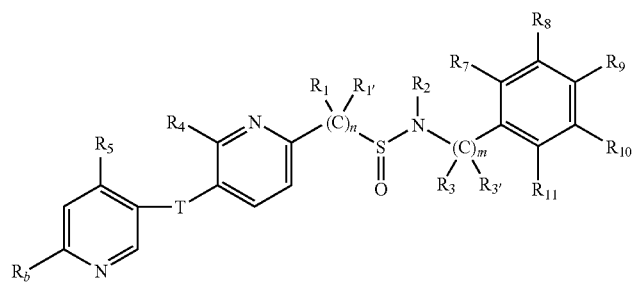
Formula CXIX:
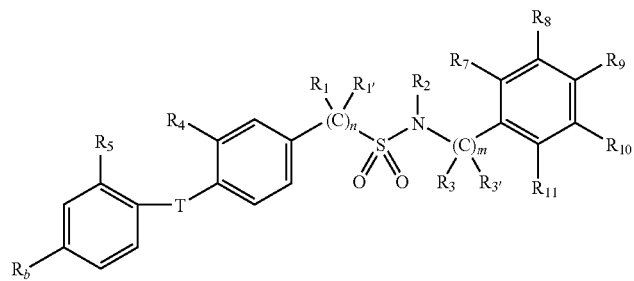

TABLE A-continued
Formula CXX:
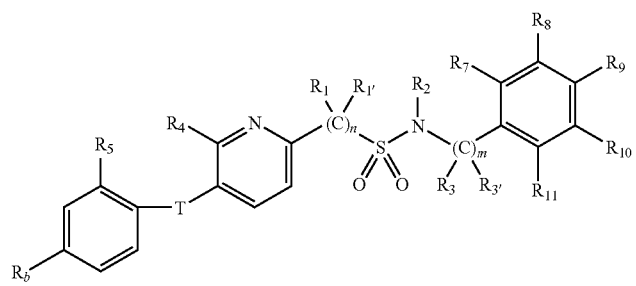
Formula CXXI:
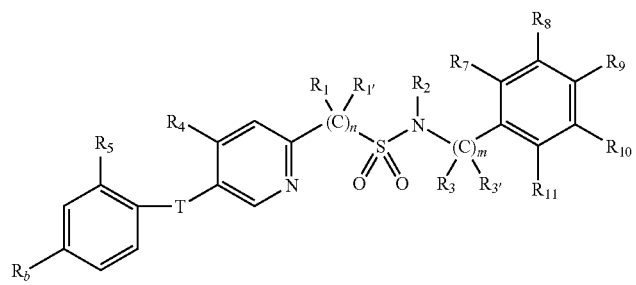
Formula CXXII:
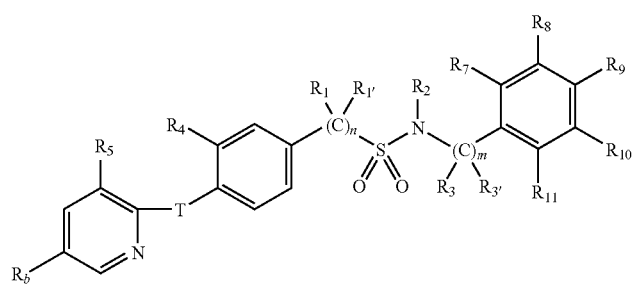
Formula CXXIII:
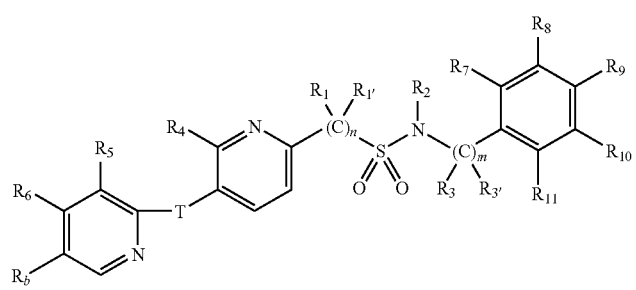
Formula CXXIV:
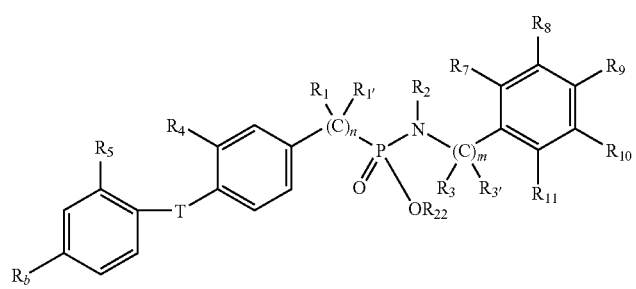

TABLE A-continued
Formula CXXV:
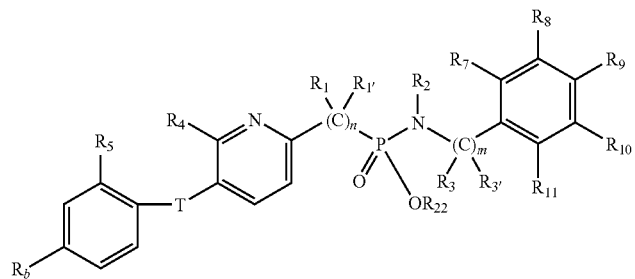
Formula CXXVI:
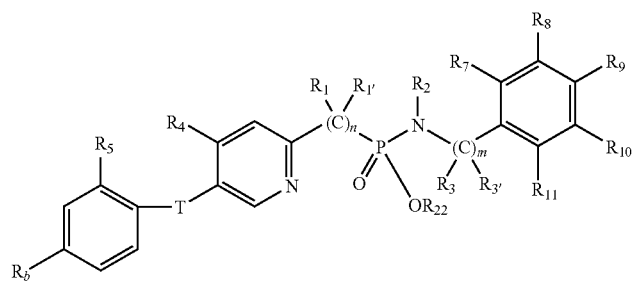
Formula CXXVII:
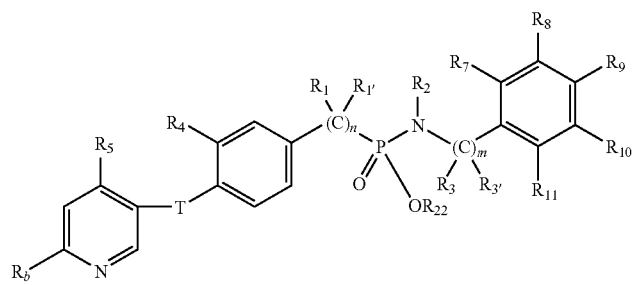
Formula CXXVIII:
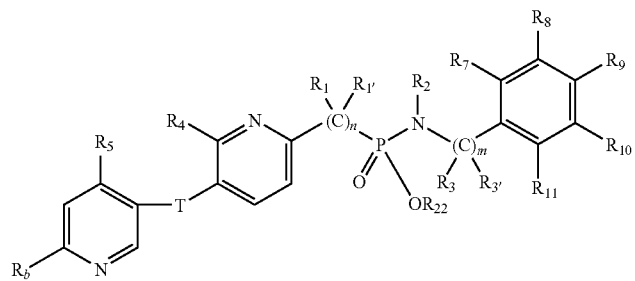

TABLE A-continued
Formula CXXIX:
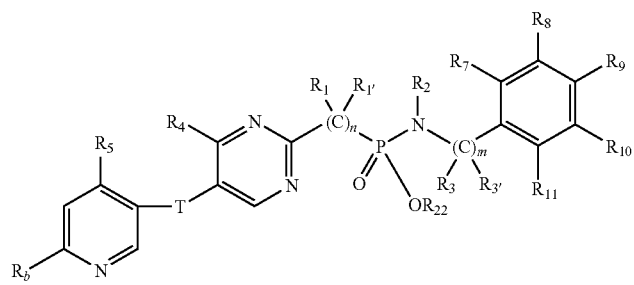
Formula CXXX:
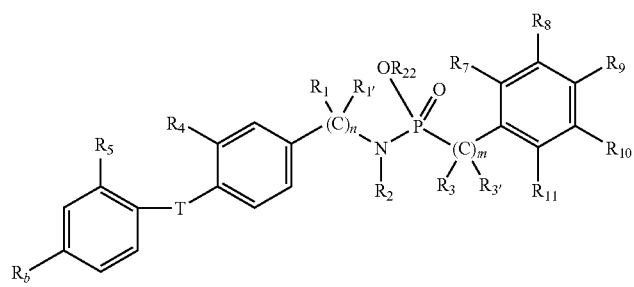
Formula CXXXI:
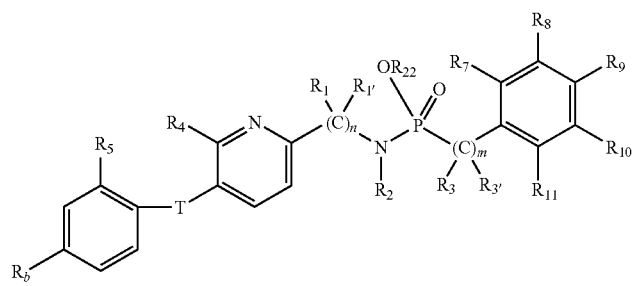
Formula CXXXII:
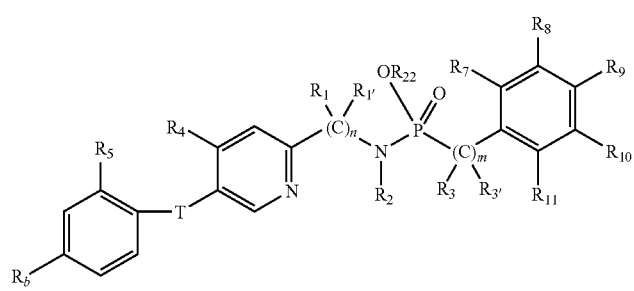
Formula CXXXIII:
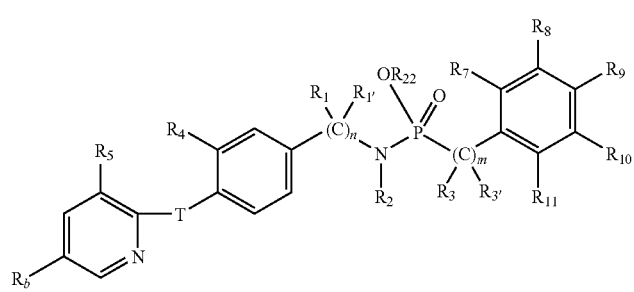

TABLE A-continued
Formula CXXXIV:
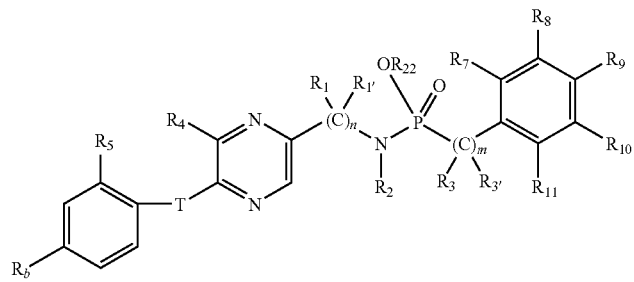
Formula CXXXV:
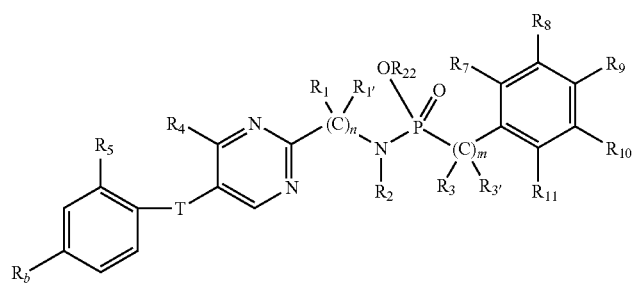
Formula CXXXVI:
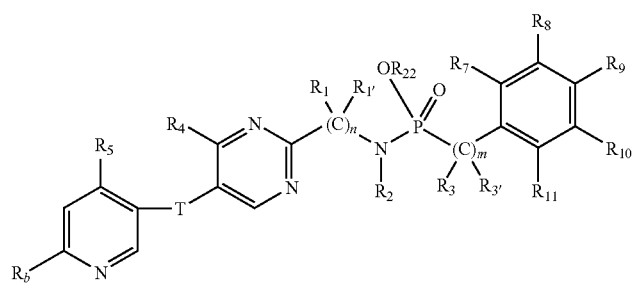
Formula CXXXVII:
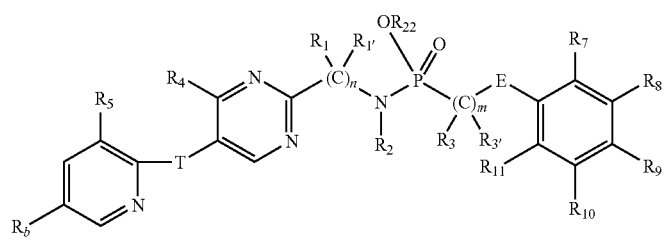
Formula CXXXVIII:
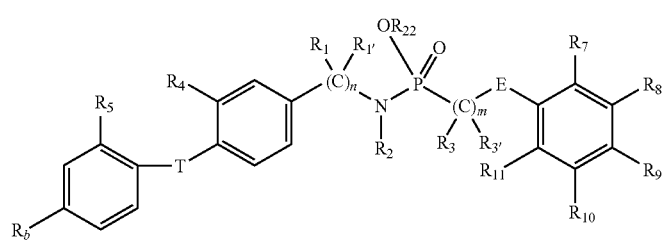

TABLE A-continued
Formula CXXXIX:
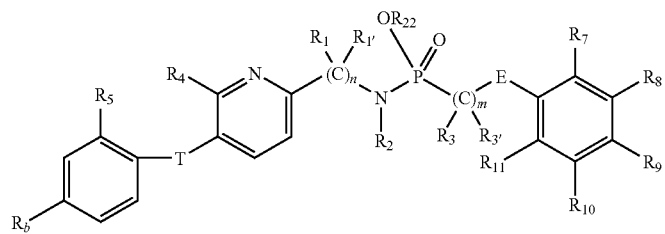
Formula CXL:
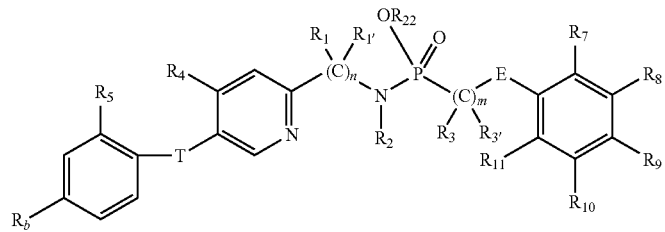
Formula CXLI:
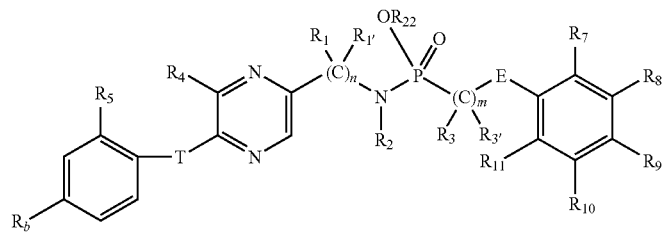
Formula CXLII:
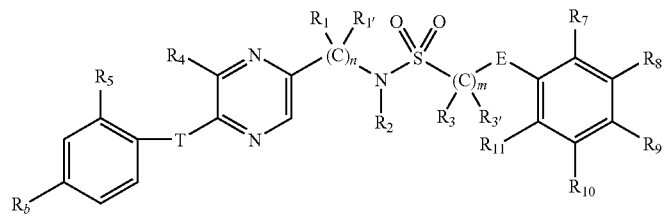
Formula CXLIII:
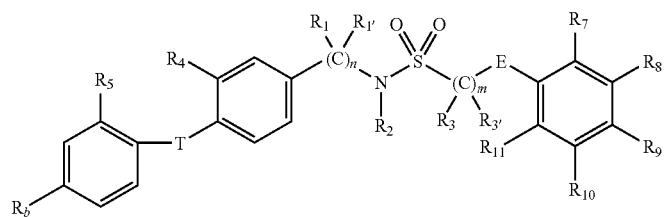
Formula CXLIV:
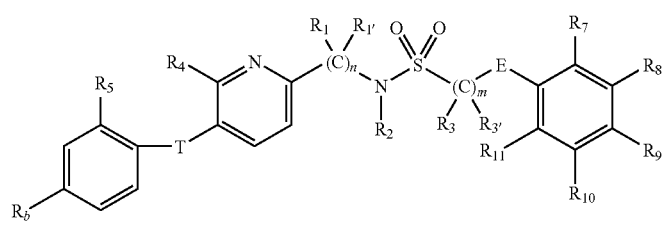

TABLE A-continued
Formula CXLV:
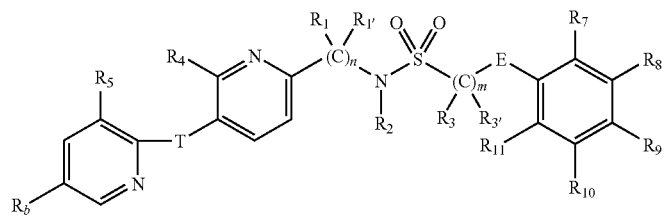
Formula CXLVI:
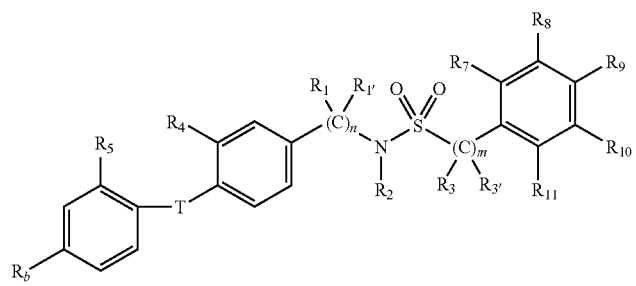
Formula CXLVII:
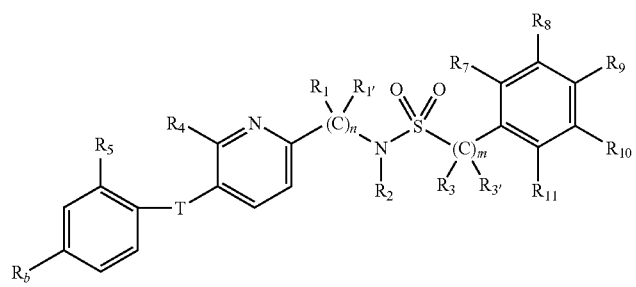
Formula CXLVIII:
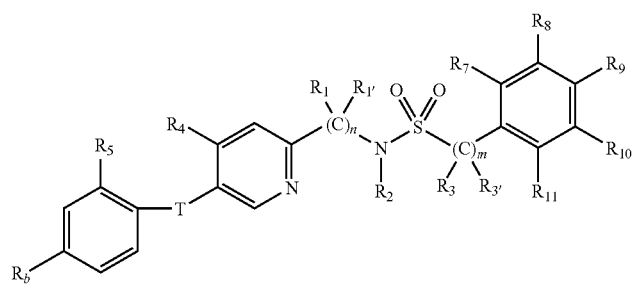
Formula CXLIX:
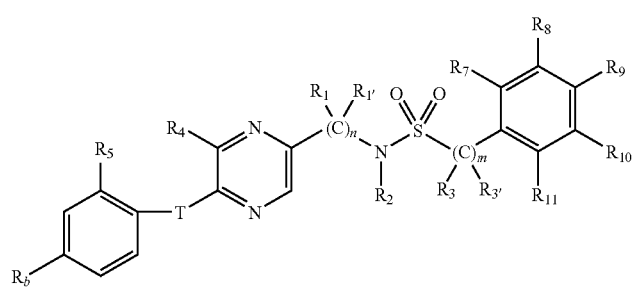

TABLE A-continued
Formula CL:
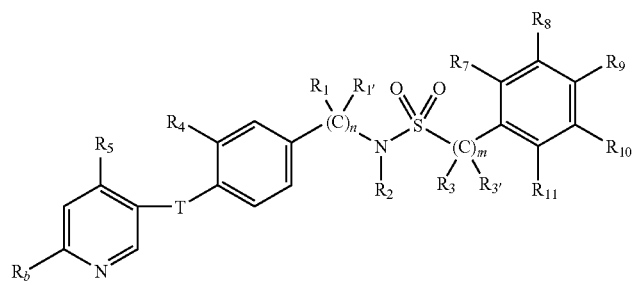
Formula CLI:
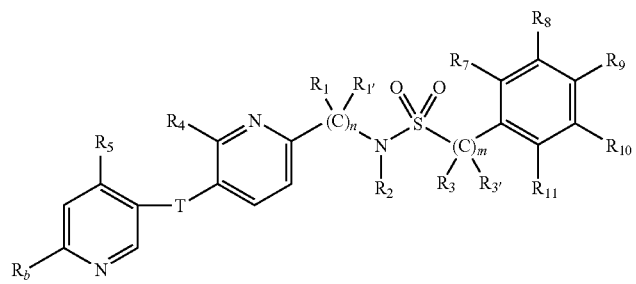
Formula CLII:
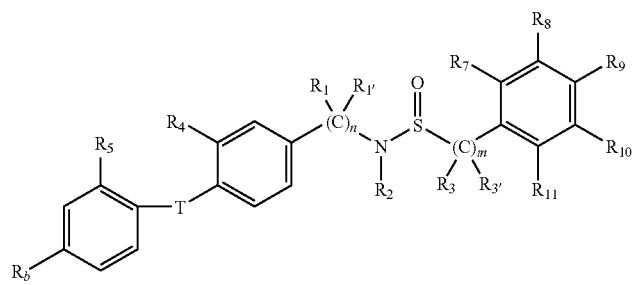
Formula CLIII:
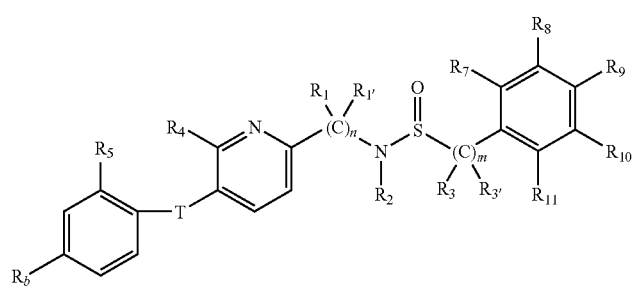
Formula CLIV:
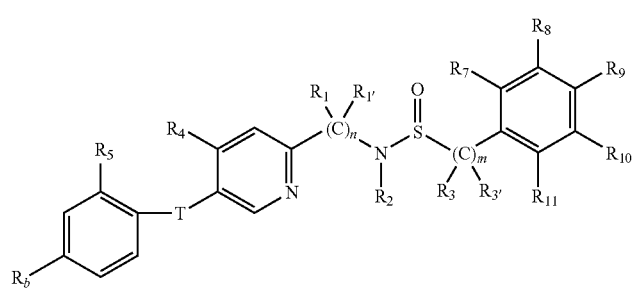

TABLE A-continued
Formula CLV:
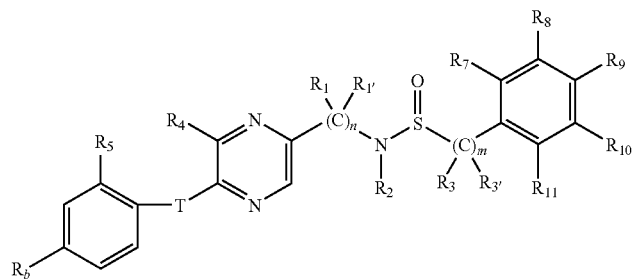
Formula CLVI:
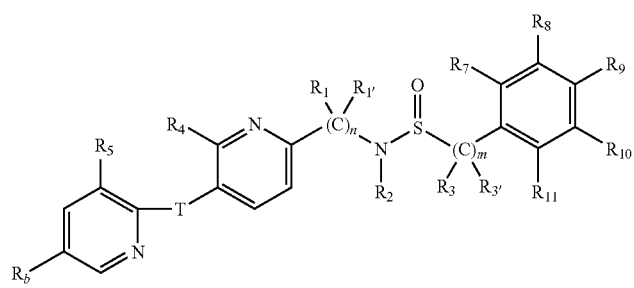
Formula CLVII:
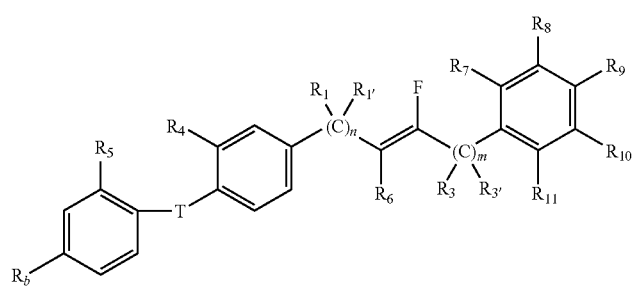
Formula CLVIII:
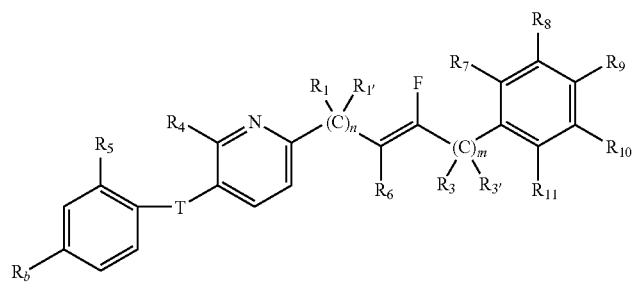

TABLE A-continued
Formula CLIX:
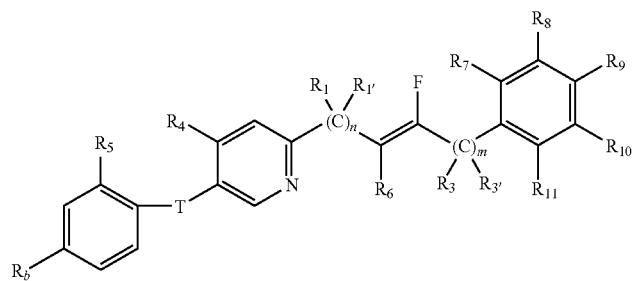
Formula CLX:
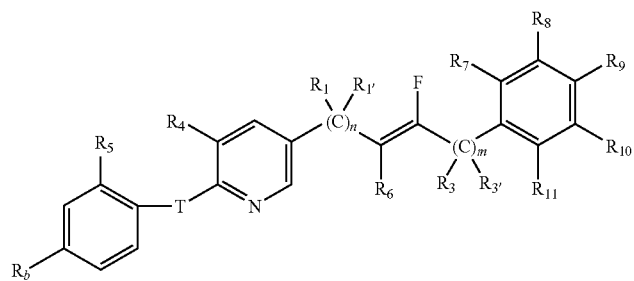
Formula CLXI:
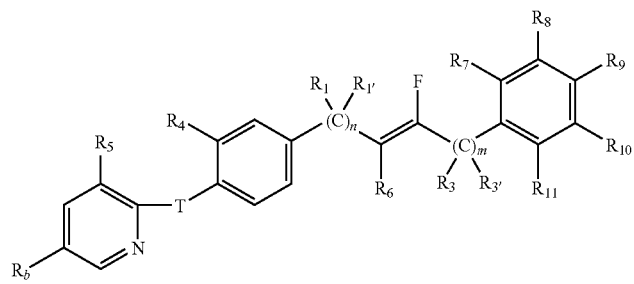
Formula CLXII:
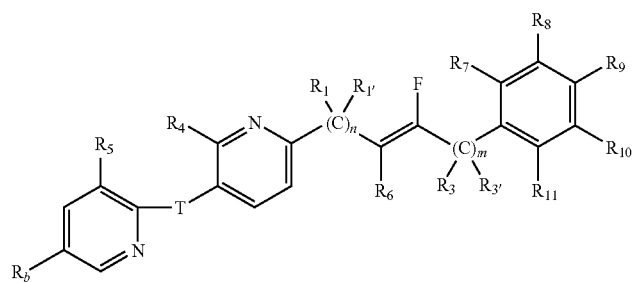
Formula CLXIII:
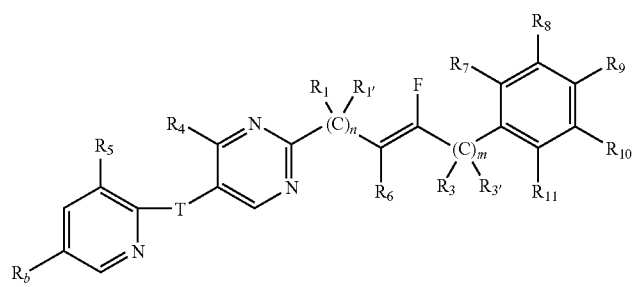

TABLE A-continued
Formula CLXIV:
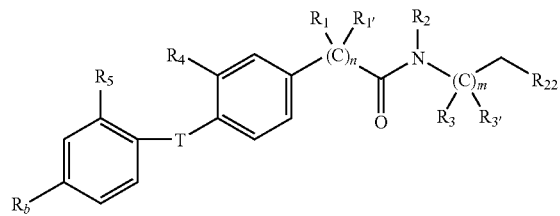
Formula CLXV:
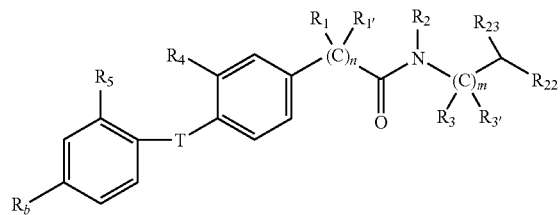
Formula CLXVI:
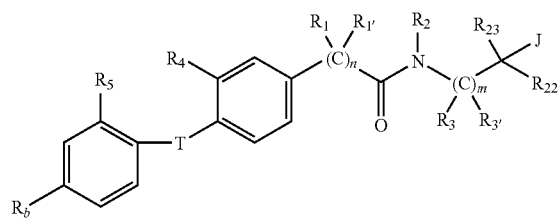
Formula CLXVII:
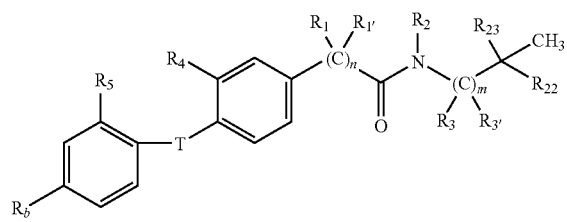
Formula CLXVIII:
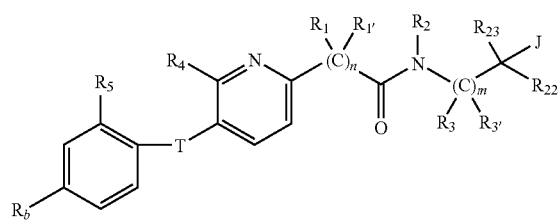
Formula CLXIX:
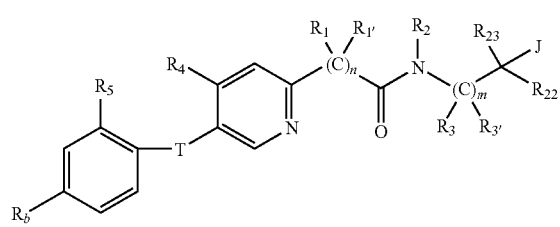

TABLE A-continued
Formula CLXX:
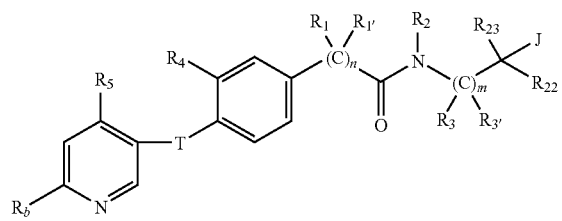
Formula CLXXI:
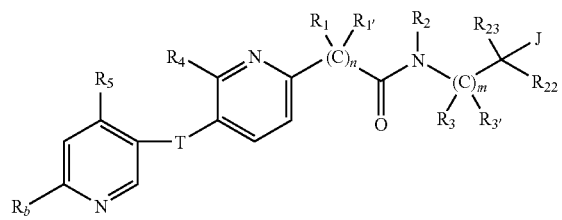
Formula CLXXII:
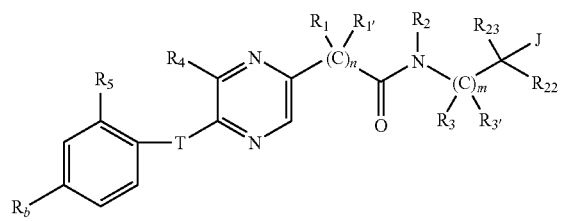
Formula CLXXIII:
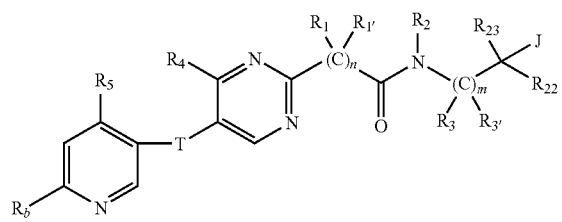
Formula CLXXIV:
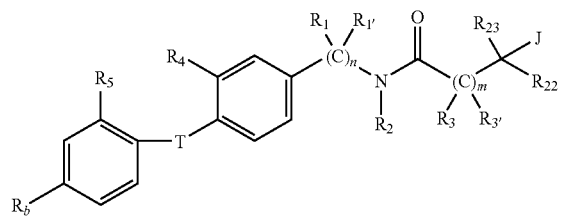
Formula CLXXV:
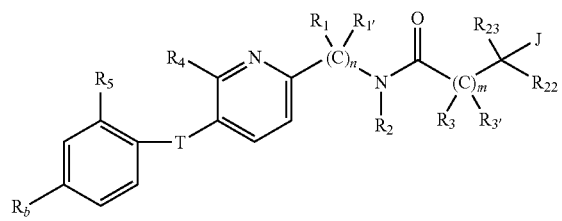

TABLE A-continued
Formula CLXXVI:
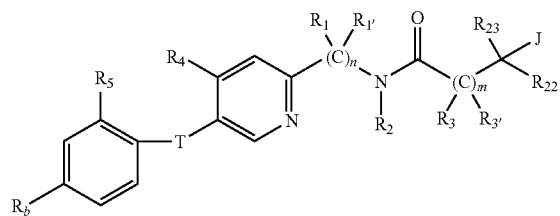
Formula CLXXVII:
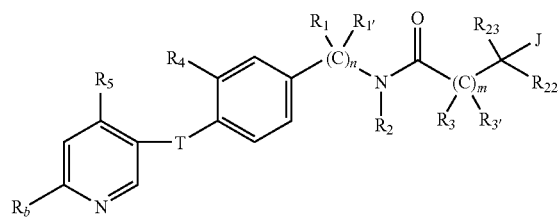
Formula CLXXVIII:
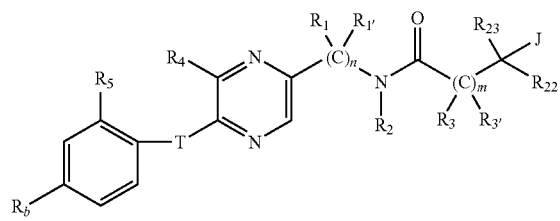
Formula CLXXIX:
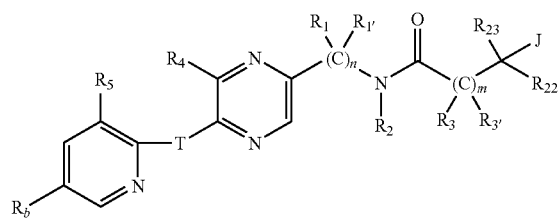
Formula CLXXX:
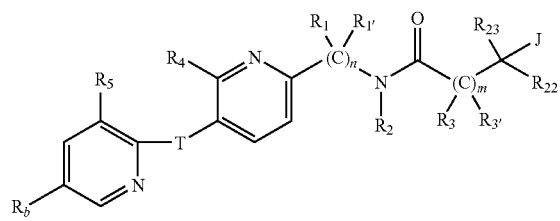
Formula CLXXI:
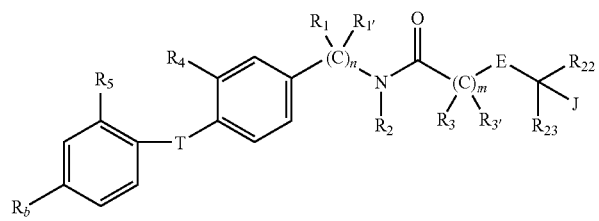

TABLE A-continued
Formula CLXXXII:
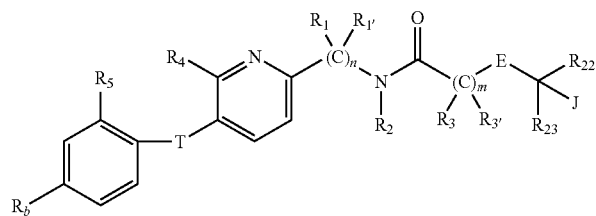
Formula CLXXIII:
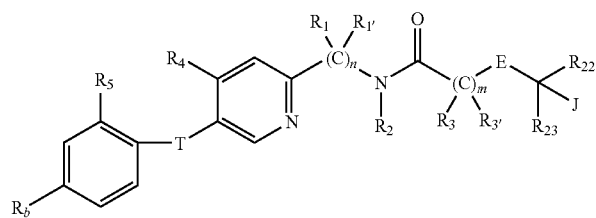
Formula CLXXXIV:
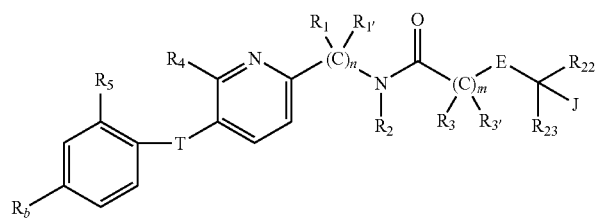
Formula CLXXV:
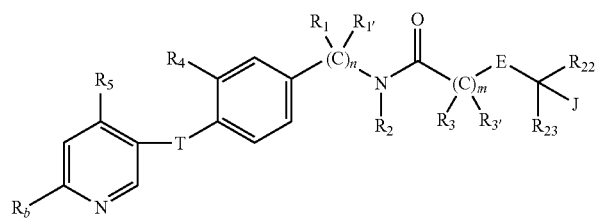
Formula CLXXXVI:
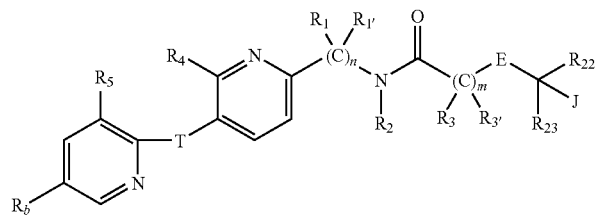
Formula CLXXVII:
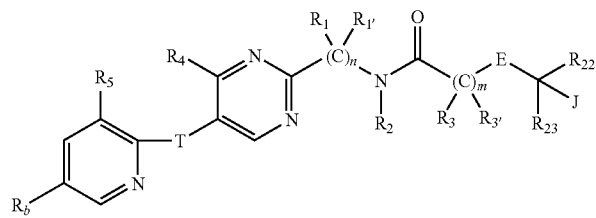

TABLE A-continued
Formula CLXXXVIII:
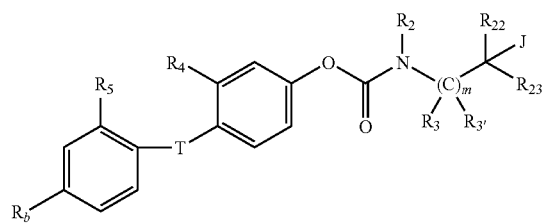
Formula CLXXXIX:
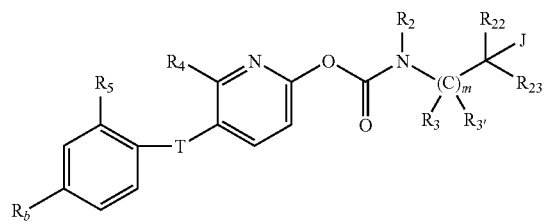
Formula CXC:
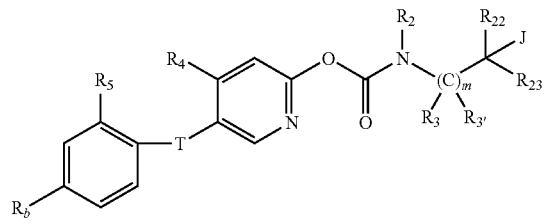
Formula CXCI:
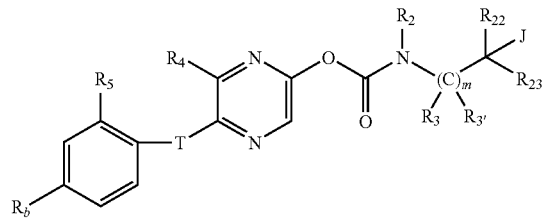
Formula CXCII:
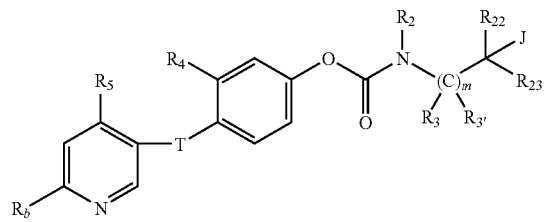
Formula CXCIII:
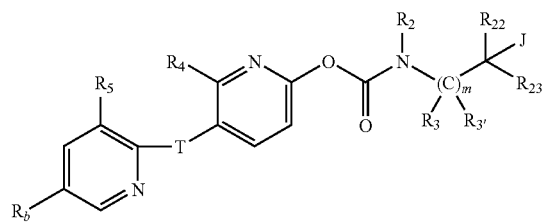

TABLE A-continued
Formula CXCIV:
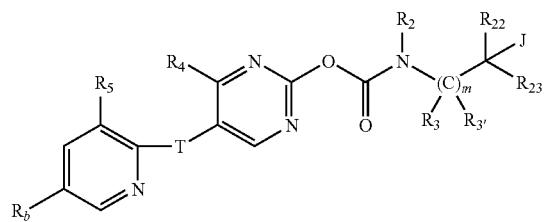
Formula CXCV:
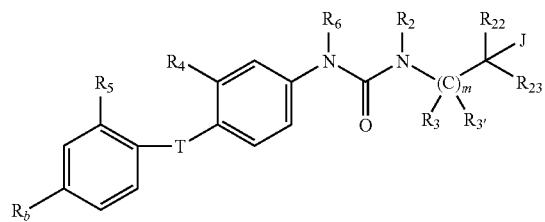
Formula CXCVI:
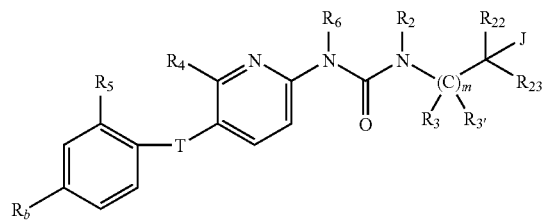
Formula CXCVII:
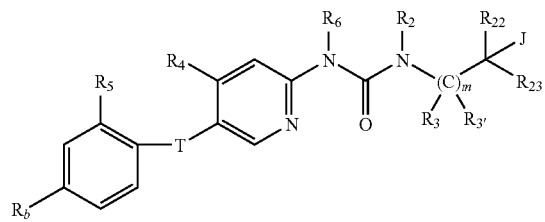
Formula CXCVIII:
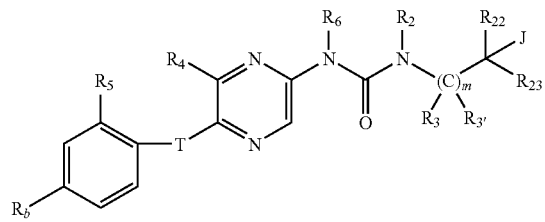
Formula CXCIX:
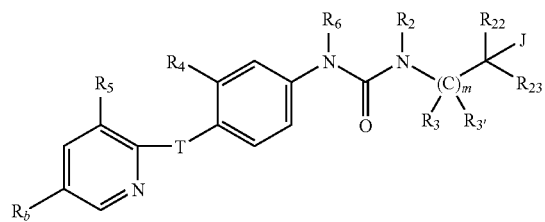

TABLE A-continued
Formula CC:
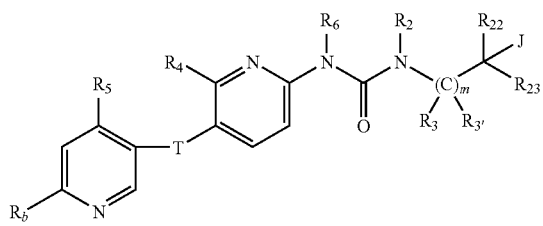
Formula CCI:
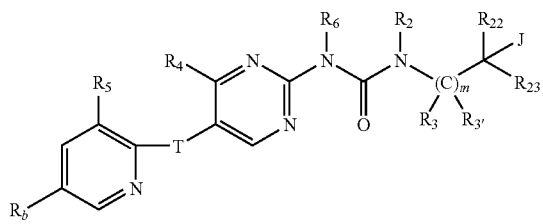
Formula CCII:
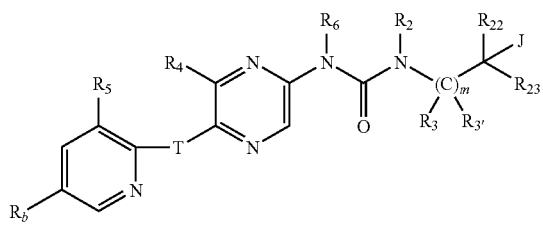
Formula CCIII:
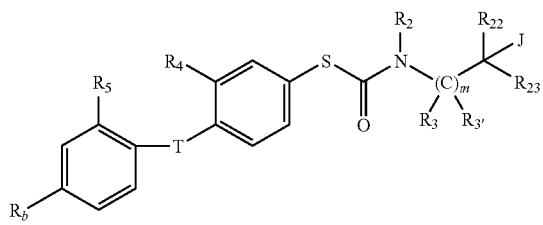
Formula CCIV:
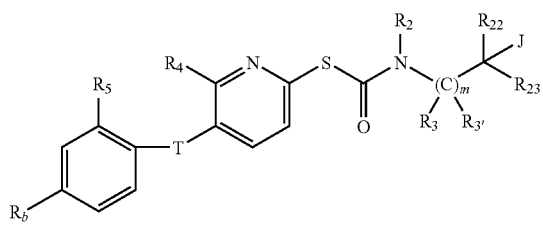
Formula CCV:
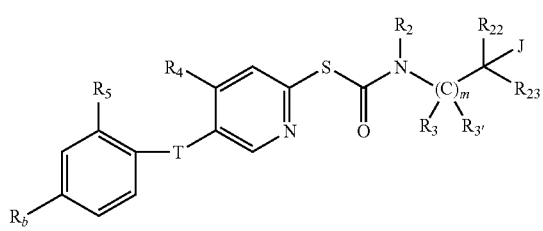

TABLE A-continued
Formula CCVI:
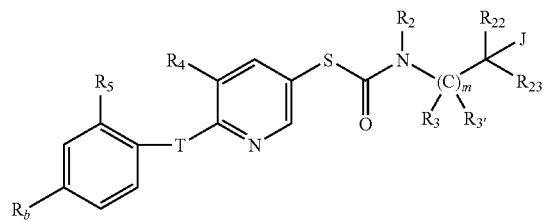
Formula CCVII:
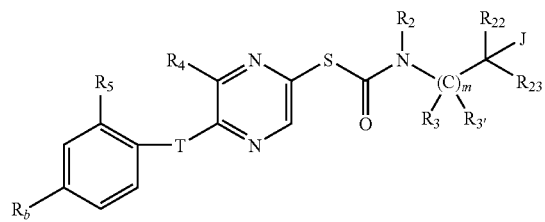
Formula CCVIII:
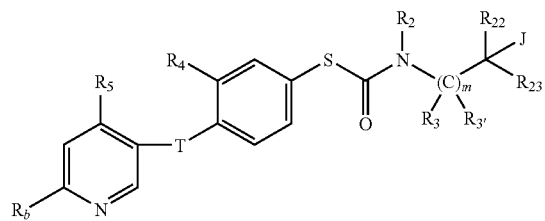
Formula CCIX:
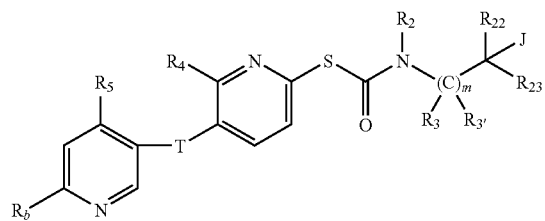
Formula CCX:
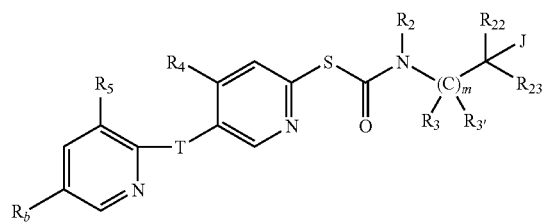
Formula CCXI:
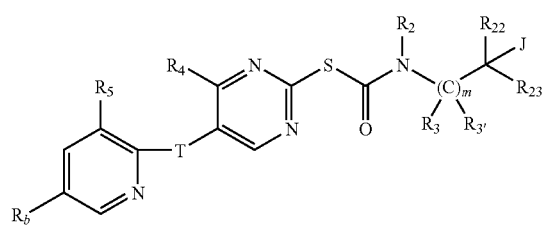

TABLE A-continued
Formula CCXII:
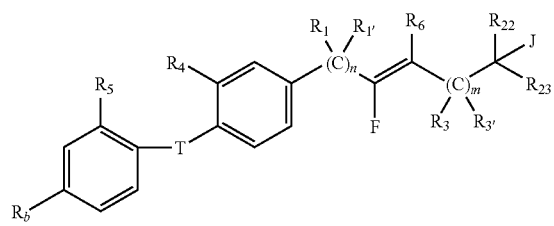
Formula CCXIII:
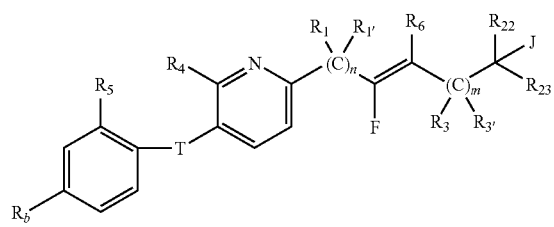
Formula CCXIV:
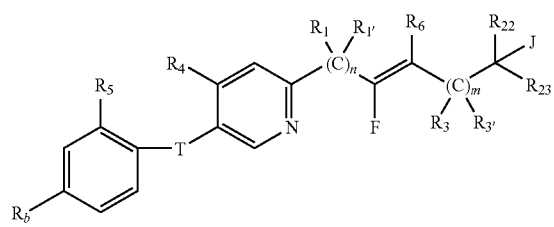
Formula CCXV:
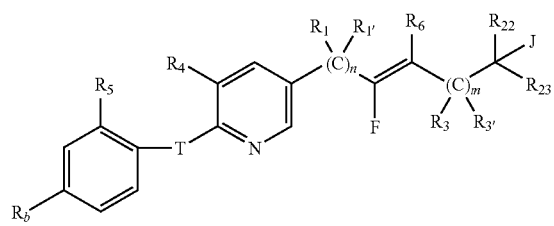
Formula CCXVI:
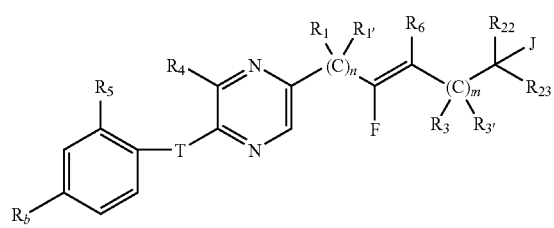
Formula CCXVII:
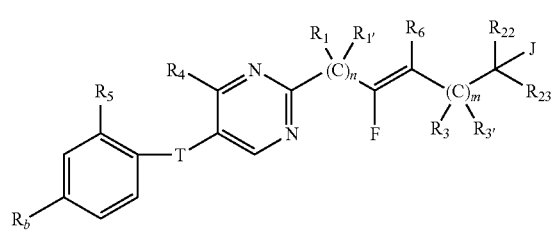

TABLE A-continued
Formula CCXVIII:
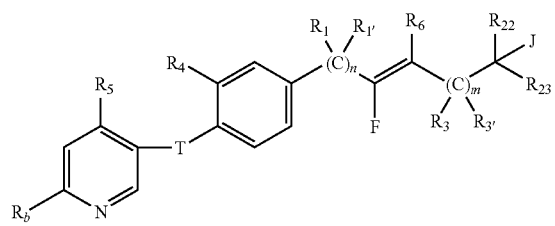
Formula CCXIX:
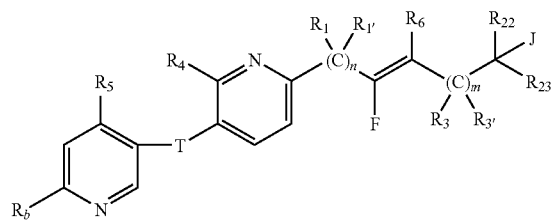
Formula CCXX:
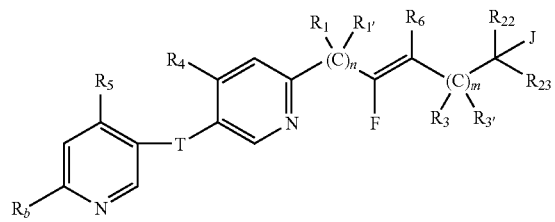
Formula CCXXI:
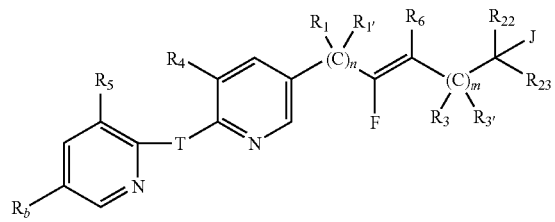
Formula CCXXII:
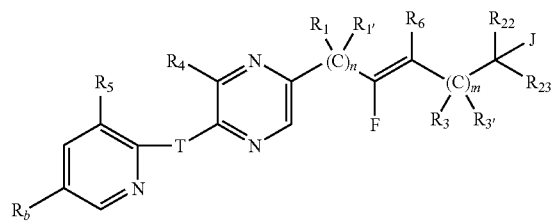
Formula CCXXIII:
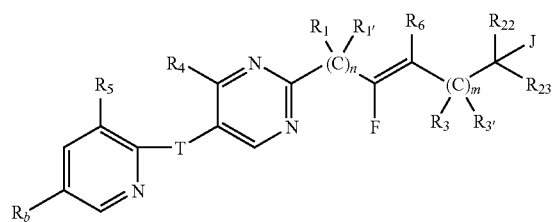

TABLE A-continued
Formula CCXXIV:
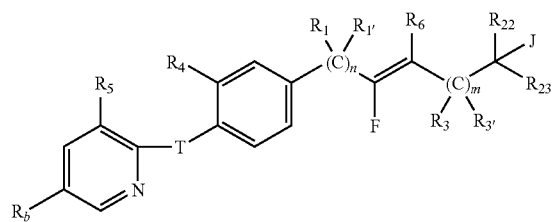
Formula CCXXV:
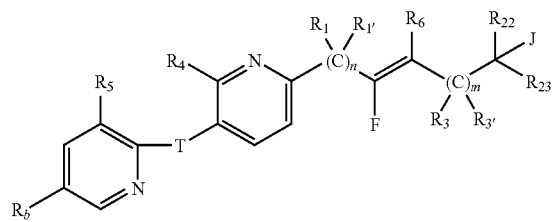
Formula CCXXVI:
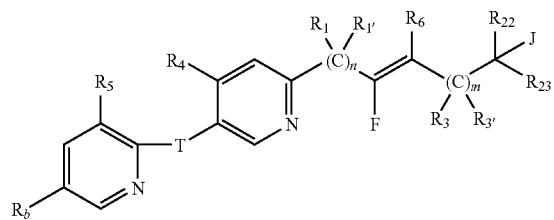
Formula CCXXVII:
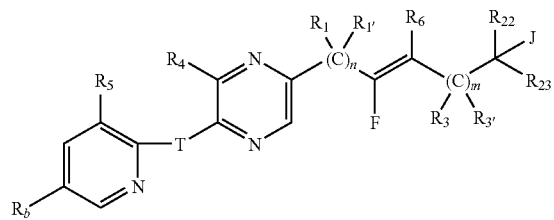
Formula CCXXVIII:
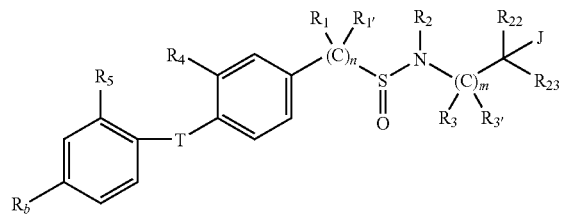
Formula CCXXIX:
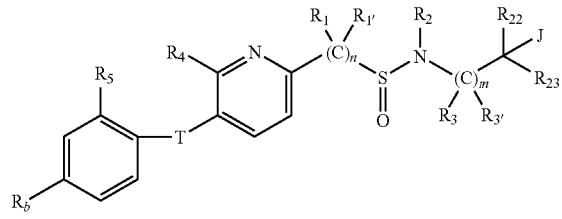

TABLE A-continued
Formula CCXXX:
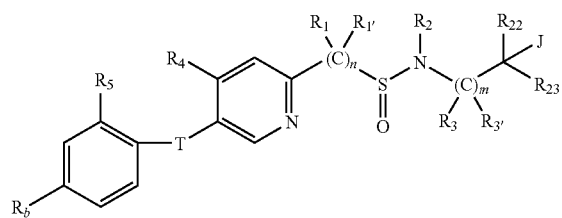
Formula CCXXXI:
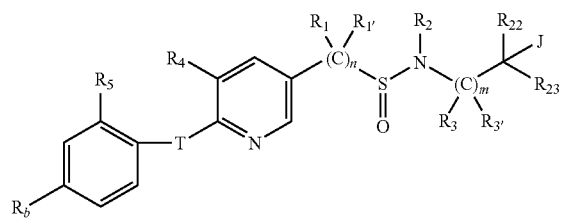
Formula CCXXXII:
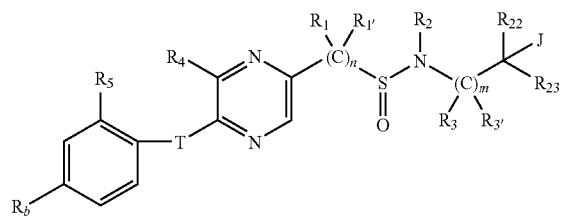
Formula CCXXXIII:
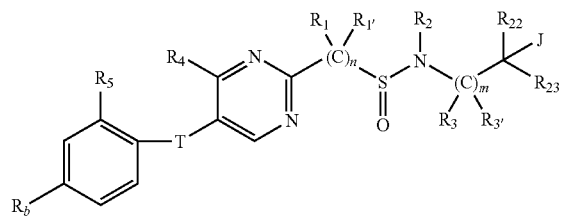
Formula CCXXXIV:
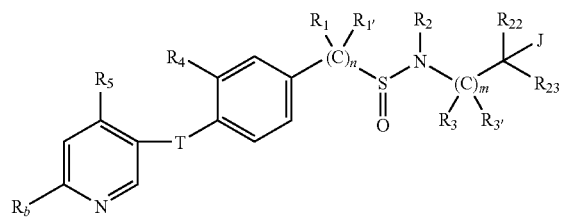
Formula CCXXXV:
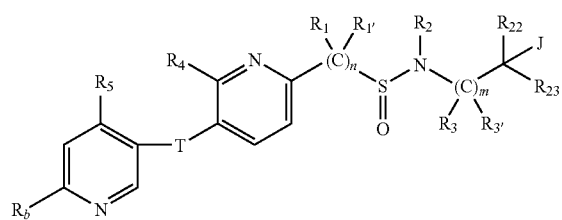

TABLE A-continued
Formula CCXXXVI:
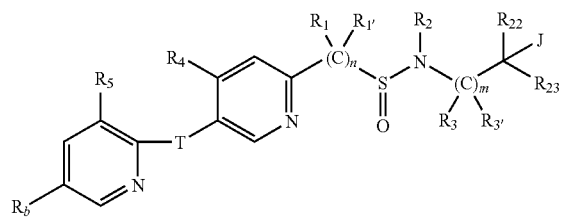
Formula CCXXXVII:
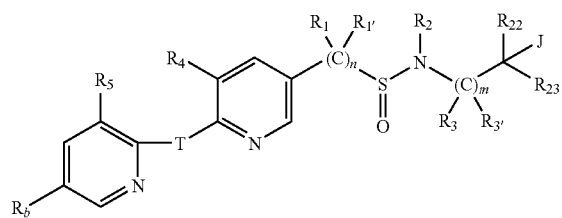
Formula CCXXXVIII:
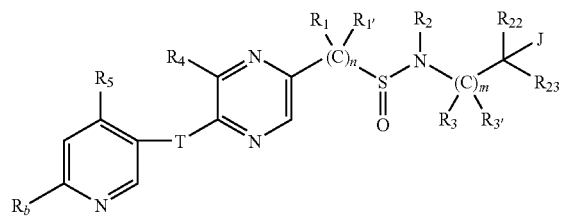
Formula CCXXXIX:
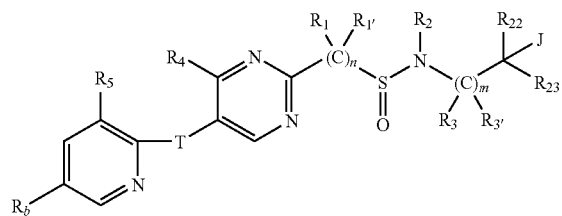
Formula CCXL:
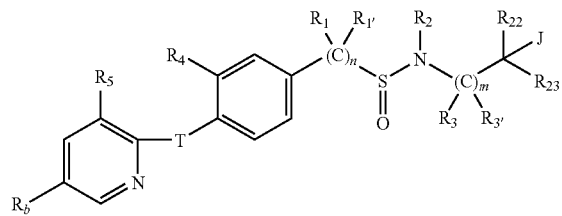
Formula CCXLI:
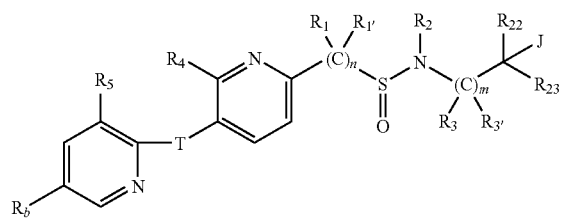

TABLE A-continued
Formula CCXLII:
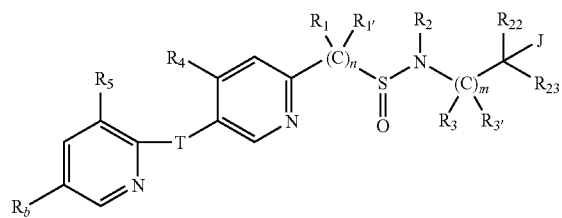
Formula CCXLIII:
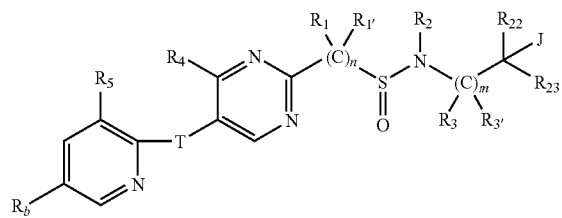
Formula CCXLIV:
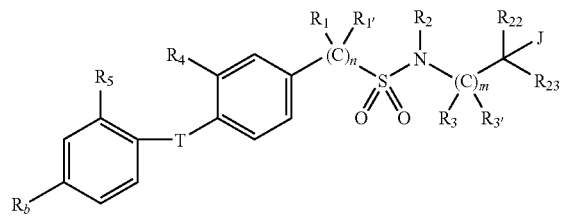
Formula CCXLV:
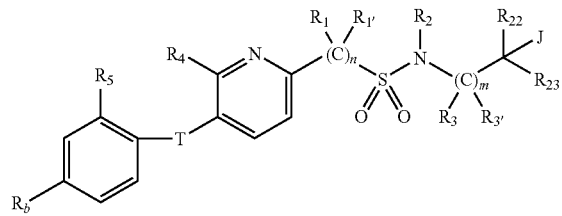
Formula CCXLVI:
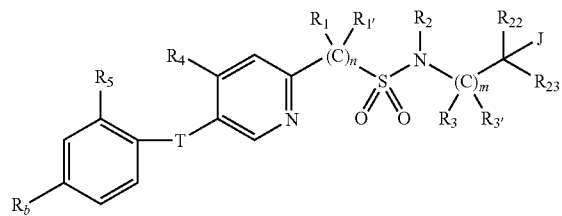
Formula CCXLVII:
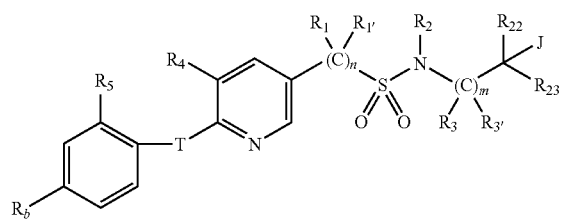

TABLE A-continued
Formula CCXLVIII:
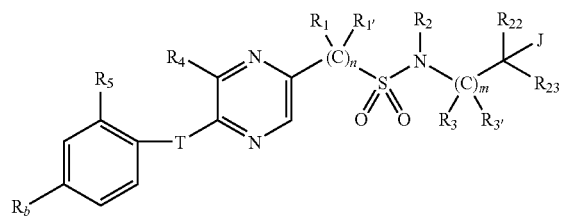
Formula CCXLIX:
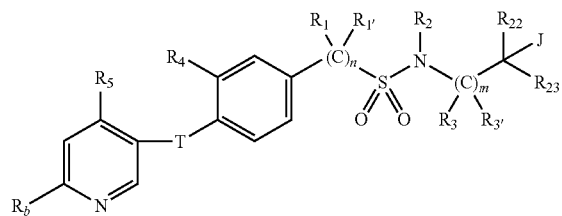
Formula CCL:
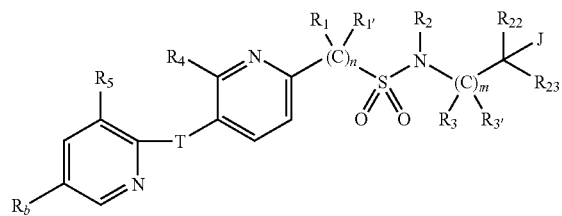
Formula CCLI:
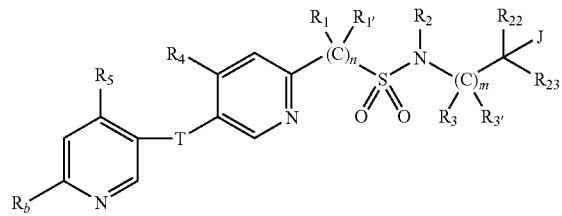
Formula CCLII:
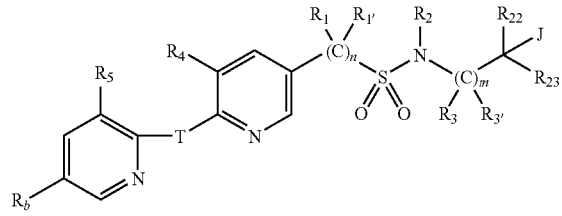
Formula CCLIII:
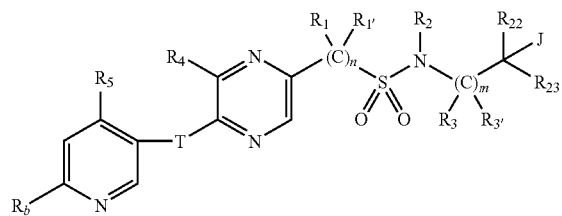

TABLE A-continued
Formula CCLIV:
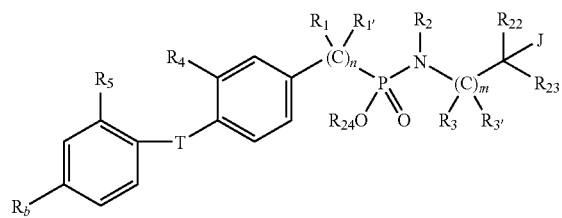
Formula CCLV:
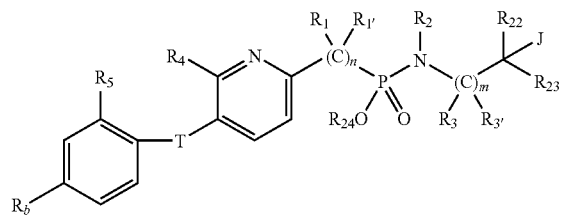
Formula CCLVI:
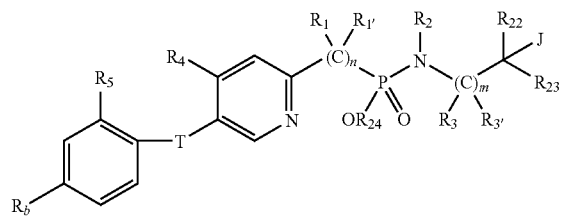
Formula CCLVII:
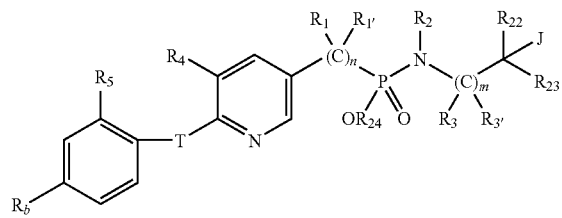
Formula CCLVIII:
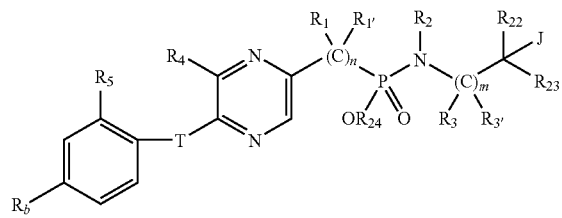
Formula CCLIX:
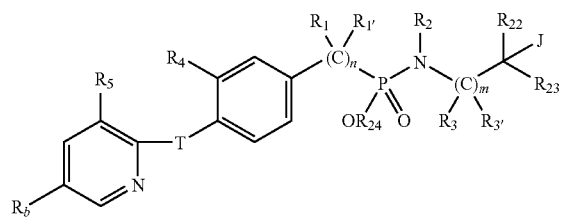

TABLE A-continued
Formula CCLX:
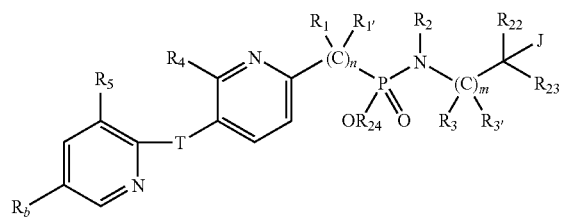
Formula CCLXI:
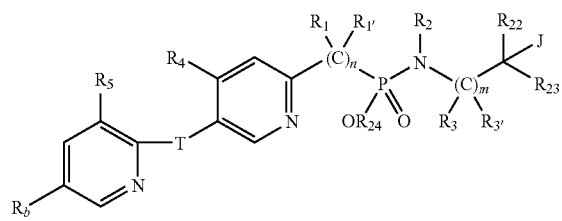
Formula CCLXII:
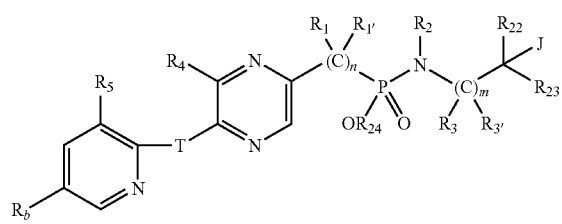
Formula CCLXIII:
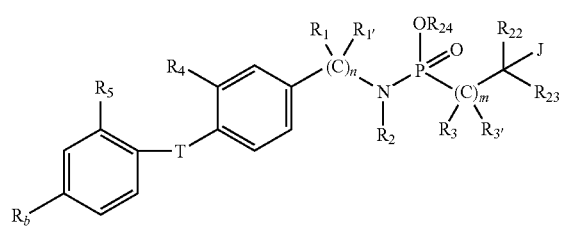
Formula CCLXIV:
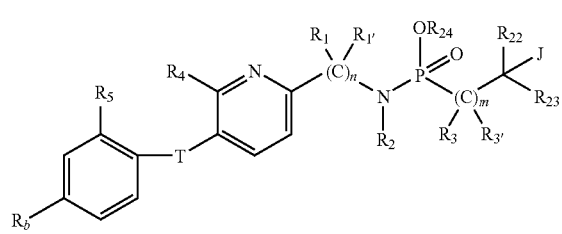
Formula CCLXV:
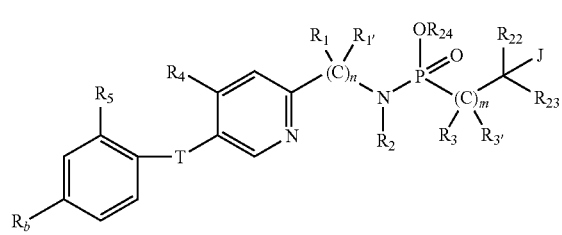

TABLE A-continued
Formula CCLXVI:
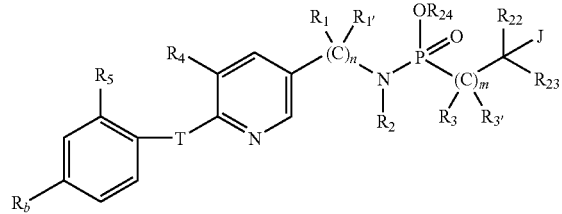
Formula CCLXVII:
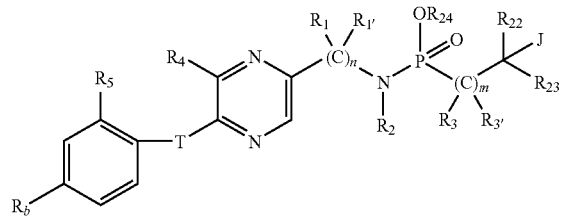
Formula CCLXVIII:
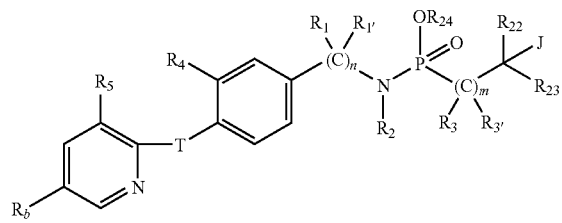
Formula CCLXIX:
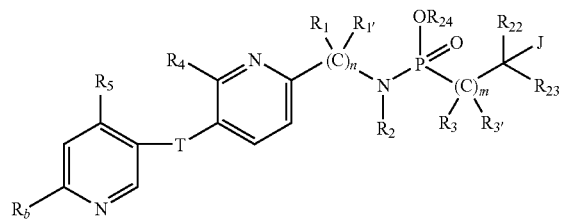
Formula CCLXX:
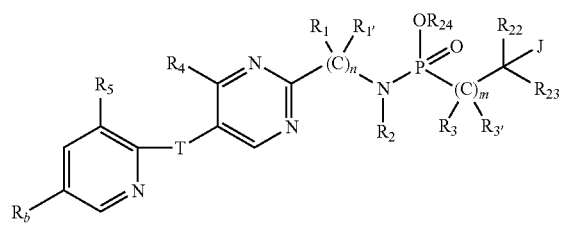
Formula CCLXXI:
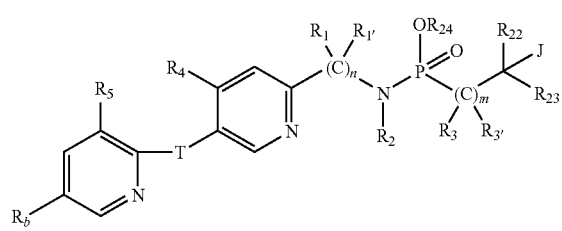

TABLE A-continued
Formula CCLXXII:
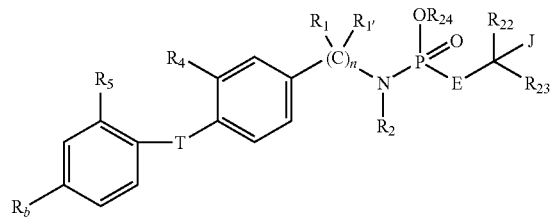
Formula CCLXXIII:
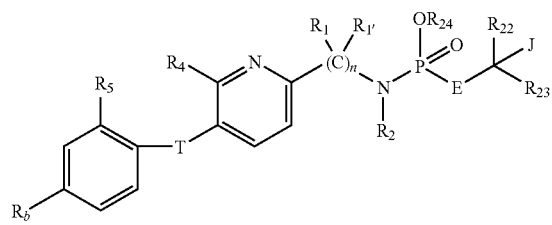
Formula CCLXXIV:
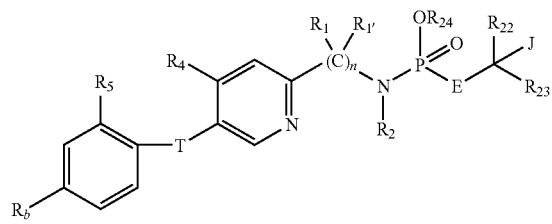
Formula CCLXXV:
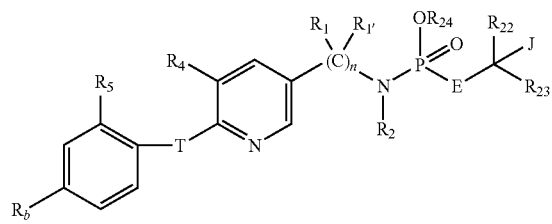
Formula CCLXXVI:
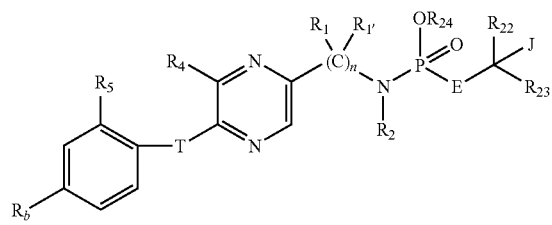
Formula CCLXXVII:
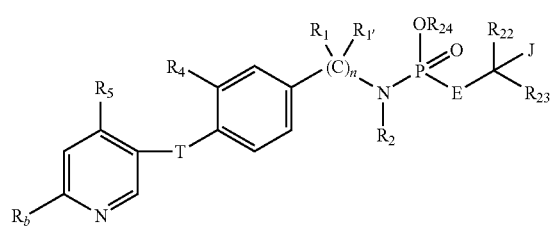

TABLE A-continued
Formula CCLXXVIII:
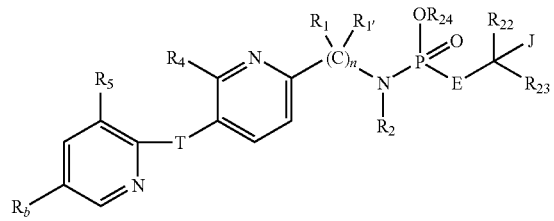
Formula CCLXXIX:
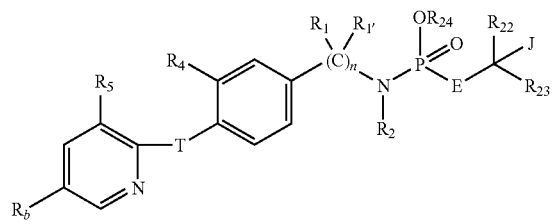
Formula CCLXXX:
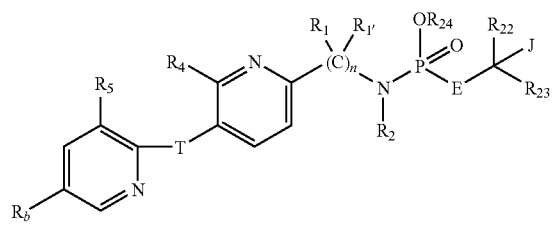
Formula CCLXXXI:
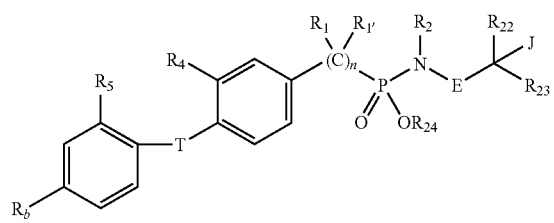
Formula CCLXXXII:
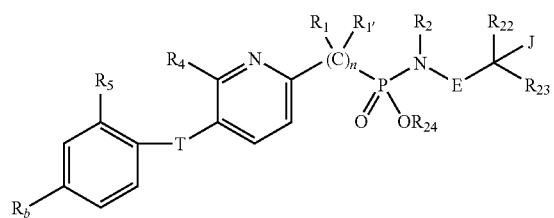
Formula CCLXXXIII:
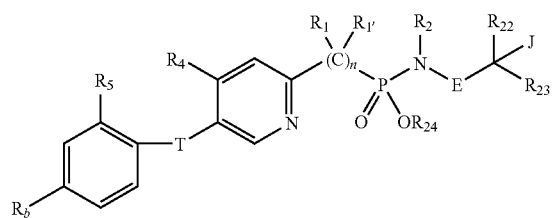

TABLE A-continued
Formula CCLXXXIV:
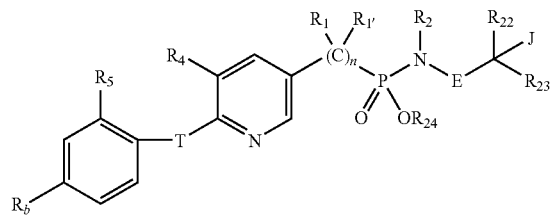
Formula CCLXXXV:
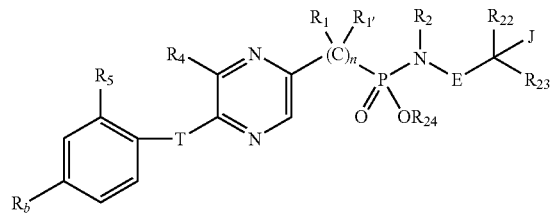
Formula CCLXXXVI:
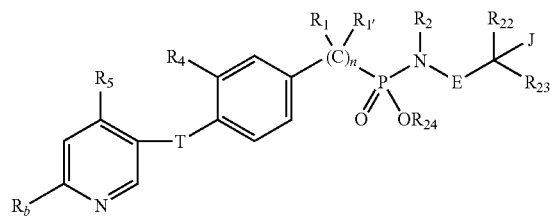
Formula CCLXXXVII:
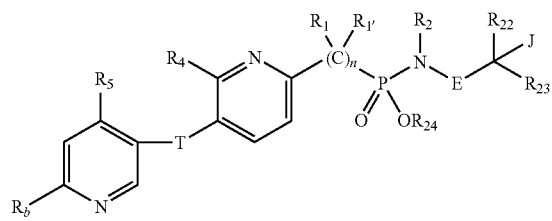
Formula CCLXXXVIII:
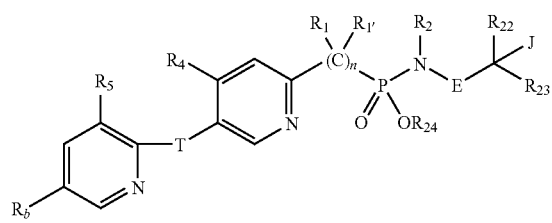
Formula CCLXXXIX:
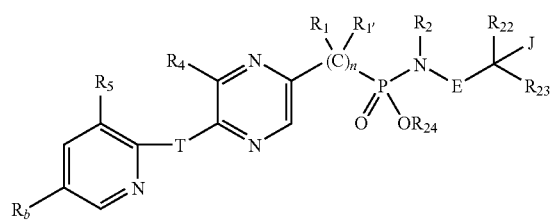

TABLE A-continued
Formula CCXC:
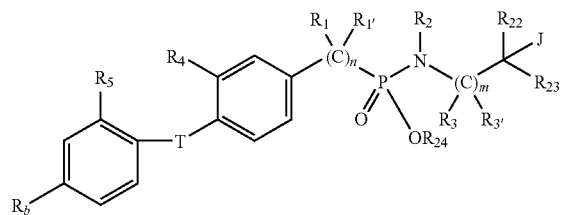
Formula CCXCI:
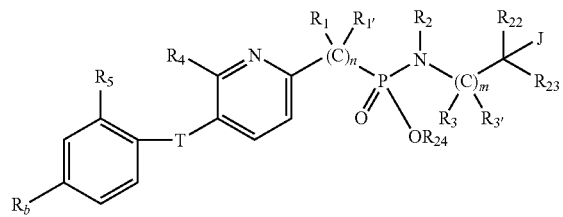
Formula CCXCII:
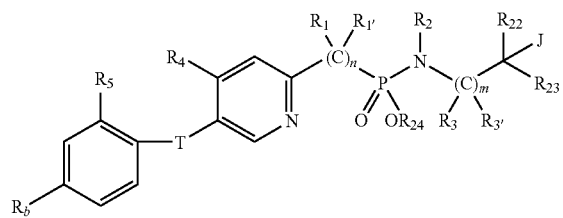
Formula CCXCIII:
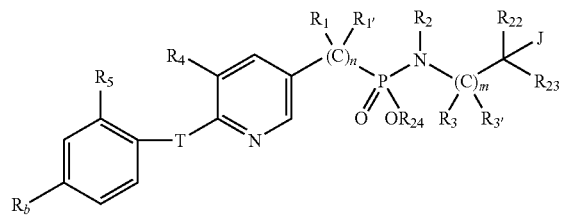
Formula CCXCIV:
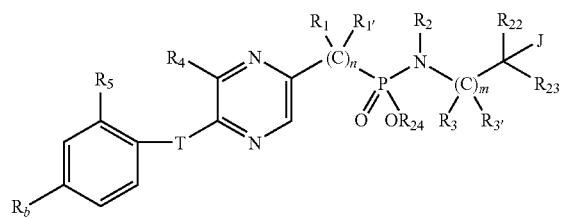
Formula CCXCV:
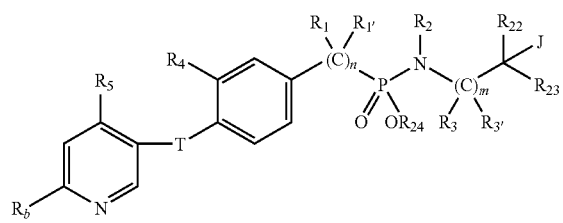

TABLE A-continued
Formula CCXCVI:
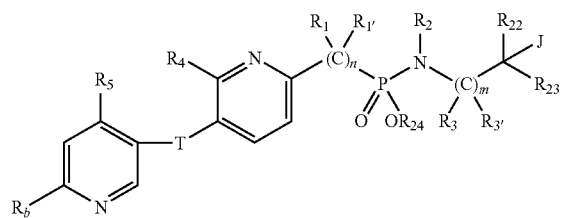
Formula CCXCVII:
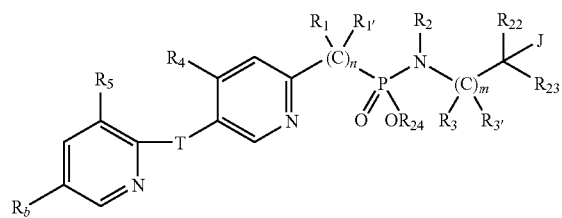
Formula CCXCVIII:
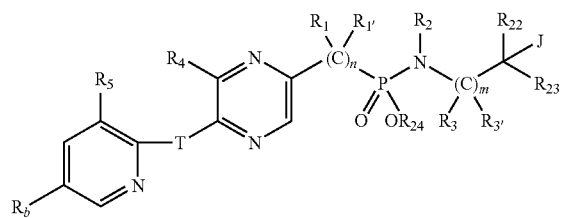
Formula CCXCIX:
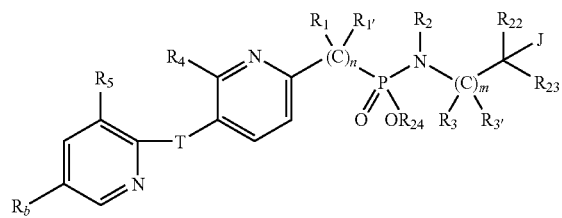
Formula CCC:
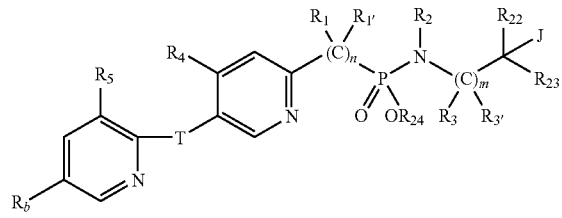
Formula CCCI:
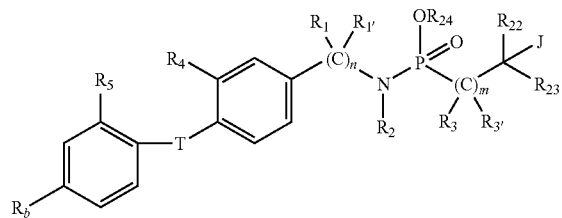

TABLE A-continued
Formula CCCII:
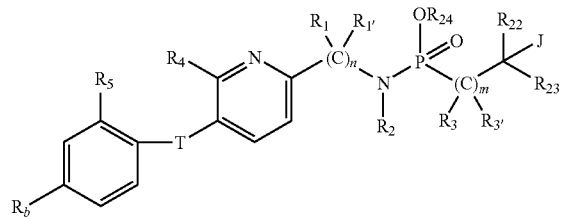
Formula CCCIII:
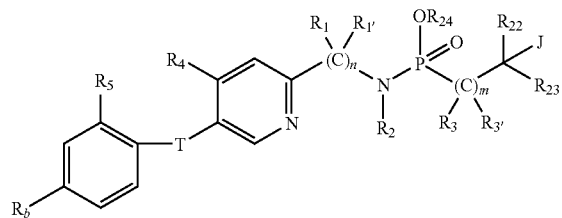
Formula CCCIV:
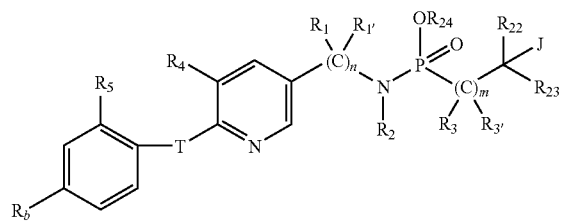
Formula CCCV:
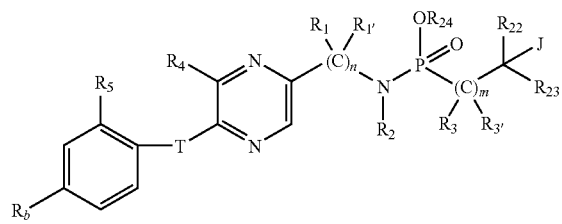
Formula CCCVI:
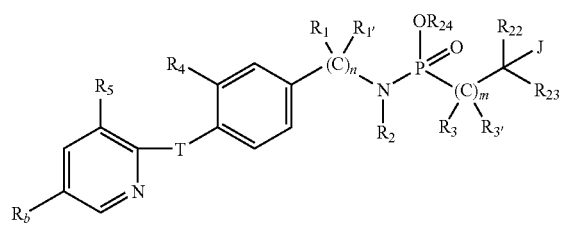
Formula CCCVII:
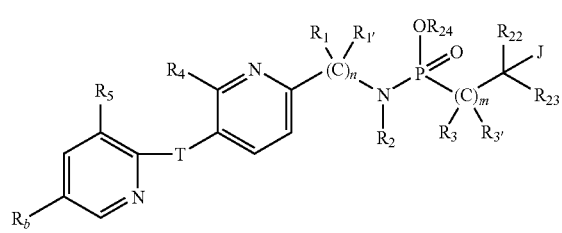

TABLE A-continued
Formula CCCVIII:
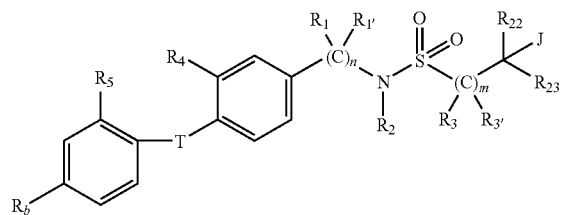
Formula CCCIX:
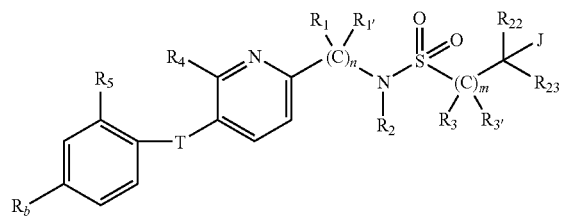
Formula CCCX:
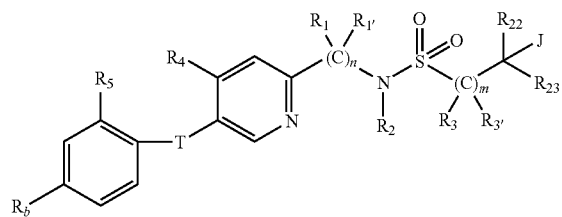
Formula CCCXI:
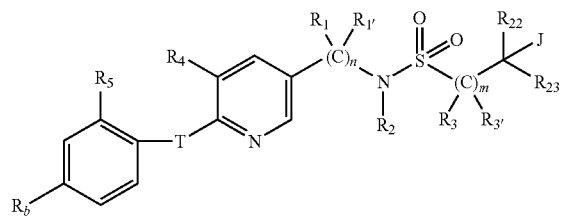
Formula CCCXII:
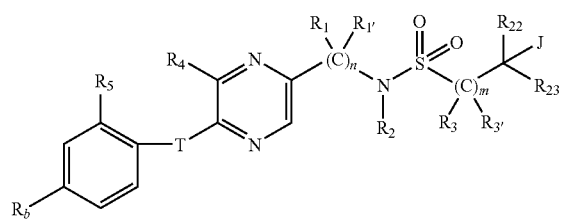
Formula CCCXIII:
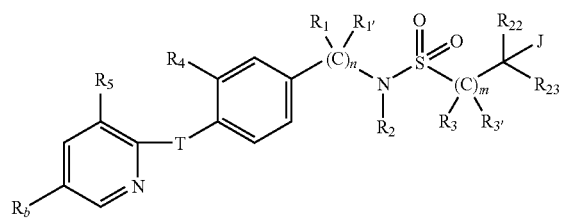

TABLE A-continued
Formula CCCXIV:
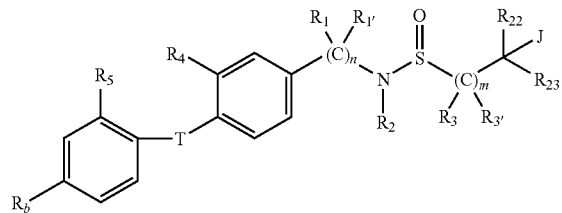
Formula CCCXV:
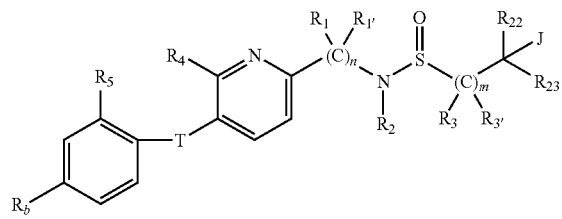
Formula CCCXVI:
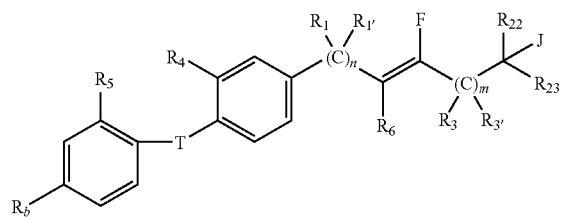
Formula CCCXVII:
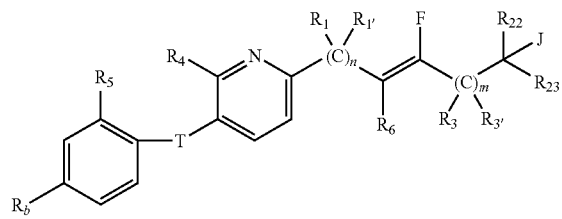
Formula CCCXVIII:
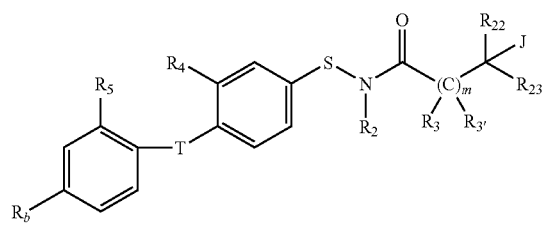
Formula CCCXIX:
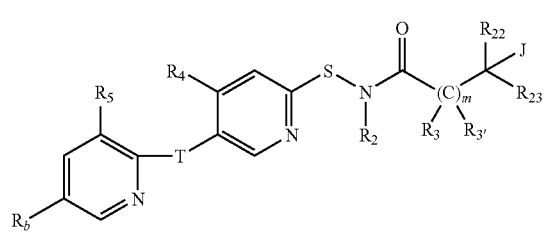

For example, in the compound of Formulae II-CCCXIX, $R_4$, or $R_5$, is hydrogen, F, Cl, Br, or I. For example F, or, in certain compounds, H.

In certain compounds of Formulae II-CCCXIX, $R_b$ is $C_1$, $C_2$, $C_3$, $C_4$, $C_5$, or $C_6$ alkoxy. For example, $R_b$ is methoxy or ethoxy.

In certain compounds of Formulae II-CCCXIX $R_b$ is hydrogen, Cl, Br, or I. In other compounds, in the compound of Formulae II-CCCXIX, $R_b$ is

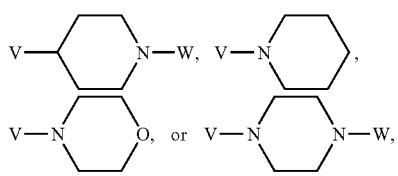

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

In certain compounds of Formulae II-CCCXIX $R_4$ is hydrogen, $C_1$, $C_2$, $C_3$, $C_4$, $C_5$, or $C_6$ alkoxy, F, Cl, Br, or I. In other compounds, in the compound of Formulae II-CCCXIX, $R_4$ is

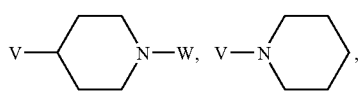

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

In certain compounds of Formulae II-CCCXIX $R_5$ is hydrogen, $C_1$, $C_2$, $C_3$, $C_4$, $C_5$, or $C_6$ alkoxy, F, Cl, Br, or I. In other compounds, of Formulae II-CCCXIX, $R_5$ is

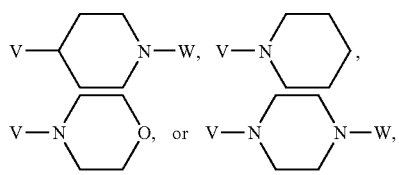

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

For example, in the compound of Formulae II-CCCXIX, W is hydrogen, or $C_1$, $C_2$, $C_3$, $C_4$, $C_5$, or $C_6$ alkyl.

In certain compounds of Formulae II-CCCXIX, T is a bond, $CR_{12}R_{13}$, C(O), O, S, S(O), $S(O)_2$, $NR_{14}$, $C(R_{15}R_{16})C(R_{17}R_{18})$, $CH_2O$, or $OCH_2$. In certain compounds of Formulae II-CCCXIX, T is a bond, O, $CH_2O$ or $OCH_2$.

Compounds of the invention include those in Table B.

TABLE B

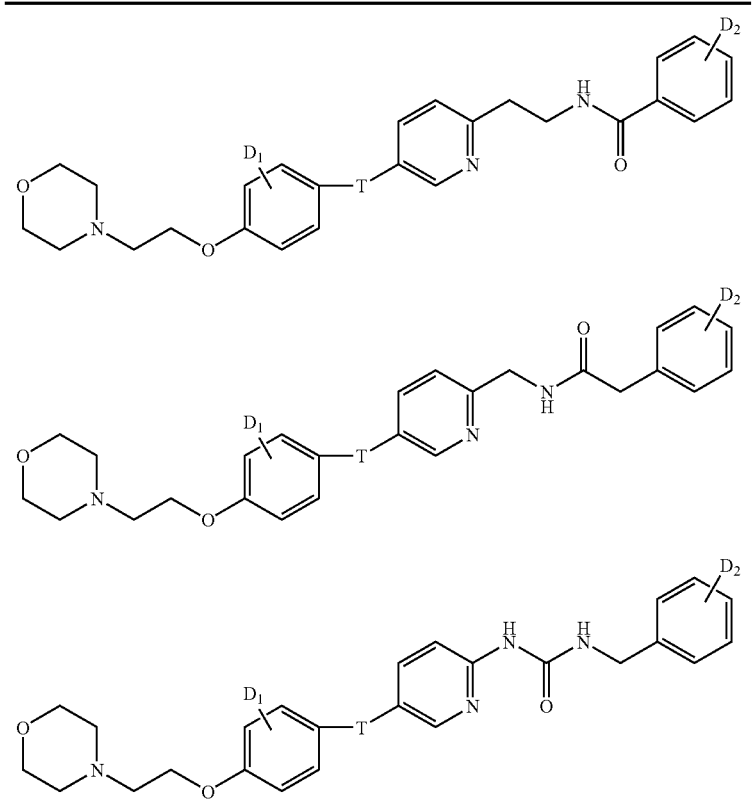

TABLE B-continued
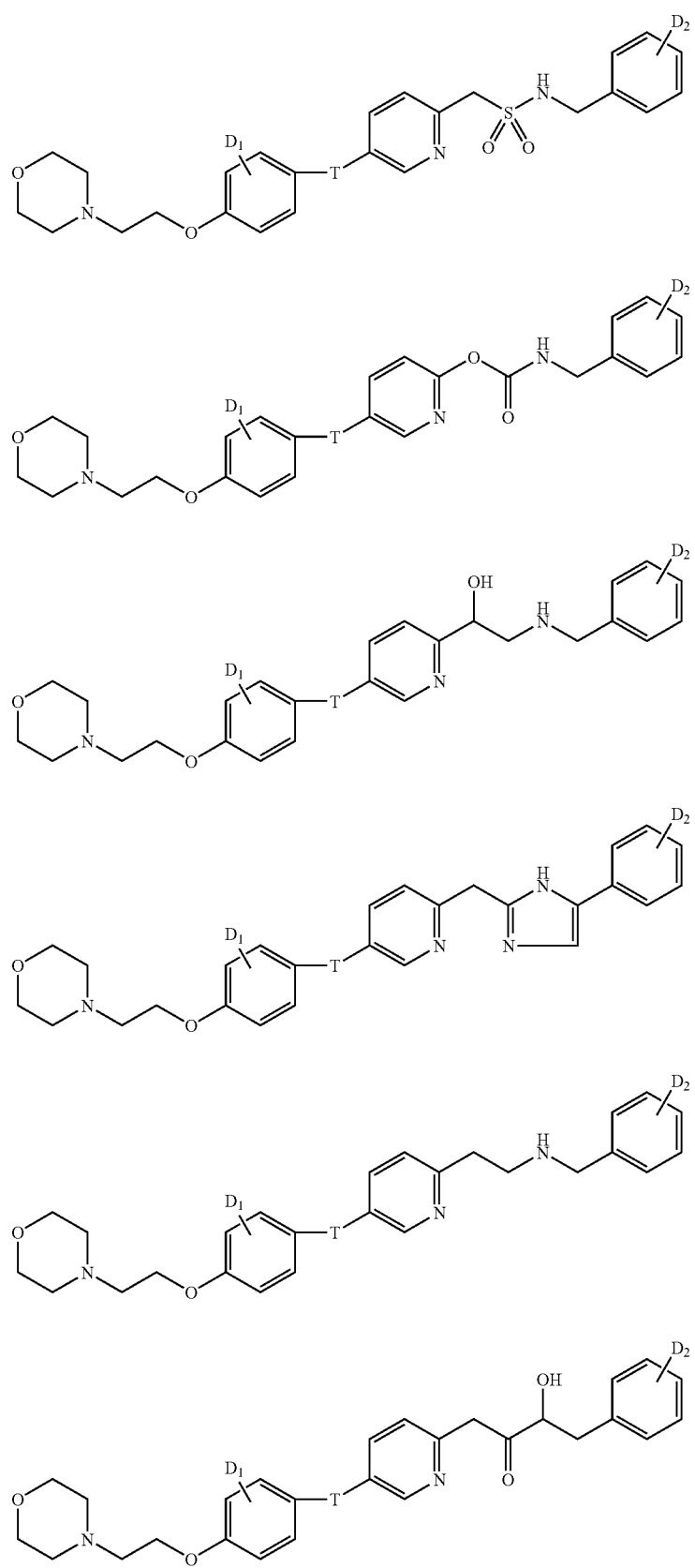

TABLE B-continued
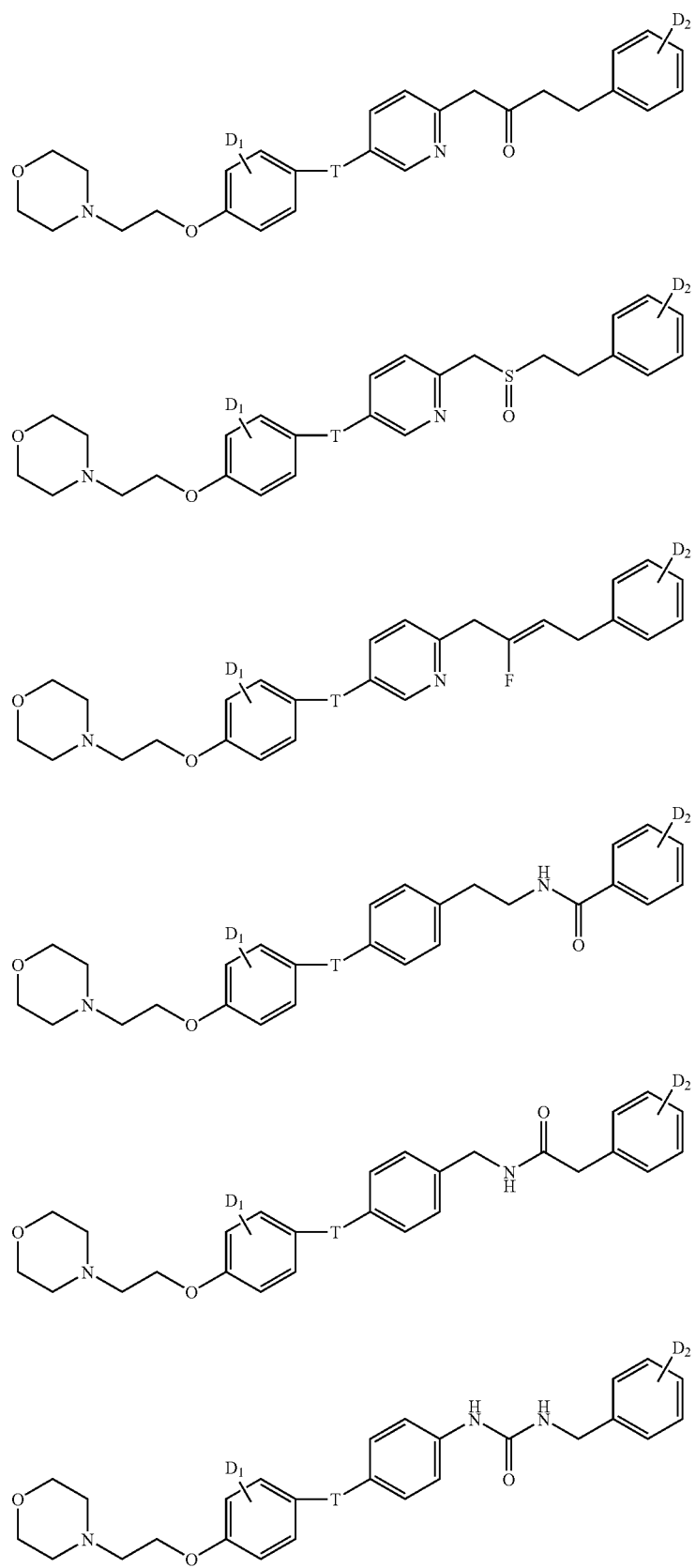

TABLE B-continued
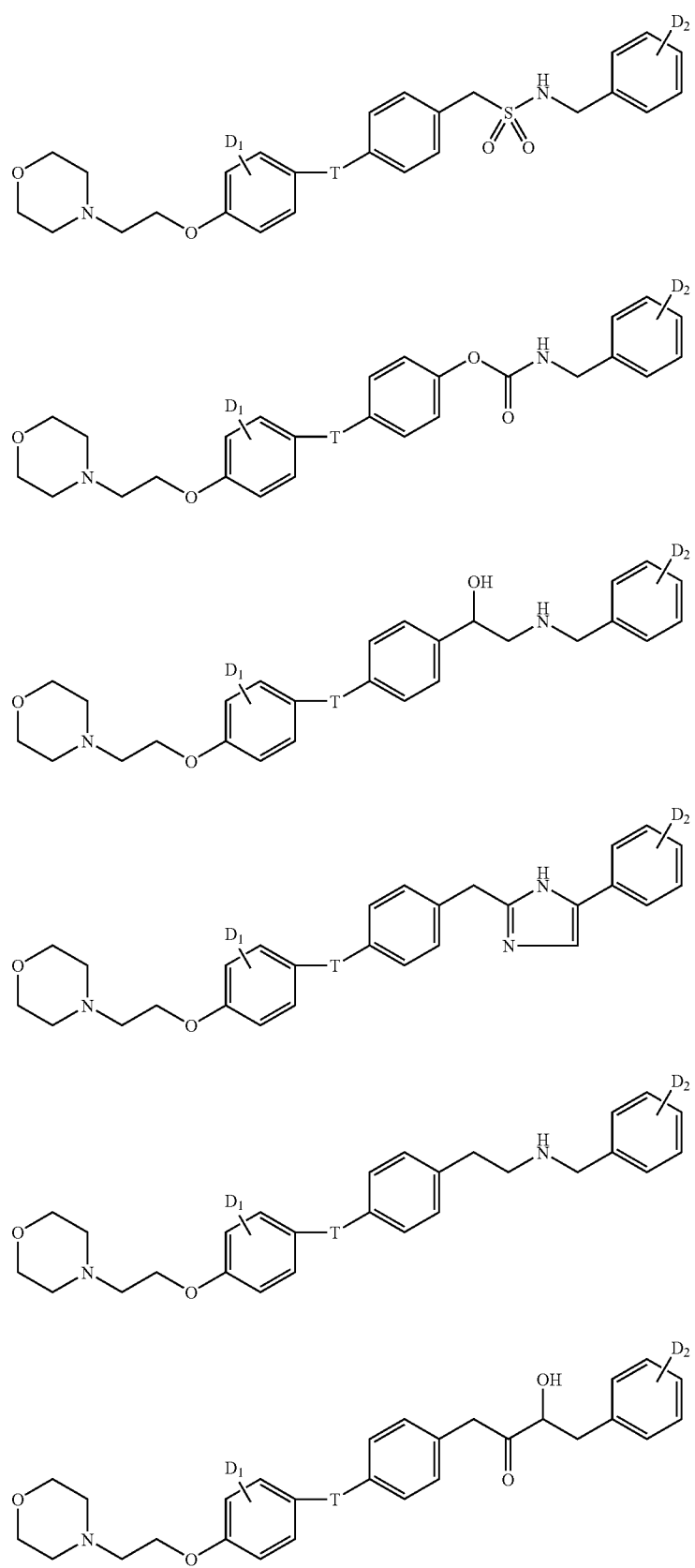

TABLE B-continued

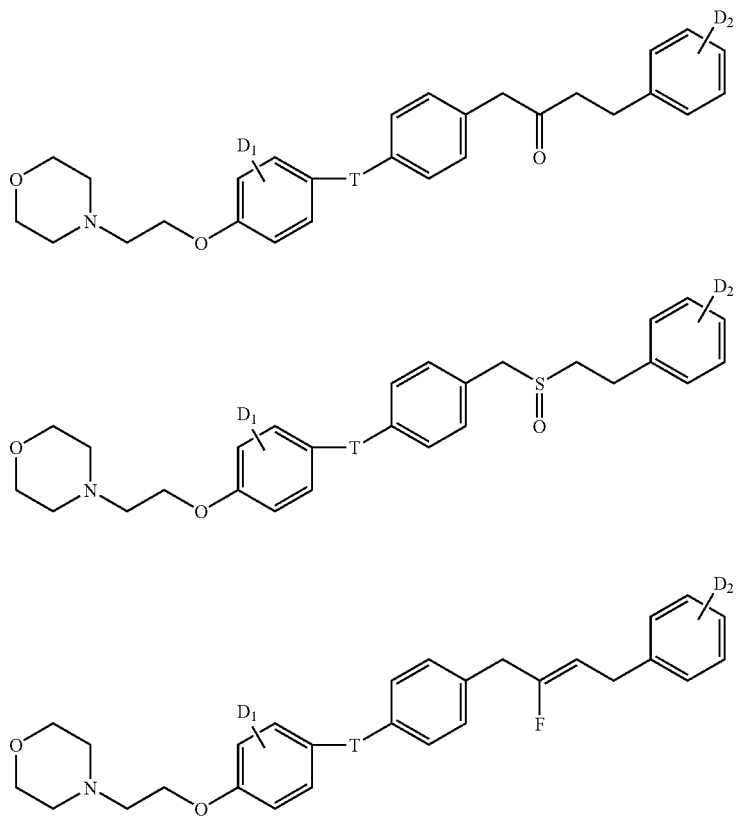

Where, in Table B, $D_1$ and $D_2$ are independently selected from hydrogen, halogen, $C_1$, $C_2$, $C_3$, $C_4$, $C_5$, or $C_6$ alkoxy, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, ($C_1$, $C_2$, $C_3$, $C_4$, $C_5$, or $C_6$)alkyl-non-aromatic heterocycle, ($C_3$, $C_4$, $C_5$, $C_6$, $C_7$, or $C_8$)cycloalkyl-non-aromatic heterocycle, ($C_1$, $C_2$, $C_3$, $C_4$, $C_5$, or $C_6$)alkyl-partially unsaturated carbocycle, ($C_3$, $C_4$, $C_5$, $C_6$, $C_7$, or $C_8$)cycloalkyl-partially unsaturated carbocycle, —$OR_{26}$, —$SR_{27}$, —$NR_{28}R_{29}$, and —$(CR_{24}R_{25})_t$—U, where U is cyano, —$OR_{26}$, —$SR_{27}$, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, $C(O)NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, or glycoside; $R_{24}$ and $R_{25}$ are independently selected from H $C_1$, $C_2$, $C_3$, $C_4$, $C_5$, or $C_6$ alkyl, and $C_3$, $C_4$, $C_5$, $C_6$, $C_7$, or $C_8$ cycloalkyl; $R_{26}$, $R_{27}$, $R_{28}$, and $R_{29}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl, or together $R_{28}$ and $R_{29}$ form a ring; $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring; t is 0, 1, 2, 3, 4, 5, or 6; p is 0, 1 or 2; and T is a bond, $CR_{12}R_{13}$, C(O), O, S, S(O), $S(O)_2$, $NR_{14}$, $C(R_{15}R_{16})C(R_{17}R_{18})$, $CH_2O$, or $OCH_2$. In another embodiment, T is a bond, O, $CH_2O$ and $OCH_2$.

Compounds of the invention include those listed in Table 1:

TABLE 1

| Compound # |
|---|
| 1 |

TABLE 1-continued
2 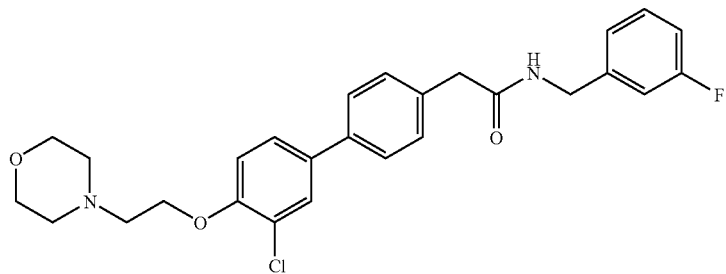
3 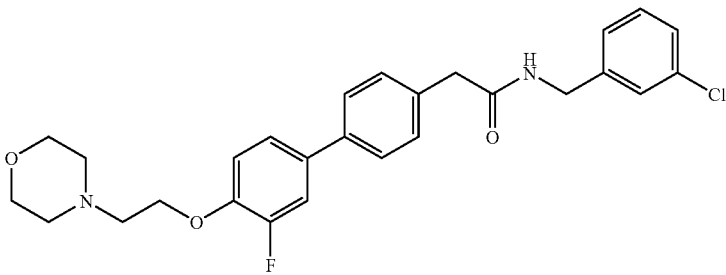
4 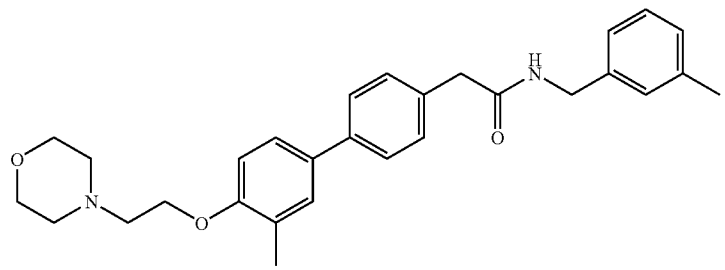
5 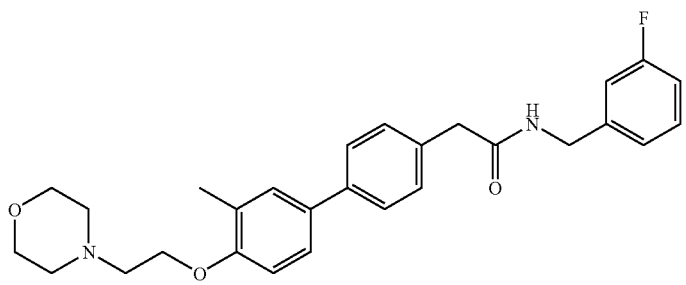
6 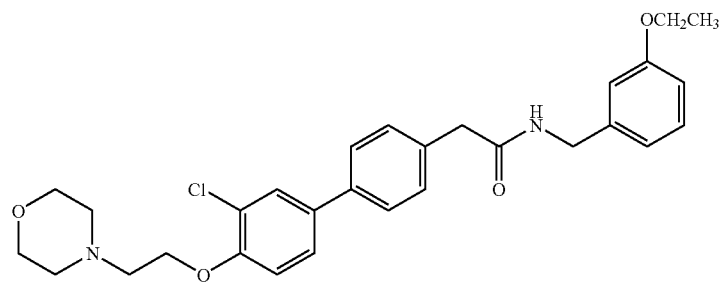
7 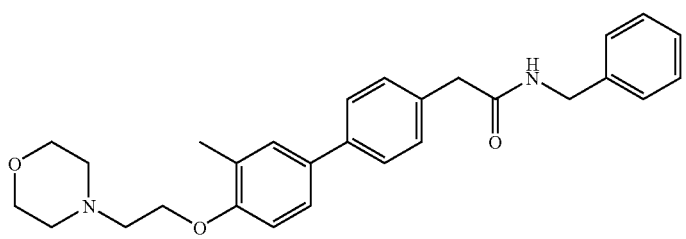

TABLE 1-continued
8
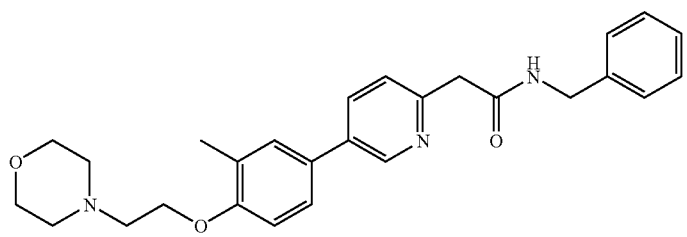
9
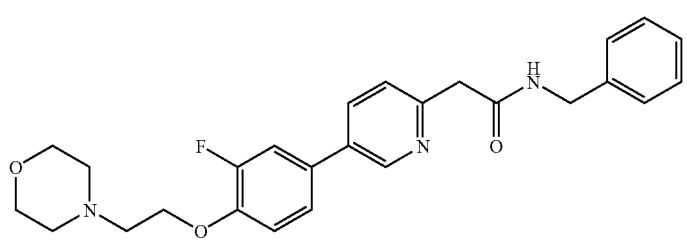
10
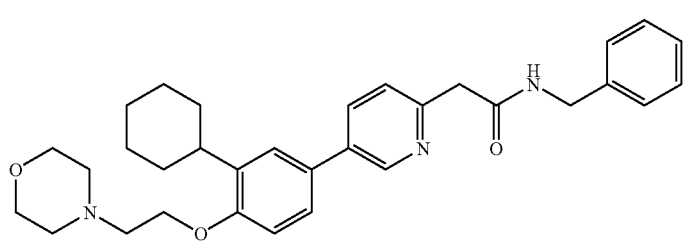
11
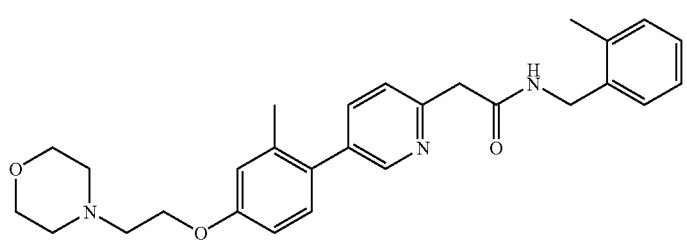
12
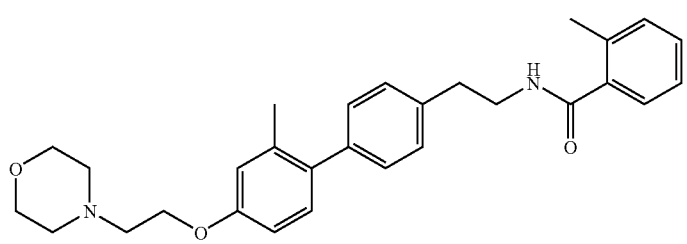
13
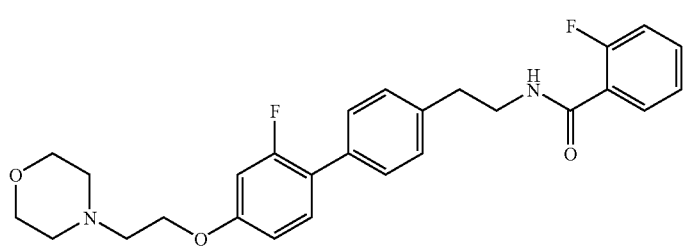

TABLE 1-continued
14
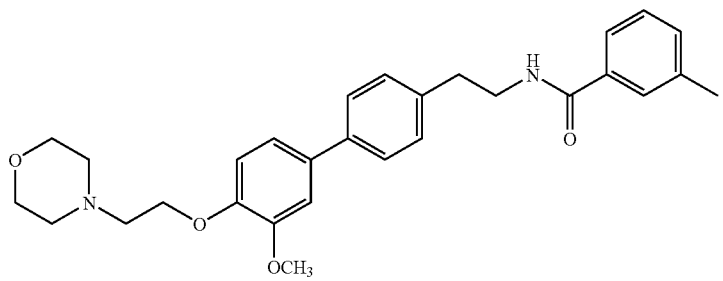
15
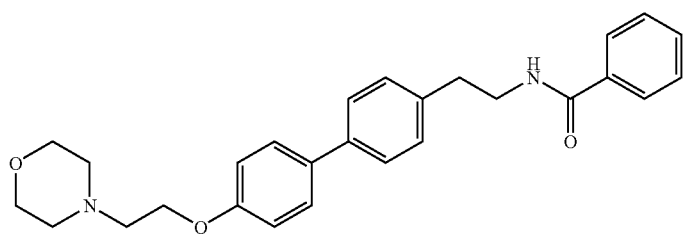
16
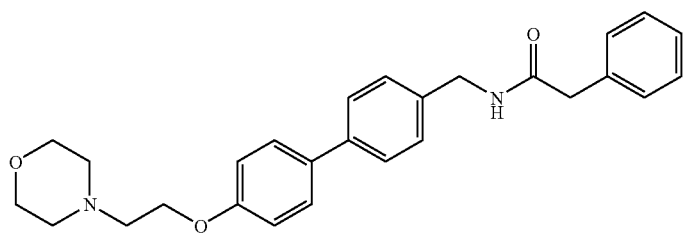
17
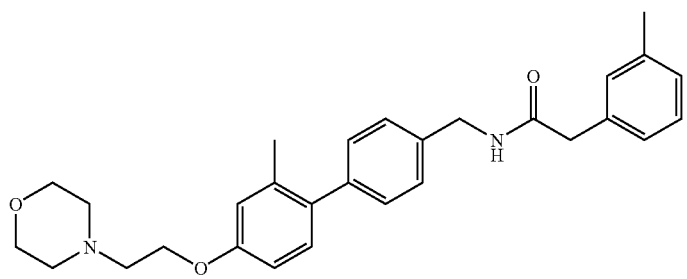
18
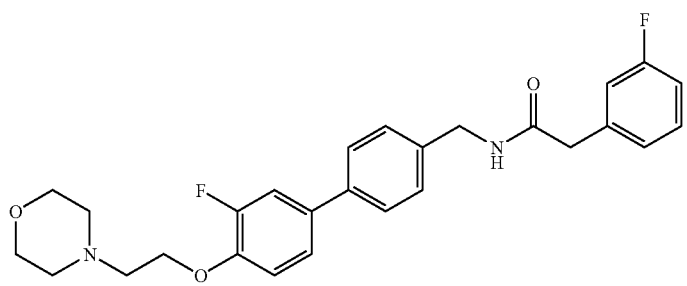
19
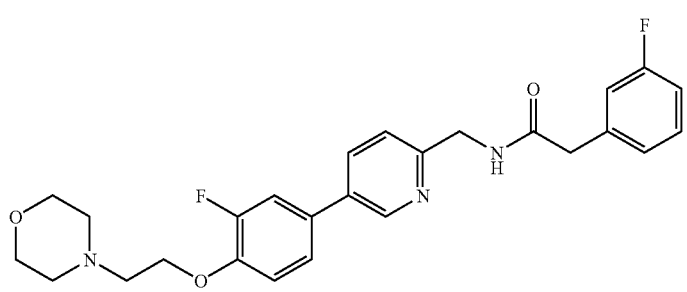

TABLE 1-continued
20
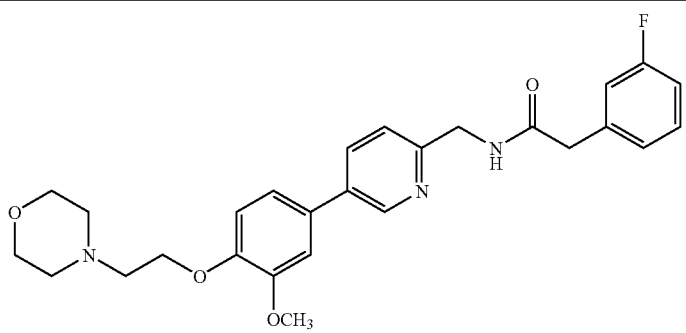
21
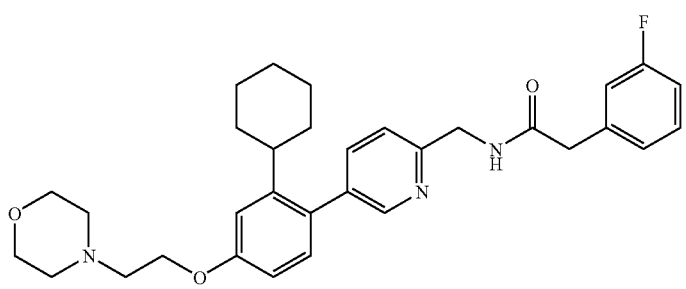
22
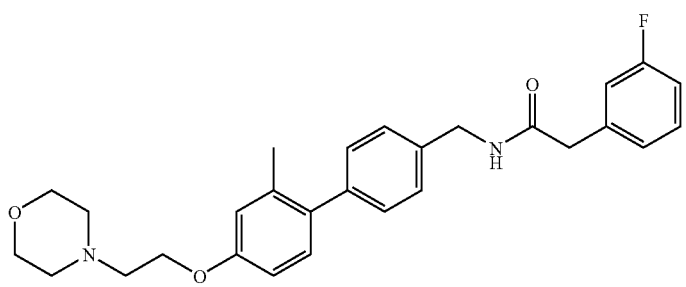
23
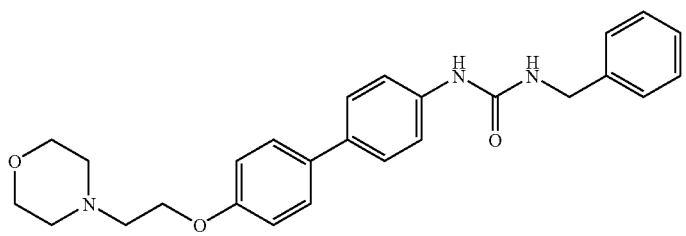
24
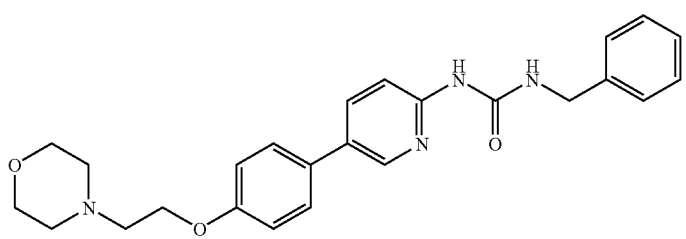
25
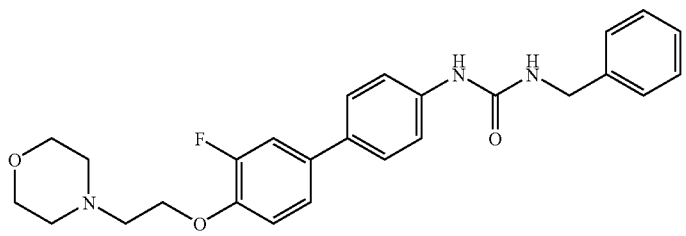

TABLE 1-continued
26
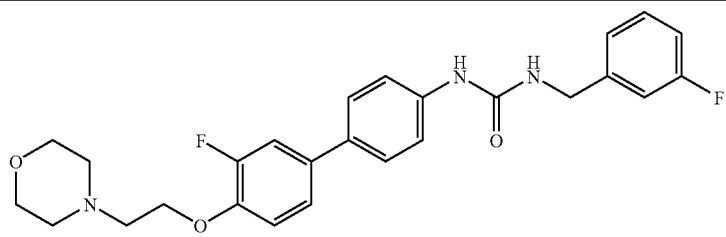
27
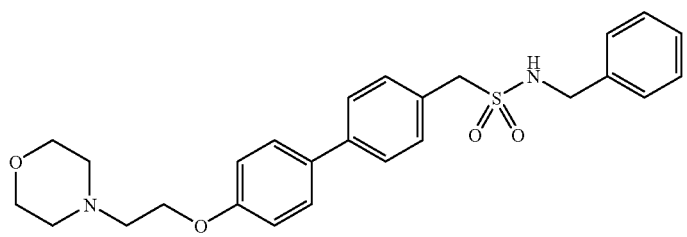
28
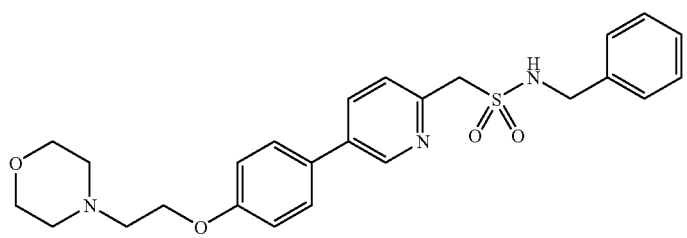
29
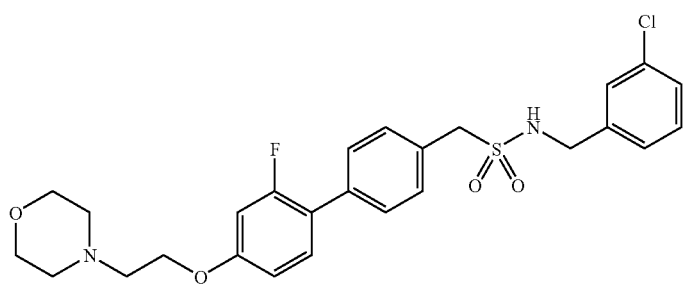
30
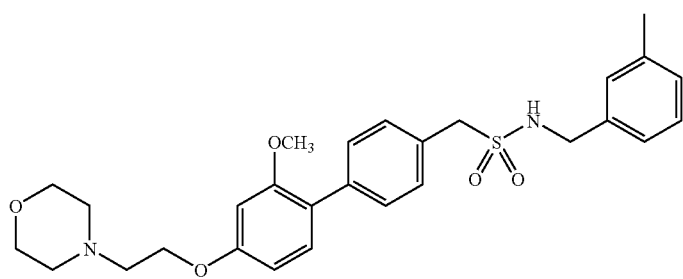
31
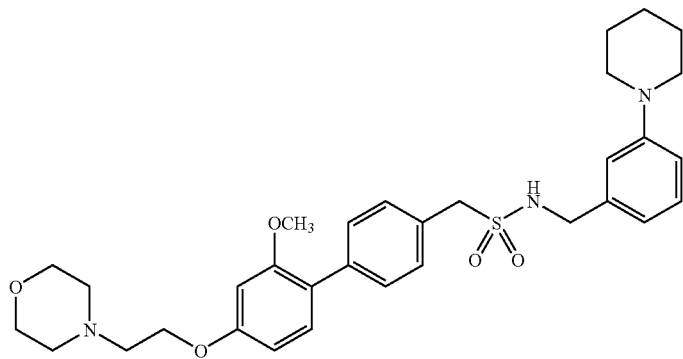

TABLE 1-continued
| 32 | 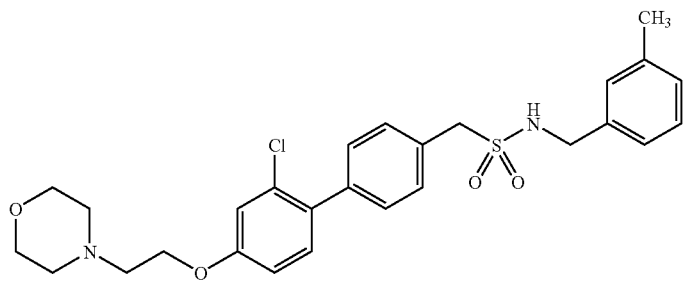 |
| 33 | 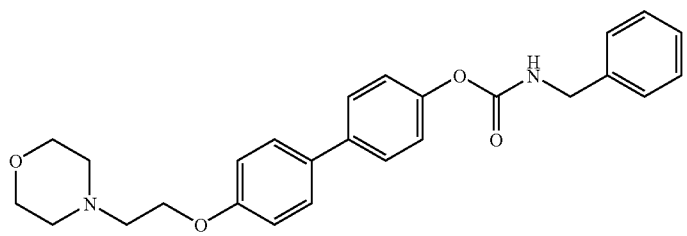 |
| 34 | 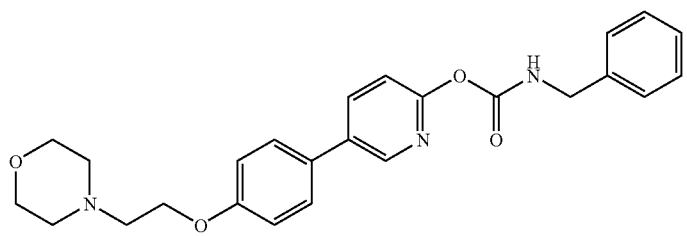 |
| 35 | 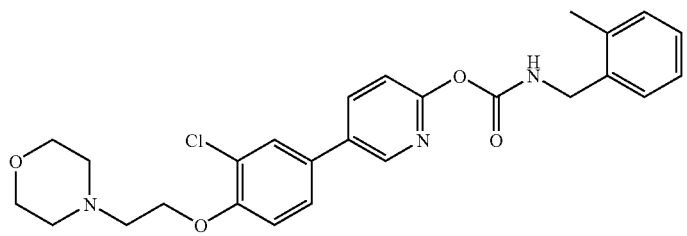 |
| 36 | 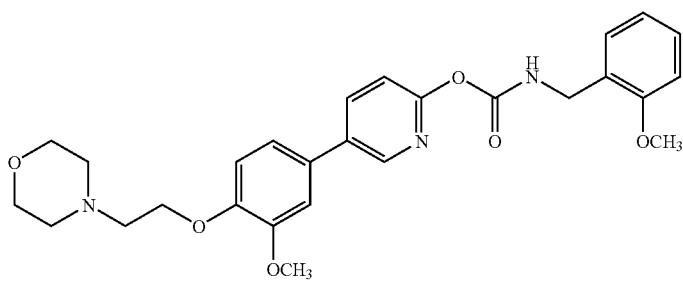 |
| 37 | 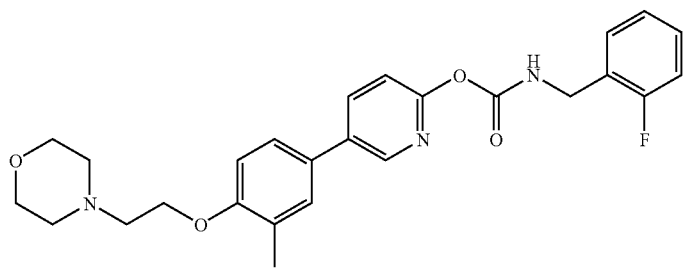 |

TABLE 1-continued
| | |
|---|---|
| 38 | 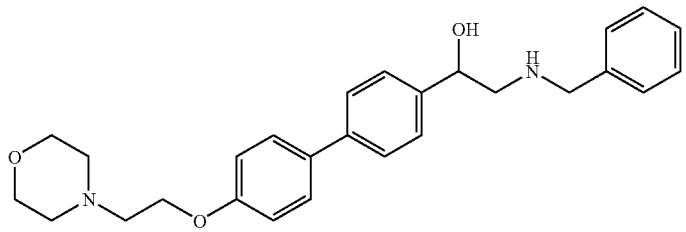 |
| 39 | 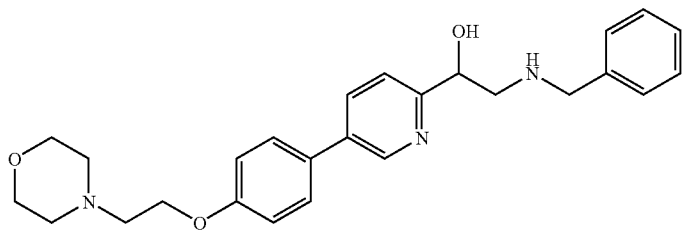 |
| 40 | 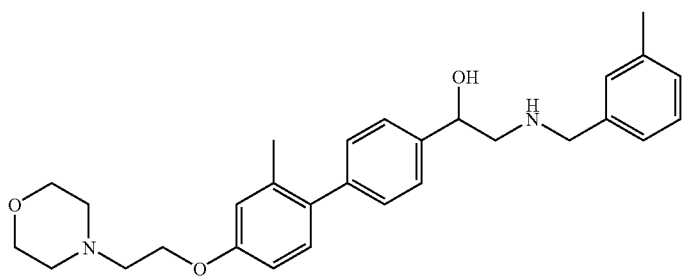 |
| 41 | 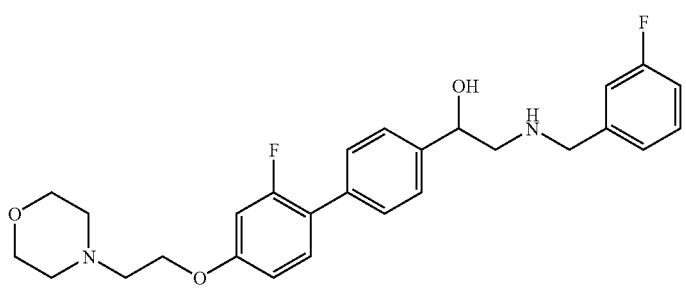 |
| 42 | 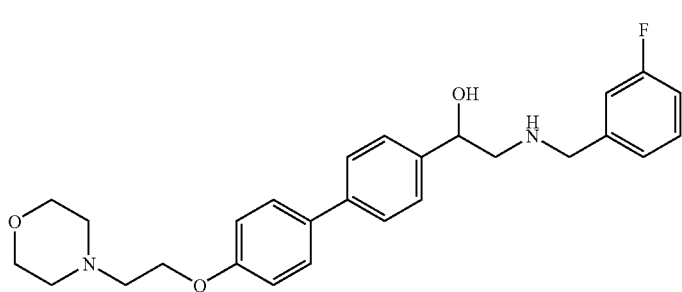 |
| 43 | 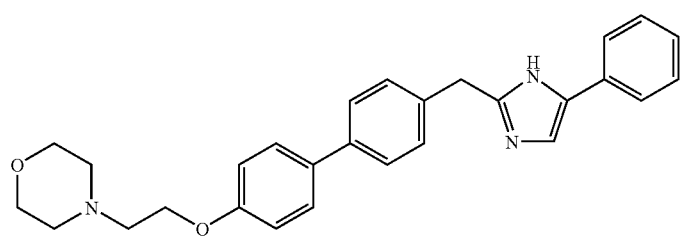 |

TABLE 1-continued
| | |
|---|---|
| 44 | 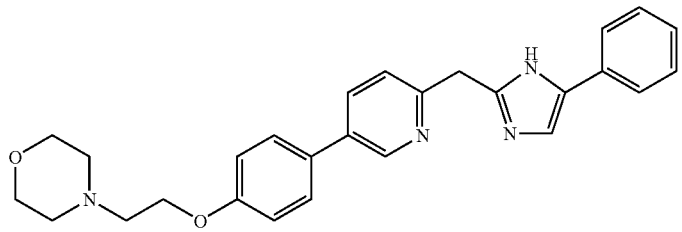 |
| 45 | 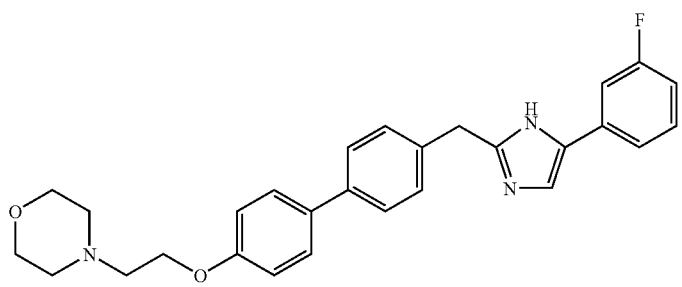 |
| 46 | 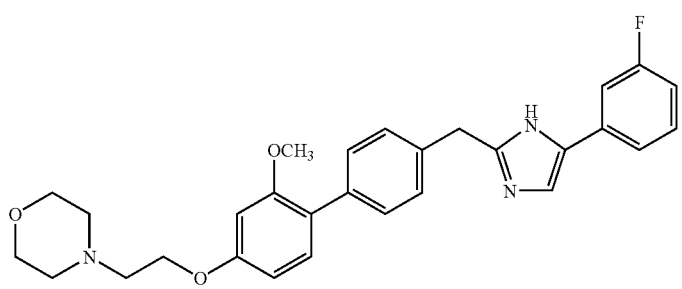 |
| 47 | 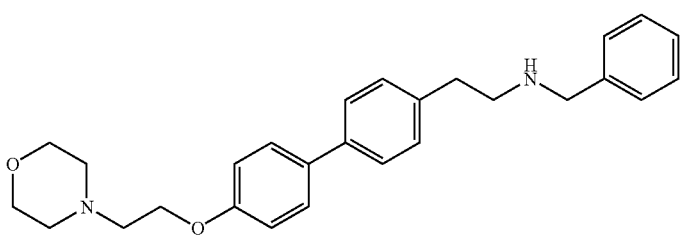 |
| 48 | 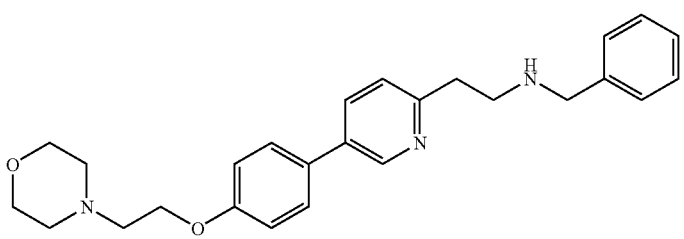 |
| 49 | 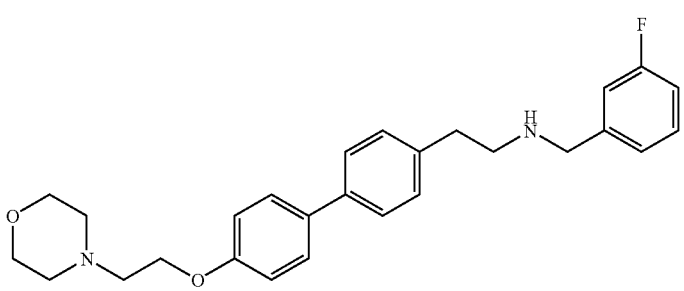 |

TABLE 1-continued
50 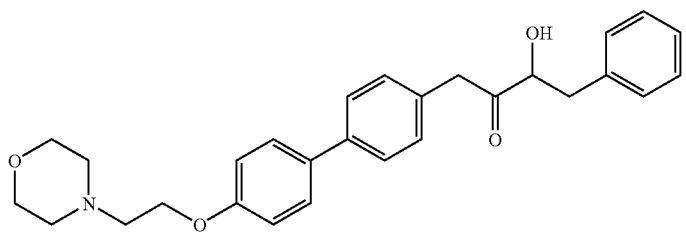
51 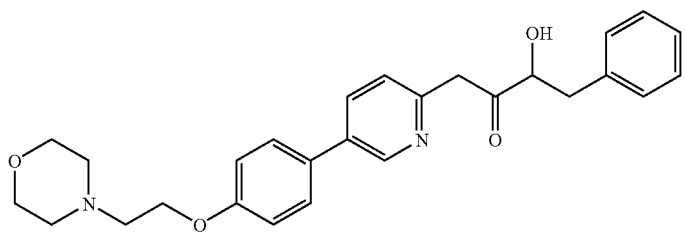
52 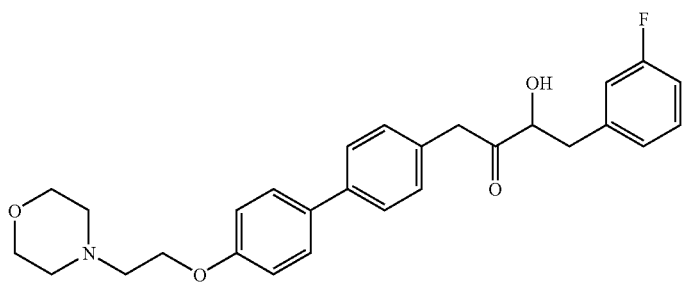
54 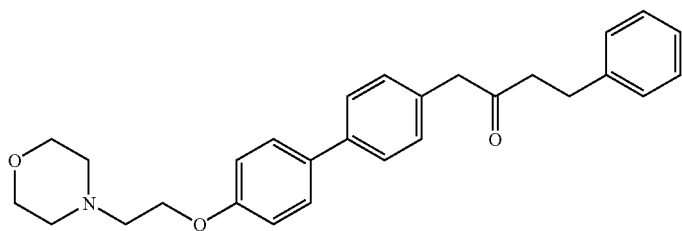
55 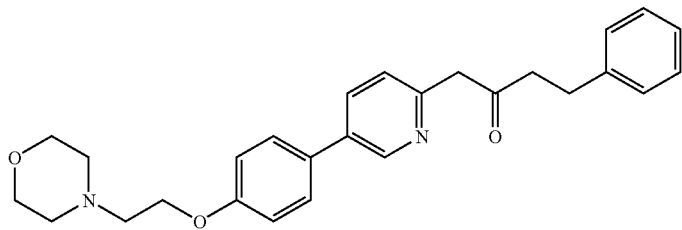
56 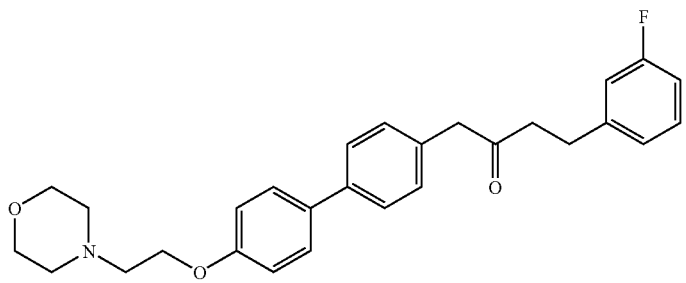

TABLE 1-continued
57
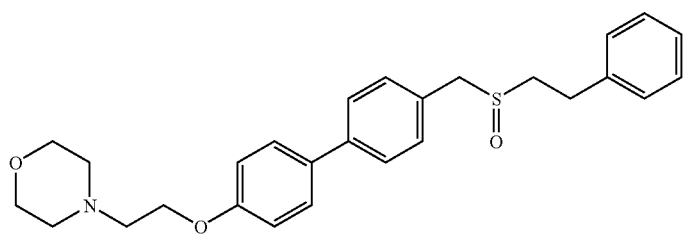
58
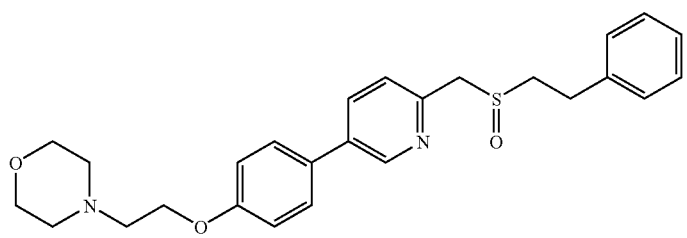
59
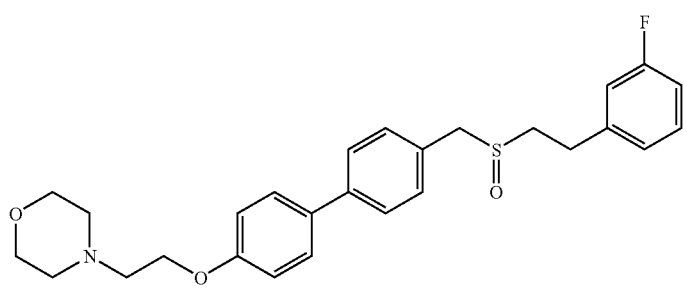
60
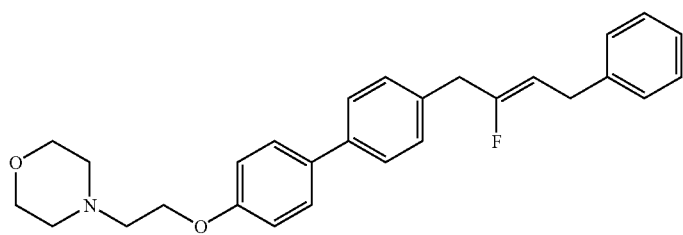
61
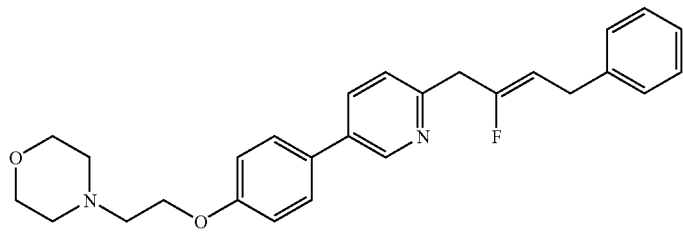
62
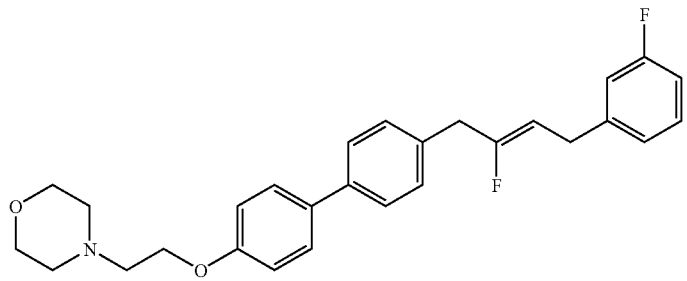

TABLE 1-continued
63 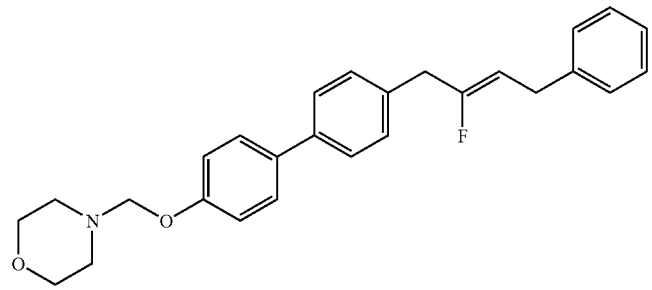
64 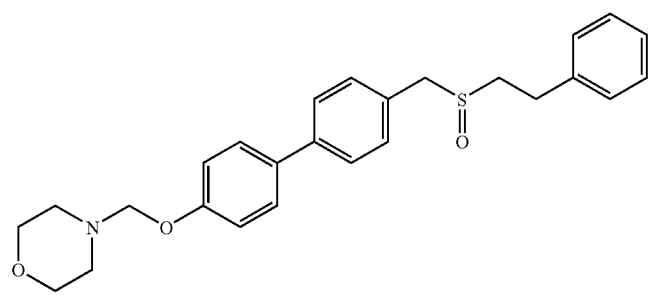
65 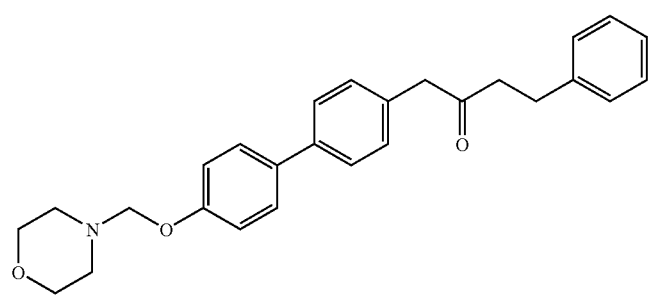
66 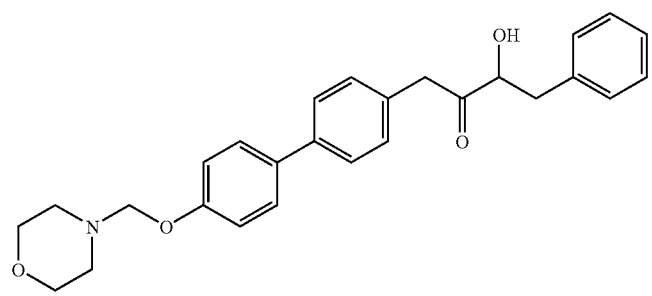
67 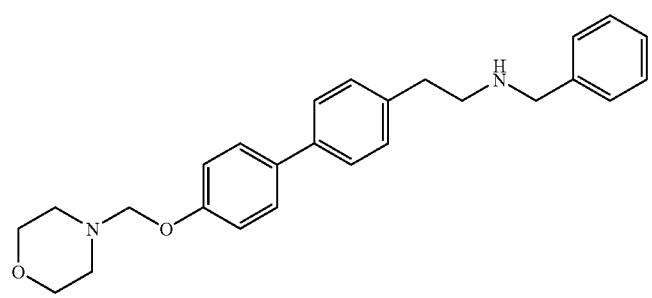

TABLE 1-continued
68
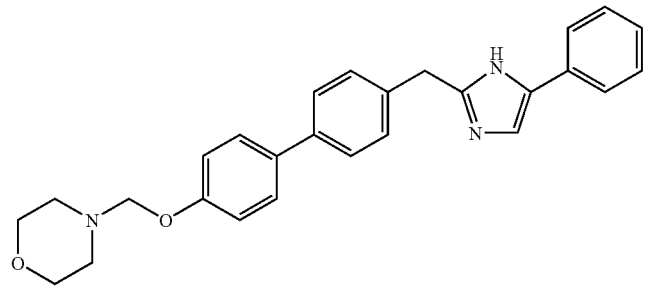
69
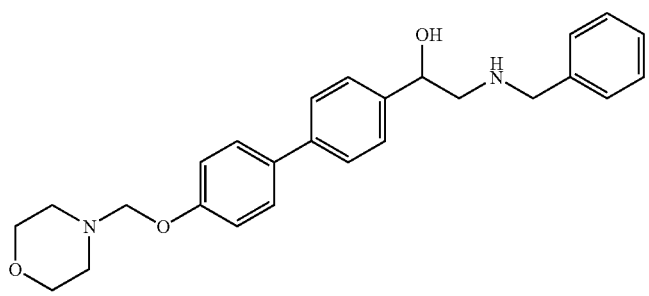
70
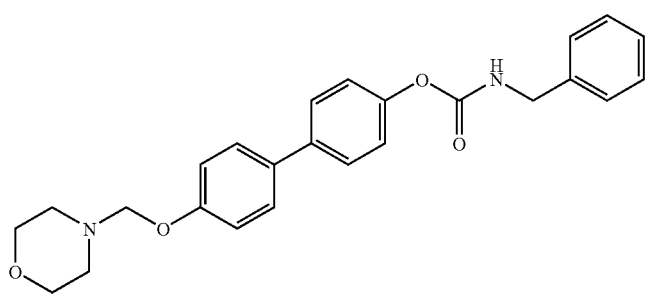
71
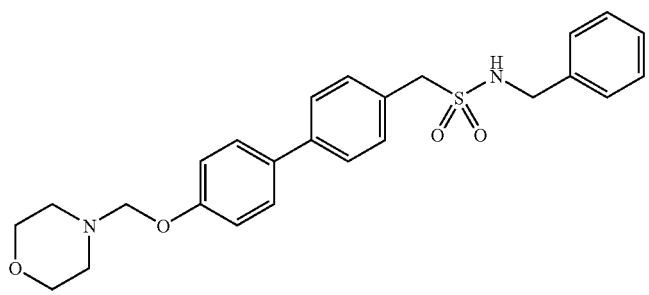
72
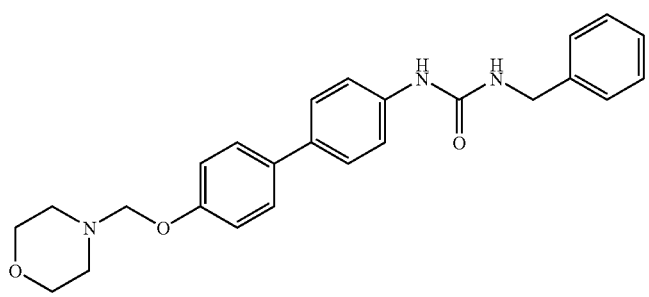

TABLE 1-continued
73
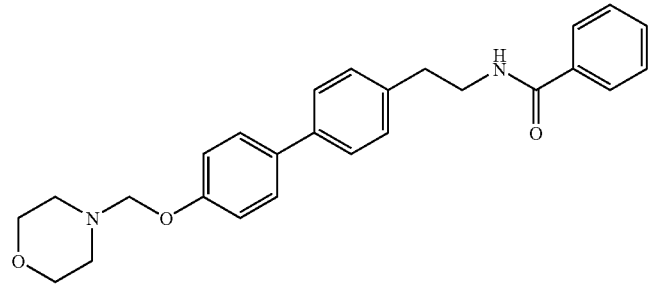
74
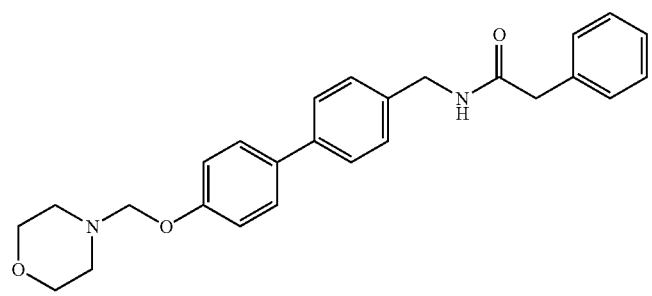
75
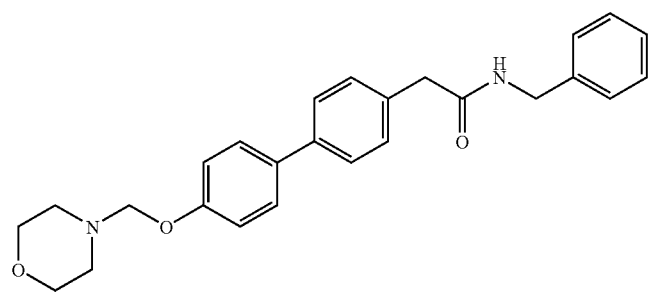
76
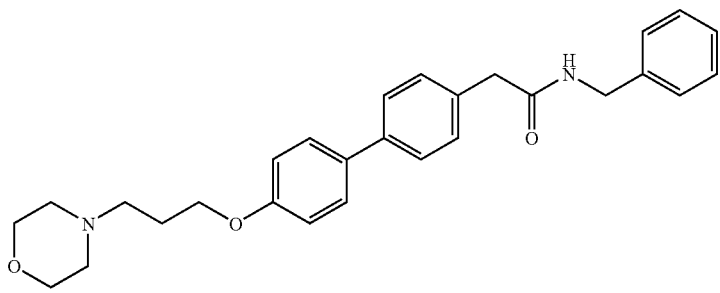
77
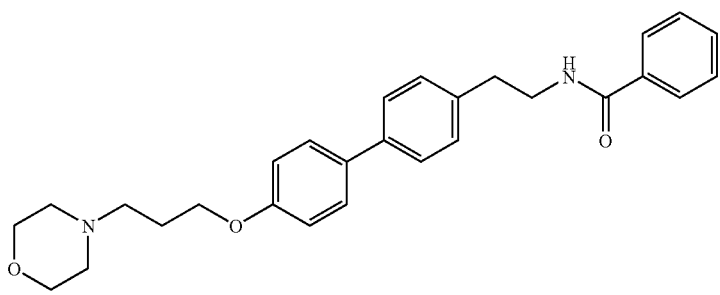

TABLE 1-continued
78
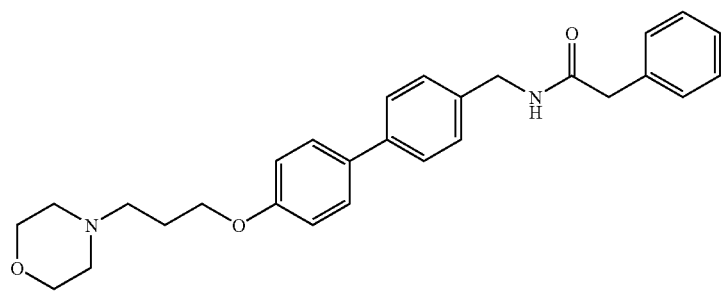
79
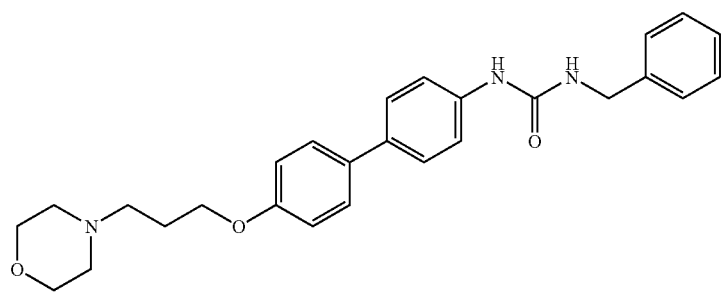
80
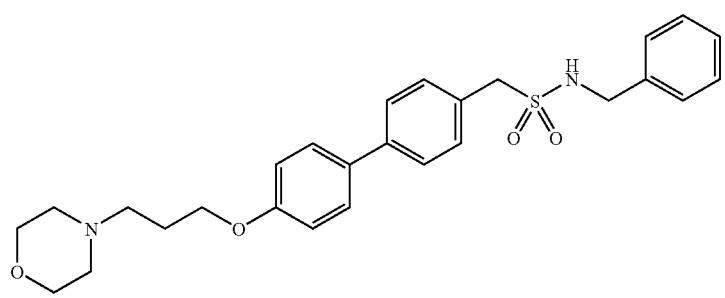
81
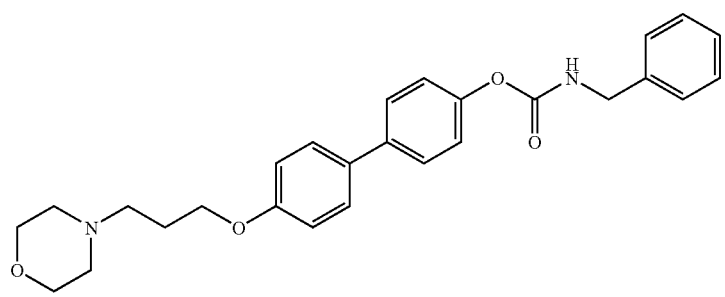
82
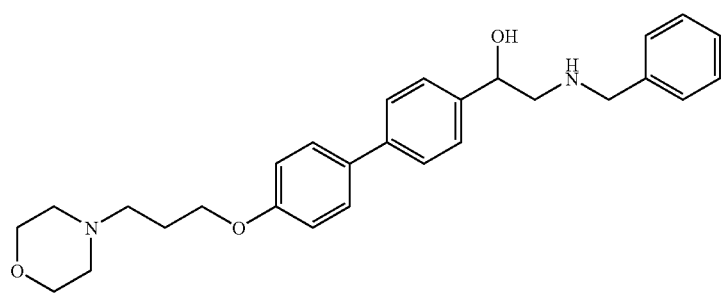

TABLE 1-continued
83
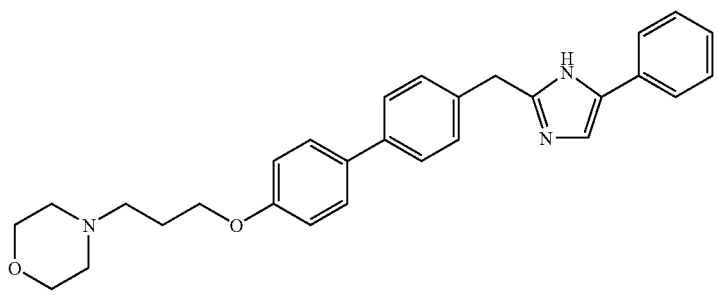
84
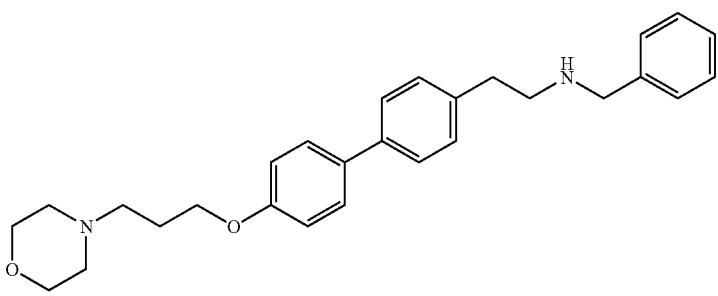
85
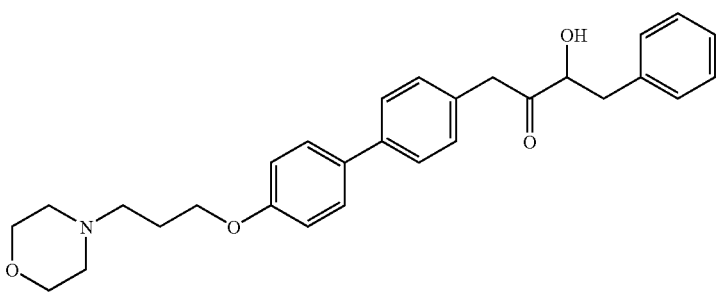
86
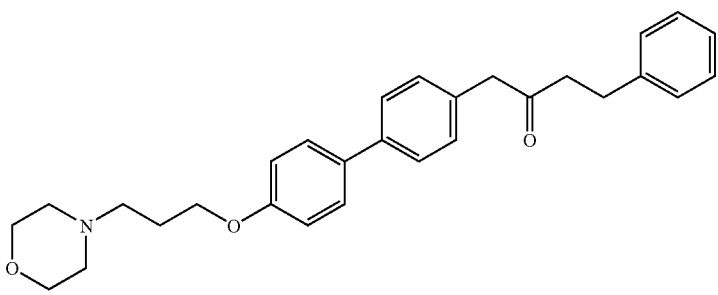
87
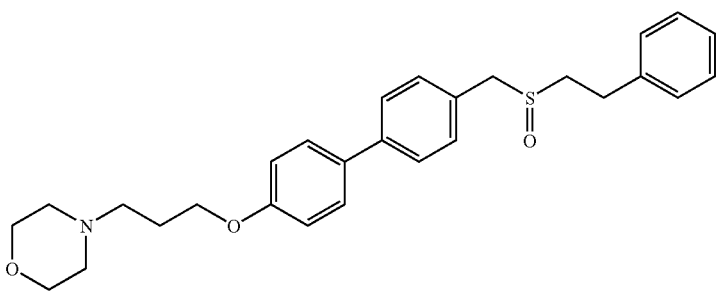

TABLE 1-continued
88
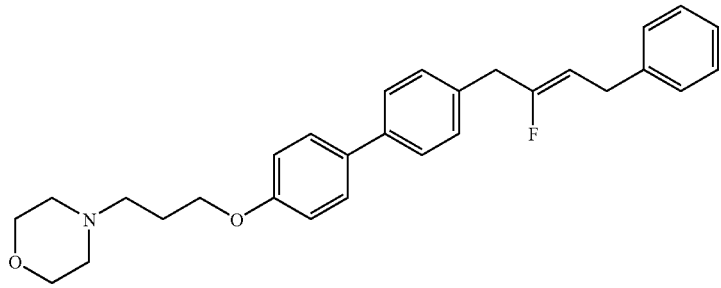
89
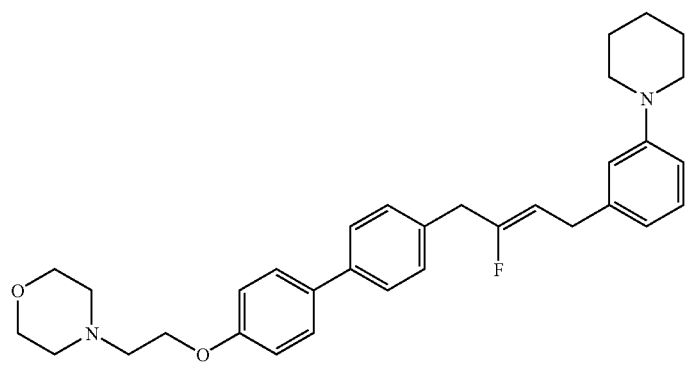
90
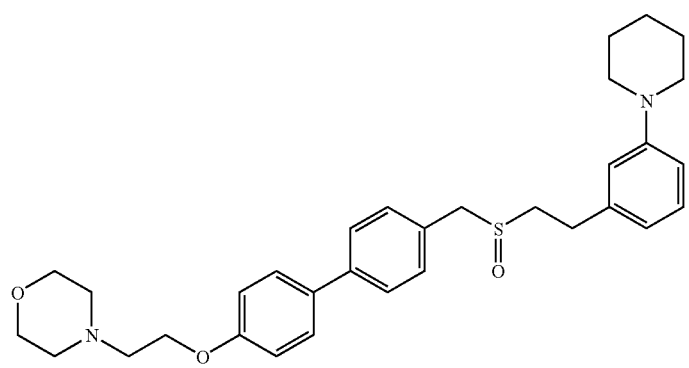
91
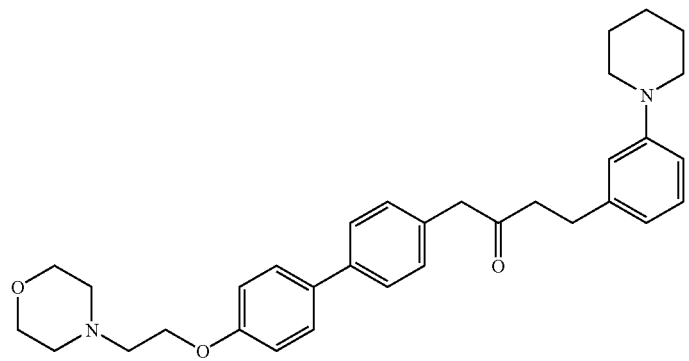

TABLE 1-continued
92
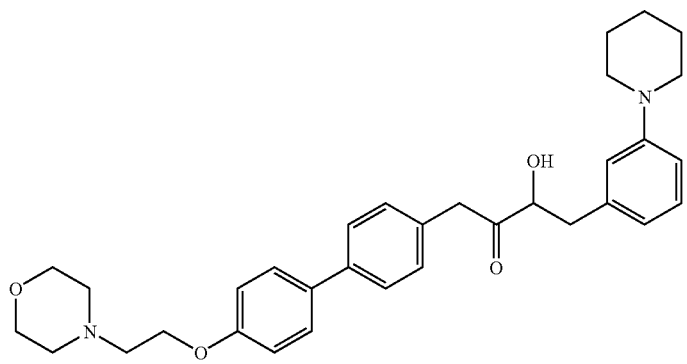
93
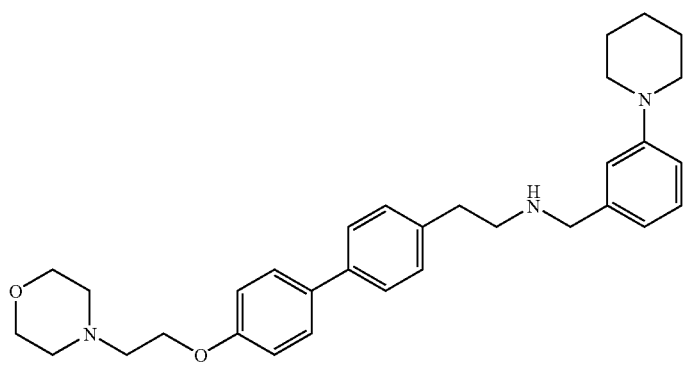
94
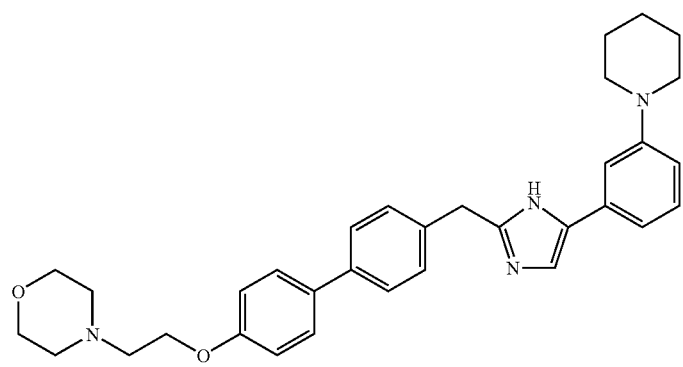
95
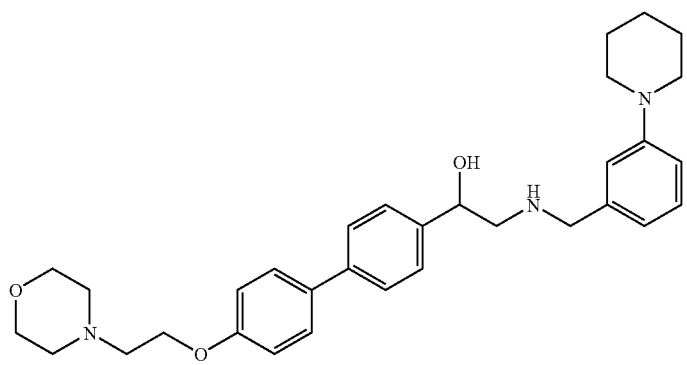

TABLE 1-continued
96
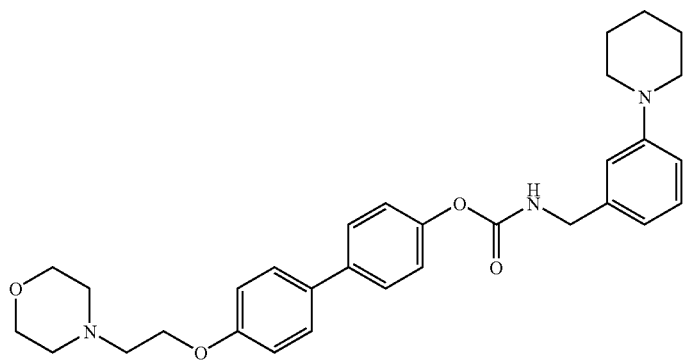
97
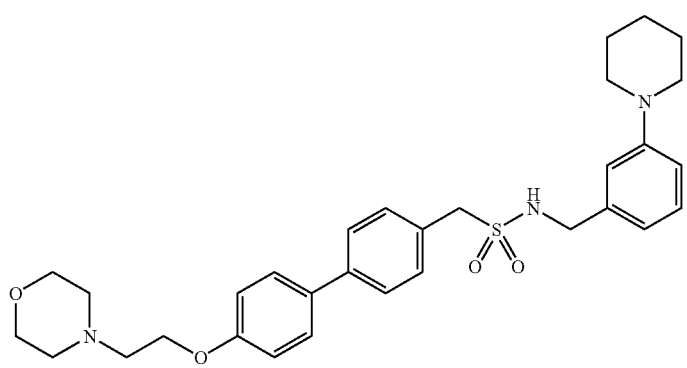
98
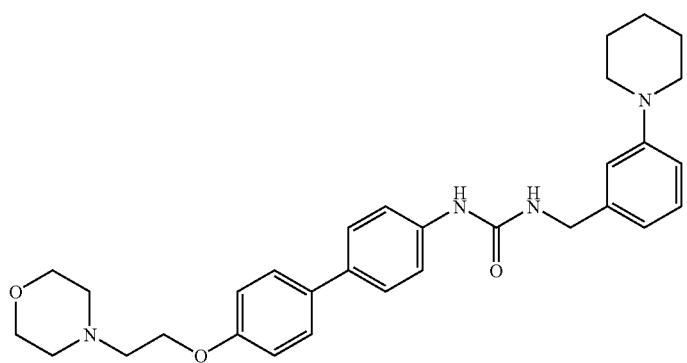
99
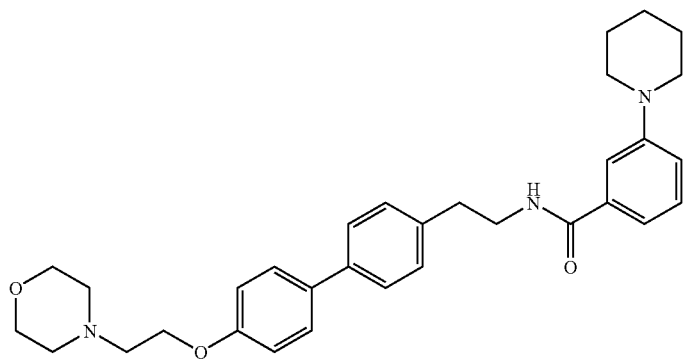

TABLE 1-continued
100
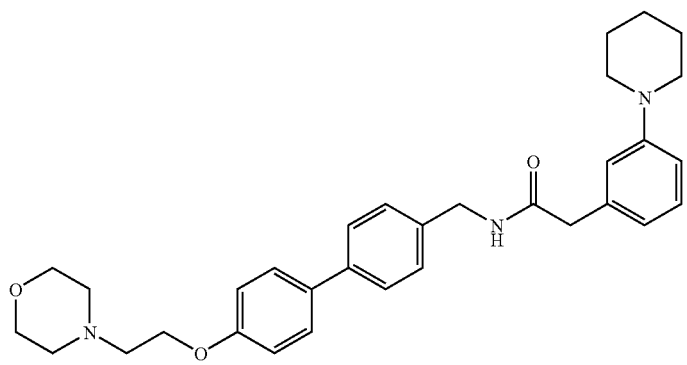
101
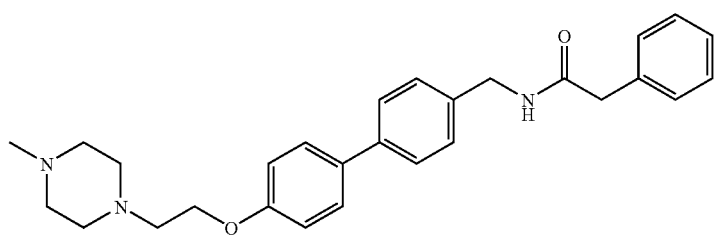
102
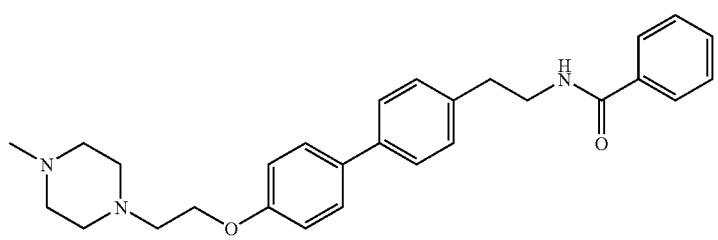
103
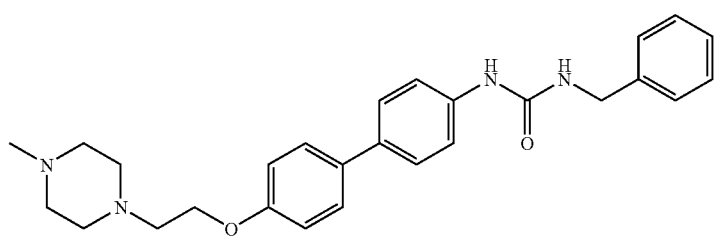
104
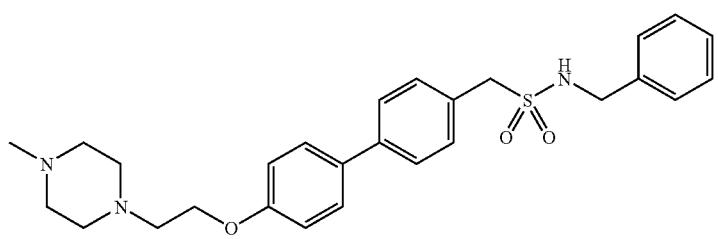
105
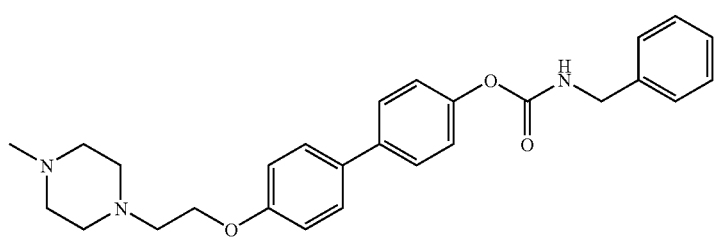

TABLE 1-continued
106
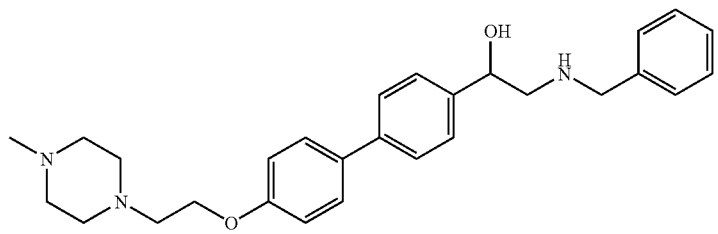
107
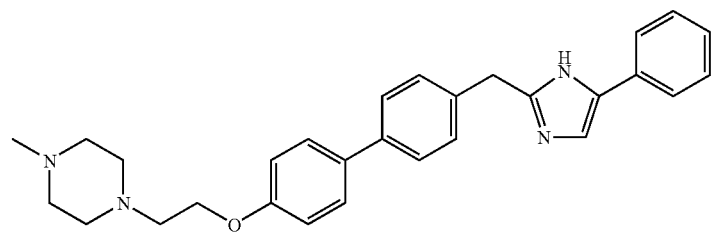
108
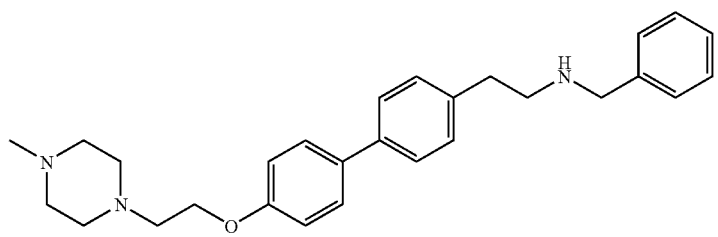
109
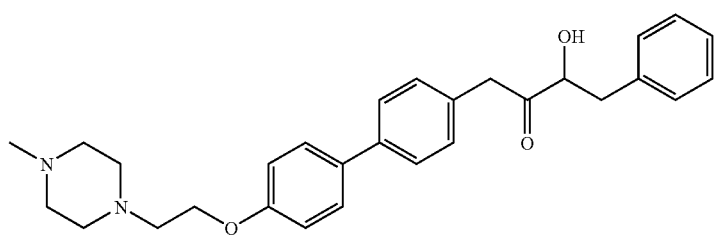
110
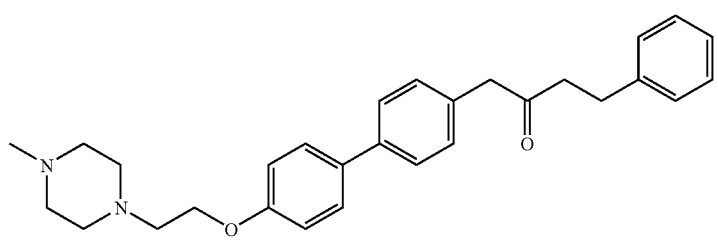
111
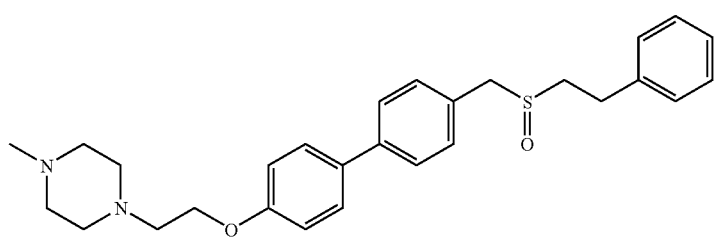

TABLE 1-continued
112
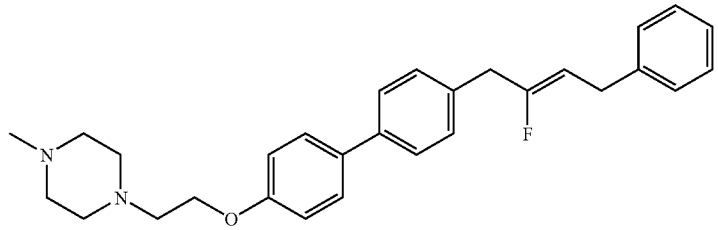
113
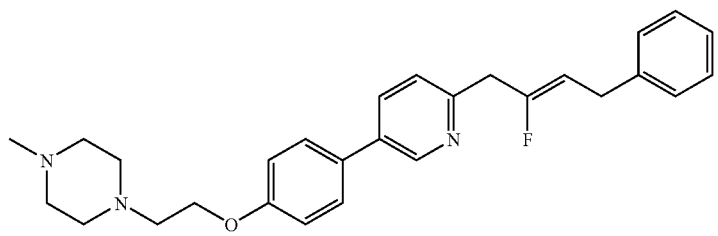
114
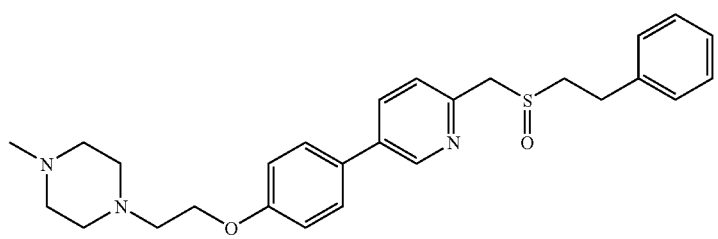
115
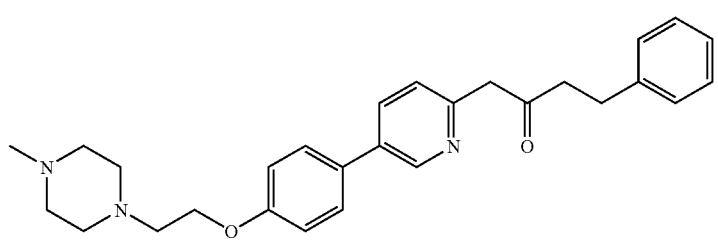
116
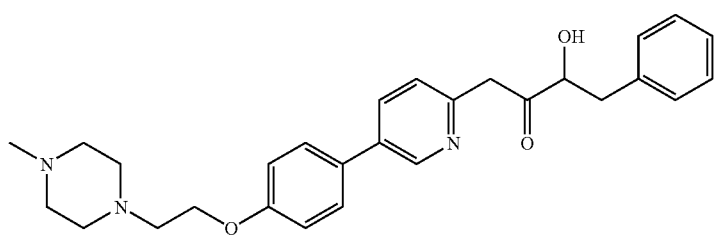
117
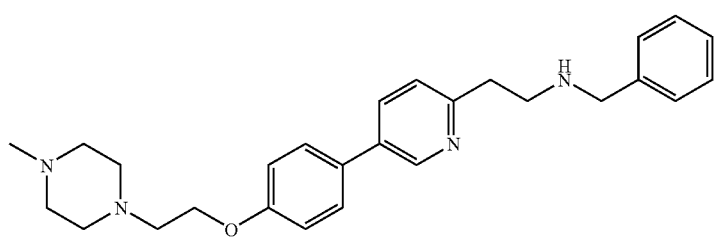

TABLE 1-continued
118
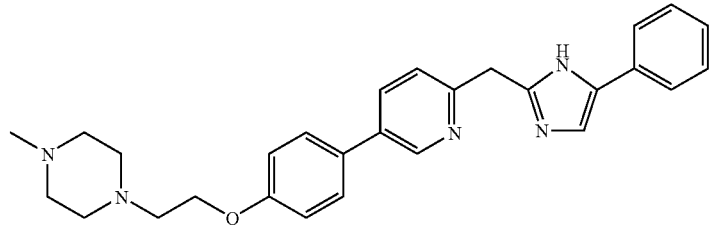
119
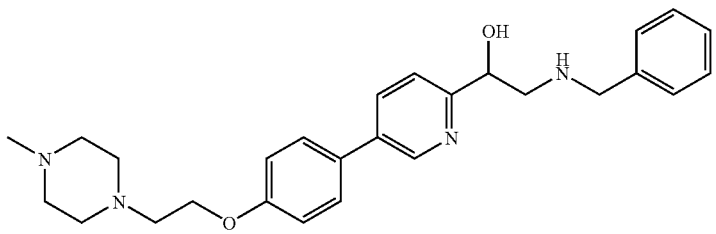
120
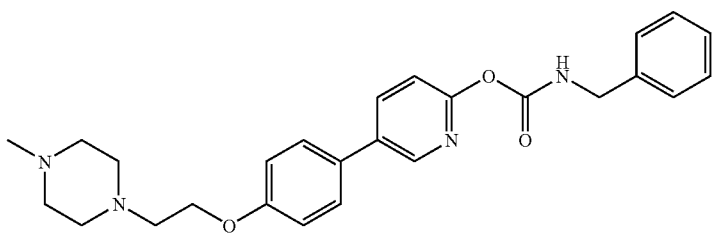
121
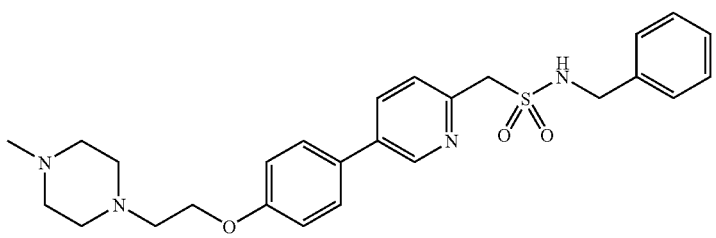
122
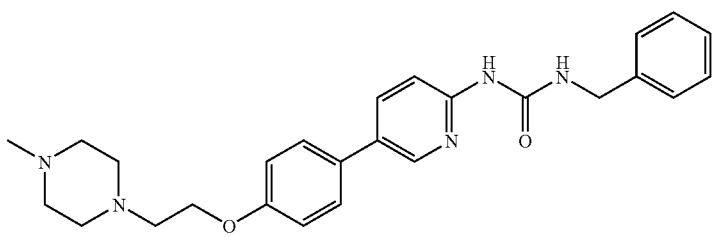
123
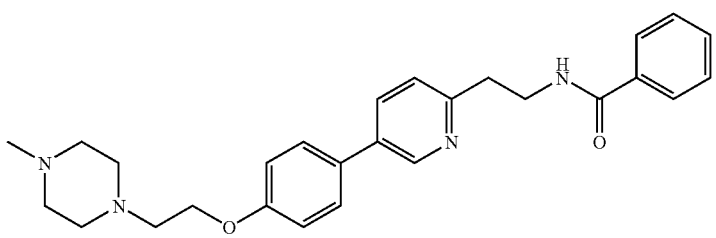

TABLE 1-continued
| 124 | 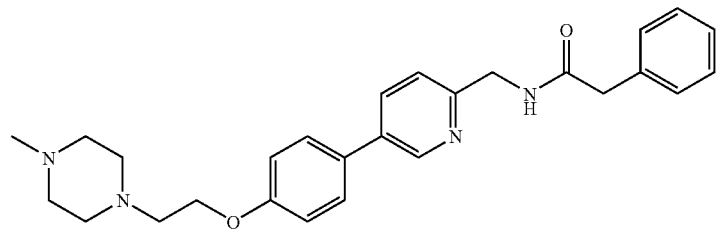 |
| CMPD # | Structure |
|---|---|
| 125 | 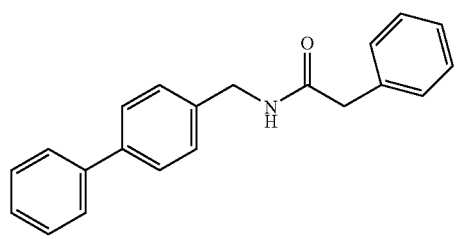 |
| 126 | 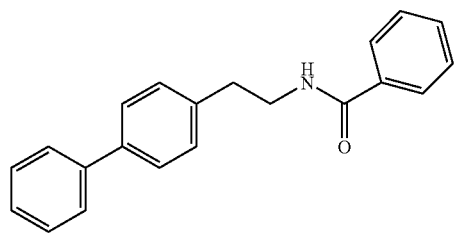 |
| 127 | 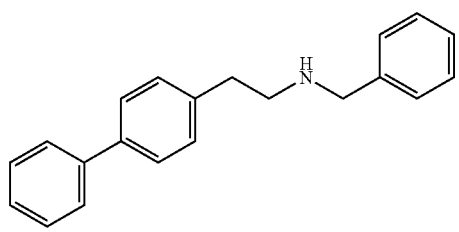 |
| 128 | 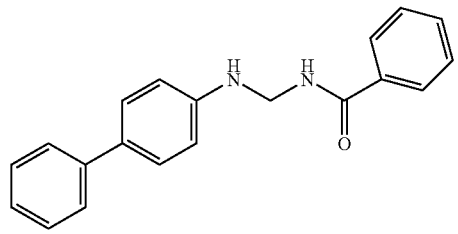 |
| 129 | 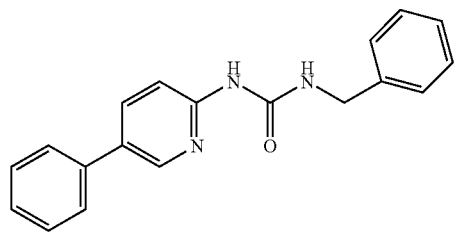 |

TABLE 1-continued
| 130 | 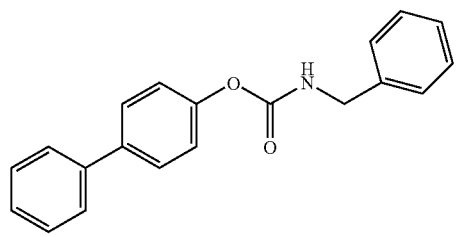 |
| 131 | 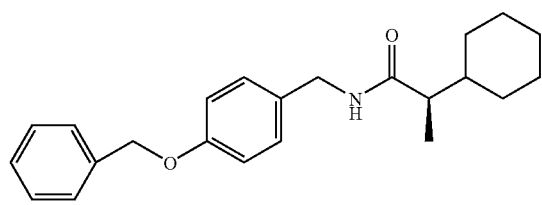 |
| 132 | 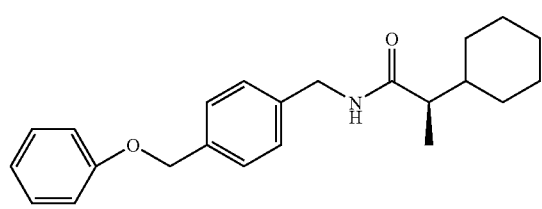 |
| 133 | 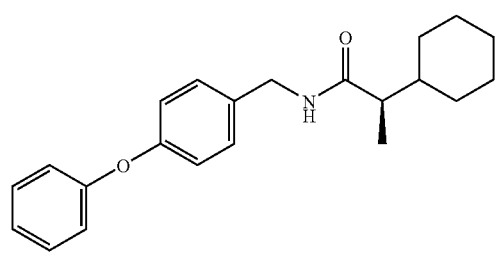 |
| 134 | 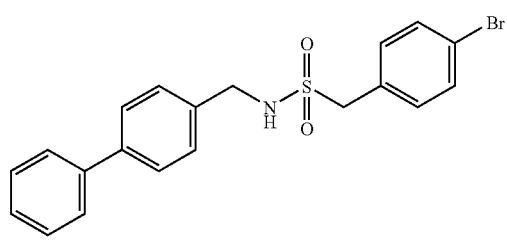 |
| 135 | 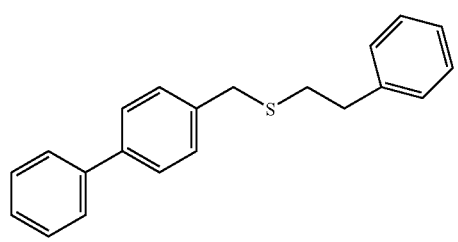 |
| 136 | 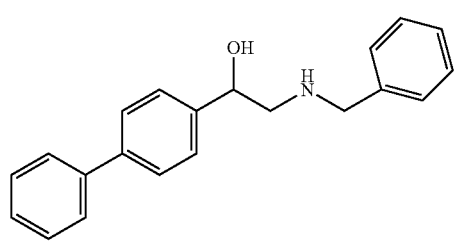 |

TABLE 1-continued
137 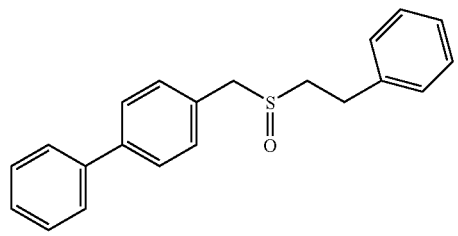
138 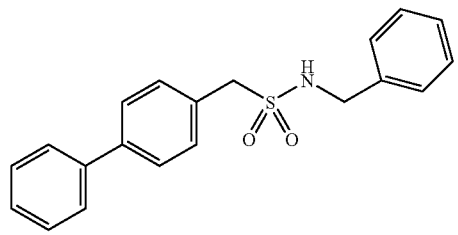
139 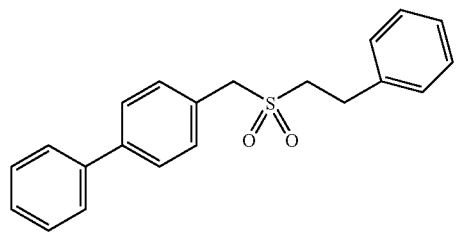
140 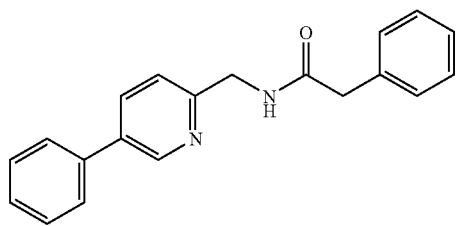
141 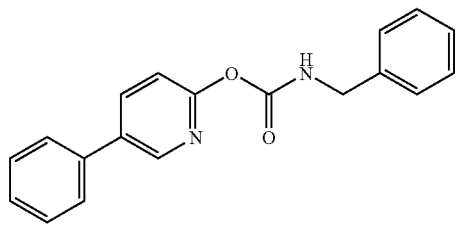
142 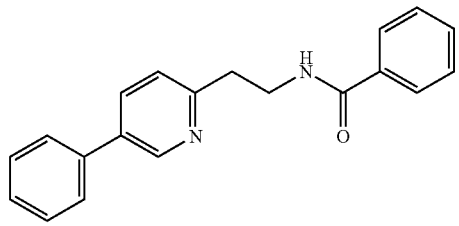
143 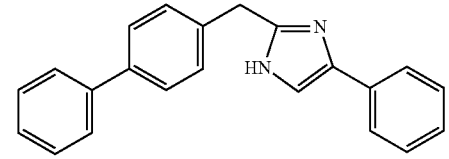

TABLE 1-continued
| | |
|---|---|
| 144 | 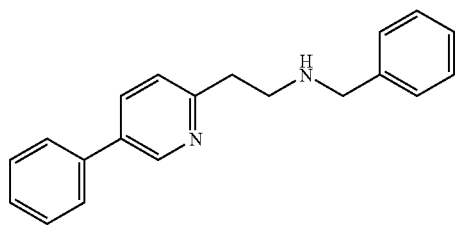 |
| 145 | 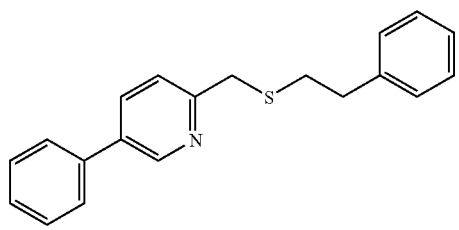 |
| 146 | 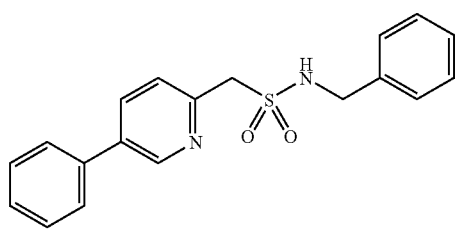 |
| 147 | 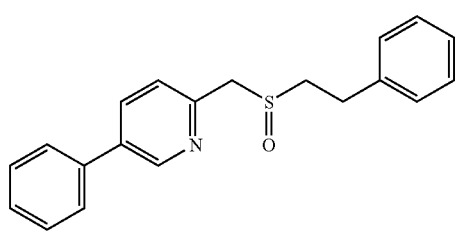 |
| 148 | 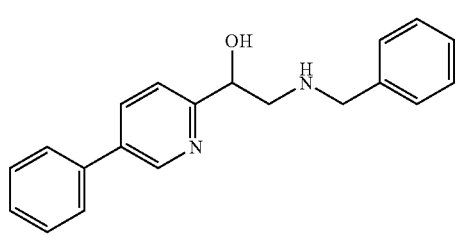 |
| 149 | 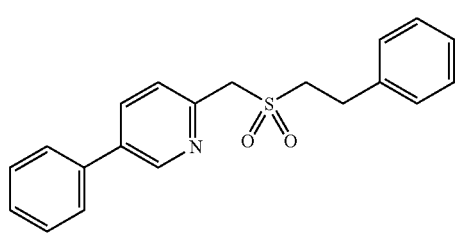 |
| 150 | 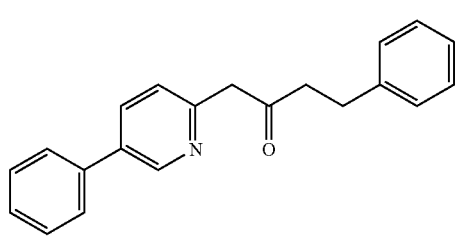 |

TABLE 1-continued
| | |
|---|---|
| 151 | 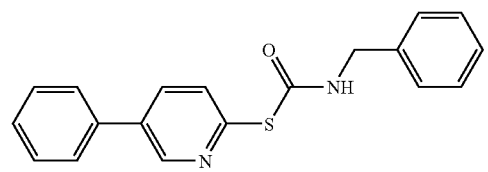 |
| 152 | 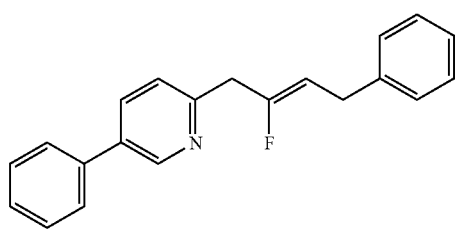 |
| 153 | 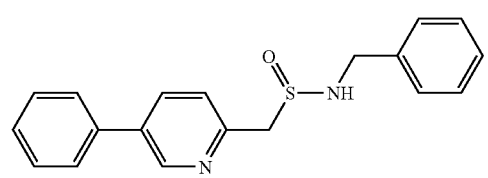 |
| 154 | 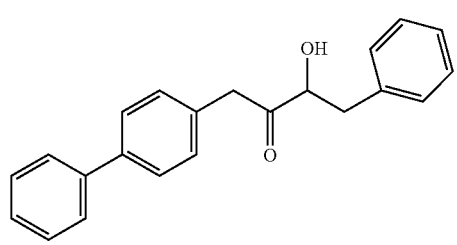 |
| 155 | 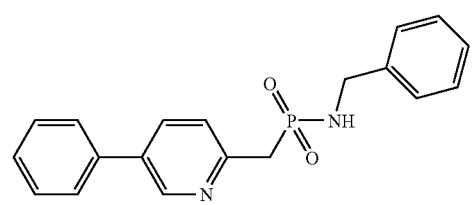 |
| 156 | 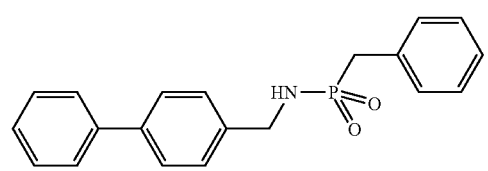 |
| 157 | 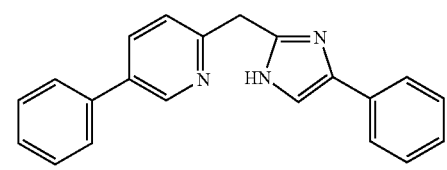 |
| 158 | 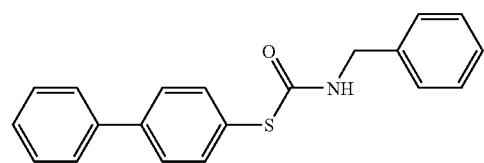 |

TABLE 1-continued
159 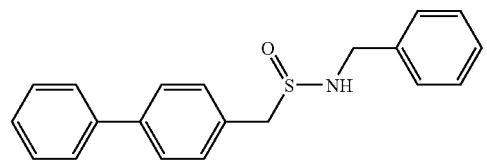
161 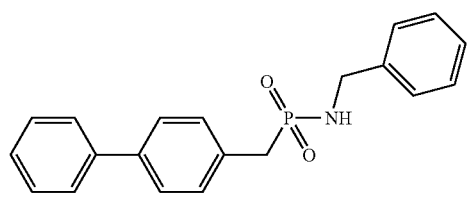
162 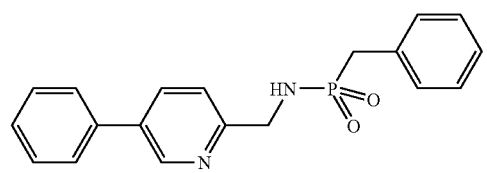
163 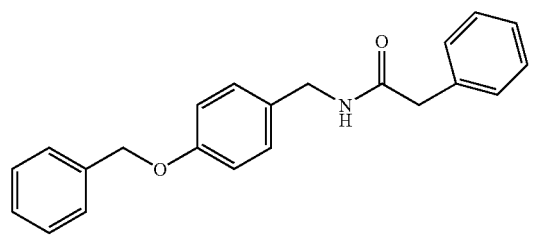
164 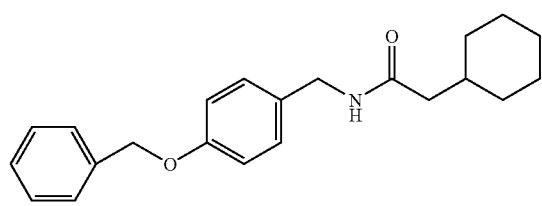
165 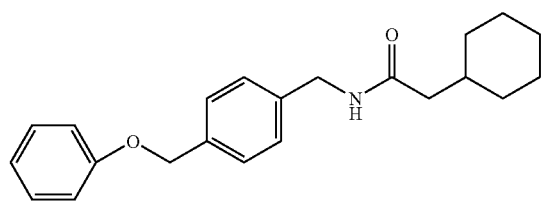
166 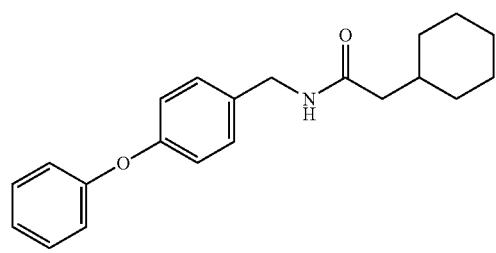

TABLE 1-continued
167
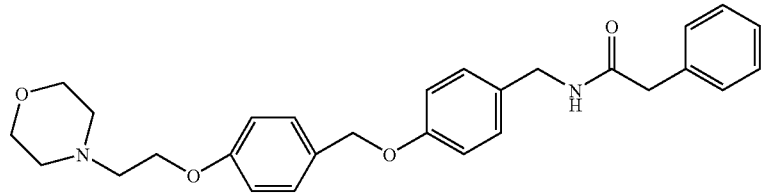
168
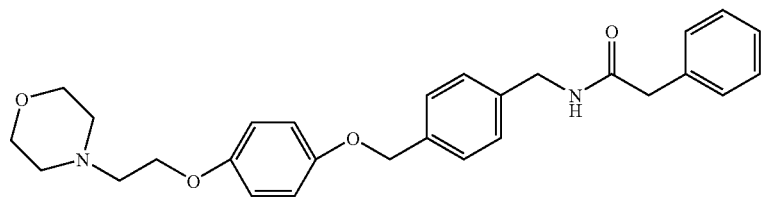
169
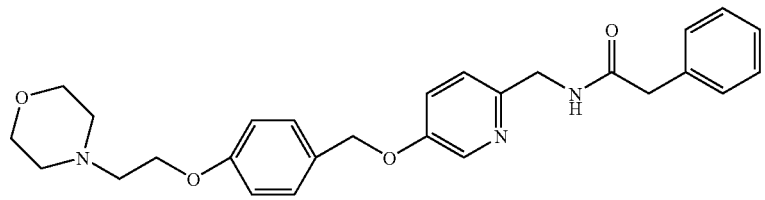
170
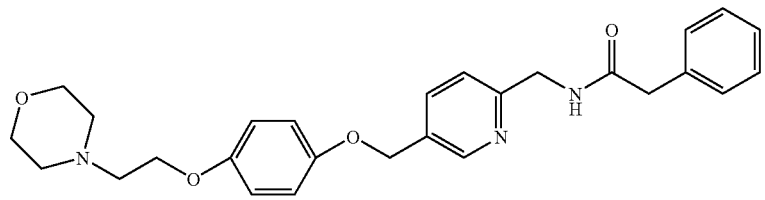
171
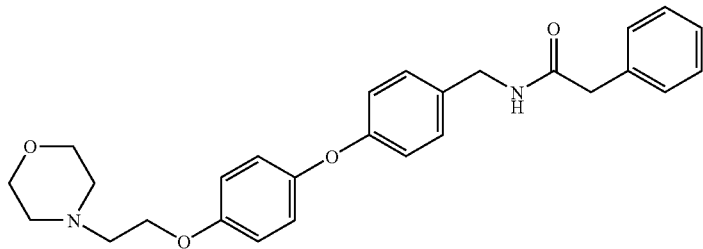
172
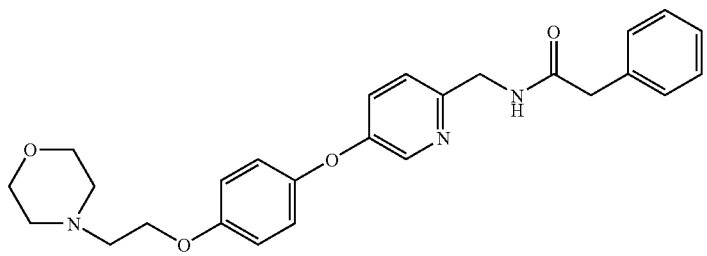
173
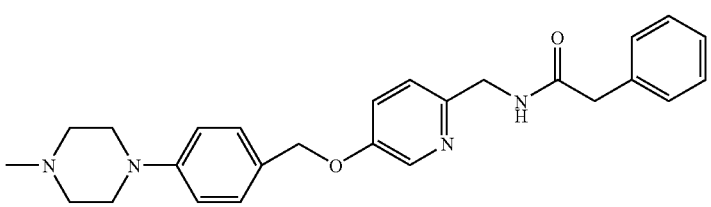

TABLE 1-continued
174
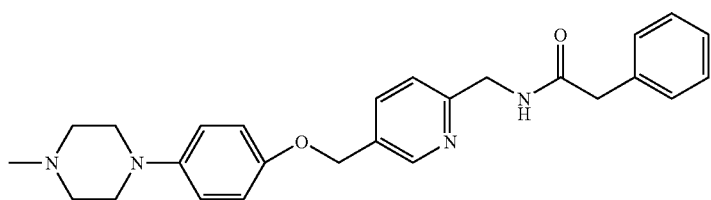
175
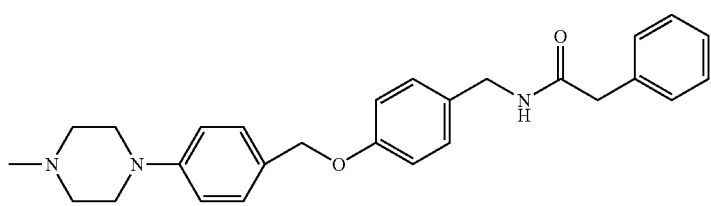
176
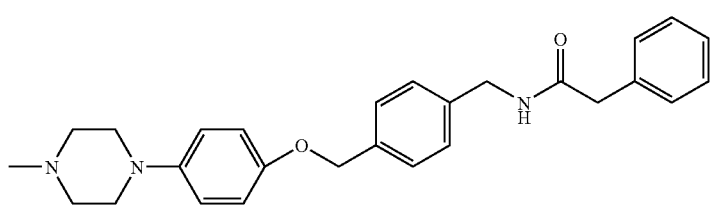
177
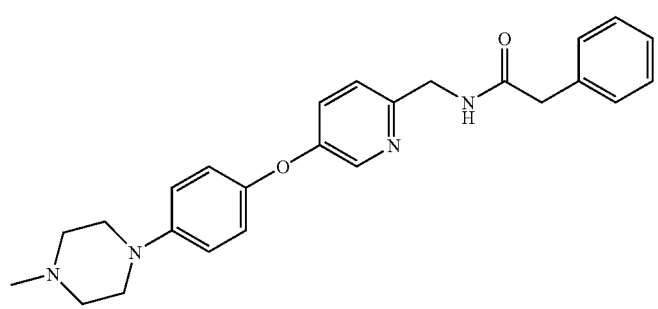
178
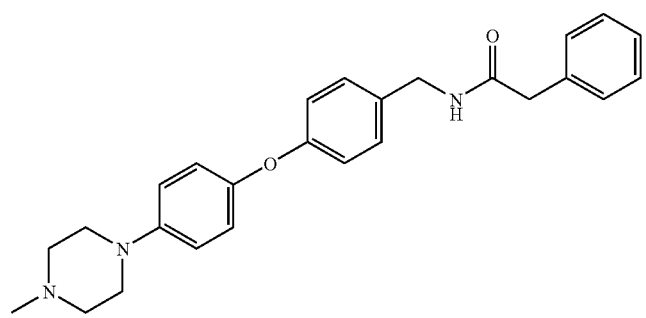
179
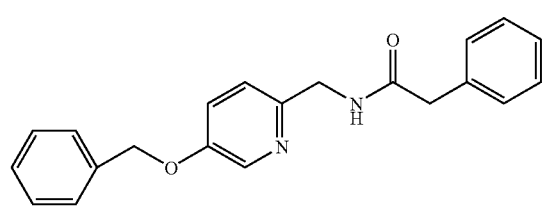

TABLE 1-continued

180

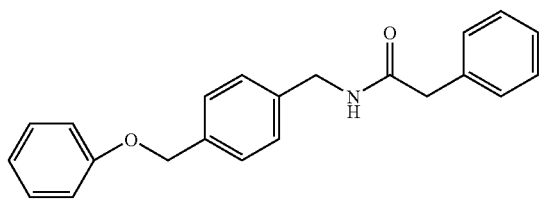

181

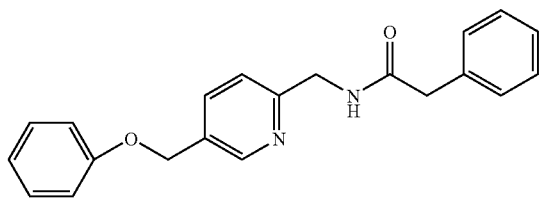

182

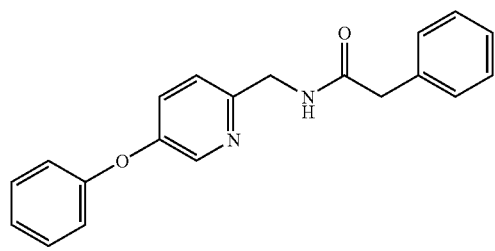

183

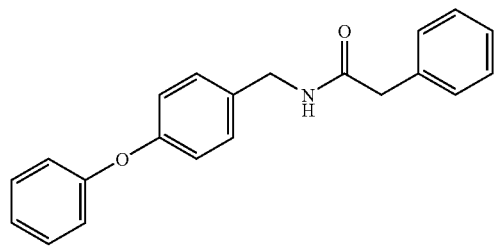

The invention includes a solvate of a compound according to Formula I. The invention includes a hydrate of a compound according to Formula I. The invention includes an acid addition salt of a compound according to Formula I. For example, a hydrochloride salt. In another embodiment, the invention includes a pharmaceutically acceptable salt. The invention includes a composition comprising a compound of Formula I and at least one pharmaceutically acceptable excipient.

The invention relates to a solvate of a compound according to one of Formulae I-CCCXIX. The invention also relates to a hydrate of a compound according to one of Formulae I-CCCXIX.

The invention also relates to an acid addition salt of a compound according to one of Formulae I-CCCXIX. For example, a hydrochloride salt e.g., a dihydrochloride salt.

Further, the invention relates to a prodrug of a compound according to one of Formulae I-CCCXIX.

The invention also relates to a pharmaceutically acceptable salt of a compound of one of Formulae I-CCCXIX.

The invention includes compositions comprising a compound according to one of Formulae I-CCCXIX and at least one pharmaceutically acceptable excipient.

Certain compounds of the invention are non-ATP competitive kinase inhibitors.

The invention also includes a method of preventing or treating a cell proliferation disorder by administering a pharmaceutical composition that includes a compound according to one of Formulae I-CCCXIX, or a salt, solvate, hydrate, or prodrug thereof, and at least one pharmaceutically acceptable excipient to a subject in need thereof. The invention also includes use of a compound of the invention in the manufacture of a medicament to prevent or treat a cell proliferation disorder.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriasis.

For example, the treatment or prevention of the proliferative disorder may occur through the inhibition of a tyrosine kinase. For example, the tyrosine kinase can be a Src kinase or focal adhesion kinase (FAK).

The invention relates to a method of treating or preventing a disease or disorder that is modulated by kinase inhibition, by administering a pharmaceutical composition that includes a compound according to one of Formulae I-CCCXIX, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection.

The pharmaceutical composition of the invention may modulate a kinase pathway. For example, the kinase pathway is a Src kinase pathway, or focal adhesion kinase pathway.

The pharmaceutical composition of the invention may modulate a kinase directly. For example, the kinase is Src kinase, focal adhesion kinase, or a JAK kinase.

Certain pharmaceutical compositions of the invention are non-ATP competitive kinase inhibitors.

For example, the compounds of the invention are useful to treat or prevent a microbial infection, such as a bacterial, fungal, parasitic or viral infection. The invention also includes use of a compound of the invention in the manufacture of a medicament to prevent or treat a microbial infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61; 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, and 183.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriasis. Anti-cancer agents include anti-metastatic agents.

The compound of the invention used as a pharmaceutical agent may be selected from Compounds 1-183. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, or 183.

In one aspect of the invention, a compound of the invention, for example, a compound of one of Formulae I-CCCXIX, is used to treat or prevent a cell proliferation disorder in an subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase or focal adhesion kinase (FAK). In another embodiment, the subject is a mammal. In another embodiment, prevention or treatment of the cell proliferation disorder, cancer or hyperproliferative disorder occurs through inhibition of JAK kinase e.g., JAK3 and/or JAK1. In one embodiment, the subject is human.

Another aspect of the invention includes a method of protecting against or treating hearing loss in a subject comprising administering a compound according to one of Formulae I-CCCXIX. The invention also includes use of a compound of the invention in the manufacture of a medicament to protect against or treat hearing loss.

In one embodiment, the compound inhibits one or more components of a kinase signaling cascade. In one embodiment, the compound is an allosteric inhibitor. In one embodiment, the compound is a peptide substrate inhibitor. In one embodiment, the compound does not inhibit ATP binding to the protein kinase. In one embodiment, the compound inhibits a Src family protein kinase. In one embodiment, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically e.g., by administering drops into the ear, intraarterially, intralesionally, by metering pump, or by application to mucous membranes. In another embodiment, the compound is administered with a pharmaceutically acceptable carrier.

In one embodiment, the compound is administered before initiation of hearing loss. In another embodiment, the compound is administered after initiation of hearing loss.

In one embodiment, the compound is administered in combination with a drug that causes hearing loss e.g., cis platinum or an aminoglycoside antibiotic. In one embodiment, the compound is administered in combination with a drug that causes hearing loss in order to reduce the amount of hearing loss. In another embodiment, the compound is administered in combination with a drug that targets hairy cells.

Another aspect of the invention includes a method of protecting against or treating osteoporosis in a subject comprising administering a compound according to one of Formulae I-CCCXIX. The invention also includes use of a compound of the invention in the manufacture of a medicament to prevent or treat osteoporosis.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before initiation of osteoporosis. In another embodiment, the compound is administered after initiation of osteoporosis.

Another aspect of the invention includes a method of protecting against or treating ophthalmic diseases e.g., macular degeneration, retinopathy, macular edema, etc. in a subject comprising administering a compound according to one of Formulae I-CCCXIX. The invention also includes use of a compound of the invention in the manufacture of a medicament to prevent or treat ophthalmic diseases.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment; the compound inhibits one or more components in the VEGF pathway. In another embodiment, the compound inhibits JAK kinase e.g., JAK1 and/or JAK3.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops to the eye), intraarterially, intralesionally, by metering pump, or by application to mucous membranes. In one embodiment, the compound is administered with a pharmaceutically acceptable carrier. In one embodiment, the compound is administered before initiation of the ophthalmic disease. In another embodiment, the compound is administered after initiation of ophthalmic disease.

Another aspect of the invention includes a method of protecting against or treating diabetes in a subject comprising administering a compound according to one of Formulae I-CCCXIX. The invention also includes use of a compound of the invention in the manufacture of a medicament to protect against or treat diabetes.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before initiation of the diabetes. In another embodiment, the compound is administered after initiation of disease.

Another aspect of the invention includes a method of protecting against or treating obesity in a subject comprising administering a compound according to one of Formulae I-CCCXIX. The invention also includes use of a compound of the invention in the manufacture of a medicament to protect against or treat obesity.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the subject is obese. In another embodiment, the compound is administered after the subject is obese.

Another aspect of the invention includes a method of protecting against or treating stroke in a subject comprising administering a compound according to one of Formulae I-CCCXIX. The invention also includes use of a compound of the invention in the manufacture of a medicament to protect against or treat stroke.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before a stroke has occurred. In another embodiment, the compound is administered after a stroke has occurred.

Another aspect of the invention includes a method of protecting against or treating atherosclerosis in a subject comprising administering a compound according to one of Formulae I-CCCXIX. The invention also includes use of a compound of the invention in the manufacture of a medicament to protect against or treat atherosclerosis.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of regulating immune system activity in a subject comprising administering a compound according to one of Formulae I-CCCXIX. The invention also includes use of a compound of the invention in the manufacture of a medicament to regulate immune system activity.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of protecting against or treating hepatitis B in a subject comprising administering a compound according to one of Formulae I-CCCXIX. The invention also includes use of a compound of the invention in the manufacture of a medicament to protect against or treat hepatitis B.

In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the subject has contracted hepatitis B. In another embodiment, the compound is administered after the subject has contracted hepatitis B.

Another aspect of the invention is a method of preventing or treating a cell proliferation disorder comprising administering to a subject in need thereof a compound having the Formulae I-CCCXIX. In one embodiment, the compound inhibits one or more components of a protein kinase signaling cascade. In another embodiment, the compound is an allosteric inhibitor. In another embodiment, the compound is a peptide substrate inhibitor. In another embodiment, the compound does not inhibit ATP binding to a protein kinase. In one embodiment, the compound inhibits a Src family protein kinase. In another embodiment, the Src family protein kinase is pp60$^{c\text{-}src}$ tyrosine kinase.

The invention is also drawn to a method of treating or preventing cancer or a proliferation disorder in a subject, comprising administering an effective amount of a compound of the invention, for example, a compound according to one of Formulae I-CCCXIX. For example, the compound of the invention may be a kinase inhibitor. The compound of the invention may be a non-ATP competitive kinase inhibitor. The compound of the invention may inhibit a kinase directly, or it may affect the kinase pathway.

In certain embodiments, the cell proliferation disorder includes any type of cancer including solid tumors and non-solid tumors. In specific embodiments the solid tumors are selected from tumors in the CNS (central nervous system), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas. In other embodiment, non-solid tumors include lymphoproliferative disorders including leukemias and lymphomas. In other embodiments a disorder is metastatic disease.

The compounds of the present invention are assayed for activity against a broad range of solid tumor cells, such as HT29 (Colon), SKOV-3 (Ovarian), PC3-MM2 (Prostate), L3.6pl (Pancreas), MDA231 (Breast), and A549 (Lung).

The compound of the present invention also may be used in the treatment of a cancer or cell proliferation disorder in combination therapy with one or more of anti-cancer treatments such as radiation therapy, and/or one or more anti-cancer agents selected from the group consisting of anti-proliferative agents, cytotoxic agents, cytostatic agents, and chemotherapeutic agents and salts and derivatives thereof. According to certain embodiments, the compound of the present invention may be used in the treatment of a cancer or cell proliferation disorder in combination therapy with any one of the drugs selected from a group consisting of an alkaloid, an alkylating agent, an antitumor antibiotic, an antimetabolite, an Bcr-Abl tyrosine kinase inhibitor, a nucleoside analogue, a multidrug resistance reversing agent, a DNA binding agent, microtubule binding drug, a toxin and a DNA antagonist. Those of skill in the art will recognize the chemotherapeutic agents classified into one or more particular classes of chemotherapeutic agents described above.

According to preferred embodiments, the compound of the present invention may be used in the treatment of a cancer or cell proliferation disorder in combination therapy with one or more agents selected from the group consisting of antimetabolites (e.g., gemcitabine), inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib), platinum complexes (e.g., oxaliplatin); and ABL kinase inhibitors (e.g., Gleevec or Imatinib).

Alkaloids include, but are not limited to, docetaxel, etoposide, irinotecan, paclitaxel (Taxol), teniposide, topotecan, vinblastine, vincristine, vindesine.

Alkylating agents include, but are not limited to, busulfan, improsulfan, piposulfan, benzodepa, carboquone, meturedepa, uredepa, altretamine, triethylenemelamine, triethylenephosphoramide, triethylenethiophosphoramide, Chlorambucil, chloranaphazine, cyclophosphamide, estramustine, ifosfamide, mechlorethamine, mechlorethamine oxide HCl, melphalan novemebichin, perfosfamide phenesterine, prednimustine, trofosfamide, uracil mustard, carmustine, chlorozotocin, fotemustine, lomustine, nimustine, semustine ranimustine, dacarbazine, mannomustine, mitobronitol, mitolactol, pipobroman, temozolomide.

Antibiotics and analogs thereof include, but are not limited to, aclacinomycins, actinomycin, anthramycin, azaserine, bleomycins, cactinomycin, carubicin, carzinophilin, cromomycins, dactinomycins, daunorubicin, 6-diazo-5-oxo-1-norleucine, doxorubicin, epirubicin, idarubicin, menogaril, mitomycins, mycophenolic acid, nogalamycine, olivomycins, peplomycin, pirarubicin, plicamycin, porfiromycin, puromycine, streptonigrin, streptozocin, tubercidin, zinostatin, zorubicin.

Antimetabolites include, but are not limited to, denopterin, edatrexate, mercaptopurine (6-MP), methotrexate, piritrexim, pteropterin, pentostatin (2'-DCF), tomudex, trimetrexate, cladribine, fludarabine, thiamiprine, ancitabine, azacitidine, 6-azauridine, carmofur, cytarabine, doxifluridine, emitefur, floxuridine, fluorouracil, gemcitabine, tegafur, hydroxyurea and urethan.

Platinum complexes include, but are not limited to, caroplatin, cisplatin, miboplatin, oxaliplatin.

Anti-mitotic agents or microtubule binding agents include, but are not limited to, vincristine, and vinblastine, and taxol.

When use in combination with additional anti-proliferation agents, the compounds of the present invention may enhance (e.g., synergize) the activity of these agents. Further, such synergism would permit the compounds of the present invention, additional anti-proliferation agents, or both to be administered at lower dosages, and/or may significantly enhance the anti-proliferation properties of the compounds at any given dose.

According to another embodiment, there is provided a method for treating leukemia in a host comprising administering to a patient a compound according to one of Formulae I-CCCXIX.

In another embodiment, there is provided a method for treating leukemia in a host comprising administering to a patient a therapeutically effective amount of a compound according to one of Formulae I-CCCXIX, as defined above, and at least one further therapeutic agent selected from the group consisting of anti-proliferative agents, cytotoxic agents, cytostatic agents, and chemotherapeutic agents and salts and derivatives thereof. According to certain embodiments, the compound of the present invention may be used in the treatment of a leukemia in combination therapy with one or more of the drugs selected from a group consisting of an alkaloid, an alkylating agent, an antitumor antibiotic, an antimetabolite, an Bcr-Abl tyrosine kinase inhibitor, a nucleoside analogue, a multidrug resistance reversing agent, a DNA binding agent, microtubule binding drug, a toxin and a DNA antagonist. Those of skill in the art will recognize the chemotherapeutic agents classified into one or more particular classes of drugs described above.

Leukemia is a malignant cancer of the bone marrow and blood and is characterized by the uncontrolled growth of blood cells. The common types of leukemia are divided into four categories: acute or chronic myelogenous, involving the myeloid elements of the bone marrow (white cells, red cells, megakaryocytes) and acute or chronic lymphocytic, involving the cells of the lymphoid lineage. Treatment of leukemia generally depends upon the type of leukemia. Standard treatment for leukemia usually involves chemotherapy and/or bone marrow transplantation and/or radiation therapy. See e.g., U.S. Pat. No. 6,645,972, hereby incorporated herein by reference in its entirety.

Chemotherapy in leukemia may involve a combination of two or more anti-cancer drugs. Approximately 40 different drugs are now being used in the treatment of leukemia, either alone or in combination. Other treatments for leukemia also include the reversal of multidrug resistance, involving the use of agents which decrease the mechanisms allowing the malignant cells to escape the damaging effects of the chemotherapeutic agent (and leads to refractoriness or relapses); and biological therapy, involving the use of monoclonal antibodies, in which toxins are attached to antibodies that react with the complementary antigen carried by the malignant cells; and cytokines (e.g., interferons, interleukins, colony-stimulating factors CSFs) which are naturally occurring chemicals that stimulate blood cell production and help restore blood cell counts more rapidly after treatment. Examples of these drugs include multidrug resistance reversing agent PSC 833, the monoclonal antibody Rituxan and the following cytokines: Erythropoetin and Epoetin, which stimulate the production of red cells; G-CSF, GM-CSF, filgrastim, and Sargramostim which stimulate the production of white cells; and thrombopoietin, which stimulate the production of platelets.

Many nucleoside analogues have been found to possess anticancer activity. Cytarabine, Fludarabine, Gemcitabine and Cladribine are some examples of nucleoside analogues which are currently important drugs in the treatment of leukemia. β-L-OddC ((−)-β-L-Dioxolane-Cytidine, Troxatyl®, from Shire BioChem. Inc.) is also a nucleoside analogue which was first described as an antiviral agent by Belleau et al. (EP 337713, herein incorporated by reference in its entirety) and was shown to have potent antitumor activity (K. L. Grove et al., Cancer Res., 55(14), 3008-11, 1995; K. L. Grove et al., Cancer Res., 56(18), 4187-4191, 1996, K. L. Grove et al., Nucleosides Nucleotides, 16:1229-33, 1997; S. A Kadhim et al., Can. Cancer Res., 57(21), 4803-10, 1997). In clinical studies, β-L-OddC has been reported to have significant activity in patients with advanced leukemia (Giles et al., J. Clin. Oncology, Vol 19, No 3, 2001).

Bcr-Abl tyrosine kinase inhibitors, such as STI-571 (Gleevec®, Imatinib mesylate, from Novartis Pharmaceuticals Corp.), have shown significant antileukemic activity and specifically in chronic myeologenous leukemia. STI-571, for example, has become a promising therapy in the group of patients targeting Bcr-Abl tyrosine kinase inhibition. However, despite significant hematologic and cytogenic responses, resistance to Bcr-Abl tyrosine kinase inhibitors occurs, particularly in the advanced phases of chronic myelogenous leukemia. Such resistance has been demonstrated for the Bcr-Abl tyrosine kinase inhibitors Imatinib, Dasatinib, AZD0530.

Accordingly, there is a great need for the further development of agents for the treatment of leukemia patients who have been previously treated with a Bcr-Abl tyrosine kinase inhibitor and have become resistant to the Bcr-Abl tyrosine kinase inhibitor. Thus, in another embodiment of the present invention, there is provide a method for treating leukemia in a host comprising administering to a patient that has been previously treated with a Bcr-Abl tyrosine kinase inhibitor and has become resistant to the Bcr-Abl tyrosine kinase inhibitor treatment, a therapeutically effective amount of a compound according to one of Formulae I-CCCXIX. Further, there is provided a method for combination therapy of leukemia in a host comprising administering to a patient a Bcr-Abl tyrosine kinase inhibitor in combination with a therapeutically effective amount of a compound according to one of Formulae I-CCCXIX. In an embodiment, the combination is administered to a patient that has become resistant to the Bcr-Abl tyrosine kinase inhibitor treatment.

The compounds of the present invention are assayed for anti-leukemia activity and can be compared to existing therapeutic agents (e.g., Dasatinib), for activity against a variety of cells, for example, K562 (CML), K562R (Gleevec resistant CML), MOLT-4 (Adult lymphoblastic leukemia), CCRF-HSB-2 (Adult lymphoblastic leukemia), Jurkat (Adult T cell leukemia), Ba/F3 (IL-3 induced), Ba/F3+WT BCR-Abl, Ba/F3+BCR-Abl E225K mutant, Ba/F3+BCR-Abl T3151 mutant.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

DEFINITIONS

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

The phrase "inhibits one or more components of a protein kinase signaling cascade" means that one or more components of the kinase signaling cascade are effected such that the functioning of the cell changes. Components of a protein kinase signaling cascade include any proteins involved directly or indirectly in the kinase signaling pathway including second messengers and upstream and downstream targets.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms or (2) relieving the disease state, i.e., causing temporary or permanent regression of the disease state or its clinical symptoms.

"Preventing" means cause the clinical symptoms of the disease state not to develop i.e., inhibiting the onset of disease, in a subject that may be exposed to or predisposed to the disease state, but does not yet experience or display symptoms of the disease state "Disease state" means any disease, disorder, condition, symptom, or indication.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

An "effective amount" of a compound of the disclosed invention is the quantity which, when administered to a subject having a disease or disorder, results in regression of the disease or disorder in the subject. Thus, an effective amount of a compound of the disclosed invention is the quantity which, when administered to a subject having a cell proliferation disorder, results in regression of cell growth in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as e.g., anti-cancer activity or anti-neoplastic activity. The combination of compounds optionally is a synergistic combination. Synergy, as described, for example, by Chou and Talalay, *Adv. Enzyme Regul*. vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

With respect to the chemical compounds useful in the present invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R^1$ at each occurrence is selected independently from the definition of $R_1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

Unless the number of carbons is otherwise specified, "lower alkyl" includes an alkyl group, as defined above, but having from one to ten, or in another embodiment from one to six, carbon atoms in its backbone structure. "Lower alkenyl" and "lower alkynyl" have chain lengths of, for example, 2-5 carbon atoms.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "substituted alkenyls" refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, aryl carbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyls" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]cyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "glycoside" means any molecule in which a sugar group is bonded through its anomeric carbon to another group. Examples of glycosides include, for example methyl α-D-glucopyranoside

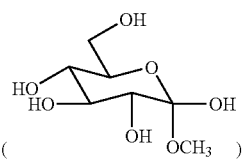

methyl β-D-glucopyranoside

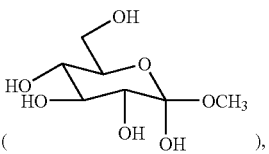

glucoside, galactoside, lactoside, lactosidoglycoside, maltoside, etc. Because a glycoside is bonded through its anomeric carbon to another group, it is also known as a non-reducing sugar (i.e., it is not subject to attack by reagents that attack carbonyl groups).

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" includes compounds and moieties that contain the acyl radical (CH$_3$CO—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "thiocarbonyl" or "thiocarboxy" includes compounds and moieties which contain a carbon connected with a double bond to a sulfur atom.

The term "ether" or "alkoxy" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In one embodiment, an anionic group is a carboxylate.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Calm et al, *Angew. Chem. Inter. Edit.* 1966, 5, 385; errata 511; Calm et al., *Angew. Chem.* 1966, 78, 413; Calm and Ingold, *J. Chem. Soc.* 1951 (London), 612; Cahn et al., *Experientia* 1956, 12, 81; Cahn, *J., Chem. Educ.* 1964, 41, 116).

"Geometric Isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorph" or "polymorph" or "crystal form" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomer" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this invention may exist in stereoisomeric form, therefore can be produced as individual stereoisomers or as mixtures.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I, where T is a bond are biaryl derivatives, and have a biaryl moiety as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996), incorporated herein by reference. Amide/peptide bioisosteres are also discussed, for example, in Ahn et al., Mini Reviews in Medicinal Chemistry 2, 463-473 (2002); Couve-Bonnaire et al., Org. Biomol. Chem. 5, 1151-1157 (2007); and Venkatesan and Kim, Curr. Med. Chem. 9, 2243-2270 (2002), each of which is incorporated herein by reference.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts thereof, is administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in. *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, the compound is prepared for oral administration, wherein the disclosed compounds or salts thereof are combined with a suitable solid or liquid carrier or diluent to form capsules, tablets, pills, powders; syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, tautomers or polymorphs thereof, can be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/ disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Synthesis

The compounds of the invention and related derivatives are synthesized by methods known to one skilled in the art.

Compound 125

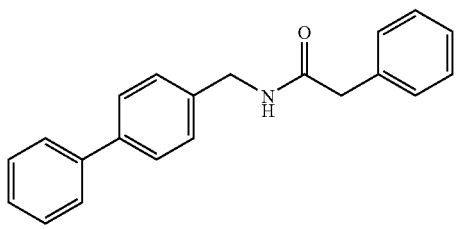

In a glass vial, phenylacetic acid (68 mg, 0.50 mmol, 1.0 eq), EDCI (106 mg, 0.55 mmol, 1.1 eq), and HOBT (68 mg, 0.50 mmol, 1.0 eq) were combined and dissolved in 1 ml DMF. DIEA (287 uL, 1.65 mmol, 3.3 eq) was added followed by 4-phenyl benzylamine (137 mg, 0.75 mmol, 1.5 eq). The mixture was stirred at 45° C. for 2 h. At the end of the two hours, the reaction mixture was poured in 10 ml 1N HCl solution and the precipitate was collected by vacuum filtration. The product was dried in a vacuum oven to give 95 mg of a colorless solid. (63% yield). $^1$H-NMR (DMSO-$d_6$) δ 3.50 (s, 2H), 4.32 (d, J=6 Hz, 2H), 7.24 (m, 1H), 7.30-7.37 (m, 7H), 7.46 (t, J=7.5 Hz, 2H), 7.63 (dd, J=8 Hz, 4H), 8.60 (t, 1H).

Compound 126

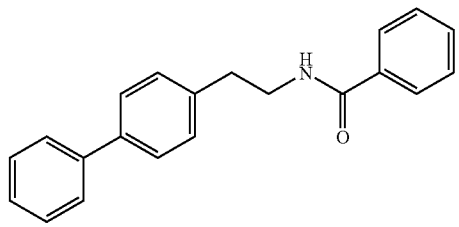

In a glass vial, benzoic acid (61 mg, 0.50 mmol, 1.0 eq), EDCI (106 mg, 0.55 mmol, 1.1 eq) and HOBT (68 mg, 0.50 mmol, 1.0 eq) were combined and dissolved in 1 ml DMF. DIEA (287 uL, 1.65 mmol, 3.3 eq) was added to the reaction followed by 4-phenyl-phenethylamine (148 mg, 0.75 mmol, 1.5 eq). The mixture was stirred at 45° C. for 2 h. At the end of the two hours, the reaction mixture was poured in 10 ml 1N HCl solution and the precipitate was collected by vacuum filtration. The product was dried in a vacuum oven to give 98 mg of a colorless solid. (67% yield). $^1$H-NMR (DMSO-$d_6$) δ 2.90 (t, J=7.5 Hz, 2H), 3.53 (q, J=7 Hz, 2H), 7.32-7.38 (m, 3H), 7.42-7.50 (m, 4H), 7.52 (t, J=7 Hz, 1H), 7.60-7.66 (dd, J=8 Hz, 4H), 7.84 (t, J=7 Hz, 2H), 8.61 (t, J=5.5 Hz, 1H).

Compound 127

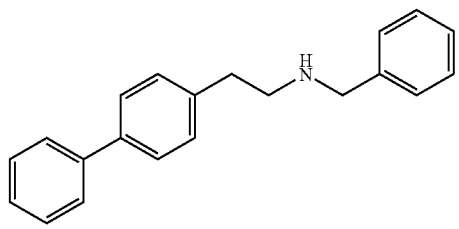

In an oven dried glass vial under an argon atmosphere 4-phenyl-phenethylamine (99 mg, 0.50 mmol, 1.0 eq) was dissolved in 2 ml of anhydrous THF. Benzaldehyde (53 mg, 0.50 mmol, 1.0 eq), sodium triacetoxyborohydride (148 mg, 0.7 mmol, 1.4 eq) and glacial acetic acid (43 uL, 0.75 mmol, 1.5 eq) were added sequentially. The reaction mixture was stirred for 2 hr at room temperature before being quenched with 5 ml 1M NaOH. The aqueous layer was extracted twice with diethyl ether. The combined ether extracts were washed with brine before being dried with anhydrous sodium sulfate. The sodium sulfate was removed by filtration prior to adding two drops of concentrated HCl. After 30 min a precipitate had formed that was isolated by filtration and dried in a vacuum oven. The hydrochloride salt of the desired product was obtained as a colorless solid 89 mg (55% yield). $^1$H-NMR (DMSO-$d_6$) δ 3.06 (m, 2H), 3.17 (m, 2H), 4.19 (s, 2H), 7.34-7.48 (m, 8H), 7.58-7.66 (m, 6H), 9.47 (bs, 2H).

Compound 128

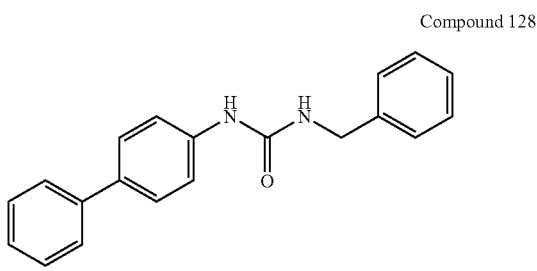

In a 10 mL microwave vial 4-phenylaniline (100 mg, 0.59 mmol, 1.0 eq) and benzylisocyanate (79 mg, 0.59 mmol, 1.0 eq) were dissolved in 3 mL of toluene. The reaction mixture was heated on a CEM microwave for 10 min at 100° C. The reaction was diluted with hexanes and the precipitate was collected by vacuum filtration. This solid was washed with hexanes and dried overnight in a vacuum oven. This gave 130 mg (73% yield) of the desired product as an off-white solid. $^1$H-NMR (DMSO-d$_6$) δ 4.32 (d, J=6, 2H), 6.66 (t, 1H), 7.26 (m, 1H), 7.30-7.35 (m, 5H), 7.43 (t, J=7.5 Hz, 2H), 7.51 (2H), 7.56 (2H), 7.62 (d, J=6 Hz, 2H), 8.68 (s, 1H).

Compound 129

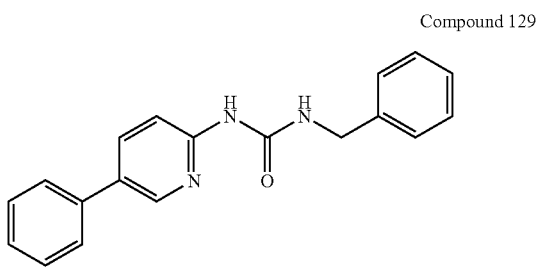

In a 10 mL microwave vial 2-amino-5-phenylpyridine (85 mg, 0.5 mmol, 1.0 eq) and benzylisocyanate (67 mg, 0.5 mmol, 1.0 eq) were dissolved in 1 ml dioxane: 3 ml toluene. The reaction mixture was heated on a CEM microwave for 10 min at 100° C. After the end of the reaction period, the reaction mixture (solution) was poured into 15 ml hexanes. The resulting precipitate was collected by vacuum filtration. This solid was recrystallized from ethanol water to give 79 mg (52% yield) of the desired product as a colorless solid. $^1$H-NMR (DMSO-d$_6$) δ 4.43 (d, J=6 Hz, 2H), 7.26 (m, 1H), 7.33-7.38 (m, 5H), 7.45-7.52 (m, 3H), 7.67 (d, J=6 Hz, 2H), 8.03 (abc sys, 1H), 8.52 (1H), 8.56 (bs, 1H), 9.43 (s, 1H).

Compound 130

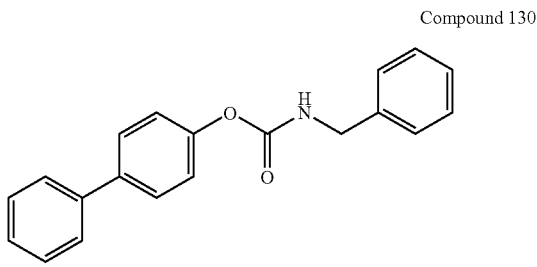

In a 10 mL microwave vial 4-phenylphenol (85 mg, 0.5 mmol, 1.0 eq), benzylisocyanate (67 mg, 0.5 mmol, 1.0 eq), and DIEA (96 uL, 0.55 mmol, 1.1 eq) were dissolved in 1 ml dioxane: 3 ml toluene. The reaction mixture was heated on a CEM microwave for 30 min at 100° C. After the end of the reaction period, the reaction mixture (solution) was poured into 15 ml hexanes. The resulting precipitate was collected by vacuum filtration. This solid was recrystallized from ethanol water to give 115 mg (76% yield) of the desired product as a colorless solid. $^1$H-NMR (DMSO-d$_6$) δ 4.31 (d, 2H), 7.20-7.40 (m, 8H), 7.48 (t, 3H), 7.67 (m, 3H), 8.40 (t, 1H).

Compound 134

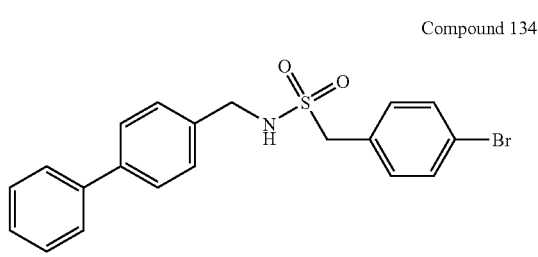

In a glass vial 4-phenylbenzylamine (92 mg, 0.5 mmol, 1.0 eq) and 4-bromobenzenesulfonyl chloride (135 mg, 0.5 mmol, 1.0 eq) were dissolved in 3 ml THF. DIEA (87 uL, 0.5 mmol, 1.0 eq) was added to the solution then the reaction was stirred at room temperature for 2 hr. The reaction mixture was poured in 10 ml 1N HCl and the resulting yellow precipitate was collected by vacuum filtration and washed with water. The desired product was purified by recrystallization from ethanol:water (1:1) to give 95 mg of a yellow solid (46% yield). $^1$H-NMR (DMSO-d$_6$) δ 4.53 (s, 2H), 7.20-7.40 (m, 5H), 7.47 (m, 3H), 7.55-7.67 (m, 6H), 9.98 (s, 1H).

Compound 135

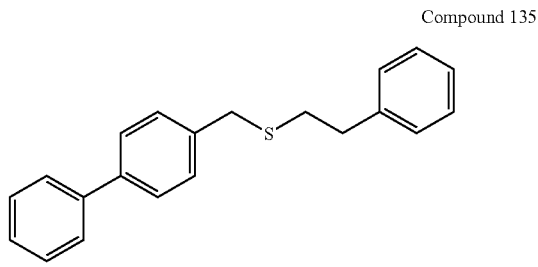

In a glass vial 4-phenybenzylbromide (247 mg, 1.0 mmol, 1.0 eq) was dissolved in 2 ml DCM. To this solution 2-phenylethanethiol (138 mg, 1.0 mmol, 1.0 eq) was added followed by DIEA (261 uL, 1.5 mmol, 1.5 eq). The reaction mixture was refluxed for 2 hr. At the end of the reaction period, the reaction mixture was diluted with DCM, washed with 1M HCl and brine before being dried anhydrous sodium sulfate. The DCM was then concentrated under vacuum and the residue was dissolved in 3 ml ethanol. This was added to 15 ml of 1M NaOH and the resulting precipitate was collected by vacuum filtration and dried in a vacuum oven overnight. This gave 185 mg of the desired product as a colorless solid (61% yield). $^1$H-NMR (DMSO-d$_6$) δ 2.66 (t, J=7.5 Hz, 2H), 2.82 (t, J=7.5 Hz, 2H), 3.81 (s, 2H), 7.20 (m, 3H), 7.28 (t, J=8 Hz, 2H), 7.36 (t, J=7 Hz, 1H), 7.40-7.48 (m, 4H), 7.60-7.68 (m, 4H).

Compound 139

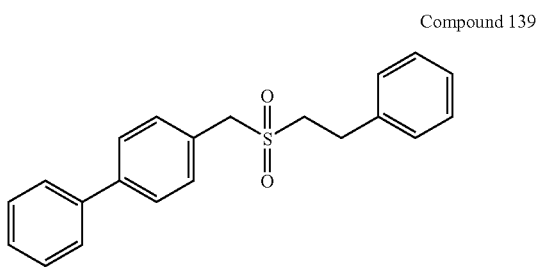

To a solution of 135 (168 mg, 0.5 mmol, 1.0 eq) in 3 ml DCM was added meta-chloroperoxybenzoic acid (70% dispersion, 371 mg, 1.5 mmol, 3.0 eq). The reaction mixture was stirred at room temperature for 2 hours. The reaction was diluted with DCM and the precipitate was filtered and dried to give 124 mg desired product as a colorless solid (74% yield). $^1$H-NMR (DMSO-d$_6$) δ 3.03 (t, J=8.5 Hz, 2H), 3.38 (t, J=8.5 Hz, 2H), 4.57 (s, 2H), 7.20-7.40 (m, 6H), 7.48 (m, 4H), 7.70 (t, 4H).

Compound 137

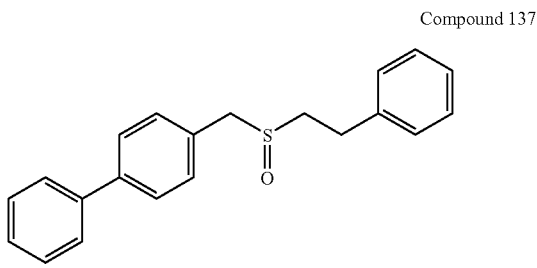

To a solution of 135 (168 mg, 0.5 mmol, 1.0 eq) in 3 ml DCM at −15 C was added meta-chloroperoxybenzoic acid (70% dispersion, 124 mg, 0.5 mmol, 1.0 eq) as a cooled solution in 1 mL DCM. The reaction was stirred at room temperature for approximately 2 hr. At the end of this period 10 ml hexane was added and the resulting precipitate was collected by vacuum filtration. This precipitate was recrystallized from ethanol: water to give 103 mg of the desired product as a colorless solid (64% yield). $^1$H-NMR (DMSO-d$_6$) δ 2.90-3.01 (m, 4H), 4.05 (d, J=8 Hz, 1H), 4.23 (d, J=8 Hz, 1H), 7.20-7.35 (m, 5H), 7.36-7.50 (m, 5H), 7.68 (d, J=7.5 Hz, 4H).

Compound 138

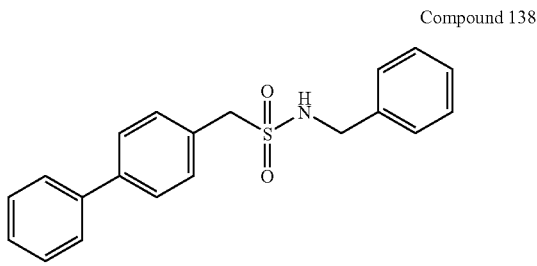

In a 10 mL microwave vial, 4-bromobenzenesulfonyl chloride (270 mg, 1.0 mmol, 1.0 eq) was dissolved in 2 ml THF. Benzylamine (321 mg, 3.0 mmol, 3.0 eq) was added to the THF solution and the mixture was stirred at room temperature for 2 hr. At the end of this period the reaction mixture was poured in 10 ml 1M HCl and the resulting precipitate was collected by vacuum filtration and dried. This yielded 302 mg of the desired bromo intermediate (89% yield). $^1$H-NMR (DMSO-d$_6$) δ 4.12 (d, J=6 Hz, 2H), 4.33 (s, 2H), 7.27-7.37 (m, 7H), 7.58 (d, J=8 Hz, 2H), 7.70 (t, 1H). This bromo intermediate (255 mg, 0.75 mmol, 1.0 eq) was combined with phenylboronic acid (137 mg, 1.125 mmol, 1.5 eq.), tetrakis (triphenylphosphine)palladium (87 mg, 0.075 mmol, 0.1 eq), and 1 ml 4M aqueous sodium carbonate solution in 3 mL 1,2-dimethoxyethane. The reaction mixture was heated on a CEM microwave reactor at 100° C. for 30 min. Upon standing crystals had formed in the reaction tube. These were isolated by vacuum filtration and dried in a vacuum oven to give 94 mg of the desired product as colorless crystals (37% yield). $^1$H-NMR (DMSO-d$_6$) δ 4.16 (d, J=6 Hz, 2H), 4.37 (s, 2H), 7.27 (m, 1H), 7.32-7.50 (m, 9H), 7.67-7.73 (m, 5H).

Compound 150

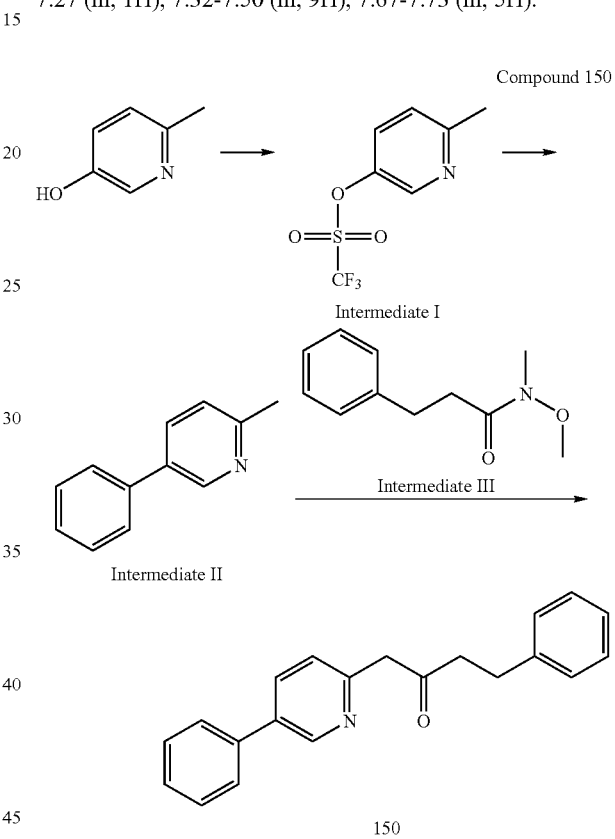

Intermediate I

In an oven dried vial under a nitrogen atmosphere 2-methyl-5-hydroxy pyridine (1.5 g, 13.8 mmol, 1.0 eq) in anhydrous pyridine (7.5 mL) was cooled to 0° C. Trifluoromethanesulfonic anhydride (3.88 g, 15.90 mmol, 1.15 eq.) was slowly added to the solution. After 30 minutes, the reaction was warmed to room temperature and stirred for 24 hours. The reaction was concentrated to half of its volume, diluted with deionized water, and extracted with ethyl acetate. The ethyl acetate layer was washed with 1M HCl and brine followed by drying with sodium sulfate. The crude product was purified by silica gel chromatography (hexanes/ethyl acetate gradient) to give 1.50 g of a brown oil (45% yield). $^1$H-NMR (CDCl$_3$) δ 2.58 (s, 3H), 7.26 (d, 8.4 Hz, 1H), 7.52 (dd, 2.8 Hz, 8.4 Hz, 1H), 8.47 (d, 2.8 Hz, 1H).

Intermediate II

In an oven dried flask under a nitrogen atmosphere 150 (Intermediate I) (1.0 g, 4.15 mmol, 1.0 eq), phenylboronic acid (0.56 g, 4.57 mmol, 1.1 eq) and tetrakis(triphenylphosphine)palladium(0) (0.24 g, 0.21 mmol, 0.1 eq) were combined. Degassed 1,2-dimethoxyethane (12 mL) and 2 M potassium carbonate in water (8.3 mL) were added. The reaction was heated to 90° C. for 24 hours. The DME was removed and the product was dissolved in ethyl acetate. The ethyl acetate was washed with brine and dried with sodium sulfate. The crude product was adsorbed onto silica gel and purified by silica gel chromatography (hexanes/ethyl acetate gradient) to give 260 mg of a colorless oil (37% yield). $^1$H-NMR (CDCl$_3$) δ 3.60 (s, 3H), 7.22 (d, 8.0 Hz, 1H), 7.38 (t, 7.2 Hz, 1H), 7.46 (t, 7.2 Hz, 2H), 7.56 (d, 8.0 Hz, 2H), 7.77 (dd, 2.4 Hz, 8.0 Hz, 1H), 8.73 (d, 2.4 Hz, 1H).

Intermediate III

In a glass vial N,O-dimethylhydroxylamine (0.49 g, 4.99 mmol, 1.0 eq), 3-phenylpropionic acid (0.75 g, 4.99 mmol, 1.0 eq), EDCI (1.05 g, 5.49 mmol, 1.1 eq), HOBT (0.68 g, 4.99 mmol, 1.0 eq), and DIEA (1.88 mL, 10.98 mmol, 2.2 eq) were combined in THF (10 mL) and DMF (1 mL) and stirred at room temperature for 48 hours. The THF was concentrated and diluted with ethyl acetate (10 mL). The reaction was washed with 1M HCl (2×10 mL), saturated sodium bicarbonate (2×10 mL), and brine (2×10 mL). The ethyl acetate layer was dried with sodium sulfate and the ethyl acetate was removed by vacuum to give the desired product as colorless solid (31% yield). $^1$H-NMR (CDCl$_3$) δ 2.80 (t, J=7.64 Hz, 2H), 3.02 (t, J=7.51, 2H), 3.24 (s, 3H), 3.66 (s, 3H), 7.24-7.37 (m, 5H).

Compound 150

In a glass vial under a nitrogen atmosphere 150 (Intermediate I) (130 mg, 0.89 mmol, 1.0 eq) was dissolved in anhydrous THF (2 mL) and cooled in an acetonitrile/dry ice bath for 30 minutes. A 1.6M solution of N-butyllithium in hexanes (0.44 mL, 0.80 mmol, 0.95 eq) was added and the reaction was stirred for 1 hour. A solution of 150 (Intermediate III) (150 mg, 0.89 mmol, 1.0 eq) in anhydrous THF (2 mL) was slowly added to the reaction and stirred continued for 1 hour. The reaction was quenched with 4 mL of 1M HCl and extracted three times with ethyl acetate. The ethyl acetate layers were combined and dried with sodium sulfate. The ethyl acetate was concentrated and purified by column chromatography (hexanes/ethyl acetate gradient) to give 51 mg of the desired product as a yellow solid (19% yield). LCMS mass ion peak 302 m/z.

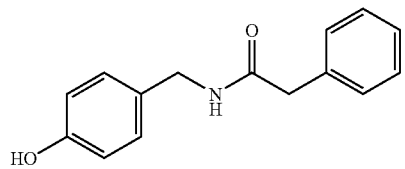

Phenol Intermediate I

In a glass vial 4-hydroxybenzylamine (1.00 g, 8.12 mmol, 1.0 eq), phenylacetic acid (1.11 g, 8.12 mmol, 1.0 eq), EDCI (1.71 g, 8.93 mmol, 1.1 eq), HOBT(1.10 g, 8.93 mmol, 1.0 eq), and DIEA (1.53 mL, 8.93 mmol, 1.1 eq) were combined in DMF (15 mL) and stirred overnight. The reaction was added to 0.5M HCl (30 mL) and stirred. The resulting precipitate was collected by vacuum filtration and placed in a vacuum oven overnight to give 1.04 g of the desired intermediate as an off-white solid (53% yield).

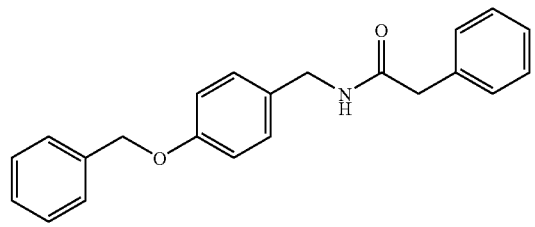

Compound 163

Phenol intermediate I (100 mg, 0.41 mmol, 1.0 eq), benzyl alcohol (50 uL, 0.43 mmol, 1.1 eq), and triphenylphosphine (140 mg, 0.52 mmol) were combined in a flame-dried vial under a nitrogen atmosphere. Anhydrous DCM (2 mL) was added and the solution was cooled to −10 C. Diisopropylazodicarboxylate (DIAD) (100 uL, 0.52 mmol, 1.25 eq) was added slowly over 5 minutes. After 30 minutes, the reaction was warmed to room temperature and stirred for 24 hours. The reaction was diluted with more DCM, washed with 1 M HCl (3×10 mL) and brine (2×10 mL), and dried over sodium sulfate. The DCM was concentrated and the residue purified by silica gel chromatography (hexanes/ethyl acetate gradient) to give 78 mg of the desired product as a colorless solid (54% yield). LCMS mass ion peak 332 m/z.

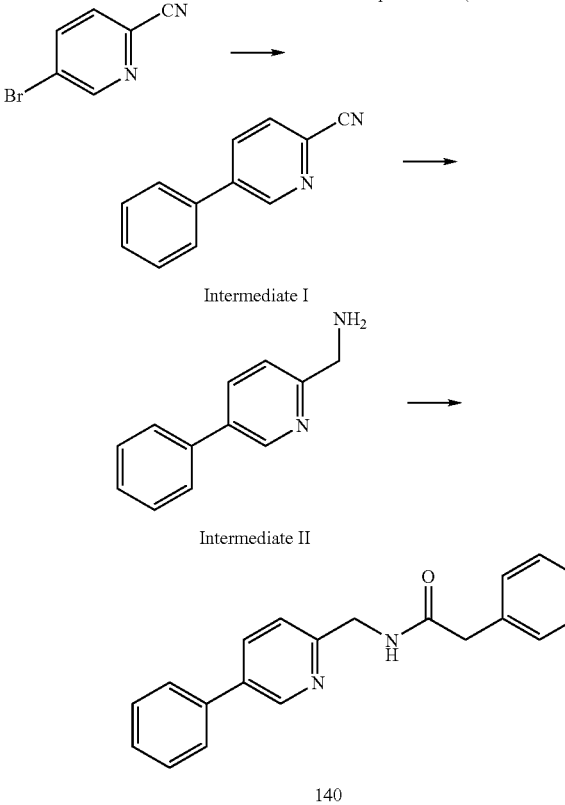

Compound 140 (Intermediate I)

140

In an oven dried flask under a nitrogen atmosphere 2-cyano-5-bromopyridine I (1.0 g, 5.46 mmol, 1.0 eq), phenylboronic acid (0.80 g, 6.55 mmol, 1.2 eq) and tetrakis(triphenylphosphine)palladium(0) (0.315 mg, 0.27 mmol, 0.05 eq) were combined. Degassed 1,2-dimethoxyethane (10 mL) and 2 M potassium carbonate in water (10 mL) were added. The reaction was heated to 90° C. for 24 hours. The DME was removed and the residue was taken up in ethyl acetate. The ethyl acetate was washed with brine and dried with sodium sulfate. The crude product was adsorbed onto silica gel and purified via column chromatography (hexanes/ethyl acetate gradient) to give 386 mg of a colorless oil (39% yield).

Compound 140 (Intermediate II)

In a Parr bottle 140 Intermediate I (386 mg, 2.14 mmol, 1.0 eq) was dissolved in methanol and a catalytic amount of Pd/C was added. The reaction was put under a hydrogen atmosphere (45-55 psi) for 48 hr. The reaction was filtered through celite and concentrated to give the desired product as a beige solid. LCMS mass ion peak 185 m/z.

Compound 140

In a glass vial 140 Intermediate II (50 mg, 0.27 mmol, 1.0 eq), phenylacetic acid (40 mg, 0.27 mmol, 1.0 eq), EDCI (50 mg, 0.30 mmol, 1.1 eq), HOBT(40 g, 0.27 mmol, 1.0 eq), and DIEA(51 µL, 0.30 mmol, 1.1 eq) were combined in DMF (1.5 mL) and stirred for 24 hours at room temperature. The reaction was diluted with ethyl acetate, washed with deionized water (3×10 mL) and brine (1×10 mL), and dried with sodium sulfate. The ethyl acetate was concentrated and purified by reverse phase C18 preparative HPLC to give 9 mg of the desired product as a brown oil (11% yield). LCMS mass ion peak 303 m/z.

Abbreviations bs—broad singlet; d—doublet; DCM—Dichloromethane; DIAD—Diisopropylazodicarboxylate; DIEA—N-ethyl-N,N-diisopropylamine; DME—1,2-dimethoxyethane; DMF—N,N-dimethylformamide; DMSO—Dimethylsulfoxide; HPLC—High pressure liquid chromatography; EDCI—1-Ethyl-3-(3'-dimethylaminopropyl)carbodiimide hydrochloride; EtOAc—Ethyl acetate; HCl—Hydrochloric acid; $^1$H-NMR—Proton Nuclear Magnetic Resonance; HOBT—Hydroxybenzotriazole; LCMS—Liquid chromatography mass spectrometry, m—multiplet; m/z—mass/charge; NaOH—Sodium hydroxide; q—quartet; s—singlet; t—triplet; THF—Tetrahydrofuran.

Example 2

Cell Growth Inhibition

The drug concentration required to block net cell growth by 50% relative to a control sample is measured as the $GI_{50}$. The $GI_{50}$s for several of the compounds of the invention are assayed as described herein.

Cell line and culture media—the human colon tumor cell line HT-29 was obtained from Dr. Irwin Gelman (Roswell Park Cancer Institute, Buffalo, N.Y.) and maintained in McCoy's 5A medium supplemented with 2% fetal bovine serum and penicillin-streptomycin. SYF/c-Src527F cell line was also obtained from Dr. Irwin Gelman and maintained in Dulbecco's modified Eagle's medium (DMEM) supplemented with 2% bovine serum and penicillin-streptomycin. Both cell lines were incubated in an atmosphere containing 5% $CO_2$ at 37° C.

Cell proliferation assay (MTT assay)-HT-29 (7,000 cells) and SYF/c-Src527F (4,000 cells) cells were plated in 120 µl of culture medium per well of 96-well plate. Cells were incubated overnight before drug treatment. Test compounds were diluted in culture medium in a separate 96-well plate to yield 10× concentrations of test dose (50 nM, 500 nM, 5 µM, 50 µM, and 500 µM). 13.3 µl of the 10× compound was added to each well of cells to achieve the final test concentrations (5 nM, 50 nM, 500 nM, 5 µM and 50 µM). After 3 days incubation, 10 µl of MTT (Thiazolyl Blue Tetrazolium Bromide, 5 mg/ml in PBS) was added to each well and incubate for 3 hours at 37° C. After removal of culture medium, 100 µl of isopropanol containing 40 mM HCl was added to each well and incubate for 10 minutes on a shaker to dissolve the MTT formazan. Optical density (OD) at 570 nm was then measured using microplate reader and cell growth inhibition (percentage of growth) by each concentration of drug was calculated as: % growth=100×[(T−$T_0$)/(C−$T_0$)] (T: OD of the test well exposure to test drug; C: OD of the control well without drug treatment; $T_0$: OD at time zero). Growth inhibition curves and GI50 were determined using GraphPad Prism 5 statistical software. Results are shown in Table 2 below.

TABLE 2

| Compound # | HT29 | SYF/c-Src527F |
| --- | --- | --- |
| 125 | 0.46 | 0.75 |
| 126 | 2.8 | 3.1 |
| 127 | 3.3 | 1.4 |
| 128 | 7.8 | 3.9 |
| 129 | 5.4 | 24.7 |
| 130 | 27.1 | 7.6 |
| 134 | 5.6 | 4.9 |
| 135 | 9.7 | 18.6 |
| 139 | 2.9 | 2.2 |
| 137 | 1.8 | 0.97 |
| 138 | 13.9 | 1.4 |
| 150 | 5.7 | 20.8 |
| 163 | 62.9 | 275.3 |
| 140 | 2.1 | 11.8 |
|  | 0.27 | 0.46 |

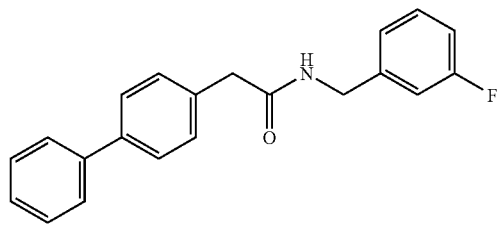

Control A

TABLE 2-continued

| Compound # | | HT29 | SYF/c-Src527F |
|---|---|---|---|
| 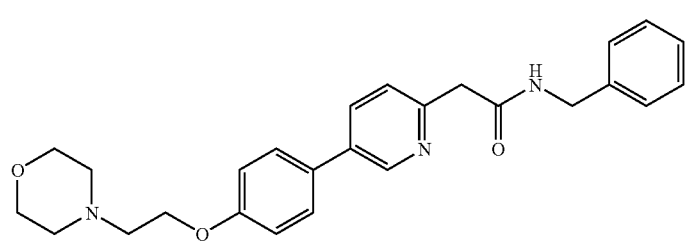 Control B | | 0.026 | 0.023 |

Example 3

Inhibition of Isolated Kinases

It is believed that the conformation of Src outside cells vs. inside cells is markedly different, because inside cells, Src is embedded in multiprotein signaling complexes. Thus, because the peptide substrate binding site is not well formed in isolated Src (as shown by Src x-ray structures), it is believed that the activity against isolated Src for a peptide substrate binding inhibitor would be weak. Binding to this site will require the inhibitor to capture the very small percentage of total Src protein in the isolated enzyme assay that is in the same conformation that exists inside cells. This requires a large excess of the inhibitor to drain significant amounts of the enzyme from the catalytic cycle in the assay.

However, inside cells this large inhibitor excess is not needed because the SH2 & SH3 domain binding proteins have already shifted the Src conformation so that the peptide substrate binding site is fully formed. Now, low concentrations of the inhibitor can remove the enzyme from the catalytic cycle since all of the enzyme is in the tight binding conformation.

KX2-328 is AstraZeneca's published ATP-competitive Src inhibitor (AZ28) and is used as a positive control in many of the'experiments described herein. Some of the compounds of the invention are expected to have weak activity against isolated kinases because the peptide binding site is not well formed outside of cells, but have very potent activity inside whole cells. Without wishing to be bound by theory, it is thought that the difference in activity is attributed to the fact that the peptide binding site is now fully formed in cells due to the allosteric effects of the binding protein partners in the multi-protein signaling complexes, relative to isolated kinase assays.

Isolated kinase activity against a variety of isolated kinases in the presence of a control, such as the AstraZeneca ATP-competitive inhibitor (KX2-328, AZ-28) relative to control (untreated) isolated kinases is measured. Isolated kinases include Abl(h), CHK1(h), EGFR(h), FGFR2(h), Fyn(h), IGF-1R(h), IR(h), Lck(h), Lyn(h), MAPK2(h), PDGFRβ(h), PKCα(h), Pyk2(h), Yes(h), ZAP-70(h), PI3 kinase., The AstraZeneca ATP competitive inhibitor shows the typical off target kinase inhibition activity for ATP-competitive inhibitors, poor selectivity as evidenced by strong inhibition of Abl, EGFRTK, Fyn, Lck, Lyn & Yes.

AZ28 is 10-100× less potent against cell growth than against isolated Src. This is typical of ATP competitive inhibitors since the concentration of competing ATP is much higher in whole cells than in the isolated enzyme assays.

Example 4

Effect of Compounds on JAK Phosphorylation/Activation Using Flow Cytometry

The protocol used to analyze the effect of compounds of the invention on JAK phosphorylation/activation is adapted from: Krutzik and Nolan, Cytometry Part A 55A:61-70 (2003).

Briefly, U-937 cells, histiocytic lymphoma cell line; ATCC No. CRL-1593.2, were treated with compounds of the invention or commercial JAK inhibitors. Cells were then stimulated with IL-4, to engage the JAK/STAT signaling pathway. Cells were fixed with formaldehyde to "freeze" the phosphorylation states of intracellular proteins. Cells were next permeabilized, and stained with mAbs directed against the phosphorylated STAT (pSTAT) proteins. The positive shift in fluorescence due to pSTAT staining serves as a surrogate to JAK phosphorylation/activation: no flow cytometric mAbs specific to JAKs exist, so the proximal downstream signaling event, STAT phosphorylation, is measured. A decrease in fluorescence, due to drug incubation prior to IL-4 stimulation, is an indirect indication of JAK inhibition. The following antibodies were used: apSTAT5-PE: monoclonal antibody to the intracellular STAT5a protein phosphorylated at Tyrosine 694; conjugated to the fluorochrome phycoerythrin (PE); BD No. 612567 and apSTAT6-Alex647: monoclonal antibody to the intracellular STAT6 protein phosphorylated at Tyrosine 641; conjugated to the fluorochrome Alexa Fluor 647; BD No. 612601. The detailed protocol is described below:

Resuspend U-937 cells @ $8 \times 10^5$ cells/mL in complete culture medium (RPMI-1640/10% FBS).

Add 0.5 mL cell suspension to each well of 24-well tissue culture plate.

Add drug treatment (compounds, controls) for 30 min @ 37° C., 5% $CO_2$.

Add cytokine/growth factor to stimulate; 15-30 min @ 37° C. (1 μL/0.5 mL cell suspension; IL-4, IL-2, IL-15=20 ng/mL)

Transfer cells to 5 mL Flow tubes.

Add 16% Formaldehyde directly to cell culture to obtain final concentration of 1.5% formaldehyde. (47 μL formaldehyde+0.5 mL cell culture)

Incubate cells in fixative for 15 min @ 37° C., 5% $CO_2$.

Add 3 mL cold "Staining Media" (PBS/1% BSA) to each tube; centrifuge cells @ 1100 RPM, 3 min. Discard supernatant.

Resuspend cells with vigorous vortexing in 200 μL ice-cold Methanol.

Incubate cells on ice, 30 min.

Wash cells twice in 2 mL "Staining Medium" (centrifuge cells @ 1100 RPM, 3 min). Discard supernatant.

Add 8 μL of fluorophore-conjugated, phosphoprotein-specific mAbs to cells. Incubate cells at RT, 60 min, in the dark.

Wash cells with 4 mL Staining Media. Centrifuge cells @ 1100 RPM, 3 min. Discard supernatant.

Resuspend cells in 350 μL Staining Media.

Acquire cellular events on BD FACSCalibur cytometer.

Results of the flow cytometry are shown in Table 3 below.

TABLE 3

| CMPD | JAK3 pStat5-PE | | JAK1 pStat6-Alexa647 | | Inhibition | |
|---|---|---|---|---|---|---|
| | Signal | Signal/ Background | Signal | Signal/ Background | JAK3 | JAK1 |
| — | 2.93 | 1.00 | 4.18 | 1.00 | NA | NA |
| IL-4 only | 5.54 | 1.89 | 29.64 | 7.09 | NA | NA |
| WHI-P131 | 3.19 | 1.09 | 33.80 | 8.09 | +++ | − |
| WHI-P154 | 1.63 | 0.56 | 14.54 | 3.48 | +++ | +++ |
| Control B | 3.42 | 1.17 | 19.03 | 4.55 | ++ | ++ |
| Control A | 4.12 | 1.41 | 23.79 | 5.69 | + | + |
| 125 | 4.58 | 1.56 | 29.48 | 7.05 | − | − |
| 126 | 5.34 | 1.82 | 30.85 | 7.38 | − | − |
| 127 | 3.38 | 1.15 | 18.81 | 4.50 | ++ | ++ |
| 128 | 3.96 | 1.35 | 20.26 | 4.84 | + | + |
| 129 | 4.15 | 1.42 | 23.06 | 5.51 | + | + |
| 130 | 5.21 | 1.78 | 31.77 | 7.60 | − | − |
| 134 | 3.66 | 1.25 | 21.47 | 5.14 | + | + |
| 135 | 3.48 | 1.19 | 17.15 | 4.10 | ++ | ++ |
| 139 | 4.41 | 1.51 | 25.08 | 6.00 | + | + |
| 137 | 3.71 | 1.27 | 22.03 | 5.27 | + | + |
| 138 | 4.10 | 1.40 | 28.65 | 6.85 | + | − |
| 150 | 3.36 | 1.27 | 14.48 | 3.81 | + | + |
| 163 | 3.24 | 1.22 | 15.35 | 4.04 | + | + |
| 140 | 3.02 | 1.14 | 13.76 | 3.62 | ++ | + |

Example 5

Effect of Compounds on Intracellular Phosphorylation Levels

The ability of compounds of the invention to inhibit Src kinase activity in whole cells is assayed, e.g., the effect of a compound of the invention on Src autophosphorylation in c-Src/NIH-3T3 cells; the effect of a compound on Src autophosphorylation in HT-29 cells; the effect of a compound on Src transphosphorylation in c-Src/NIH-3T3 cells; or the effect of a compound on Src autophosphorylation in HT-29 cells. Similar whole cell inhibition results are obtained for additional transphosphorylation substrates, i.e., FAK Y925 and paxillin Y31. Phosphorylations of PDGF Y572/574, EGF Y845, JAK1 Y1022/1023 & JAK2 Y1007/1008, Lck Y405 & ZAP70 Y319 are also assayed.

HT29 (colon cancer) and c-Src527F/NIH-3T3 (Src transformed) cell lines are treated with a compound of the invention or with AstraZeneca's ATP competitive Src inhibitor AZ28. AZ28 serves as a positive comparator to show what a validated Src inhibitor should do in these assays. After treatment with compound, cells are lysed, subjected to PAGE and probed with a battery of antibodies. The antibodies are selected to determine whether compounds caused changes in phosphorylation of known Src substrates. In addition, off-target protein phosphorylation is also investigated. Further, induction of apoptosis is evaluated via Caspase 3 cleavage. Multiple doses of each compound are tested because the trends in response to increasing drug concentration are the most reliable indicator of activity.

A dose response curve for a compound of the invention is generated using the $GI_{50}$ for this compound in each of the two cell lines as the 1× concentration. Three additional doses 0.2×, 5× & 25× multiples the $GI_{50}$'s are also tested in addition to a no drug control. The same range of multiples of the $GI_{50}$ for AZ28 in these two cell lines is run as a comparison. A dose response for Src-Y416 autophosphorylation indicates that a compound is a Src inhibitor inside cells.

Phosphorylation of FAK Tyr 925, a known Src transphorylation substrate within cells is also assayed. Inhibition of Src trans-phosphorylation indicates that a compound is a Src inhibitor inside cells.

Phosphorylation of Shc Y239/240, a known Src transphorylation substrate within cells is also assayed. Inhibition of Src trans-phosphorylation indicates that a compound is a Src inhibitor inside cells.

Phosphorylation of Paxillin Y-31, a known Src transphorylation substrate within cell, is also assayed. Inhibition of Src trans-phosphorylation indicates that a compound is a Src inhibitor inside cells.

Cleavage of Caspase-3 is a good measure of induction of apoptosis. It is known that AZ28 is not effective in inducing apoptosis in HT29 (colon cancer) and c-Src527F/NIH-3T3 (Src transformed) cell lines. Cleavage of Caspase-3 is assayed for the compounds of the invention. Effective cleavage indicates that a compound is effective in inducing apoptosis.

Since Src activity is very high in both HT29 (colon cancer) and c-Src527F/NIH-3T3 (Src transformed) cell lines, one would expect to see a reduction in the total phosphotyrosine levels when Src activity is inhibited. Phosphotyrosine levels are assayed for compounds of the invention and AZ28.

PDGF receptor tyrosine kinase autophosphorylates on Y572/574. This is thought not to be a direct Src substrate in cells. It is known that AZ28 is not a potent inhibitor of isolated PDGF receptor tyrosine kinase. Nevertheless, a dose response reduction in PDGF receptor autophosphorylation is seen with AZ28. This suggests that this is an indirect effect. Indirect PDGF autophoshorylation inhibition is assayed for the compounds of the invention.

FAK Y397 is mainly a FAK autophosphorylation site and only a poor Src transphorylation site. AZ28 is not a potent FAK inhibitor, nevertheless, some inhibition of FAK autophosphorylation in c-Src527F/NIH3T3 cells with AZ28 is seen. Inhibition of FAK autophosphorylation in c-Src527F/NIH3T3 and the NCI human colon cancer cell line HT29 is assayed for the compounds of the invention.

AZ28 is a potent EGFR tyrosine kinase inhibitor and AZ28 potently inhibits EGFR tyrosine kinase autophosphorylation. This site is not a direct Src phosphorylation site. The off target autophosphorylation of EGFRTK is assayed for the compounds of the invention.

The inhibition of autophosphorylation and transphosphorylation is correlated with the $GI_{50}$'s of compounds of the invention.

Example 6

Selectivity for Protein Tyrosine Kinases in Whole Cells

The selectivity of compounds of the invention for protein tyrosine kinases (PTKs) is assayed using methods described herein, and is compared to that of Dasatinib, an ATP-competitive Src inhibitor currently in clinical trials.

The selectivity of compounds for protein tyrosine kinases (PTKs) is assayed in whole cells such as SYF cells, which are mouse fibroblasts that lack the Src kinase family members Src, Yes and Fyn.

Example 7

IC$_{50}$ of Compounds and Dasatinib in Dasatinib-resistant Cell Lines

Cancer cell lines reported in current literature to be Dasatinib-resistant (i.e., COLO-320DM, H460, H226, and HCT-116) are cultured in the presence of the compound of the invention or Dasatinib control in order to determine the effect of the compound on cell growth inhibition. Cell proliferation/growth inhibition is assessed using a MTT colorimetric assay. Additionally, the IC$_{50}$ of both the compound of the invention and Dasatinib control is determined. Table 4 provides a list of the cell lines used in this growth inhibition study.

TABLE 1

| NAME | ATCC No. | TYPE |
|---|---|---|
| H460 | HTB-177 | NSCLC |
| H226 | CRL-5826 | NSCLC |
| COLO-320DM | CCL-220 | colorectal adenocarcinoma |
| HCT116 | CCL-247 | colorectal carcinoma |

COLO-320DM, H460, H226, and HCT-116 human cancer cell lines are routinely cultured and maintained in basal medium containing 2% FBS at 37° C., 5% CO$_2$. For the experiments, cells are seeded at 4.0×10$^3$/190 μL and 8.0×10$^3$/190 μL per well of 96-well plate in basal medium/1.5% FBS. Cells are cultured overnight (16 h) in 96-well plates at 37° C. in appropriate CO$_2$ conditions prior to test compound or Dasatinib addition.

For test compound or Dasatinib (BMS354825) dilutions, 20 mM stock solution samples are diluted serially in basal medium/1.5% FBS using 1:3 dilutions, yielding 20× concentrations in the 131 μM to 0.74 nM range. 10 μL of 20× dilutions are then added to appropriate wells containing 190 μL cancer cell lines, yielding 6561 nM to 0.037 nM range of final concentrations. The following controls are used: Vehicle control of cells and no sample; Medium Control of cells, no sample, and 0.03% DMSO.

Treated cancer cells are incubated for 3 Days (78 hours) at 37° C., appropriate CO$_2$ conditions. On Day 3, 10 μL MTT (5 mg/mL) is added to each well. Cells are then incubated in the presence of MTT for 4 hours at 37° C., appropriate CO$_2$ conditions. After this incubation period, 90 μL 10% SDS(+ HCl) is added to each well to lyse cells and solubilize formazan. Cells are then incubated overnight at 37° C., appropriate CO$_2$ conditions.

The OD$_{570}$ is measured using a microplate reader. Growth inhibition curves and EC$_{50}$/IC$_{50}$ are determined using GraphPad Prism 4 statistical software. Data is normalized to represent percent of maximum response. See, e.g., Johnson et al., Clin. Cancer Res 2005; 11(19) δ 6924-6932, Oct. 1, 2005 and Puputti et al., Mol Cancer Ther. 2006; 5 (12): 927-934, December 2006.

Example 8

Effect of Compounds on Dasatinib and Imatinib Resistant Leukemia Cells

Ba/F3 cells (See e.g., Palacios et al., Nature 309: 126-131 (1984); Palacios et al., Cell 41: 727-734 (1985)) are cultured in 96-well plates in complete media+IL-3. Cultures of Ba/F3 cells are also transfected to express wild-type (WT) Bcr-Abl, E255K mutation of Bcr-Abl, or T315I mutation of Bcr-Abl and cultured in 96-well plates in complete media without IL-3. The Ba/F3 cell line is rendered Gleevec resistant when the mutation in the Bcr/Abl tyrosine kinase E225K is present. The Ba/F3 cell line is rendered both Gleevec and Dasatinib resistant when the Bcr/Abl tyrosine kinase T315I mutation is present.

The cells of each group are treated with no drug, 0.1-10,000 nM Dasatinib, or 0.1-10,000 nM test compound in 10-fold dilutions for 96 hrs. MTT assays are performed (plate read) at 570 nM.

Dasatinib, also known as BMS-354825, is a drug produced by Bristol-Myers Squibb and sold under the trade name Sprycel®. Dasatinib is an oral dual BCR/ABL and Src family tyrosine kinases inhibitor approved for use in patients with chronic myelogenous leukemia (CML) after imatinib treatment and Philadelphia chromosome-positive acute lymphoblastic leukemia (Ph+ ALL). It is also being assessed for use in metastatic melanoma.

Imatinib is a drug used to treat certain types of cancer. It is currently marketed by Novartis as Gleevec (USA) or Glivec (Europe/Australia) as its mesylate salt, imatinib mesylate. It is used in treating chronic myelogenous leukemia (CML), gastrointestinal stromal tumors (GISTs) and a number of other malignancies.

Example 9

GI$_{50}$s/BrdU Assay

Evaluation of the GI50s in five cell lines (SKOV-3, K562, HT-29, A549 & MDA-MB-231) with a test compound or Dasatinib is assayed at T=0 and T=72 using BrdU.

For these experiments, cells are seeded in two 96-well plates per cell line with the cell number indicated below in 200 μL growth media containing 1.5% FBS. Cell lines being evaluated are: SKOV-2, K562, HT-29, A549, and MDA231. All are seeded at 1000 cells per well except HT-29 (2000 cells) and MDA MB 231 (5000 cells). The plates are incubated for 24 hours after seeding at 37° C.+5% CO$_2$. Except MDA231, this line is grown at 37° C. and 0% CO$_2$.

After 24 hours post-seeding, a test compound or Dasatinib is added at 128 nM, 64 nM, 32 nM, 16 nM, 8 nM, 4 nM, 2 nM, or 1 nM to 1 plate of each cell line. The test compound and Dasatinib treated sets of cell line plates are incubated for 72 hours at 37° C.+5% CO$_2$, except MDA231, this line is grown at 37° C. and 0% CO$_2$. The Brdu assay is performed at T=0 and T=72.

Growth Inhibition. The BrdU data is used to determine the % growth inhibition for each sample concentration using the formula:

$$GI=[(T_1-T_0)/(Con-T_0)]\times 100$$

where $T_0$=Fluorescence of cells at time 0; $T_1$=Fluorescence of treated cells at x hours; Con=Fluorescence of control cells at x hours. $T_1$ values$\leq T_0$ values are designated as T, cytotoxicity. The GI$_{50}$ is estimated using XLFit excluding $T_1$ values$\leq T_0$ (cytotoxicity).

Example 10

Combination GI$_{50}$ of Gemzar and Test Compound in the L3.6pl Cell Line Using the BrdU Assay Gemcitabine (Gemzar®) is a chemotherapy drug that is given as a treatment for types of cancer such as non-small cell lung cancer, pancreatic, bladder and breast cancer.

This study involves the evaluation of the $GI_{50}$ of Gemzar±Test Compound in the L3.6pl cell line assayed at T=0 and T=72 using the BrdU Assay (Roche: Catalog Number, 11647229001). L3.6pl cells, a human pancreatic cancer cell line, are seeded in three 96-well plates with 2000 cells/well for L3.6pl in 190 µl, growth media containing 1.5% FBS. L3.6pl cells are previously described in Trevino et al. Am J Pathol. 2006 March; 168(3):962-72, hereby incorporated herein by reference in its entirety. The cells are incubated for 18-24 hours after seeding at 37° C.+5% $CO_2$. After 24 hours, Gemzar+Compound, Gemzar, or Compound is added to the L3.6pl cells. Gemzar is evaluated at various concentrations, e.g., 8 nM, 4 nM, 2 nM, 1 nM, 0.5 nM, 0.25 nM, 0.125 nM, 0.063 nM. Compounds of the invention are evaluated at concentrations of, e.g., 100 nM, 50 nM, 25 nM, 12.5 nM, 6.25 nM, 3.125 nM, 1.56 nM, and 0.78 nM. Each sample treated plate is incubated for 72 hours at 37° C.+5% $CO_2$. The BrdU assay is performed at T=0 and again after 72 hours of incubation, T=72.

Example 11

Orthotopic Prostate Model for Measuring In Vivo Metastases

Nu/Nu mice (8-12 weeks of age) are injected with PC3-MM2 prostate cancer cells into the prostate as described previously in Pettaway et al., Clin Cancer Res 1996, 2:1627-1636, hereby incorporated herein by reference in its entirety. Fourteen days after orthotopic injection of PC3-MM2 cells, the mice are randomized into three groups: Dasatinib (15 mg/kg/day) treatment; Compound of the invention (e.g., 5 mg/kg/day or 10 mg/kg/day) treatment; and control (vehicle). Dasatinib, Compound, or vehicle is administered by oral gavage. All mice are sacrificed by cervical dislocation on about day 42. Tumor volume (measured by caliper), weight, and incidence of regional (celiac or para-aortal) lymph node metastases are recorded.

The human prostate cancer cell line, PC-3, is available from the American Type Culture Collection (ATCC; Manassas, Va.). The highly metastatic variant line (PC-3MM2) was established by several cycles of in vivo orthotopic implantation-metastatic selection, as previously described (Kim et al., Clinical Cancer Research 2003; 1200-10; Pettaway et al., Clinical Cancer Research 1996; 1627-36). For in vivo bioluminescence imaging, the PC-3MM2GL cells are produced by stably transfecting the green-fluorescent protein and luciferase (GL) fusion gene using vesicular stomatitis virus-G-pseudotyped retrovirus produced in 293GPG packaging cells (Ory et al., Proceedings of the National Academy of Sciences of the United States of America 1996; 11400-6).

Briefly, production of the retrovirus by the GL-transfected packaging cell line is initiated by replacing the tetracycline-containing media with fresh media. Virus containing supernatants are collected at two consecutive three-day intervals, filtered through 0.22 µm low protein-binding filters, and assayed for virus titer. PC-3MM2 cells are plated in 10 cm plates at a density of $2 \times 10^4/cm^2$ to achieve 50% confluence in 24 hours. A 1:1 mixture of retroviral supernatant and Dulbecco's Modified Eagle Media (DMEM)/Ham's F-12 media supplemented with 10% fetal bovine serum is added to the culture in presence of polybrene (6 µg/ml). After 48 hours incubation, the virus-containing supernatant is replaced with fresh media, and the cells are incubated additionally for 48 hours. The monolayer culture are then expanded into 15 cm dishes and assayed for green-fluorescent protein (GFP) expression by fluorescence-activated cell sorting (FACSCalibur; BD Bioscience, San Jose, Calif.). GFP-expressing cells are selected by FACSAria cell sorter (BD Bioscience, San Jose, Calif.) to enrich the population of GL-expressing PC-3MM2 cells. Two rounds of cell sorting enhances the percentage of GFP-positive cells to 88%. PC-3MM2GL cells are measured for luciferase activity by IVIS™ 200 bioluminescence imaging system (Xenogen Co., Alameda, Calif.). PC-3MM2GL cells maintain the metastatic potentials of the parental cells, determined by in vivo orthotopic mouse model.

Cells are maintained as monolayer cultures in DMEM/Ham's F-12 media supplemented with 10% fetal bovine serum and 1× penicillin-streptomycin (Gibco® Invitrogen Co., Carlsbad, Calif.), and incubated in 5% $CO_2$/95% air at 37° C. Cultures are free of mycoplasma and the following murine viruses: reovirus type 3; pneumonia virus; K virus; Theiler's encephalitis virus; Sendai virus; min virus; mouse adenovirus; mouse hepatitis virus; lymphocytic choriomeningitis virus; ectromelia virus; and lactate dehydrogenase virus (e.g., as assayed by M. A. Bioproducts, Walkersville, Md.).

Male athymic nude mice (NCr-nu/nu) are purchased from the National Cancer Institute-Frederick Animal Production Area (Frederick, Md.). The animals are housed and maintained under specific pathogen-free conditions. The mice are used at 8 to 12 weeks of age in accordance with the University of Texas M. D. Anderson Cancer Center institutional guidelines.

PC-3MM2GL cells are detached from subconfluent cultures by a brief exposure to 0.25% trypsin (Gibco® Invitrogen Co., Carlsbad, Calif.). Fresh media supplemented with 10% fetal bovine serum are added to produce single-cell suspension. Cell viability is determined by trypan blue exclusion, and only viable cells are counted using a hemacytometer under microscope. A desired number of cells are centrifuged and resuspended with $Ca^{2+}$- and $Mg^{2+}$-free Hank's Balanced Salt Solution (Gibco® Invitrogen Co., Carlsbad, Calif.).

Mice are anesthetized with pentobarbital sodium i.p. (0.5 mg per 1 g body weight) (Nembutal®, Abbott Laboratories, North Chicago, Ill.), and placed in a supine position. A midline incision is made on the lower abdomen and the prostate is exteriorized. Fifty microliters of HBSS containing 50,000 cells is injected into dorsum of the prostate. The incision is closed with surgical metal clips (Braintree Scientific Inc., Braintree, Mass.).

Three days after xenograft injection, mice are randomized into three groups receiving control vehicle, test compound (5.0 or 10.0 mg/kg body weight/day) or Dasatinib (15 mg/kg body weight/day). For oral administration, compounds are dissolved in double-distilled $H_2O$ or appropriate buffer, e.g., Dasatinib is dissolved in 80 mM citrate buffer (pH=3.1) according to the manufacturer's instruction. Total daily dosage of drug is divided by two and administered p.o. at 12-hour intervals, using 20-gauge gavage needle. Control group mice are administered with the equal volume of water by the same gavage technique. Mice are treated for 28 days.

At the end of four-week's treatment, mice are euthanized by pentobarbital sodium overdose (1 mg per 1 g body weight) four hours after the final drug or control diluent administration. Lymph node metastasis is assessed macroscopically and enlarged lymph nodes are harvested for pathologic examination. Tumors are surgically excised and weighed, followed by fixation in phosphate-buffered 10% formaldehyde. A part of tumor tissue is embedded in O.C.T. compound (Sakura Finetek, Torrance, Calif.), snap-frozen in liquid nitrogen, and stored at −80° C.

Statistical analyses are performed in SPSS 12.0 for windows (SPSS Inc., Chicago, Ill.). Mann-Whitney U test was conducted to compare differences in tumor weight. Incidences of tumors and lymph node metastases are compared between groups with Fisher's exact test. All statistical tests are two-sided.

Example 12

Protection Against Noise-Induced Hearing Loss Using PTK Inhibitors

Chinchillas are used in studies of noise-induced hearing loss. The animals' hearing sensitivity is measured using standard electrophysical techniques before the experimental manipulation. In particular, hearing thresholds are measured through evoked potentials from recording electrodes chronically implanted in the inferior colliculus, following standard laboratory procedures. Animals are anesthetized, the auditory bullae are opened, and the left and right cochleas are visualized. The round window leading to the scala tympani of the cochlea is used as the access point for drug application. Animals are treated with a compound of the invention or a control, such as AZ28, a non-ATP competitive inhibitor from AstraZeneca (KX2-238), emulsified in DMSO, in 1000 mM of saline solution, which is placed on the round window of one ear.

A control solution of 3 mM DMSO in 1000 mM of saline solution is placed on the round window of the other ear. The solution is allowed to set on the round window for 30 minutes, then the auditory bullae are closed. Subsequently, the animals are exposed to 4 kHz band noise at 105 dB SPL for four hours. Following the noise exposure, the animals' hearing is tested at day 1, day 7, and day 21 to determine evoked potential threshold shifts. Permanent threshold shift is assessed at day 21.

Average threshold shifts after exposure to 0.5 kHz, 1 kHz, 2 kHz, 4 kHz, and 8 kHz band noise on day 1 after experimental manipulation are assayed. Average threshold shifts after exposure to 0.5 kHz, 1 kHz, 2 kHz, 4 kHz, and 8 kHz band noise on day 7 after experimental manipulation are also assayed. Average threshold shifts after exposure to 0.5 kHz, 1 kHz, 2 kHz, 4 kHz, and 8 kHz band noise on day 21 after experimental manipulation are also assayed. If the average dB threshold shifts for ears treated with a compound of the invention are lower, it is an indication that the compound reduces the level of hearing loss in treated animals relative to the untreated control animals.

Example 13

Protection Against Cisplatin-Induced Hearing Loss Using PTK Inhibitors

The effects of high level noise and ototoxic drugs, such as cisplatin or the class of aminoglycosides, share several common features in the inner ear. First, the noise and/or drugs alter the free radical/antioxidant levels in the cochlea (inner ear). The increase in free radicals has been shown to be a causative factor in the apoptotic death of the sensory cells. Guinea pigs are used in studies of cisplatin-induced hearing loss. The animals' hearing sensitivity is measured using standard electrophysical techniques before the experimental manipulation. In particular, hearing thresholds are measured through evoked potentials from recording electrodes chronically implanted in the inferior colliculus, following standard laboratory procedures. Animals are anesthetized and treated with cisplatin. Subsequently, the animals' hearing is tested to determine evoked potential threshold shifts.

Threshold shifts for a number of guinea pigs after exposure to 2 kHz, 4 kHz, 8 kHz, 12 kHz, 16 kHz and 20 kHz band noise after treatment with cisplatin are assayed. Animals are treated subcutaneously with a compound of the invention prior to the cisplatin-induced hearing loss. Median CAP thresholds after cisplatin-induced hearing loss for both the untreated control animals and the treated animals are assayed.

The average threshold shifts (dB) in treated guinea pig cochleas and untreated control guinea pig cochleas after exposure to 2 kHz, 4 kHz, 8 kHz, 12 kHz, 16 kHz and 20 kHz band noise after treatment with cisplatin are measured.

Example 14

Effect of Compounds on Osteoclast Formation

To determine the effect of the compounds on osteoclast formation, the compounds are added to osteoclast precursors derived from spleen cells. For the generation of spleen-derived osteoclasts, spleen cells comprising osteoclast precursors are treated with Rapamycin, a compound of the invention, or a control, such as KX2-328 (AstraZeneca compound AZ28), for 5 days in the presence of receptor activator of nuclear factor-KB ligand (RANKL) and macrophage colony-stimulating factor (M-CSF). In in vitro murine or human osteoclast models, soluble RANKL enables osteoclast precursors to differentiate in the presence of M-CSF (Quinn, et al.; 1998, *Endocrinology*, 139, 4424-4427; Jimi, et al.; 1999, *J. Immunol.*, 163, 434-442). The untreated control cells are incubated in the presence of RANKL and M-CSF alone. Rapamycin is used as a positive control for the inhibition of osteoclast formation. Increasing concentrations of Rapamycin (e.g., 0.0001 µM, 0.001 µM, 0.01 µM, or 0.1 µM), test compound (e.g., 0.5 µM, 2.5 µM, 12.5 µM, or 20 µM), or KX2-328 (e.g., 0.02 µM, 0.1 µM, 0.5 µM, or 2.5 µM), are added to the spleen cells. The cells are then stained, and assessed for inhibition of osteoclast formation compared to the untreated control.

For generating spleen-derived osteoclasts, spleen cells are treated as described above. Increasing concentrations of Rapamycin (e.g., 0.1 nM, 1 nM, 10 nM, or 100 nM), test compound (e.g., 0.5 µM, 2.5 µM, 12.5 µM, or 20 µM), or AZ control KX2-328 (e.g., 0.02 µM, 0.1 µM, 0.5 µM, or 2.5 µM), are added to the spleen cells. Cells are then stained with the osteoclast marker, tartrate-resistant acid phosphatase (TRAP) to visualize differentiated cells. A reduction in the number of TRAP-positive osteoclasts relative to the number of TRAP-positive osteoclasts in the untreated control (Ctr) is measured.

Example 15

Effect of Compounds on Osteoclast Survival

To determine the effect of the compounds on osteoclast survival, osteoclasts are treated with Rapamycin, test compound, or AZ28 control, KX2-328 for 48 hours in the presence of RANKL and M-CSF. The untreated, control cells are incubated in the presence of RANKL and M-CSF alone. Rapamycin is used as a positive control for the inhibition of osteoclast survival. Increasing concentrations of Rapamycin (e.g., 0.001 µM, 0.01 µM, 0.1 µM, or 1 µM), test compound (e.g., 0.5 µM, 2.5 µM, 12.5 µM, or 20 µM), or AZ28 control, KX2-328 (e.g., 0.02 µM, 0.1 µM, 0.5 µM, or 2.5 µM) are added to the osteoclasts. The cells are stained and assayed for inhibition of the survival of osteoclasts compared to the untreated control.

As described above, osteoclasts are treated with Rapamycin, test compound, or AZ28 (KX2-328) 48 hours in the presence of RANKL and M-CSF. Increasing concentrations of Rapamycin (e.g., 0.1 nM, 1 nM, 10 nM, or 100 nM), test compound (e.g., 0.5 µM, 2.5 µM, 12.5 µM, or 20 µM), or AZ28 (e.g., 0.02 µM, 0.1 µM, 0.5 µM, or 2.5 µM) are added to the osteoclasts. Cells are then stained with TRAP and the number of TRAP-positive osteoclasts is counted.

Example 16

Effect of Compounds on Bone Resorption In Vitro

To determine the effects of the compounds on osteoclast formation on bone slices, the bone slices are treated with Rapamycin, test compound, or AZ28 (KX2-328). Increasing concentrations of Rapamycin (e.g., 0.1 nM, 1 nM, or 10 nM), test compound (e.g., 2.5 µM, 12.5 µM, or 20 µM), AZ28 (e.g., 0.1 µM, 0.5 µM, or 2.5 µM) are added to the bone slices. The number of osteoclasts on the bone slices is counted. The number of osteoclasts on the bone slices compared to the untreated control (Ctr) is counted.

During the resorption of bone, osteoclasts form resorption pits. To determine the effects of the compounds on resorption pit formation on bone slices, the bone slices are treated with Rapamycin, test compound, or AZ28, as described above. Increasing concentrations of Rapamycin (e.g., 0.1 nM, 1 nM, or 10 nM), test compound (e.g., 2.5 µM, 12.5 µM, or 20 µM), or AZ28 (e.g., 0.1 µM, 0.5 µM, or 2.5 µM) are added to the bone slices. The number of resorption pits on the bone slices is determined. A reduction in the number of resorption pits on the bone slices compared to the untreated control (Ctr) is measured.

Bone slices are treated as indicated above. Increasing concentrations of Rapamycin (e.g., 0.001 µM, 0.01 µM, or 0.1 µM), test compound (e.g., 2.5 µM, 12.5 µM, or 20 µM), or AZ28 (e.g., 0.1 µM, 0.5 µM, or 2.5 µM) are added to the bone slices. The bone slices are then stained with TRAP. A reduction in the number of TRAP-positive osteoclasts on the bone slices is compared to the untreated control.

Bone slices are treated as indicated above. Increasing concentrations of Rapamycin (e.g., 0.001 µM, 0.01 µM, or 0.1 µM), test compound (e.g., 2.5 µM, 12.5 µM, or 20 µM), or AZ28 (e.g., 0.1 µM, 0.5 µM, or 2.5 µM) are added to the bone slices. The bone slices are stained with Toluidine Blue to reveal resorption pits, which are indicators of osteoclast-mediated resorption of bone. A reduction in the number of resorption pits on the bone slices compared to the untreated control is measured.

Example 17

Effect of Compounds on Osteoblasts

The enzyme alkaline phosphatase has been used as an indicator of osteoblast activity, as it is involved in making phosphate available for calcification of bone. To determine the effects of the compounds of the invention on osteoblast activity, osteoblasts are treated with test compound (e.g., 0.5 µM, 2.5 µM, 12.5 µM, or 20 µM), or AZ28 (e.g., 0.02 µM, 0.1 µM, 0.5 µM, or 2.5 µM) and alkaline phosphatase expression is determined (nM alkaline phosphatase protein/min. As controls, osteoblasts are treated with medium alone, dimethyl sulfoxide (DMSO), or bone morphogenic protein-2 (BMP2). BMPs, defined as osteoinductive by their ability to induce osteogenesis when implanted in extraskeletal sites, are thought to mediate the transformation of undifferentiated mesenchymal cells into bone-producing osteoblasts.

To determine the effects of the compounds on osteoblast activity and protein expression, osteoblasts are treated with medium, DMSO, BMP2, test compound, or AZ28 (KX2-328) as indicated above. The protein concentration in cell lysates is determined (µg/10 µl).

Example 18

Effect of Compounds on Obesity

The following example illustrates that the compounds of the present invention could be used to treat obesity. The compounds are tested using a method described previously (Minet-Ringuet, et al.; 2006, *Psychopharmacology*, Volume 187, Number 4/September, 2006, pages 447-454, incorporated herein by reference). Male Sprague-Dawley rats initially weighing 175-200 g are housed in individual Plexiglas cages with an artificial 12:12-h light-dark cycle (lights on at 08:00 h) in a room maintained at 24±1° C. and 55±5% humidity. Food and water are available ad libitum throughout. All rats are fed with a medium fat diet (metabolizable energy 17.50 kJ/g) composed of 140 g/kg of whole milk protein, 538.1 g/kg of cornstarch, 87.6 g/kg of sucrose, and 137 g/kg of soya bean oil, and this diet is supplemented with minerals and vitamins (mineral salts 35 g/kg, vitamins 10 g/kg, cellulose 50 g/kg, and choline 2.3 g/kg). This food, named P14-L, which resembles the usual human diet (14% proteins, 31% lipids, and 54% carbohydrates) is prepared in the laboratory in the form of a powder.

Several doses of the compound of the instant invention are tested: e.g., 0.01, 0.1, 0.5, and 2 mg/kg, in addition to the control solution. The compound is solubilized in water and then incorporated into the diet. The basal food intake is recorded during the adaptation period and used to determine the daily quantity of the compound of the instant invention incorporated into food. The compound is mixed into the food in the laboratory. After 1 week of adaptation to the laboratory conditions, the rats are separated into five groups with homogenous weight and receive the compound of the instant invention in their food for 6 weeks. Weight is recorded three times per week. Body composition is measured at the end of the study by dissection and by weighing the main organs and tissues. Briefly, rats are deeply anesthetized by an intraperitoneal injection of an overdose of anesthetic (sodium pentobarbital 48 mg/kg) and heparinized (100 U heparin/100 g body weight). They are bled (to avoid coagulation in tissues) by sectioning the vena cava and abdominal aorta before removal and weighing of the main fresh organs (liver, spleen, kidneys, and pancreas) and tissues (perirenal and scapular brown adipose tissue, epididymal, retroperitoneal, visceral, and subcutaneous white adipose tissues (WATs), and carcass defined by muscles and skeleton). The compounds which reduce the body weight of the animals, may be used to treat obesity in a subject.

Example 19

Effect of Compounds on Insulin-Induced GLUT4 Translocation in 3T3-L1 Adipocytes

The following example illustrates that the compounds of the present invention could be used to treat diabetes. The compounds are tested using a method described previously (Nakashima, et al.; 2000, *J. Biol. Chem.*, 275, 12889-12895). Either control IgG, or the compound of the instant invention is injected into the nucleus of differentiated 3T3-L1 adipocytes on coverslips. Glutathione S-transferase fusion proteins are each coinjected with 5 mg/ml sheep IgG for detection purposes. Prior to staining, the cells are allowed to recover for a period of 1 h. Cells are starved for 2 hr in serum-free medium, stimulated with or without insulin (e.g., 0.5 nM or 17 nM) for 20 min and fixed.

Immunostaining is performed using rabbit polyclonal anti-GLUT4 (F349) (1 µg/ml). Each fluorescein isothiocyanate-positive microinjected cell is evaluated for the presence of plasma membrane-associated GLUT4 staining. Control cells are injected with preimmune sheep IgG and then processed in the same way as experimentally injected cells. As quantitated by immunofluorescent GLUT4 staining, insulin leads to an increase in GLUT4 translocation to the plasma membrane. Cells are incubated with wortmannin as a control to block basal and insulin-induced GLUT4 translocation. The compounds of the instant invention could stimulate insulin-induced GLUT4 translocation, which could indicate that administration of the compounds of the invention inhibited kinase activity, e.g., PTEN function, resulting in an increase in intracellular phosphatidylinositol 3,4,5-triphosphate levels, which stimulates GLUT4 translocation.

Example 20

Effect of Compounds on Retinal Neovascularization

The following example illustrates that the compounds of the present invention could be used to treat eye diseases, e.g., macular degeneration, retinopathy and macular edema. The effect of compounds on retinal neovascularization is determined using a model of retinal neovascularization as previously described (Aiello, et al.; 1995, *Proc. Natl. Acad. Sci.*, 92, 10457-10461). Briefly, C57Bl/6J mice are exposed to 75% $O_2$ from postnatal day 7 (P7) to P12 along with nursing mothers. At P12, the mice are returned to room air. Intraocular injections are performed at P12 and sometimes P14 as described below. At P17 the mice are sacrificed by cardiac perfusion of 4% paraformaldehyde in phosphate-buffered saline and the eyes are enucleated and fixed in 4% paraformaldehye overnight at 4° C. before paraffin embedding.

Mice are deeply anesthetized with tribromoethanol for all procedures. The lid fissure is opened (e.g., using a no. 11 scalpel blade) and the eye is proptosed. Intravitreal injections are performed by first entering the left eye with an Ethicon TG140-8 suture needle at the posterior limbus. A 32-gauge Hamilton needle and syringe are used to deliver the compound of the instant invention diluted in Alcon balanced salt solution through the existing entrance site. The eye is then repositioned and the lids are approximated over the cornea. Repeat injections are performed through a previously unmanipulated section of limbus 2 days later. As a control, equal amounts of saline are injected to the right eye.

Over 50 serial 6-µm paraffin-embedded axial sections are obtained starting at the optic nerve head. After staining with periodic acid/Schiff reagent and hematoxylin (Pierce, et al.; 1995, *Proc. Natl. Acad. Sci. USA.*, 92, 905-909; Smith et al.; 1994, *Invest. Ophthal. Vis. Sci.*, 35, 101-111), 10 intact sections of equal length, each 30 µm apart, are evaluated for a span of 300 p.m. Eyes exhibiting retinal detachment or endophthalmitis are excluded from evaluation. All retinal vascular cell nuclei anterior to the internal limiting membrane are counted in each section by a fully masked protocol. The mean of all 10 counted sections yield average neovascular cell nuclei per 6-µm section per eye. No vascular cell nuclei anterior to the internal limiting membrane are observed in normal, unmanipulated animals (Smith et al.; 1994, *Invest. Ophthal. Vis. Sci.*, 35, 101-111). Reduced neovascularization in the eyes treated with the compounds of the instant invention as compared to the eyes in the saline control group indicates, a positive result.

Example 21

Identification of Compounds that Modulate Kinase Signaling Cascade Associated with Stroke Many animal models for stroke have been developed and characterized, see e.g., Andaluz, et al., Neurosurg. Clin. North Am., vol. 13:385-393 (2002); Ashwal, S. and W. J. Pearce., Curr. Opin. Pediatr., vol. 13:506-516 (2001); De Lecinana, et al., Cerebrovasc. Dis., vol. 11(Suppl. 1):20-30 (2001); Ginsberg and Busto, Stroke, vol. 20:1627-1642 (1989); Lin, et al., J. Neurosci. Methods, vol. 123:89-97 (2003); Macrae, I. M., Br. J. Clin. Pharmacol., vol. 34:302-308 (1992); McAuley, M. A., Cerebrovasc. Brain Metab. Rev., vol. 7:153-180 (1995); Megyesi, et al., Neurosurgery, vol. 46:448-460 (2000); Stefanovich, V. (ed.)., Stroke: animal models. Pergamon Press, Oxford (1983); and Traystman, R. J., ILAR J. 44:85-95 (2003), each of which is hereby incorporated by reference in its entirety. For a review of animal models of focal (stroke) and global (cardiac arrest) cerebral ischemia, see e.g., Traystman, ILAR J., vol. 44(2):85-95 (2003) and Carmichael, NeuroRx®: The Journal of the American Society for Experimental NeuroTherapeutics, vol. 2:396-409 (2005, each of which is hereby incorporated by reference in its entirety.

Compounds that modulate cell death in stroke are identified using any of the art-recognized models for stroke. In the studies described herein, intra-arterial suture occlusion of the middle cerebral artery (MCA), a procedure known as MCAo, through the internal carotid artery is used as a model for cell death in stroke. In the control and test group of rats, the external carotid artery is transected, the common carotid artery is tied off, and the external carotid artery is then used as a pathway to pass a suture through the internal carotid artery, wherein the suture lodges in the junction of the anterior and middle cerebral arteries. To reduce subarachnoid hemorrhage and premature reperfusion, the suture is preferably coated with an agent such as silicone. The suture is used to occlude the MCA, e.g., for a duration of 60, 90, or 120 minutes and to permanently occlude the MCA.

In the test group, rats are administered a compound of the invention at a variety of times prior to, during and after occlusion of the MCA with the suture. The effects of the compound on the test group is compared to the effects observed in the control group, for example, by measuring the extent of cell death in each MCAo group. Typically, in the control group, the pattern of cell death follows a progression from early infarction in the striatum to delayed infarction in the dorsolateral cortex overlying the striatum. Striatal is mostly necrotic and occurs rapidly. The pattern of cell-death in the test group is compared to that of the control group to identify compounds that modulate cell death in stroke.

Example 22

Identification of Compounds that Modulate Kinase Signaling Cascade Associated with Atherosclerosis Many animal models for atherosclerosis have been developed and characterized. For a review of animal models of atherosclerosis, restenosis and endovascular graft research, see e.g., Narayanaswamy et al., JVIR, vol. 11(1): 5-17 (2000), which is hereby incorporated by reference in its entirety. Atherosclerosis is induced in a suitable animal model using a high fat/high cholesterol (HFHC) diet. The test animal is an animal that contains cholesterol ester transferase, such as the rabbit or the swine. The HFHC diet is produced, e.g., using commercial chow supplemented with fat. Cholesterol intake is between 0.5-2.0% of the diet. A test group of animals, e.g., rabbits or swine, receives a compound of the invention. The effect of the test compound is compared to the effects of atherosclerosis in the untreated, control group of animals. Effects that are compared include, for example, the degree of plaque formation, the number and/or frequency of myocardial infarctions observed in each group of animals, and the extent of tissue damage secondary to myocardial infarction exhibited in coronary tissue.

Myocardial infarction is studied using a variety of animal models such as rats and mice. The majority of myocardial infarctions result from acute transbotic occlusion of pre-existing atherosclerotic plaques of coronary arteries, which is mimicked in animal models by ligation of the left coronary artery in e.g., rats and mice. Myocardial infarction induces global changes in the ventricular architecture, a process called ventricular remodeling. The infarcted heart progressively dilates and accelerates the deterioration of ventricular dysfunction that eventually results in heart failure.

Myocardial ischemia is induced in test and control groups of animals, e.g., mice or rats, by ligating the left anterior descending coronary artery. The affected heart tissue is contacted with a compound of the invention, for example, by intraperitoneal (i.p.) injections, after the induction of ischemia. High resolution magnetic resonance imaging (MRI), dry weight measurements, infarct size, heart volume, and area at risk are determined 24 hours postoperatively. Survival rates and echocardiography are determined at various times postoperatively in the rats receiving injections of the compound of the invention. Other effects of the test compound are compared to the control group of rats. For example, changes in left ventricular geometry and function are characterized using echocardiography to compare end-diastolic diameters, relative wall thickness, and the percentage of fractional shortening. In excised hearts, the infarct size calculated and expressed as a percentage of left ventricular surface area.

Example 23

Identification of Compounds that Modulate Kinase Signaling Cascade Associated with Neuropathic Pain Many animal models for neuropathic pain, such as chronic neuropathic pain, have been developed and characterized, see e.g., Bennett & Xie, Pain, vol. 33, 87-107 (1988); Seltzer et al., Pain, vol. 43, 205-18 (1990); Kim & Chung, Pain, vol. 50, 355-63 (1992); Malmberg & Basbaum, Pain, vol. 76, 215-22 (1998); Sung et al., Neurosci Lett., vol. 246, 117-9 (1998); Lee et al., Neuroreport, vol. 11, 657-61 (2000); Decosterd & Woolf, Pain, vol. 87, 149-58 (2000); Vadakkan et al., J Pain, vol. 6, 747-56 (2005), each of which is hereby incorporated by reference in its entirety. For a review of animal models used for neuropathic pain, see e.g., Eaton, J. Rehabilitation Research and Development, vol. 40(4 Supplement):41-54 (2003), the contents of which are hereby incorporated by reference in their entirety.

Compounds that modulate neuropathic pain are identified using any of the art-recognized models for neuropathic pain. For example, the models for neuropathic pain generally involve injury to the sciatic nerve, although the method used to induce injury varies. For example, the sciatic nerve is injured due to partial constriction, complete transection, freezing of the nerve, and metabolic, chemical, or immune insults to the nerve. Animals with these types of nerve injury have been shown to develop abnormal pain sensations similar to those reported by neuropathic pain patients. In the studies described herein, the sciatic nerve of test and control groups of subjects, such as mice, are injured. In the test group, subjects are administered a compound of the invention at a variety of times prior to, during and after injury to the sciatic nerve. The effects of the compound on the test group are compared to the effects observed in the control group, e.g., through physical observation and examination of the subjects. For example, in mice, the subject's hindpaw is used to test the response to non-noxious stimuli, such as tactile stimulation, or to test the subject's response to stimuli that would be noxious in the course of ordinary events, for example, radiant heat delivered to the hindpaw. Evidence of allodynia, a condition in which ordinarily nonpainful stimuli evoke pain, or a hyperalgesia, the excessive sensitiveness or sensibility to pain, in the test subjects indicates that test compound is not effectively modulating neuropathic pain in the test subjects.

Example 24

Identification of Compounds that Modulate Kinase Signaling Cascade Associated with Hepatitis B Many animal models for hepatitis B have been developed and characterized. For a review of animal models of hepatitis B, see e.g., Guha et al., Lab Animal, vol. 33(7):37-46 (2004), which is hereby incorporated by reference in its entirety. Suitable animal models include, for example, the chimpanzee, tree shrews (non-rodent small animals that are phylogenetically close to primates, see Walter et al., Hepatology, vol. 24(1):1-5 (1996), which is hereby incorporated by reference in its entirety), and surrogate models such as the woodchuck, duck and ground squirrel. (See e.g., Tennant and Gerin, ILAR Journal, vol. 42(2):89-102 (2001), which is hereby incorporated by reference in its entirety).

For example, primary hepatocytes are isolated from livers of the tree shrew species tupaia belangeri and are infected with HBV. In vitro infection results in viral DNA and RNA synthesis in hepatocytes and secretion hepatitis B surface antigen (HBsAg) and hepatitis B e antigen (HBeAg) into culture medium. Tupaias can also be infected with HBV in vivo, resulting in viral DNA replication and gene expression in tupaia livers. Similar to acute, self-limited hepatitis B in humans HBsAg is rapidly cleared from serum, followed by seroconversion to anti-HBe and anti-HBs.

Compounds that modulate hepatitis B are identified using any of the art-recognized models for hepatitis B. In the studies described herein, test and control groups of animals, e.g., chimpanzees or tree shrews, are infected with HBV. In the test group, subjects are administered a compound of the invention at a variety of times prior to, during and after exposure to HBV. The effects of the compound on the test group are compared to the effects observed in the control group, e.g., through physical observation and examination of the subjects and through blood or serum analysis to determine at what point in time the infection is cleared from the subject. For example, assays are run to detect the presence and/or amount of hepatitis B virus called surface antigens and fragments thereof. Alternatively or in addition, the subject's liver is analyzed. Liver function tests analyze levels of certain proteins and enzymes, such as, for example, aspartate aminotransferase (AST, formerly serum glutamic-oxaloacetic transaminase (SGOT)) and alanine aminotransferase (ALT, formerly serum glutamate-pyruvate transaminase (SGPT)).

Example 25

The Effect of Compounds on Autoimmune Disease

The following example illustrates that the compounds of the present invention may be used to treat autoimmune diseases. The compounds are tested using a method described previously (Goldberg, et al.; 2003, *J. Med. Chem.*, 46, 1337-1349). The kinase activity is measured using DELFIA (dissociation enhanced lanthanide fluoroimmunoassay), which utilizes europium chelate-labeled anti-phosphotyrosine antibodies to detect phosphate transfer to a random polymer, poly-Glu4-Tyr1 (PGTYR). The kinase assay is performed in a neutravidin-coated 96-well white plate in kinase assay buffer (50 mM HEPES, pH 7.0, 25 mM MgCl2, 5 mM MnCl2, 50 mM KCl, 100 µM Na3VO4, 0.2% BSA, 0.01% CHAPS). Test samples (compounds of the instant invention) initially dissolved in DMSO at 1 mg/mL are prediluted for dose response (10 doses with starting final concentration of 1 µg/mL, 1-3.5 serial dilutions) with the assay buffer. A 25 µL aliquot of this diluted sample and a 25 µL aliquot of diluted enzyme (lck) (0.8 nM final concentration) are sequentially added to each well. The reaction is started with a 50 µL/well of a mixture of substrates containing 2 µM ATP (final ATP concentration is 1 µM) and 7.2 ng/µL PGTYR-biotin in kinase buffer. Background wells are incubated with buffer and substrates only. Following 45 min of incubation at room temperature, the assay plate is washed three times with 300 µL/well DELFIA wash buffer. A 100 µL/well aliquot of europium-labeled anti-phosphotyrosine (Eu$^{3+}$-PT66, 1 nM, Wallac CR04-100) diluted in DELFIA assay buffer is added to each well and incubated for 30 min at room temperature. Upon completion of the incubation, the plate is washed four times with 300 µL/well of wash buffer and 100 µL/well of DELFIA wash buffer. Enhancement solution (Wallac) is added to each well. After 15 min, timeresolved fluorescence is measured on the LJL's analyst (excitation at 360 nm, emission at 620 nm, EU 400 dichroic mirror) after a delay time of 250 µs. A compound of the instant invention that inhibits the kinase activity of lck indicates that the compound may be used to treat autoimmune disease in a subject.

Example 26

HBV Primary Assay

The HBV primary assay is conducted similarly to that described by Korba et al., (Antiviral Res. 15: 217-228 (1991) and Antiviral Res. 19: 55-70 (1992)) with the exception that viral DNA detection and quantification are improved and simplified (Korba et al., Antiviral Res. 19: 55-70 (1992)).

Compounds are evaluated for potential anti-HBV activity using a single high-test concentration of compounds in the standardized HepG2-2.2.15 antiviral assay. The HepG2-2.2.15 is a stable cell line producing high levels of the wild-type ayw1 strain of HBV. Briefly, HepG2-2.2.15 cells are plated in 96-well plates. Only the interior wells are utilized to reduce "edge effects" observed during cell culture; the exterior wells are filled with complete medium to help minimize sample evaporation. On the following day, the confluent monolayer of HepG2-2.2.15 cells is washed and the medium is replaced with complete medium containing test concentrations of a test article in triplicate. 3TC is used as the positive control, while media alone is added to cells as the untreated control. Three days later the culture medium is replaced with fresh medium containing the appropriately diluted Compound or control. Six days following the initial administration of the test compound, the cell culture supernatant is collected, treated with pronase and DNAse and then used in a real-time quantitative TaqMan PCR assay for direct measurement of HBV DNA copies using an ABI Prism 7900 sequence detection system (Applied Biosystems, Foster City, Calif.).

The antiviral activity of each test compound is calculated by comparing its HBV DNA copies against that of the untreated control cells (100%) to derive percent inhibition level. After removing the supernatant, the remaining cells are subject to CellTiter 96 Aqueous One (Promega, Madison, Wis.) solution cell proliferation assay (MTS-based) to measure cell viability. Cytotoxicity of the compound is determined by comparing its cell viability with that of the untreated cell control to derive percentage of the cell control.

Example 27

HCV Primary Assay

The ability of compounds of the invention to treat HCV is assayed e.g., according to the method of Pietschmann, et al., J. Virol. 76:4008-4021. The ET cell line is a human hepatoma cell line, Huh-7, harboring an HCV RNA replicon (genotype 1b) with a stable luciferase (Luc) reporter and three cell culture-adaptive mutations. The cells are grown in Dulbecco's modified essential media (DMEM), 10% fetal bovine serum (FBS), 1% penicillin-streptomycin (pen-strep), 1% glutamine, 5 mg/ml G418 in a 5% $CO_2$ incubator at 37° C. Cell culture reagents are from e.g., Mediatech (Herndon, Va.).

Example 28

Inhibition of Human IL-2 Dependent T-Cell Blast Proliferation

Therapeutic immunosuppression (TI) remains vital for prevention of chronic rejection of transplanted organs or tissues. Since JAK kinases play a critical role in the activation of T-cells, the JAK-selective inhibitory compounds described herein are used to treat and/or prevent many aspects of transplant rejection, and are particularly useful in the treatment and/or prevention of rejection reactions that are mediated, at least in part, by T-cells, such as the host versus graft reaction (HVGR). Modulation of immune activity through this novel mechanism is useful in the treatment of T cell proliferative disorders such as transplant rejection and autoimmune diseases. In one aspect, the JAK-selective compounds are used to treat and/or prevent chronic rejection in transplant recipients, such as renal transplant recipients.

JAK3 is a member of the Janus family of protein kinases. Although the other members of this family are expressed by essentially all tissues, JAK3 expression is limited to hematopoietic cells. This is consistent with its essential role in signaling through the receptors for IL-2, IL-4, IL-7, IL-9 and IL-15 by non-covalent association of JAK3 with the gamma chain common to these multichain receptors. X-Linked Severe Combined Immunodeficiency (XSCID) patient populations have been identified with severely reduced levels of JAK3 protein or with genetic defects to the common gamma chain, suggesting that immunosuppression should result from blocking signaling through the JAK3 pathway. Animal studies have suggested that JAK3 not only plays a critical role in B and T lymphocyte maturation, but that JAK3 is constitutively required to maintain T cell function.

Compounds of the invention are assayed in a screen which measures the inhibitory effect of compounds on IL-2 dependent T-Cell blast proliferation in vitro. Since signaling through the IL-2 receptor requires JAK-3, cell active inhibitors of JAK-3 should inhibit IL-2 dependent T-Cell blast proliferation. The cells for this assay are isolated from fresh human blood. After separation of the mononuclear cells using, e.g., Accuspin System-Histopaque-1077 (Sigma #A7054), primary human T-Cells are isolated by negative selection using, e.g., Lympho-Kwik T (One Lambda, Inc., Cat #LK-50T). T-Cells are cultured at 1–2×10$^6$/ml in Media (RPMI+10% heat-inactivated fetal calf serum (Hyclone Cat #A-1111-L)+1% Penicillin/Streptomycin (Gibco)) and induced to proliferate by the addition of 10 ug/ml PHA (Murex Diagnostics, Cat #HA 16). After 3 days at 37° C. in 5% $CO_2$, cells are washed 3 times in Media, resuspended to a density of 1-2×10$^6$ cells/ml in Media plus 100 Units/ml of human recombinant IL-2 (R&D Systems, Cat #202-IL). After 1 week, the cells are IL-2 dependent and can be maintained for up to 3 weeks by feeding twice weekly with equal volumes of Media+100 Units/ml of IL-2.

To assay for a test compound's ability to inhibit IL-2 dependent T-Cell proliferation, IL-2 dependent cells are washed 3 times, resuspended in media and then plated (50,000 cells/well/0.1 ml) in a Flat-bottom 96-well microtiter plate (Falcon #353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% $CO_2$ for 72 hours. Plates are then pulsed with $^3$H-thymidine (0.5 uCi/well) (NEN Cat #NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An $IC_{50}$ value (uM) is determined from this plot.

Suitable animal models of transplant rejection, such as models of the host versus graft reaction (HVGR) are described in O'Shea et al, 2004, Nature Reviews Drug Discovery 3:555-564; Cetkovic-Curlje & Tibbies, 2004, Current Pharmaceutical Design 10:1767-1784; and Chengelian et al, 2003, Science 302:875-878. Ordinarily skilled artisans can routinely adapt such information to determine dosages suitable for human administration.

Example 29

Effect of Compounds on Experimental Allergic Encephalomyelitis (EAE)

In order to determine whether a JAK inhibitor of the present invention is involved in the activation or inhibition of lymphocytes, such as "CD28" and "CTLA-4," model rats for experimental allergic encephalomyelitis (EAE), a model for multiple sclerosis (MS), are produced, and the effect of the JAK inhibitor compounds in the model are analyzed.

An emulsion to be used as immunogen is prepared by mixing Hartley guinea pig cerebrospinal homogenate (800 mg/ml physiological saline) with the same amount of Freund's complete adjuvant. Immunization is performed by intradermally injecting the emulsion into left and right foot pads of 15 Lewis rats (female, 6-week-old) in an amount of 0.25 ml per footpad. The administration (immunization) is adjusted so as for the dosages of the homogenate prepared to be 200 mg per rat. This immunization so induces experimental allergic encephalomyelitis (EAE).

The rats so immunized are divided into three groups of five rats each, and any one of (1) to (3) below is intravenously injected into mice of each group immediately after immunization (day 0), and 3, 6, 9, and 12 days after the immunization.
(1) Test compound JAK kinase inhibitor (dosage: 2 mg/ml PBS, 5 mg/kg)
(2) Prednisolone, steroid agent (dosage: 4 mg/ml PBS, 10 mg/kg)
(3) Control (dosage: 2 mg/ml PBS, 5 mg/kg)

Symptoms are observed in the course of time after the immunization. After the onset of EAE is been found, the degree of the symptoms are estimated by scoring, based on the following criteria.
(Score 1) Disappearance of tension of a tail
(Score 2) Dragging of hind legs, and slight paralysis
(Score 3) Dragging of hind legs, and serious paralysis
(Score 4) Paralysis of the whole body, or death In the group to which the control is administered, the symptom of EAE is expected to reach the peak (maximum score) at day 11 to 15 after the immunization, and then gradually recover. In contrast, in the presence of a JAK kinase inhibitor, the symptom of EAE at day 11 after the immunization is significantly inhibited. This inhibitory effect is expected to be higher than that in the prednisolone-administered group.

Results of these experiments indicate whether a compound is a JAK inhibitor, and if it functions in the induction of immune response such as the lymphocyte activation induced by immunization by foreign antigens, potentially indicating a compound useful for treating multiple sclerosis.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:
1. A compound according to Formula I

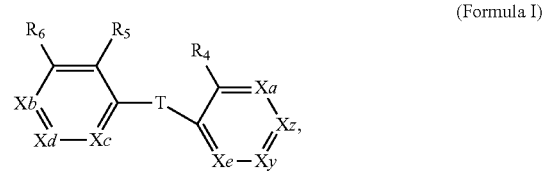

(Formula I)

or a salt thereof, wherein:
T is a bond;
$X_y$ is CY, N, or N—O;
$X_z$ is CZ;
Y is selected from hydrogen, hydroxyl, halogen, $C_1$, $C_2$, $C_3$, $C_4$, $C_5$, or $C_6$ alkyl, $C_3$, $C_4$, $C_5$, $C_6$, $C_7$ or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$)alkyl-aryl, ($C_3$, $C_4$, $C_5$, $C_6$, $C_7$, or $C_8$)cycloalkyl-aryl, and O-benzyl;
$X_a$ is $CR_a$;
$X_b$ is $CR_b$;

$X_c$ is $CR_c$;

$X_d$ is $CR_d$;

$X_e$ is $CR_e$;

$R_a$, $R_d$, $R_e$, $R_4$, and $R_6$ are, independently, hydrogen, hydroxyl, halogen, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COOH, COO—($C_1$, $C_2$, $C_3$, $C_4$, $C_5$, or $C_6$) alkyl, $SO_2H$, $SO_2$—($C_1$, $C_2$, $C_3$, $C_4$, $C_5$, or $C_6$) alkyl,

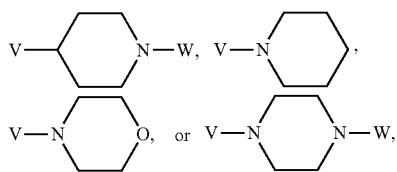

wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_b$ is hydroxyl, halogen, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COOH, COO—($C_1$, $C_2$, $C_3$, $C_4$, $C_5$, or $C_6$) alkyl, $SO_2H$, $SO_2$—($C_1$, $C_2$, $C_3$, $C_4$, $C_5$, or $C_6$) alkyl,

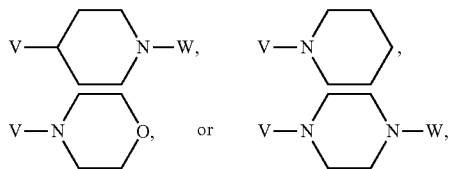

wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—;

or T is $OCH_2$, or $CH_2O$; wherein $R_b$ is hydrogen, hydroxyl, halogen, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COOH, COO—($C_1$, $C_2$, $C_3$, $C_4$, $C_5$, or $C_6$) alkyl, $SO_2H$, $SO_2$—($C_1$, $C_2$, $C_3$, $C_4$, $C_5$, or $C_6$) alkyl,

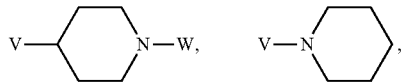

-continued

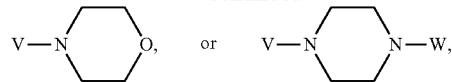

wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_c$ and $R_5$ are, independently, hydrogen, hydroxyl, halogen, $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkoxy, O—($C_1$, $C_2$, $C_3$, $C_4$, $C_5$, or $C_6$) alkyl-aryl, O—($C_3$, $C_4$, $C_5$, $C_6$, $C_7$, or $C_8$) cycloalkyl-aryl, O-benzyl, $C_1$, $C_2$, $C_3$, $C_4$, $C_5$, or $C_6$ alkyl-OH, $C_3$, $C_4$, $C_5$, $C_6$, $C_7$, or $C_8$ cycloalkyl-OH, COO—($C_1$, $C_2$, $C_3$, $C_4$, $C_5$, or $C_6$) alkyl, $SO_2H$, $SO_2$—($C_1$, $C_2$, $C_3$, $C_4$, $C_5$, or $C_6$) alkyl,

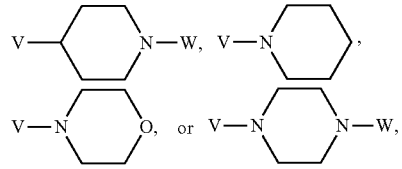

wherein W is H, or $C_1$, $C_2$, $C_3$, $C_4$, $C_5$, or $C_6$ alkyl, $C_3$, $C_4$, $C_5$, $C_6$, $C_7$, or $C_8$ cycloalkyl, $C_1$, $C_2$, $C_3$, $C_4$, $C_5$, or $C_6$ alkyl-aryl, $C_3$, $C_4$, $C_5$, $C_6$, $C_7$ or $C_8$ cycloalkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

Z is —$(CR_1R_{1'})_n$—$NR_2$—C(O)—$(CR_3R_{3'})_m$—B,

B is Ar or —$(CR_{22}R_{23})_s$-J;

Ar is unsubstituted aryl, unsubstituted nitrogen-containing heteroaryl group, aryl substituted with D, or nitrogen-containing heteroaryl group substituted with D;

J is selected from $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, COOH, $COOR_{30}$, and $CONR_{31}R_{32}$; further wherein alkyl, cycloalkyl, non-aromatic heterocycle, and partially unsaturated carbocycle are optionally substituted with D;

D is selected from halogen, $C_1$, $C_2$, $C_3$, $C_4$, $C_5$, or $C_6$ alkoxy, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, ($C_1$, $C_2$, $C_3$, $C_4$, $C_5$, or $C_6$)alkyl-non-aromatic heterocycle, ($C_3$, $C_4$, $C_5$, $C_6$, $C_7$, or $C_8$)cycloalkyl-non-aromatic heterocycle, ($C_1$, $C_2$, $C_3$, $C_4$, $C_5$, or $C_6$)alkyl-partially unsaturated carbocycle, ($C_3$, $C_4$, $C_5$, $C_6$, $C_7$, or $C_8$)cycloalkyl-partially unsaturated carbocycle, —$OR_{26}$, —$SR_{27}$, —$NR_{28}R_{29}$, and —$(CR_{24}R_{25})_t$—U;

U is cyano, —$OR_{26}$, —$SR_{27}$, $C_1$, $C_2$, $C_3$, $C_4$, $C_5$, or $C_6$ alkyl, $C_3$, $C_4$, $C_5$, $C_6$, $C_7$, or $C_8$ cycloalkyl, non-aromatic heterocycle, partially unsaturated carbocycle, C(O)$NR_{28}R_{29}$, COOH, $SO_3H$, $OSO_3H$, $PO_3H_2$, $OPO_3H_2$, $NH_2$, $NHR_{19}$, $NR_{19}R_{20}$, $SO_2R_{21}$, or glycoside;

$R_{22}$ and $R_{23}$ are independently selected from H, $C_1$, $C_2$, $C_3$, $C_4$, $C_5$, or $C_6$ alkyl, and $C_3$, $C_4$, $C_5$, $C_6$, $C_7$, or $C_8$ cycloalkyl;

R$_{24}$ and R$_{25}$ are independently selected from H C$_1$, C$_2$, C$_3$, C$_4$, C$_5$, or C$_6$ alkyl, and C$_3$, C$_4$, C$_5$, C$_6$, C$_7$, or C$_8$ cycloalkyl;

R$_{26}$, R$_{27}$, R$_{28}$, and R$_{29}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl, or together R$_{28}$ and R$_{29}$ form a ring;

R$_{30}$, R$_{31}$ and R$_{32}$ are independently selected from H, C$_1$, C$_2$, C$_3$, C$_4$, C$_5$, or C$_6$ alkyl, and C$_3$, C$_4$, C$_5$, C$_6$, C$_7$, or C$_8$ cycloalkyl, or together R$_{31}$ and R$_{32}$ form a ring;

s is 0, 1, 2, 3, 4, 5, 6, 7, 8, 9, or 10;

t is 0, 1, 2, 3, 4, 5, or 6;

p is 0, 1 or 2;

m is 1 or 2;

n is 0, 1 or 2; and

R$_1$, R$_{1'}$, R$_2$, R$_3$, and R$_{3'}$ are independently H or C$_1$, C$_2$, C$_3$, C$_4$, C$_5$, or C$_6$ alkyl, or C$_3$, C$_4$, C$_5$, C$_6$, C$_7$, or C$_8$ cycloalkyl.

2. The compound of claim 1, wherein m and n are independently selected from 1 and 2.

3. The compound of claim 1, wherein R$_1$ and R$_{1'}$ are both hydrogen.

4. The compound of claim 1, wherein R$_2$ is hydrogen.

5. The compound of claim 1, wherein R$_3$ and R$_{3'}$ are both hydrogen.

6. The compound of claim 1, wherein X$_y$ is N.

7. The compound of claim 1, wherein T is a bond.

8. The compound of claim 1, wherein B is Ar.

9. The compound of claim 1, wherein B is —(CR$_{22}$R$_{23}$)$_s$-J.

10. The compound of claim 9, wherein J is non-aromatic heterocycle.

11. A composition comprising a compound of claim 1 and at least one pharmaceutically acceptable carrier or excipient.

12. The compound of claim 1, wherein T is OCH$_2$, or CH$_2$O, and R$_b$ is hydrogen.

13. The compound of claim 1, wherein Xy is CY, further wherein Y is hydrogen.

14. The compound of claim 1, wherein n and m are both 1.

15. The compound of claim 1, wherein R$_4$, R$_5$, and R$_6$ are each hydrogen.

16. The compound of claim 1, wherein R$_2$ is hydrogen.

17. The compound of claim 8, wherein Ar is substituted with D, wherein D is selected from halogen, C$_1$, C$_2$, C$_3$, C$_4$, C$_5$, C$_6$ alkyl and non-aromatic heterocycle.

18. A compound selected from

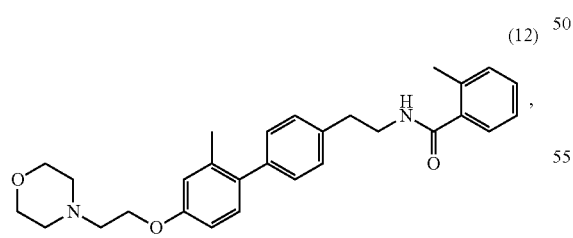

(12)

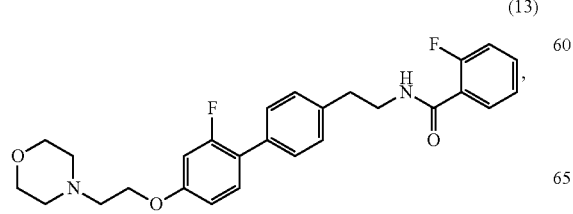

(13)

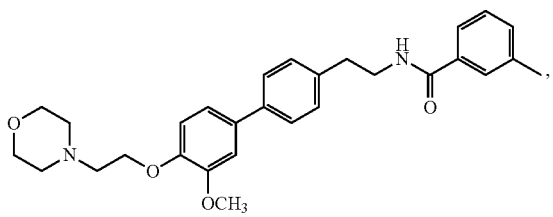

(14)

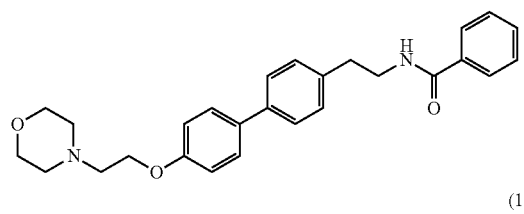

(15)

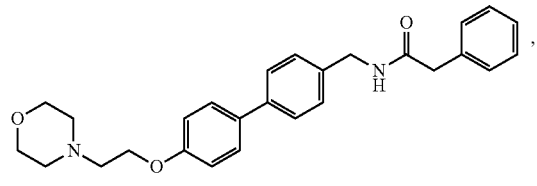

(16)

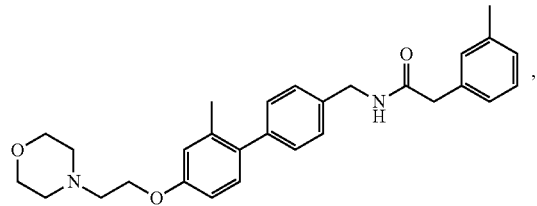

(17)

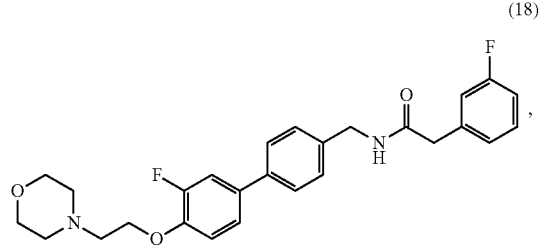

(18)

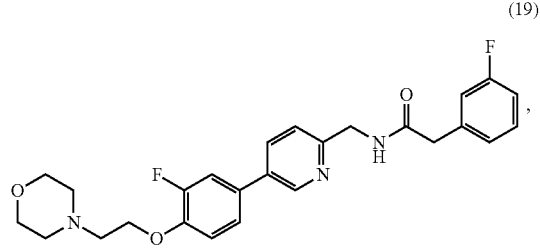

(19)

(20)
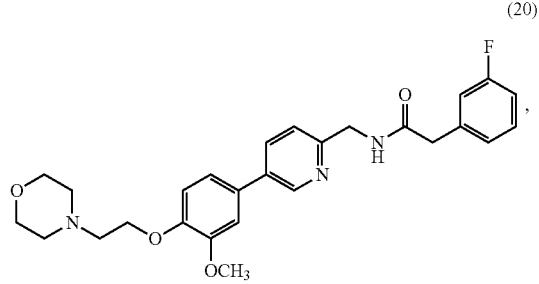
(21)
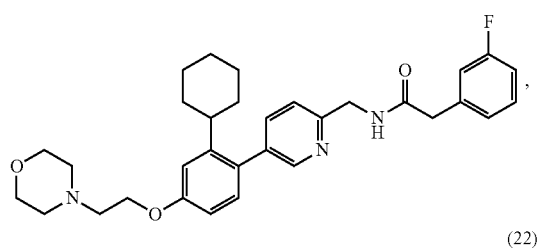
(22)
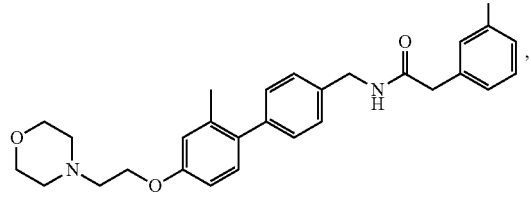
(73)
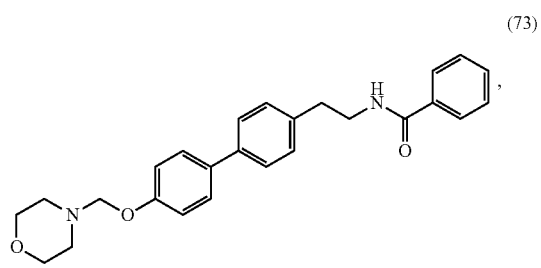
(74)
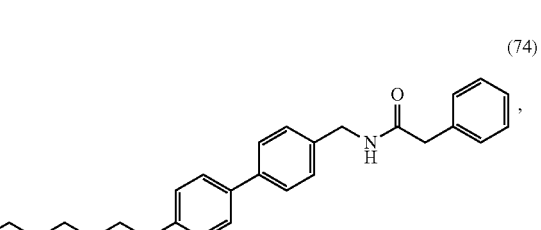
(77)
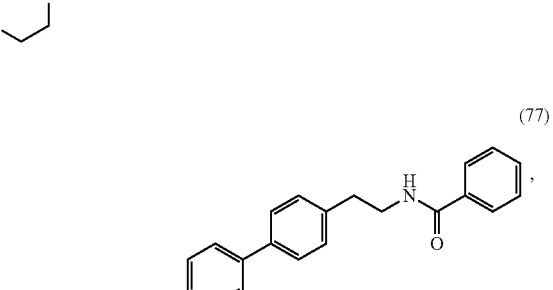
(78)
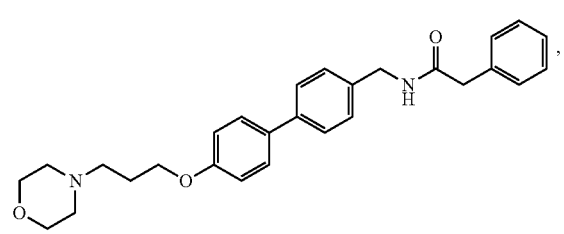
(99)
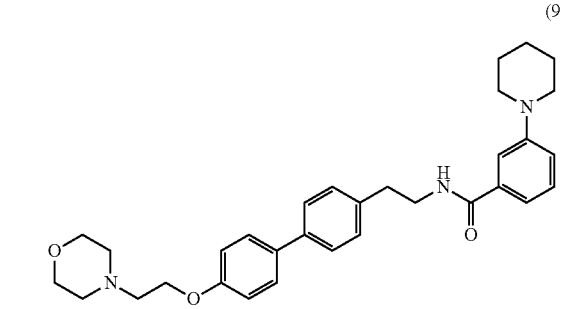
(100)
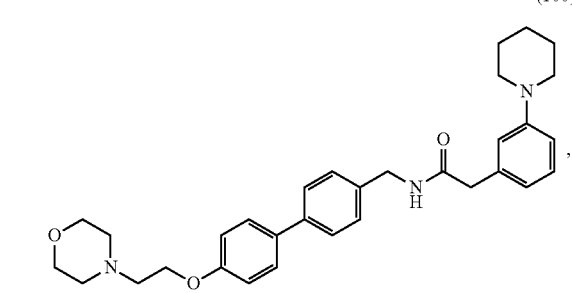
(101)
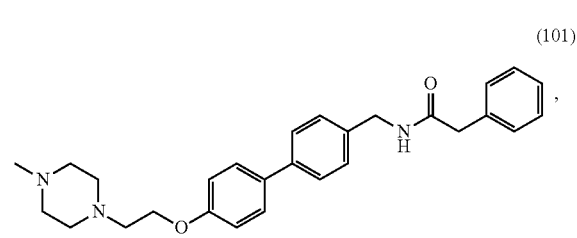
(102)
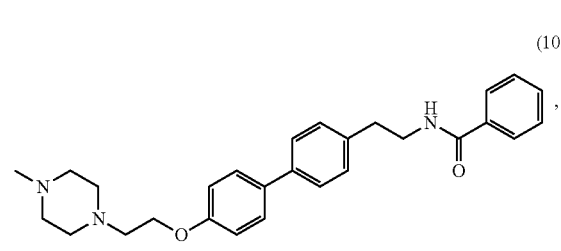
(123)
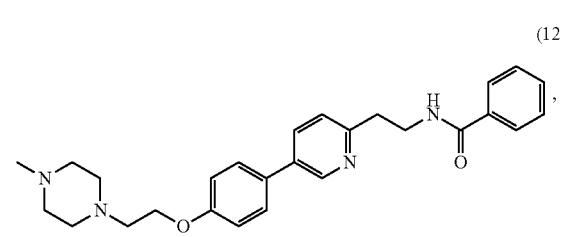

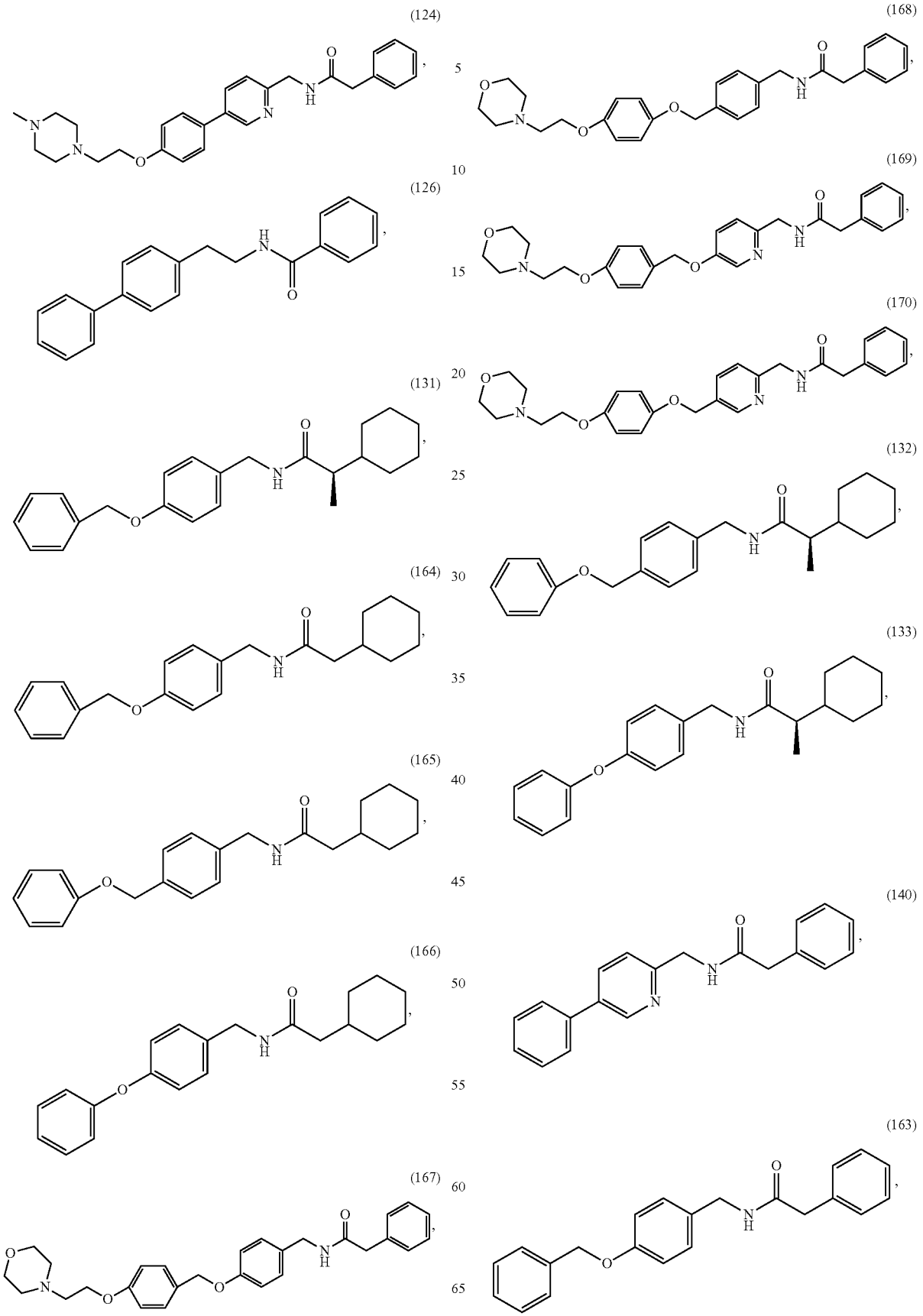

-continued
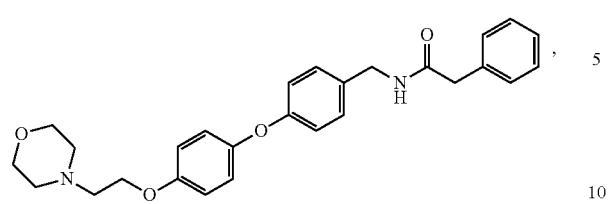
-continued
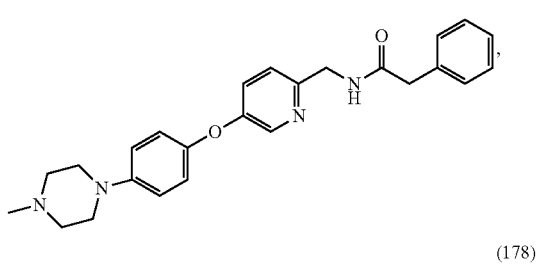

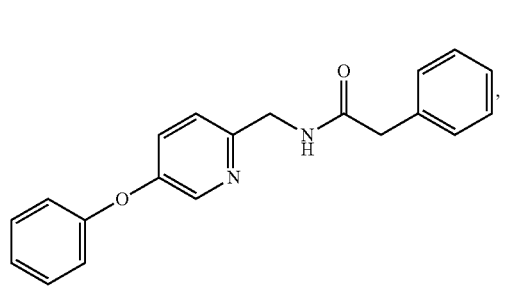
(182)
, and
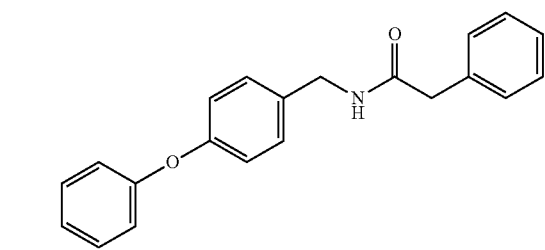
(183)
or a salt thereof.
* * * * *

UNITED STATES PATENT AND TRADEMARK OFFICE
CERTIFICATE OF CORRECTION

PATENT NO. : 8,124,605 B2  Page 1 of 1
APPLICATION NO. : 12/217721
DATED : February 28, 2012
INVENTOR(S) : David G. Hangauer, Jr.

It is certified that error appears in the above-identified patent and that said Letters Patent is hereby corrected as shown below:

Claim 18, column 310, lines 36-42, compound 180 should be amended as follows:

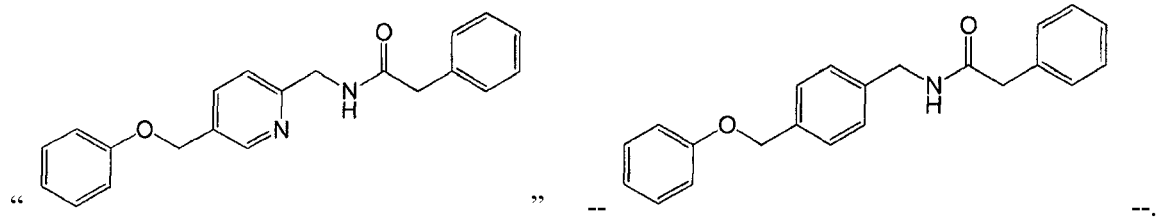

Claim 18, column 310, lines 46-54, compound 142 should be amended as follows:

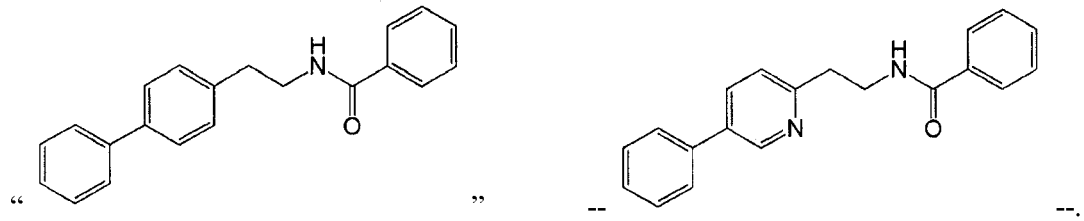

Signed and Sealed this
Nineteenth Day of June, 2012

David J. Kappos
*Director of the United States Patent and Trademark Office*